US011873485B2

(12) United States Patent
Hochrein et al.

(10) Patent No.: US 11,873,485 B2
(45) Date of Patent: Jan. 16, 2024

(54) ALLOSTERIC CONDITIONAL GUIDE RNAS FOR CELL-SELECTIVE REGULATION OF CRISPR/CAS

(71) Applicant: California Institute of Technology, Pasadena, CA (US)

(72) Inventors: Lisa Hochrein, Chicago, IL (US); Mikhail H. Hanewich-Hollatz, Pasadena, CA (US); Zhewei Chen, Pasadena, CA (US); Heyun Li, Pasadena, CA (US); Shashank Gandhi, Pasadena, CA (US); Marianne Bronner, Pasadena, CA (US); Niles A. Pierce, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 17/584,237

(22) Filed: Jan. 25, 2022

(65) Prior Publication Data
US 2022/0348909 A1 Nov. 3, 2022

Related U.S. Application Data

(60) Provisional application No. 63/181,808, filed on Apr. 29, 2021, provisional application No. 63/141,865, filed on Jan. 26, 2021.

(51) Int. Cl.
*C12N 15/11* (2006.01)
*C12N 9/22* (2006.01)

(52) U.S. Cl.
CPC .............. *C12N 15/11* (2013.01); *C12N 9/22* (2013.01); *C12N 2310/15* (2013.01); *C12N 2310/20* (2017.05); *C12N 2310/344* (2013.01); *C12N 2310/531* (2013.01); *C12N 2310/532* (2013.01); *C12N 2800/80* (2013.01)

(58) Field of Classification Search
None
See application file for complete search history.

(56) References Cited

U.S. PATENT DOCUMENTS

| | | |
|---|---|---|
| 4,714,680 A | 12/1987 | Civin |
| 4,868,105 A | 9/1989 | Urdea et al. |
| 4,897,355 A | 1/1990 | Eppstein et al. |
| 4,965,204 A | 10/1990 | Civin |
| 5,057,410 A | 10/1991 | Kawasaki et al. |
| 5,061,620 A | 10/1991 | Tsukamoto et al. |
| 5,118,801 A | 6/1992 | Lizardi et al. |
| 5,124,246 A | 6/1992 | Urdea et al. |
| 5,270,163 A | 12/1993 | Gold et al. |
| 5,312,728 A | 5/1994 | Lizardi et al. |
| 5,424,413 A | 6/1995 | Hogan et al. |
| 5,459,127 A | 10/1995 | Felgner et al. |
| 5,563,256 A | 10/1996 | Chakraborty et al. |
| 5,571,670 A | 11/1996 | Urdea et al. |
| 5,579,793 A | 12/1996 | Gajewski et al. |
| 5,624,802 A | 4/1997 | Urdea et al. |
| 5,635,352 A | 6/1997 | Urdea et al. |
| 5,643,741 A | 7/1997 | Tsukamoto et al. |
| 5,656,731 A | 8/1997 | Urdea |
| 5,677,136 A | 10/1997 | Simmons et al. |
| 5,681,697 A | 10/1997 | Urdea et al. |
| 5,681,702 A | 10/1997 | Collins et al. |

(Continued)

FOREIGN PATENT DOCUMENTS

| | | |
|---|---|---|
| AU | 2003226729 A1 | 10/2003 |
| CA | 2994958 A1 | 2/2017 |

(Continued)

OTHER PUBLICATIONS

Siu and Chen, Riboregulated toehold-gated gRNA for programmable CRISPR-Cas9 function. Nature Chemical Biology (2019), 15: 217-220 (Year: 2019).*
Jin et al., Programmable CRISPR-Cas Repression, Activation, and Computation with Sequence-Independent Targets and Triggers. ACS Synth. Biol. (2019), 8: 1583-1589 (Year: 2019).*
Nowak et al., Guide RNA engineering for versatile Cas9 functionality. Nucleic Acids Research (2016), 44(20): 9555-9564 (Year: 2016).*
Jinek et al., A Programmable Dual-RNA-Guided DNA Endonuclease in Adaptive Bacterial Immunity. Science (2012), 337: 816-821 (Year: 2012).*

(Continued)

*Primary Examiner* — Samuel C Woolwine
*Assistant Examiner* — Catherine Konopka
(74) *Attorney, Agent, or Firm* — Knobbe, Martens, Olson & Bear, LLP

(57) ABSTRACT

Programmable guide RNAs (gRNAs) play a central role in the CRISPR revolution sweeping biology and medicine by directing the function of a Cas protein effector to a target gene of choice. To achieve programmable control over regulatory scope, the activity of a conditional guide RNA (cgRNA) depends on the presence or absence of an RNA trigger, allowing for cell-selective regulation of CRISPR/Cas function. Unlike a standard gRNA, a cgRNA is programmable at multiple levels, with the target-binding sequence controlling the target of Cas activity (edit, silence, induce, or bind a gene of choice) and the trigger binding sequence controlling the scope of Cas activity. cgRNA mechanisms that are allosteric allow for independent design of the target and trigger sequences, providing the flexibility to select the regulatory target and scope independently. Disclosed herein are allosteric cgRNA mechanisms for both ON→OFF logic (conditional inactivation by an RNA trigger) and OFF→ON logic (conditional activation by an RNA trigger). Allosteric cgRNAs enable restriction of CRISPR/Cas function to a desired cell type, tissue, organ, or disease state. Allosteric cgRNAs provide a versatile platform for cell-selective and tissue-selective research tools, biotechnologies, diagnostics, and therapeutics.

2 Claims, 81 Drawing Sheets

Specification includes a Sequence Listing.

(56) References Cited

U.S. PATENT DOCUMENTS

| | | | |
|---|---|---|---|
| 5,691,145 A | 11/1997 | Pitner et al. |
| 5,710,264 A | 1/1998 | Urdea et al. |
| 5,716,827 A | 2/1998 | Tsukamoto et al. |
| 5,750,397 A | 5/1998 | Tsukamoto et al. |
| 5,780,610 A | 7/1998 | Collins et al. |
| 5,784,487 A | 7/1998 | Cooperman |
| 5,849,481 A | 12/1998 | Urdea et al. |
| 5,876,924 A | 3/1999 | Zhang et al. |
| 5,902,724 A | 5/1999 | Lane et al. |
| 5,928,913 A | 7/1999 | Efstathiou et al. |
| 5,989,823 A | 11/1999 | Jayasena et al. |
| 6,007,994 A | 12/1999 | Ward et al. |
| 6,128,587 A | 10/2000 | Sjolander |
| 6,130,047 A | 10/2000 | Nadeau et al. |
| 6,232,462 B1 | 5/2001 | Collins et al. |
| 6,242,246 B1 | 6/2001 | Gold et al. |
| 6,255,469 B1 | 7/2001 | Seeman et al. |
| 6,261,783 B1 | 7/2001 | Jayasena et al. |
| 6,264,825 B1 | 7/2001 | Blackburn et al. |
| 6,361,944 B1 | 3/2002 | Mirkin et al. |
| 6,361,945 B1 | 3/2002 | Becker et al. |
| 6,485,965 B1 | 11/2002 | Klatzmann et al. |
| 6,506,559 B1 | 1/2003 | Fire et al. |
| 6,555,367 B1 | 4/2003 | Spence et al. |
| 6,696,285 B1 | 2/2004 | Mills, Jr. |
| 6,899,871 B2 | 5/2005 | Kasahara et al. |
| 7,033,834 B2 | 4/2006 | Valerio et al. |
| 7,632,641 B2 | 12/2009 | Dirks et al. |
| 7,709,198 B2 | 5/2010 | Luo et al. |
| 7,727,721 B2 | 6/2010 | Pierce et al. |
| 7,960,357 B2 | 6/2011 | Dirks et al. |
| 8,105,778 B2 | 1/2012 | Dirks et al. |
| 8,124,751 B2 | 2/2012 | Pierce et al. |
| 8,241,854 B2 | 8/2012 | Yin et al. |
| 8,318,921 B2 | 11/2012 | Pierce et al. |
| 8,478,543 B2 | 7/2013 | Pierce et al. |
| 8,497,364 B2 | 7/2013 | Pierce et al. |
| 8,507,204 B2 | 8/2013 | Pierce et al. |
| 8,604,182 B2 | 12/2013 | Luo et al. |
| 8,658,361 B2 | 2/2014 | Luo et al. |
| 8,658,780 B2 | 2/2014 | Pierce et al. |
| 8,877,438 B2 | 11/2014 | Yin |
| 8,951,726 B2 | 2/2015 | Luo et al. |
| 8,962,241 B2 | 2/2015 | Yin et al. |
| 8,962,582 B2 | 2/2015 | Dirks et al. |
| 9,217,151 B2 | 11/2015 | Yin et al. |
| 9,315,862 B2 | 4/2016 | Smolke et al. |
| 9,353,404 B2 | 5/2016 | Fletcher |
| 9,834,439 B2 | 12/2017 | Yin et al. |
| 9,856,472 B2 | 1/2018 | Pierce et al. |
| 10,450,599 B2 | 10/2019 | Pierce et al. |
| 10,815,519 B2 | 10/2020 | Husain et al. |
| 2001/0014445 A1 | 8/2001 | Urnovitz |
| 2001/0026918 A1 | 10/2001 | Collins et al. |
| 2002/0051769 A1 | 5/2002 | Zhang |
| 2002/0102584 A1 | 8/2002 | Hester et al. |
| 2002/0137035 A1 | 9/2002 | Stender et al. |
| 2002/0172950 A1 | 11/2002 | Kenny et al. |
| 2003/0056177 A1 | 3/2003 | Nara et al. |
| 2003/0092162 A1 | 5/2003 | Shankara et al. |
| 2003/0129611 A1 | 7/2003 | Bao et al. |
| 2003/0207295 A1 | 11/2003 | Gunderson et al. |
| 2003/0215821 A1 | 11/2003 | Gunderson et al. |
| 2004/0005552 A1 | 1/2004 | Lane et al. |
| 2004/0009510 A1 | 1/2004 | Seiwert et al. |
| 2004/0018491 A1 | 1/2004 | Gunderson et al. |
| 2004/0043386 A1 | 3/2004 | Pray et al. |
| 2004/0115686 A1 | 6/2004 | Dolginow et al. |
| 2004/0126773 A1 | 7/2004 | Beske et al. |
| 2004/0223953 A1 | 11/2004 | Kung et al. |
| 2004/0265934 A1 | 12/2004 | Stender et al. |
| 2005/0089864 A1 | 4/2005 | Li et al. |
| 2005/0100893 A1 | 5/2005 | Gunderson et al. |
| 2005/0112614 A1 | 5/2005 | Cook |
| 2005/0233332 A1 | 10/2005 | Collis |
| 2005/0239061 A1 | 10/2005 | Marshall et al. |
| 2005/0260635 A1 | 11/2005 | Dirks et al. |
| 2006/0035375 A1 | 2/2006 | Head et al. |
| 2006/0088864 A1 | 4/2006 | Smolke et al. |
| 2006/0156226 A1 | 7/2006 | Dejean et al. |
| 2006/0228733 A1 | 10/2006 | Pierce et al. |
| 2006/0234261 A1 | 10/2006 | Pierce et al. |
| 2007/0072215 A1 | 3/2007 | Seelig et al. |
| 2007/0087334 A1 | 4/2007 | Dirks et al. |
| 2007/0117109 A1 | 5/2007 | Rothemund |
| 2008/0038725 A1 | 2/2008 | Luo et al. |
| 2008/0183958 A1 | 7/2008 | Cheriton |
| 2008/0214488 A1 | 9/2008 | Pierce et al. |
| 2009/0011956 A1 | 1/2009 | Yin et al. |
| 2009/0123914 A1 | 5/2009 | Erikson et al. |
| 2009/0197271 A1 | 8/2009 | Kotlikoff et al. |
| 2009/0227774 A1 | 9/2009 | Turberfield et al. |
| 2009/0247615 A1 | 10/2009 | Pierce et al. |
| 2009/0311799 A1 | 12/2009 | Sotzing et al. |
| 2010/0021901 A1 | 1/2010 | Yin et al. |
| 2010/0021904 A1 | 1/2010 | Pierce et al. |
| 2010/0035233 A1 | 2/2010 | Yin et al. |
| 2010/0047926 A1 | 2/2010 | Dirks et al. |
| 2011/0059064 A1 | 3/2011 | Possani-Potsay et al. |
| 2011/0104676 A1 | 5/2011 | Pierce et al. |
| 2011/0287557 A1 | 11/2011 | Zhang et al. |
| 2011/0288148 A1 | 11/2011 | Pierce et al. |
| 2011/0288832 A1 | 11/2011 | Pierce et al. |
| 2011/0313030 A1 | 12/2011 | Dirks et al. |
| 2012/0021410 A1 | 1/2012 | Peng et al. |
| 2012/0022243 A1 | 1/2012 | Peng et al. |
| 2012/0022244 A1 | 1/2012 | Peng |
| 2012/0190835 A1 | 7/2012 | Pierce et al. |
| 2012/0251583 A1 | 10/2012 | Rothemund |
| 2012/0324341 A1 | 12/2012 | Dejean et al. |
| 2013/0171621 A1 | 7/2013 | Luo et al. |
| 2014/0032558 A1 | 1/2014 | Renders et al. |
| 2014/0107983 A1 | 4/2014 | Wolfe et al. |
| 2014/0270545 A1 | 9/2014 | Ghessassi |
| 2014/0280167 A1 | 9/2014 | Ghessassi |
| 2014/0301644 A1 | 10/2014 | Koh et al. |
| 2015/0004615 A1 | 1/2015 | Pierce et al. |
| 2015/0154347 A1 | 6/2015 | Wolfe et al. |
| 2017/0009278 A1 | 1/2017 | Soderberg et al. |
| 2017/0022499 A1 | 1/2017 | Lu et al. |
| 2017/0037432 A1* | 2/2017 | Donohoue ............... C12N 9/22 |
| 2017/0067096 A1 | 3/2017 | Wassie et al. |
| 2017/0124217 A1 | 5/2017 | Hassanzadeh |
| 2017/0166952 A1 | 6/2017 | Wang et al. |
| 2017/0327888 A1 | 11/2017 | Ong et al. |
| 2018/0066303 A1 | 3/2018 | Pierce et al. |
| 2018/0362944 A1 | 12/2018 | Hanewich-Hollathz et al. |
| 2019/0073345 A1 | 3/2019 | Jain et al. |
| 2019/0141203 A1 | 5/2019 | Morita et al. |
| 2019/0163750 A1 | 5/2019 | Sage et al. |
| 2019/0233806 A1 | 8/2019 | de Loubresse et al. |
| 2019/0382758 A1* | 12/2019 | Aoki ................... C12N 15/907 |
| 2020/0239879 A1 | 7/2020 | Choudhary et al. |
| 2022/0090163 A1 | 3/2022 | Pierce et al. |
| 2022/0282300 A1 | 9/2022 | Pierce et al. |

FOREIGN PATENT DOCUMENTS

| | | |
|---|---|---|
| EP | 0070685 | 1/1982 |
| EP | 0070685 A2 | 1/1983 |
| EP | 0273085 | 7/1988 |
| EP | 1071023 A1 | 1/2001 |
| EP | 0731848 B1 | 5/2003 |
| EP | 1479766 | 11/2004 |
| EP | 1634890 | 3/2006 |
| EP | 2155770 | 5/2008 |
| EP | 2055781 | 5/2009 |
| EP | 1730161 | 9/2010 |
| EP | 1931806 | 10/2011 |
| EP | 2460893 A1 | 6/2012 |
| EP | 2630260 B1 | 11/2015 |
| EP | 1910572 B1 | 12/2015 |
| EP | 2500439 B2 | 8/2017 |
| EP | 2529030 B1 | 3/2019 |

(56) References Cited

FOREIGN PATENT DOCUMENTS

| | | |
|---|---|---|
| EP | 3507296 A1 | 7/2019 |
| EP | 3638789 A2 | 4/2020 |
| EP | 3943613 | 1/2022 |
| EP | 3507296 B1 | 10/2022 |
| HK | 40062706 | 6/2022 |
| HK | 40008988 | 7/2022 |
| IL | 264831 | 3/2019 |
| IL | 290679 | 4/2022 |
| IL | 264152 | 6/2022 |
| WO | WO 92/03464 | 3/1992 |
| WO | WO 93/15102 | 8/1993 |
| WO | WO 94/01550 | 1/1994 |
| WO | WO 99/31276 | 6/1999 |
| WO | WO 01/40516 | 6/2001 |
| WO | WO 2001/094632 | 12/2001 |
| WO | WO 03/083131 | 10/2003 |
| WO | WO 2005/098049 | 10/2005 |
| WO | WO 2006/002167 A2 | 1/2006 |
| WO | WO 2006/048025 A1 | 5/2006 |
| WO | WO 2007/008276 | 1/2007 |
| WO | WO 2007/044727 | 4/2007 |
| WO | WO 2007/141809 A1 | 12/2007 |
| WO | WO 2007/148337 A2 | 12/2007 |
| WO | WO 2008/106658 | 2/2008 |
| WO | WO 2008/144562 | 5/2008 |
| WO | WO 2011/126996 | 4/2011 |
| WO | WO 2014/074648 A2 | 5/2014 |
| WO | WO 2015/035139 A2 | 3/2015 |
| WO | WO 2015/118029 A1 | 8/2015 |
| WO | WO 2015/168404 A1 | 11/2015 |
| WO | WO 2016/011089 A1 | 1/2016 |
| WO | WO 2016/022866 A1 | 2/2016 |
| WO | WO 2016/094867 A1 | 6/2016 |
| WO | WO 2017/004261 A1 | 1/2017 |
| WO | WO 2017/189525 A1 | 11/2017 |
| WO | WO 2017/223449 A1 | 12/2017 |
| WO | WO 2018/009463 A3 | 1/2018 |
| WO | WO 2018/044939 | 3/2018 |
| WO | WO 2018/217905 A1 | 11/2018 |
| WO | WO 2018/231730 A2 | 12/2018 |
| WO | WO 2021/221789 A2 | 11/2021 |
| WO | WO 2022/164796 A1 | 8/2022 |

OTHER PUBLICATIONS

International Search Report and Written Opinion in International PCT Application No. PCT/US2022/13693 dated Jun. 27, 2022 in 21 pages.
Hanewich-Hollatz et al. "Conditional Guide RNAs: Programmable Conditional Regulation of CRISPR/Cas Function in Bacterial and Mammalian Cells via Dynamic RNA Nanotechnology" ACS Cent Sci., Jul. 24, 2019, vol. 5, No. 7, pp. 1241-1249.
Jin et al. "Programmable CRISPR-Cas Repression, Activation, and Computation with Sequence-Independent Targets and Triggers" ACS Cent Sci., Jul. 19, 2019, vol. 8, No. 7, pp. 1583-1589.
Hao et al. "Programmable Live-Cell CRISPR Imaging with Toehold-Switch-Mediated Strand-Displacement" Angew Chem Int Ed, Nov. 9, 2020, vol. 59, No. 46, pp. 20612-20618.
Ablain, J.; Durand, E. M.; Yang, S.; Zhou, Y.; Zon, L. I. A CRISPR/Cas9 Vector System for Tissue-Specific Gene Disruption in Zebrafish. Dev. Cell 2015, 32 (6), 756-764. https://doi.org/10.1016/j.devcel.2015.01.032.
Anzalone, A. V.; Randolph, P. B.; Davis, J. R.; Sousa, A. A.; Koblan, L. W.; Levy, J. M.; Chen, P. J.; Wilson, C.; Newby, G. A.; Raguram, A.; Liu, D. R. Search-and-Replace Genome Editing without Double-Strand Breaks or Donor DNA. Nature 2019, 576 (7785), 149-157. https://doi.org/10.1038/s41586-019-1711-4.
Aubrey, B. J.; Kelly, G. L.; Kueh, A. J.; Brennan, M. S.; O'Connor, L.; Milla, L.; Wilcox, S.; Tai, L.; Strasser, A.; Herold, M. J. An Inducible Lentiviral Guide RNA Platform Enables the Identification of Tumor-Essential Genes and Tumor-Promoting Mutations in Vivo. Cell Rep. 2015, 10 (8), 1422-1432.
Bertero, A.; Pawlowski, M.; Ortmann, D.; Snijders, K.; Yiangou, L.; Cardoso de Brito, M.; Brown, S.; Bernard, W. G.; Cooper, J. D.; Giacomelli, E.; Gambardella, L.; Hannan, N. R. F.; Iyer, D.; Sampaziotis, F.; Serrano, F.; Zonneveld, M. C. F.; Sinha, S.; Kotter, M.; Vallier, L. Optimized Inducible ShRNA and CRISPR/Cas9 Platforms for in Vitro Studies of Human Development Using HPSCs. Development 2016, 143 (23), 4405.
Briner, A. E.; Donohoue, P. D.; Gomaa, A. A.; Selle, K.; Slorach, E. M.; Nye, C. H.; Haurwitz, R. E.; Beisel, C. L.; May, A. P.; Barrangou, R. Guide RNA Functional Modules Direct Cas9 Activity and Orthogonality. Mol Cell 2014, 56 (2), 333-339. https://doi.org/10.1016/j.molcel.2014.09.019.
Chavez, A.; Scheiman, J.; Vora, S.; Pruitt, B. W.; Tuttle, M.; Iyer, E. P. R.; Lin, S.; Kiani, S.; Guzman, C. D.; Wiegand, D. J.; Ter-Ovanesyan, D.; Braff, J. L.; Davidsohn, N.; Housden, B. E.; Perrimon, N.; Weiss, R.; Aach, J.; Collins, J. J.; Church, G. M. Highly Efficient Cas9-Mediated Transcriptional Programming. Nat. Methods 2015, 12 (4), 326-328. https://doi.org/10.1038/nmeth.3312.
Chen, B.; Gilbert, L. A.; Cimini, B. A.; Schnitzbauer, J.; Zhang, W.; Li, G .-W.; Park, J.; Blackburn, E. H.; Weissman, J. S.; Qi, L. S.; Huang, B. Dynamic Imaging of Genomic Loci in Living Human Cells by an Optimized CRISPR/Cas System. Cell 2013, 155 (7), 1479-1491.
Chen, T.; Gao, D.; Zhang, R.; Zeng, G.; Yan, H.; Lim, E.; Liang, F. Chemically Controlled Epigenome Editing through an Inducible DCas9 System. J. Am. Chem. Soc. 2017, 139 (33), 11337-11340. https://doi.org/10.1021/jacs.7b06555.
Cong, L.; Ran, F. A.; Cox, D.; Lin, S.; Barretto, R.; Habib, N.; Hsu, P. D.; Wu, X.; Jiang, W.; Marraffini, L. A.; Zhang, F. Multiplex Genome Engineering Using CRISPR/Cas Systems. Science 2013, 339 (6121), 819-823. https://doi.org/10.1126/science.1231143.
Ferry, Q. R. V.; Lyutova, R.; Fulga, T. A. Rational Design of Inducible CRISPR Guide RNAs for de Novo Assembly of Transcriptional Programs. Nat Commun 2017, 8, 2109.
Gao, Z.; Herrera-Carrillo, E.; Berkhout, B. Delineation of the Exact Transcription Termination Signal for Type 3 Polymerase III. Mol. Ther. Nucleic Acids 2018, 10, 36-44.
Gaudelli, N. M.; Komor, A. C.; Rees, H. A.; Packer, M. S.; Badran, A. H.; Bryson, D. I.; Liu, D. R. Programmable Base Editing of A•T to G•C in Genomic DNA without DNA Cleavage. Nature 2017, 551 (7681), 464-471. https://doi.org/10.1038/nature24644.
Gilbert, L. A.; Larson, M. H.; Morsut, L.; Liu, Z.; Brar, G. A.; Torres, S. E.; Stern-Ginossar, N.; Brandman, O.; Whitehead, E. H.; Doudna, J. A.; Lim, W. A.; Weissman, J. S.; Qi, L. S. CRISPR-Mediated Modular RNA-Guided Regulation of Transcription in Eukaryotes. Cell 2013, 154 (2), 442-451.
Hanewich-Hollatz, M. H.; Chen, Z.; Hochrein, L. M.; Huang, J.; Pierce, N. A. Conditional Guide RNAs: Programmable Conditional Regulation of CRISPR/Cas Function in Bacterial and Mammalian Cells via Dynamic RNA Nanotechnology. ACS Cent. Sci. 2019, 5 (7), 1241-1249.
Hilton, I. B.; D'Ippolito, A. M.; Vockley, C. M.; Thakore, P. I.; Crawford, G. E.; Reddy, T. E.; Gersbach, C. A. Epigenome Editing by a CRISPR-Cas9-Based Acetyltransferase Activates Genes from Promoters and Enhancers. Nat Biotechnol 2015, 33, 510.
Hirosawa, M.; Fujita, Y.; Parr, C. J. C.; Hayashi, K.; Kashida, S.; Hotta, A.; Woltjen, K.; Saito, H. Cell-Type-Specific Genome Editing with a MicroRNA-Responsive CRISPR-Cas9 Switch. Nucleic Acids Res 2017, 45 (13), e118.
Hochrein, L. M.; Li, H.; Pierce, N. A. High-Performance Allosteric Conditional Guide RNAs for Mammalian Cell-Selective Regulation of CRISPR/Cas. ACS Synth. Biol. 2021, 10 (5), 964-971. https://doi.org/10.1021/acssynbio.1c00037.
Jain, P. K.; Ramanan, V.; Schepers, A. G.; Dalvie, N. S.; Panda, A.; Fleming, H. E.; Bhatia, S. N. Development of Light-Activated CRISPR Using Guide RNAs with Photocleavable Protectors. Angew. Chem. Int. Ed. 2016, 55 (40), 12440-12444.
Kieft, J. S.; Rabe, J. L.; Chapman, E. G. New Hypotheses Derived from the Structure of a Flaviviral Xrn1-Resistant RNA: Conservation, Folding, and Host Adaptation. RNA Biol 2015, 12 (11), 1169-1177. https://doi.org/10.1080/15476286.2015.1094599.

(56) References Cited

OTHER PUBLICATIONS

Knight, S. C.; Tjian, R.; Doudna, J. A. Genomes in Focus: Development and Applications of CRISPR-Cas9 Imaging Technologies. Angew Chem Int Ed 2018, 57 (16), 4329-4337.

Knott, G. J.; Doudna, J. A. CRISPR-Cas Guides the Future of Genetic Engineering. Science 2018, 361 (6405), 866-869.

Kundert, K.; Lucas, J. E.; Watters, K. E.; Fellmann, C.; Ng, A. H.; Heineike, B. M.; Fitzsimmons, C. M.; Oakes, B. L.; Qu, J.; Prasad, N.; Rosenberg, O. S.; Savage, D. F.; El-Samad, H.; Doudna, J. A.; Kortemme, T. Controlling CRISPR-Cas9 with Ligand-Activated and Ligand-Deactivated SgRNAs. Nat Commun 2019, 10 (1), 2127. https://doi.org/10.1038/s41467-019-09985-2.

Larson, M. H.; Gilbert, L. A.; Wang, X.; Lim, W. A.; Weissman, J. S.; Qi, L. S. CRISPR Interference (CRISPRi) for Sequence-Specific Control of Gene Expression. Nat Protoc 2013, 8, 2180-2196.

Lee, Y. J.; Hoynes-O'Connor, A.; Leong, M. C.; Moon, T. S. Programmable Control of Bacterial Gene Expression with the Combined CRISPR and Antisense RNA System. Nucleic Acids Res. 2016, 44 (5), 2462-2473.

Liu, X. S.; Wu, H.; Krzisch, M.; Wu, X.; Graef, J.; Muffat, J.; Hnisz, D.; Li, C. H.; Yuan, B.; Xu, C.; Li, Y.; Vershkov, D.; Cacace, A.; Young, R. A.; Jaenisch, R. Rescue of Fragile X Syndrome Neurons by DNA Methylation Editing of the FMR1 Gene. Cell 2018, 172 (5), 979-992.e6. https://doi.org/10.1016/j.cell.2018.01.012.

Liu, Y.; Zou, R. S.; He, S.; Nihongaki, Y.; Li, X.; Razavi, S.; Wu, B.; Ha, T. Very Fast CRISPR on Demand. Science 2020, 368 (6496), 1265-1269.

Ma, H.; Tu, L.-C.; Naseri, A.; Huisman, M.; Zhang, S.; Grunwald, D.; Pederson, T. Multiplexed Labeling of Genomic Loci with DCas9 and Engineered SgRNAs Using CRISPRainbow. Nat. Biotechnol. 2016, 34 (5), 528-530. httgs://doi.org/10.1038/nbt.3526.

Mali, P.; Aach, J.; Stranges, P. B.; Esvelt, K. M.; Moosburner, M.; Kosuri, S.; Yang, L.; Church, G. M. CAS9 Transcriptional Activators for Target Specificity Screening and Paired Nickases for Cooperative Genome Engineering. Nat. Biotechnol. 2013, 31, 833-838.

Mali, P.; Yang, L.; Esvelt, K. M.; Aach, J.; Guell, M.; DiCarlo, J. E.; Norville, J. E.; Church, G. M. RNA-Guided Human Genome Engineering via Cas9. Science 2013, 339 (6121), 823.

Misteli, T.; Spector, D. L. Applications of the Green Fluorescent Protein in Cell Biology and Biotechnology. Nat Biotech 1997, 15 (10), 961-964.

Morgan, S. L.; Mariano, N. C.; Bermudez, A.; Arruda, N. L.; Wu, F.; Luo, Y.; Shankar, G.; Jia, L.; Chen, H.; Hu, J.-F.; Hoffman, A. R.; Huang, C.-C.; Pitteri, S. J.; Wang, K. C. Manipulation of Nuclear Architecture through CRISPR-Mediated Chromosomal Looping. Nat. Commun. 2017, 8 (1), 15993. https://doi.org/10.1038/ncomms15993.

Moroz-Omori, E. V.; Satyapertiwi, D.; Ramel, M.-C.; Høgset, H.; Sunyovszki, I. K.; Liu, Z.; Wojcieohowski, J. P.; Zhang, Y.; Grigsby, C. L.; Brito, L.; Bugeon, L.; Dallman, M. J.; Stevens, M. M. Photoswitohable GRNAs for Spatiotemporally Controlled CRISPR-Cas-Based Genomic Regulation. ACS Cent. Sci. 2020, 6 (5), 695-703. https://doi.org/10.1021/acscentsci.9b01093.

Mückl, A.; Schwarz-Schilling, M.; Fischer, K.; Simmel, F. C. Filamentation and Restoration of Normal Growth in *Escherichia coli* Using a Combined CRISPRi SgRNA/Antisense RNA Approach. PLoS One 2018, 13 (9), e0198058.

Myers, S. A.; Wright, J.; Peckner, R.; Kalish, B. T.; Zhang, F.; Carr, S. A. Discovery of Proteins Associated with a Predefined Genomic Locus via DCas9-APEX-Mediated Proximity Labeling. Nat. Methods 2018, 15 (6), 437-439. https://doi.org/10.1038/s41592-018-0007-1.

Nihongaki, Y.; Otabe, T.; Sato, M. Emerging Approaches forSpatiotemporal Control of Targeted Genome with Inducible CRISPR-Cas9. Anal Chem 2018, 90 (1), 429-439.

Nissim, L.; Perli, S. D.; Fridkin, A.; Perez-Pinera, P.; Lu, T. K. Multiplexed and Programmable Regulation of Gene Networks with an Integrated RNA and CRISPR/Cas Toolkit in Human Cells. Mol. Cell 2014, 54 (4), 698-710.

Nowak, C. M.; Lawson, S.; Zerez, M.; Bleris, L. Guide RNA Engineering for Versatile Cas9 Functionality. Nucleic Acids Res 2016, 44 (20), 9555-9564.

Oesinghaus, L.; Simmel, F. C. Switching the Activity of 035123 Using Guide RNA Strand Displacement Circuits. Nat. Commun. 2019, 10 (1), 1-11. https://doi.org/10.1038/541467-019-09953-w.

Qi, L. S.; Larson, M. H.; Gilbert, L. A.; Doudna, J. A.; Weissman, J. S.; Arkin, A. P.; Lim, W. A. Repurposing CRISPR as an RNA-Guided Platform for Sequence-Specific Control of Gene Expression. Cell 2013, 152 (5), 1173-1183. https://doi.org/10.1016/j.cell.2013.02.022.

Regulation of CRISPR/Cas Function in Bacterial and Mammalian Cells via Dynamic RNA Nanotechnology. ACS Cent. Sci. 2019, 5 (7), 1241-1249. (27) Liu, Y.; Zhan, Y.; Chen, Z.; He, A.; Li, J.; Wu, H.; Liu, L.; Zhuang, C.; Lin, J.; Guo, X.; Zhang, Q.; Huang, W.; Cai, Z. Directing Cellular Information Flow via CRISPR Signal Conductors. Nat Methods 2016, 13, 938-944.

Shagin, D. A.; Barsova, E. V.; Yanushevioh, Y. G.; Fradkov, A. F.; Lukyanov, K. A.; Labas, Y. A.; Semenova, T. N.; Ugalde, J. A.; Meyers, A.; Nunez, J. M.; Widder, E. A.; Lukyanov, S. A.; Matz, M. V. GFP-like Proteins as Ubiquitous Metazoan Superfamily: Evolution of Functional Features and Structural Complexity. Mol. Biol. Evol. 2004, 21 (5), 841-850. https://doi.org/10.1093/molbev/msh079.

Shen, Z.; Zhang, X.; Chai, Y.; Zhu, Z.; Yi, P.; Feng, G.; Li, W.; Ou, G. Conditional Knockouts Generated by Engineered CRISPR-Cas9 Endonuclease Reveal the Roles of Coronin in C. Elegans Neural Development. Dev. Cell 2014, 30 (5), 625-636.

Siu, K.- H.; Chen, W. Riboregulated Toehold-Gated GRNA for Programmable CRISPR-Cas9 Function. Nat. Chem. Biol. 2019, 15 (3), 217-220. https://doi.org/10.1038/s41589-018-0186-1.

Tang, W.; Hu, J. H.; Liu, D. R. Aptazyme-Embedded Guide RNAs Enable Ligand-Responsive Genome Editing and Transcriptional Activation. Nat Commun 2017, 8, 15939.

Tsien, R. Y. The Green Fluorescent Protein. Annu Rev Biochem 1998, 67 (1), 509-544. https://doi.org/10.1146/annurev.biochem.67.1.509.

Wang, D.; Zhang, C.; Wang, B.; Li, B.; Wang, Q.; Liu, D.; Wang, H.; Zhou, Y.; Shi, L.; Lan, F.; Wang, Y. Optimized CRISPR Guide RNA Design for Two High-Fidelity Cas9 Variants by Deep Learning. Nat Commun 2019, 10 (1), 4284. https://doi.org/10.1038/s41467-019-12281-8.

Wang, X.- W.; Hu, L.- F.; Hao, J.; Liao, L.- Q.; Chiu, Y.-T.; Shi, M.; Wang, Y. A MicroRNA-Inducible CRISPR-Cas9 Platform Serves as a MicroRNA Sensor and Cell-Type-Specific Genome Regulation Tool. Nat. Cell Biol. 2019, 21 (4), 522-530. https://doi.org/10.1038/s41556-019-0292-7.

Wolfe, B. R.; Pierce, N. A. Sequence Design for a Test Tube of Interacting Nucleic Acid Strands. ACS Synth. Biol. 2015, 4 (10), 1086-1100.

Wolfe, B. R.; Porubsky, N. J.; Zadeh, J. N.; Dirks, R. M.; Pierce, N. A. Constrained Multistate Sequence Design for Nucleic Acid Reaction Pathway Engineering. J. Am. Chem. Soc. 2017, 139 (8), 3134-3144.

Zadeh, J. N.; Steenberg, C. D.; Bois, J. S.; Wolfe, B. R.; Pierce, M. B.; Khan, A. R.; Dirks, R. M.; Pierce, N. A. NUPACK: Analysis and Design of Nucleic Acid Systems. J. Comput. Chem. 2011, 32 (1), 170-173. https://doi.org/10.1002/jcc.21596.

Zadeh, J. N.; Wolfe, B. R.; Pierce, N. A. Nucleic Acid Sequence Design via Efficient Ensemble Defect Optimization. J. Comput. Chem. 2011, 32, 439-452. https://doi.org/10.1002/jcc.21633.

Zetsche, B.; Heidenreich, M.; Mohanraju, P.; Fedorova, I.; Kneppers, J.; DeGennaro, E. M.; Winblad, N.; Choudhury, S. R.; Abudayyeh, O. O.; Gootenberg, J. S.; Wu, W. Y.; Scott, D. A.; Severinov, K.; van der Oost, J.; Zhang, F. Multiplex Gene Editing by CRISPR-Cpf1 Using a Single CrRNA Array. Nat Biotechnol 2016, 35, 31-34.

Zimmer, M. Green Fluorescent Protein (GFP): Applications, Structure, and Related Photophysical Behavior. Chem Rev 2002, 102 (3), 759-782. https://doi.org/10.1021/cr010142r.

(56) References Cited

OTHER PUBLICATIONS

Aagaard et al., "RNAi Therapeutics: Principles, Prospects and Challenges." Advanced Drug Delivery Reviews 59 (2007): 75-86.
Abudayyeh,.O et al. C2c2 is a single-component programmable RNA-guided RNA-targeting CRISPR effector', Science, (2016).
Acloque, H. et al., "In situ hybridization analysis of chick embryos in whole-mount and tissue sections," Methods in Cell Biology, vol. 87, pp. 169-185, 2008.
Acharya, A, Multiplexed Analysis of Diverse RNA Classes via Hybridization Chain Reaction. PhD Thesis, California Institute of Technology, 2016.
Allan et al., "A Concise Total Synthesis of (-)-Quinocarcin via Aryne Annulation." Journal of American Chemical Society 130 (2008) 17270-17271.
Amarzguioui et al., "Rational design and in vitro and in vitro delivery of Dicer substrate siRNA,", Nature Protocols, vol. 1, No. 2, pp. 508-517, 2006.
An, C. I.; Trinh, V. B.; Yokobayashi, Y. "Artificial control of gene expression in mammalian cells by modulating RNA interference through aptamer-small molecule interaction" RNA 2006, 12, 710-716.
Andronescu et al., "A New Algorithm for RNA Secondary Structure Design", J. Mol. Biol., vol. 336, pp. 607-624, 2004.
Antao et al., In Situ Hybridization Using the bDNA Technology. In: Patterson B.K. (eds) Techniques in Quantification and Localization of Gene Expression. Birkhauser, Boston, MA. (Year: 2000). Appendix Feb. 12, 2020, Feb. 12, 2020.
Asbury, C.L., "Kinesin: world's tiniest biped", Current Opinion in Cell Biology, vol. 17, pp. 89-97, 2005.
Bayer Versant® HIV-1 RNA 3.0 Assay (bDNA) FDA coversheet (approval date 2002).
Bayer Versant® HIV-1 RNA 3.0 Assay (bDNA) FDA Summary of Safety and Effectiveness (approval date 2002).
Bayer Versant® HCV RNA 3.0 Assay (bDNA) product manual (date 2003).
Bayer Versant (TM) HCV RNA 3.0 Assay (BONA), Premarket Approval (PMA) Notice, 2004.
Barish, R.D.; Schulman, R.; Rothemund, P.W.K.; Winfree, E., "An Information-Bearing seed for nucleating algorithmic self assembly." Proceedings of the National Academy of Sciences 2009, 106, 6054.
Barrangou, R, et al., 2007. 'CRISPR Provides Acquired Resistance Against Viruses in Prokaryotes', Science, 315, pp. 1709-1712, (2007).
Barroso-Chinea, P. et al., "Detection of two different mRNAs in a single section by dual in situ hybridization: A comparison between colorimetric and fluorescent detection," Journal of Neuroscience Methods, vol. 162, Issues 1-2, pp. 119-128, May 15, 2007.
Bates, M.; Huang, B.; Dempsey, G.T.; and Zhuang, X. "Multicolor super-resolution imaging with photo-switchable fluorescent probes." Science, 317: 1749-1759, 2007.
Bath et al., "DNA nanomachines", Nature Nanotechnology, vol. 2, pp. 275-284, May 2007.
Beisel, C. L.; Bayer, T. S.; Hoff, K. G.; Smolke, C. D. "Model-guided design of ligand-regulated RNAi for programmable control of gene expression" Mol. Syst. Biol. 2008, 4, 224.
Beisel, C. L.; Chen, Y. Y.; Culler, S. J.; Hoff, K. G.; Smolke, C. D. "Design of small molecule-responsive microRNAs based on structural requirements for Drosha processing" Nucleic Acids Res. 2011, 39, 2981-2994.
Berry et al., "HIV-1 and HIV-2 Molecular Diagnosis", HIV and the New Viruses Second Edition, pp. 207-222, Copyright@ 1999 Academic Press.
Behenna et al., "The Enantioselective Tsuji Allylation." Journal of American Chemical Society 126.46 (2004): 15044-15045.
Bhatia et al., Icosahedral DNA Nanocapsules by Modular Assembly, Angew. Chem. Int. Ed., vol. 48, pp. 4134-4137, 2009.
Bloomfield et al., "Nucleic Acids: Structures, Properties, and Functions." University Science Books (2000).
Boehm et al., Interrogating the Degradation Pathways of Unstable MRNAs with XRN1-Resistant Sequences. Nat. Commun. 2016, 7 (1), 13691. https://doi.org/10.1038/ncomms13691.
Bois et al., "Topological constraints in nucleic acid hybridization kinetics", Nucleic Acids Research, vol. 33, No. 13, pp. 4090-4095, 2005.
Bois J.S., "Analysis of interacting nucleic acids in dilute solutions" Ph.D. Thesis. California Institute of Technology. (2007).
Bolt et al., Differential Reactivities of the mono- and di-epoxide of 1,3-butadiene. Toxicology 113 (1996): 294-296.
Bonnet et al. Thermodynamic basis of the enhanced specificity of structured DNA probes, Proc. Natl. Acad. Sci. USA vol. 96 (May 1999), pp. 6171-6176.
Bouchard, H, et al., Antibody-drug conjugates: A new wave of cancer drugs. Bioorganic & Medicinal Chemistry Letters, vol. 24, No. 23, pp. 5357-5367, (2014).
Brummelkamp, T. R.; Bernards, R.; Agami, R. "A system for stable expression of short interfering RNAs in mammalian cells" Science 2002, 296, 550-553.
Bumcrot et al., "RNAi Therapeutics: A Potential New Class of Pharmaceutical Drugs." Nature Chemical Biology 2.12 (Dec. 2006): 711-719.
Bushnell et al., "ProbeDesigner: for the design of probesets for branched DNA (bDNA) signal amplification assays," Bioinformatics, 15(5), pp. 348-355, 1999.
Butterfoss et al., Computer-Based Design of Novel Protein Structures, Annu. Rev. Biophys. Biomol. Struct., vol. 35, pp. 49-65, 2006.
Caltech News Release, "Caltech Scientists Create New Process to Program", Sep. 6, 2010.
Caplen, "RNAi as a gene therapy approach", Expert Opin. Biol. Ther., vol. 3, No. 4, pp. 575-586, 2003.
Capodieci, P. et al., "Gene expression profiling in single cells within tissue," Nat Methods, vol. 2, No. 9, pp. 663-665, Sep. 2005.
Carbonell-Ballestero et al., Dealing with the Genetic Load in Bacterial Synthetic Biology Circuits: Convergences with the Ohm's Law. Nucleic Acids Res. 2016, 44 (1), 496-507. https://doi.org/10.1093/nar/gkv1280.
Castanotto et al., "The Promises and Pitfalls of RNA-Interface-Based Therapeutics." Nature 457 (Jan. 22, 2009):426-433.
Cerutti et al., "On the Origin and Functions of RNA-Mediated Silencing: From Protists to Man." Current Genetics 50 (2006) 81-99.
Chan, PM et al., "Method for multiplex cellular detection of mRNAs using quantum dot fluorescent in situ hybridization," Nucleic Acids Research, vol. 33, Issue 18, pp. e161, Jan. 1, 2005.
Chapell, et al., Renaissance in RNA Synthetic Biology: New Mechanisms, Applications and Tools for the Future. Curr Opin Chem Biol 28, 47-56, 2015.
Chappell et al., The Centrality of RNA for Engineering Gene Expression. Biotechnol. J.m 8 (12), 1379-1395. https://doi.org/Doi 10.1002/Biot.201300018, 2013.
Chappell et al., Creating Small Transcription Activating RNAs. Nat. Chem. Biol., 11 (3), 214-220. https://doi.org/10.1038/nchembio.1737, 2015.
Chapman et al., The Structural Basis of Pathogenic Subgenomic Flavivirus RNA (SfRNA) Production. Science 2014, 344 (6181), 307-310. https://doi.org/10.1126/science.1250897.
Check, "RNA to the rescue?", Nature, vol. 425, pp. 10-12, Sep. 4, 2003.
Chen, H.L.; Cheng, Q.; Goel, A.; Huang, M.D.' Espanes, P.M.d. "Invadable self-assembly: Combining robustness with efficiency." In Proceedings of the 15th annual ACM-SIAM Symposium on Discrete Algorithms (SODA); 2004.
Chen Y.; Liu, H.P.; Ye, T.; Kim, J.; Mao, C.D. "DNA-Directed Assembly of Single-Wall Carbon Nanotubes." J.Am. Chem. Soc. 2007,129.
Chen, Y et al. Profiling of Multiple Glycans on Whole Living Cell Suraces, Analytical Chemistry, vol. 85, No. 22, pp. 11153-11158, (2013).
Chernoff et al., "Quantification of Cytomegalovirus DNA in Peripheral Blood Leukocytes by a Branched-DNA Signal Amplification Assay", Journal of Clinical Microbiology, vol. 35, No. 11, p. 2740-2744, Nov. 1997.

(56) References Cited

OTHER PUBLICATIONS

Choi et al., Nature Biotechnology 28(11): 1208-1214, 2010.
Choi, H, et al. Programmable in Situ Amplification for Multiplexed Imaging of mRNA Expression, Nature Biotechnology, vol. 28, No. 11, pp. 1206-1212, (2010).
Choi, H. et al., Next-generation in situ hybridization chain reaction: higher gain, lower cost, greater durability, vol. 8, No. 5, pp. 4284-4294 (2014).
Choi and Love et al., Immuno-Hybridization Chain Reaction for Enhancing Detection of Individual Cytokine-Secreting Human Peripheral Mononuclear Cells, Analytical Chemistry 83 :6890-6895 , 2011.
Clay, H. et al., "Multiplex fluorescent in situ hybridization in zebrafish embryos using tyramide signal amplification," Zebrafish, vol. 2, No. 2, pp. 105-111, Aug. 2005.
Cleve et al., "Direct quantitation of HIV by flow cytometry using branched DNA signal amplification", Molecular and Cellular Probes, vol. 12, pp. 243-247, 1998.
Coburn et al., "siRNAs: a new wave of RNA-based therapeutics", Journal of Antimicrobial Chemotherapy, vol. 51, pp. 753-756, 2003.
Coleman, R.S. and Pires, R.M. Covalent cross-linking of duplex DNA using 4-thio-2'-deoxyuridine as a readily modifiable platform for introduction of reactive functionality into oligonucleotides. Nucleic Acids Research, 1997. 25: p. 4771-4777.
Coleman et al., "Template-Directed Corss-Linking of Oligonucleotides: Site-Specific Covalent Modification of dG-N7 Within Duplex DNA." J. Org. Chem. 60 (1995): 6252-6253.
Collingwood et al., Chemical Modification Patterns Compatible with High Potency Dicer-Substrate Small Interfering RNAs. Oligonucleotides 2008, 18 (2), 187-199.
Collins et al., "A branched DNA signal amplification assay for quantification of nucleic acid targets below 100 molecules/ml," Nucleic Acids Res, 25(15), pp. 2979-2984, 1997.
Collins et al., "Branched DNA (bDNA) Technology for Direct Quantification of Nucleic Acids: Design and Performance", pp. 205-223, 1998.
Communication pursuant to Article 94(3) EPC dated Nov. 7, 2012 from Application No. 08.755764.1, filed May 16, 2008.
Communication regarding Supplementary European Search Report dated Jan. 8, 2020 received in European application No. 17824 751.6.
Communication regarding Supplementary European Search Report dated Feb. 25, 2020 received in European application No. 17847401. 1.
Coppelli et al., "Oligonucleotides as Anticancer Agents: From the Benchside to the Clinic and Beyond", Current Pharmaceutical Design, vol. 11, pp. 2825-2840, 2005.
Cox, K.H. et al., "Detection of mRNAs in sea urchin embryos by in situ hybridization using asymmetric RNA probes," Developmental Biology, vol. 101, Issue 2, pp. 485-502, Feb. 1984.
Cullen et al., "Genome-wide Screening for Gene Function Using RNAi in Mammalian Cells." Immunology and Cell Biology 83 (2005) 217-223.
Czauderna et al., "Structural Variations and Stabilising Modifications of Synthetic siRNAs in Mammalian Cells." Nucleic Acids Research 31.11 (2003): 2705-2716.
Dabby NL, Chen HL, Schaeffer JM, Winfree E. "The kinetics of toehold-mediated four-way branch migration." California Institute of Technology Thesis, Chapter 5 (2013), pp. 75-105.
Dabby et al., Synthetic Molecular Machines for Active Self-Assembly: Prototype Algorithms, Designs, and Experimental Study. thesis, 2013.
Darnell, D.K. et al., "GEISHA: an in situ hybridization gene expression resource for the chicken embryo," Cytogenetic and Genome Research, vol. 117, No. 1-4, pp. 30-35, Jul. 2007.
Dailey et al., "Quantification of HCV RNA in Liver Tissue by bDNA Assay", Methods in molecular medicine, vol. 19, No. 1543-1894, pp. 119-129, 1998.

Decroly et al., Conventional and Unconventional Mechanisms for Capping Viral MRNA. Nat. Rev. Microbiol. 2012, 10 (1), 51-65. https://doi.org/10.1038/nrmicro2675.
De Matos, et al., Heparanase expression in lung carcinoid tumors by immunohistochemistry. Ejc Supplements , vol. 3, No. 2, pp. 342 (2005).
Definition for "substantial" from Merriam-Webster Online Dictionary. Downloaded from merriam-webster.com; downloaded on Mar. 5, 2008.
Delebecque et al., Organization of Intracellular Reactions with Rationally Designed RNA Assemblies. Science 2011, 333 (6041), 470-474. https://doi.org/10.1126/science.1206938.
Delebecque et al., Designing and Using RNA Scaffolds to Assemble Proteins in Vivo. Nat. Protoc. 2012, 7 (10), 1797-1807. https://doi.org/Doi10.1038/Nprot.2012.102.
Denkers, N. et al., "FISHing for chick genes: Triple-label whole-mount fluorescence in situ hybridization detects simultaneous and overlapping gene expression in avian embryos," Developmental Dynamics, vol. 229, Issue 3, DD. 651-657, Mar. 2004.
Detmer et al., "Accurate Quantification of Hepatitis C Virus (HCV) RNA from All HCV Genotypes by Using Branched-DNA Technology", Journal of Clinical Microbiology, vol. 34, No. 4, pp. 901-907, Apr. 1996.
Dicarlo, J et al.. 'RNA-guided gene drives can efficiently bias inheritance in wild yeast', bioRxiv, (2015).
Dias et al., "Antisense Oligonucleotides: Basic Concepts and Mechanisms." Molecular Cancer Therapeutics 1 (Mar. 2002) 347-355.
Dietz et al., "Folding DNA into Twisted and Curved Nanoscale Shapes." Science 2009, 325, 725-730.
Dirks et al., "An Algorithm for Computing Nucleic Acid Base-Pairing Probabilities Including Pseudoknots." Journal of Computational Chemistry 25.10 (2004): 1295-1304.
Dirks et al., "A Partition Function Algorithm for Nucleic Acid Secondary Structure Including Pseudoknots." Journal of Computational Chemistry 24.13 (2003) 1664-1677.
Dirks et al., "Paradigms for computational nucleic acid design," Nucleic Acids Research, vol. 32, No. 4, pp. 1392-1403, Oxford University Press, 2004.
Dirks et al., Retraction for "Selective cell death mediated by small conditional RNAs" (which appeared in issue 39, Sep. 28, 2010 of Proc Natl Acad Sci USA), Proc Natl Acad Sci USA, Jan. 2, 2013 vol. 110, No. 1, p. 384.
Dirks et al., "Thermodynamic Analysis of Interacting Nucleic Acid Strands." SIAM Review 49.1 (2007): 65-88.
Dirks et al., "Triggered amplification by hybridization chain reaction," PNAS, vol. 101, No. 43, pp. 15275-15278, Oct. 26, 2004.
Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.
Douglas et al., "DNA-nanotube-induced alignment of membrane proteins for NMR structure determination", PNAS, vol. 104, No. 16, pp. 6644-6648, Apr. 17, 2007.
Douglas et al., "Self-assembly of DNA into nanoscale three-dimensional shapes", Nature, vol. 459, pp. 414-418, May 21, 2009.
Du Qa, Thonberg H, Wang J, Wahlestedt C, Liang ZC (2005) A systematic analysis of the silencing effects of an active siRNA at all single-nucleotide mismatched target sites. Nucleic Acids Res 33:1671-1677.
Duckworth et al., "A Universal Method for the Preparation of Covalent Protein-DNA Conjugates for Use in Creating Protein Nanostructures", Agnew. Chem. Int. Ed., vol. 46, pp. 8819-8822, 2007.
Dunn JJ, Studier FW (1983) Complete nucleotide-sequence of bacteriophage—TY DNA and the locations of T7 genetic elements. J Mol Biol 166:477-535.
Eckstein, F. "Phosphrothioate oligodeooxynucleotides: what is their origin and what is unique about them?" Antisense Nucleic Acid Drug Dev., 10:117-121, 2000.
Eddy, S.R. "Non-coding RNA genes and the modern RNA world." Nature Reviews, 2: 919-929, 2001.

(56) References Cited

OTHER PUBLICATIONS

Elbashir et al., "Functional anatomy of siRNAs for mediating efficient RNAi in *Drosophila melanogaster* embryo lysate", The EMBO Journal, vol. 20, No. 23, pp. 6877-6888, 2001.
Elbeik et al., Quantitative and Cost Comparison of Ultrasensitive Human Immunodeficiency Virus Type 1 RNA Viral Load Assays: Bayer bDNA Quantiplex Versions 3.0 and 2.0 and Roche PCR Amplicor Monitor Version 1.5, Journal of Clinical Microbiology, vol. 38, No. 3, pp. 1113-1120, Mar. 2000.
Elghanian et al.,"Selective colorimetric detection of polynucleotides based on the distance-dependent optical properties of gold nanoparticles, " Science, 277(5329), pp. 1078-1081, 1997.
Ellington et al., "In vitro selection of RNA molecules that bind specific ligands," Nature 346, pp. 818-822, 1990.
Elmén et al., "Locked Nucleic Acid (LNA) Mediated Improvements in siRNA Stability and Functionality." Nucleic Acids Research 33.1 (2005): 439-447.
Engel et al., "Detection of circulating tumour cells in patients with breast or ovarian cancer by molecular cytogenetics", British Journal of Cancer, vol. 81, No. 7, pp. 1165-1173, 1999.
Enquist et al.., "The Total Synthesis of ( − )-Cyanthiwigin F by Means of Double Catalytic Enantioselective Alkylation." Nature 453.7199 (Jun. 26, 2008) 1228-1231.
Evanko, "Hybridization chain reaction", Nature Methods, vol. 1, No. 3, pp. 186-187, Dec. 2004.
Feldkamp et al., "Rational Design of DNA Nanoarchitectures", Angew. Chem. Int. Ed., vol. 45, pp. 1856-1876, 2006.
Felgner, et al., "Nomenclature for Synthetic Gene Delivery Systems", Human Gene Therapy, vol. 8, pp. 511-512, Mar. 20, 1997.
Femino et al., "Visualization of Single Molecules of mRNA in Situ." Methods of Enzymology 361 (2003): 245-304.
Femino, A. et al., "Visualization of single RNA transcripts in situ," Science, vol. 280, Issue 5363, pp. 585-590, Apr. 24, 1998.
Ferkol et al., "Gene Transfer into the Airway Epithelium of Animals by Targeting the Polymeric Immunoglobulin Receptor", J. Clin. Invest., vol. 95, pp. 493-502, Feb. 1995.
Ferkol et al., "Regulation of the phosphoenolpyruvate carboxykinase/human factor IX gene introduced into the lives of adult rats by receptor-mediated gene transfer", The FASEB Journal, vol. 7, pp. 1081-1091, Aug. 1993.
Ferre, F., "Gene Quantification",@ Birkhauser Boston 1998, Foreword by Edwin Southern (Advanced biomedical technologies) , 379 pages.
Ferreira et al., "The Palladium-Catalyzed Oxidative Kinetic Resolution of Secondary Alcohols with Molecular Oxygen." Journal of American Chemical Society 123.31 (2001): 7725-7726.
Fire et al., "Potent and specific genetic interference by double-stranded RNA in Caenorhabditis elegans", Nature, vol. 391, pp. 806-811, Feb. 19, 1998.
Flamm et al., "RNA folding at elementary step resolution," RNA, vol. 6, pp. 325-338, 2000.
Fox et al., "Antiviral treatment normalizes neurophysiological but not movement abnormalities in simian immunodeficiency virus-infected monkeys", J Clin Invest., vol. 106, No. 1, pp. 37-45, 2000.
Friedrich et al., A Cellular Screening Assay to Test the Ability of PKR to Induce Cell Death in Mammalian Cells, Molecular Therapy, vol. 12, No. 5, pp. 969-975, Nov. 2005.
Friedrich et al., "RNA molecules as anti-cancer agents", Seminars in Cancer Biology, vol. 14, pp. 223-230, 2004.
Fu et al., "DNA Double-Crossover Molecules", Biochemistry, vol. 32, pp. 3211-3220, 1993.
Gall, J. et al., "Formation and detection of RNA-DNA hybrid molecules in cytological preparations," Proc Natl Acad Sci USA, vol. 63, No. 2, pp. 378-383, Jun. 1, 1969.
Garcia et al., "Impact of Protein Kinase PKR in Cell Biology: from Antiviral to Antiproliferative Action." Microbiology and Molecular Biology Reviews vol. 70, No. 4 (Dec. 2006): pp. 1032-1060.
Garg et al., "Development of an Enantiodivergent Strategy for the Total Synthesis of (+)- and (−)-Dragmacidin F from a Single Enantiomer of Quinic Acid." Journal of American Chemical Society 127 (2005) 5970-5978.
Garg et al., "A Ligand-free Solid-supported System for Sonogashira Couplings: Applications in Nucleoside Chemistry." Chem. Commun. (2005) 4551-4553.
Gasparro et al., Site-specific targeting of psoralen photoadducts with a triple helix-forming oligonuicleotide: characterization of psoralen monoadduct and crosslink formation. Nucleic Acids Research 22 (1994), pp. 2845-2852.
Geary et al., A Single-Stranded Architecture for Cotranscriptional Folding of RNA Nanostructures. Science 2014, 345 (6198), 799-804.
Gilman et al., "The Biological Actions and Therapeutic Applications of the B-Chloroethyl Amines and Sulfides." Science 103.2675 (Apr. 5, 1946): 409-415.
Glick et al., Metabolic Load and Heterologous Gene Expression. Biotechnol. Adv. 1995, 13 (2), 247-261. https://doi.org/10.1016/0734-9750(95)00004-A.
Goodman, R.P.; Schaap, I.A.T.; Tardin, C.F.; Erben, C.M.; Berry, R.M.; Schmidt, C.F.; and Turberfield, A.K. "Rapid chiral assembly of rigid DNA blocks for molecular nanofabrication." Science, 310, 2005.
Green et al., "DNA Hairpins: Fuel for Autonomous DNA Devices", Biophysical Journal, vol. 91, pp. 2966-2975, Oct. 2006.
Green et al., Toehold Switches: De-Novo-Designed Regulators of Gene Expression. Cell 2014, 159 (4), 925-939.
Gross-Thebing et al., "Simultaneous high-resolution detection of multiple transcripts combined with localization of proteins in whole-mount embryos", BMC Biology, vol. 12, No. 55, 2014.
Ha et al., Regulation of microRNA biogenesis, Nature Reviews Molecular Cell Biology 15, 509-524. Jul. 16, 2014.
Hayat, Comparison of Immunohistochemistry, in situ Hybridization, Fluorescence in situ Hybridization, and chromogenic in situ Hybridization, Handbook of Immunohistochemistry and in Situ Hybridization of Human Carcinomas, 1st Edition, Molecular Genetics; Lung and Breast Carcinomas, 2004.
Hansma et al., "DNA Binding to Mica Correlates with Cationic Radius: Assay by Atomic Force Microscopy", Biophysical Journal, vol. 70, pp. 1933-1939, Apr. 1996.
Harland, R.M., "In situ hybridization : an improved whole-mount method for Xenopus embryos," Methods Cell Biol., vol. 36, pp. 685-695, 1991.
Hartley et al., "Detection Of Chemical-Induced Differential Expression Of Rat Hepatic Cytochrome P450 MRNA Transcripts Using Branched DNA Signal Amplification Technology", Drug Metabolism and Disposition, vol. 28, No. 5, 2000, pp. 608-616.
Hashimoto et al., "Recent Progress in Diazirine-Based Photoaffinity Labeling." Eur. J. Org. Chem. (2008): 2513-2523.
Haugland RP. The Handbook: A Guide to Fluorescent Probes and Labeling Technologies. 10th Ed. Molecular Probes/Invitrogen; 2005.
Hawkins et al., "Comparison of Plasma Virus Loads among Individuals Infected with Hepatitis C Virus (HCV) Genotypes 1, 2, and 3 by Quantiplex HCV RNA Assay Versions 1 and 2, Roche Monitor Assay, and an In-House Limiting Dilution Method", Journal of Clinical Microbiology, vol. 35, No. 1, pp. 187-192, Jan. 1997.
He et al., Hierarchical self-assembly of DNA into symmetric supramolecular polyhedral, Nature, vol. 452, pp. 198-202, 2008.
Hearst et al., "Psoralen Photochemistry." Ann. Rev. Biophys. Bioeng. 10 (1981): 69-86.
Heidel, J.D., "Targeted, systematic non-viral delivery of small interfering RNA in vivo", Doctoral thesis, California Institute of Technology, pp. 1-128, 2005.
Hell, S.W. "Far-field optical nanoscopy." Science, 316: 1153-1158, 2007.
Hendricks et al., "Quantitation of HBV DNA in Human Serum Using a Branched DNA (bDNA) Signal Amplification Assay", American journal of clinical pathology, vol. 104, No. 5, pp. 537-546, 1995.
Herath et al., "Synthesis of Acrimarins from 1,3,5-Trioxygenated-9-acridone Derivatives." Journal of Heterocyclic Chem. 41 (2004): 23-28.

(56) References Cited

OTHER PUBLICATIONS

Higuchi et al. Selective regulation of mutant K-ras mRNA expression by photo-cross-linking antisense oligonucleotide. Nucleic Acids Symposium Series (2007) vol. 51 (1) pp. 443-444.
Hochrein et al., Signal Transduction in Human Cell Lysate via Dynamic RNA Nanotechnology. ACS Synth. Biol. 2018, 7 (12), 2796-2802.
Hochrein et al., "Conditional Dicer Substrate Formation via Shape and Sequence Transduction with Small Conditional RNAs," J. Am. Chem. Soc. 2013, 135, 17322-17330.
Hodinka et al. , The clinical utility of viral quantitation using molecular methods, Clinical and Diagnostic Virology, vol. 10, No. 1, pp. 25-47, 1998.
Hofacker et al., "Fast folding and comparison of RNA secondary structures," Monatshefte für Chemie, vol. 125, pp. 167-188, 1994.
Hokaiwado et al., "RNAi-based drug discovery and its application to therapeutics", IDrugs, vol. 11, No. 4, pp. 274-278, 2008.
Horvath, P et al.. 'CRISPR/Cas, the Immune System of Bacteria and Archaea', Science, 327: 167-70, (2010).
Hughes et al., "Double Labeling wit Fluorescence In Situ Hybridization in Drosophila Whole-Mount Embryos," BioTechniques, 24(4), pp. 530-532, 1998.
Huizenga et al., "A DNA Aptamer That Binds Adenosine and ATP." Biochemistry 34, pp. 656-665, 1995.
Huss, D. et al., "Combinatorial analysis of mRNA expression patterns in mouse embryos using hybridization chain reaction." Cold Spring Harbor Protocols, pp. 259-269 (2015).
Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma." Cancer Research 65.19 (Oct. 1, 2005): 8984-8992.
Idrovo et al., "Hepatitis C virus RNA quantification in right and left lobes of the liver in patients with chronic hepatitis C", Journal of Viral Hepatitis, vol. 3, pp. 239-246, 1996.
Isaacs et al., RNA Synthetic Biology. Nat. Biotechnol. 2006, 24 (5), 545-554. https://doi.org/10.1038/nbt1208.
Iqbal, J. et al., The hybridization chain reaction in the development of ultrasensitive nucleic acid assays, Trac-Trends in Analytical Chemistry vol. 64, pp. 86-99, (2015).
Iqbal et al., "A review of molecular recognition technologies for detection of biological threat agents", Biosensors & Bioelectronics, vol. 15, pp. 549-578, 2000.
Jacob et al., "Comparison of Quantitative HCV RNA Assays in Chronic Hepatitis C", Microbiology and Infectious Disease, American journal of clinical pathology, vol. 107, No. 3, pp. 362-367, Mar. 1997.
Jagus et al., "PKR, apoptosis and cancer", The International Journal of Biochemistry & Cell Biology, vol. 31, pp. 123-138, 1999.
Jayasena, "Aptamers: An Emerging Class of Molecules That Rival Antiodies in Diagnostics", Clinical Chemistry, vol. 45, No. 9, pp. 1628-1650, 1999.
Jhaveri et al., "In vitro selection of signaling aptamers", Nature Biotechnology, vol. 18, pp. 1293-1297, Dec. 2000.
Jinek M, Doudna JA (2009) A three-dimensional view of the molecular machinery of RNA interference. Nature 457:405-412.
Johnston et al., "Psoralen-DNA Photoreaction: Controlled Production of Mono- and Diadducts with Nanosecond Ultraviolet Laser Pulses," Science, New Series, vol. 197, No. 4306, pp. 906-908, Aug. 26, 1977.
Jones et al., The 5' -→ 3' Exoribonuclease XRN1/Pacman and Its Functions in Cellular Processes and Development: The 5' -→ 3' Exoribonuclease XRN1/Pacman and Its Functions. Wiley Interdiscip. Rev. RNA 2012, 3(4), 455-468. https://doi.org/10.1002/wrna.1109.
Jonoska et al., DNA cages with icosahedral symmetry bionanotechnology, Algorithmic Bioprocesses', 2008.
Judge et al., "Design of Noninflammatory Synthetic siRNA Mediating Potent Gene Silencing in Vivo." Molecular Therapy 13.3 (Mar. 2006): 494-505.

Judge et al., "Overcoming the Innate Immune Response to Small Interfering RNA", Human Gene Therapy, vol. 19, pp. 111-124, Feb. 2008.
Julian et al., "Biomimetic Approaches to Gas Phase Peptide Chemistry: Combining Selective Binding Motifs with Reactive Carbene Precursors to Form Molecular Mousetraps." International Journal of Mass Spectrometry 228 (2003): 851-864.
Julian et al., "Molecular Mousetraps: Gas-Phase Studies of the Covalent Coupling of Noncovalent Complexes Initiated by Reactive Carbenes Formed by Controlled Activation of Diazo Precursors." Agnew. Chem.Int. Ed. 42.9 (2003) 1012-1015.
Jung, C. et al., Diagnostic applications of nucleic acid circuits, Accounts of Chemical Research, vol. 47, No. 6, pp. 1825-183, (2014).
Kadnikov et al., "Synthesis of Coumarins via Palladium-Catalyzed Carbonylative Annulation of Internal Alkynes by o-Iodophenols." Organic Letters 2.23 (2000): 3643-3646.
Ke et al. "Scaffolded DNA Origami of a DNA Tetrahedron Molecular Container," Nanoletters, 2009. 9(6): 2445-2447.
Kenny et al., Detection of Viral Infection and Gene Expression in Clinical Tissue Specimens Using Branched DNA (BONA) In Situ Hybridization, vol. 50, No. 9, pp. 1219-1227, 2002.
Kern et al., An Enhanced-Sensitivity Branched-DNA Assay for Quantification of Human Immunodeficiency Virus Type 1 RNA in Plasma, Journal of Clinical Microbiology, vol. 34, No. 12, pp. 3196-3202, 1996.
Kerstens, H.M. et al., "A novel in situ hybridization signal amplification method based on the deposition of biotinylated tyramine," The Journal of Histochemistry and Cytochemistry, vol. 43, No. 4, pp. 347-352, 1995.
Killops, K.L., Campos, L.M., Hawker, C.J. Robust, Efficient, and Orthogonal Synthesis of Dendrimers via Thiol-ene "Click" Chemistry. Journal of the American Chemical Society, 2008. 130: p. 5062-5064.
Kim J. et al., "Construction of an in vitro bistable circuit from synthetic transcriptional switches." Mol Syst Biol, vol. 2, pp. 68, 2006.
Kim et al., "Synthetic dsRNA Dicer substrates enhance RNAi potency and efficacy", Nature Biotechnology, vol. 23, No. 2, pp. 222-226, Feb. 2005.
Kim et al., "Strategies for Silencing Human Disease Using RNA Interference." Nature Review Genetics 8 (Mar. 2007) 173-184.
Kim et al., CRISPR/Cas-Based Devices for Mammalian Synthetic Biology. Curr. Opin. Chem. Biol. 2019, 52, 23-30. https://doi.org/10.1016/j.cbpa.2019.04.015.
Kim et al., RNA Therapy: Current Status and Future Potential. Chonnam Med. J. 2020, 56 (2), 87. https://doi.org/10.4068/cmj.2020.56.2.87.
Kislauskis et al. "Isoform-specific 3'-untranslated Sequences Sort α-cardiac and ß-cytoplasmic Actin Mesenger RNAs to Different ytoplasmic Compartments," The Journal of Cell Biology, 123(1), pp. 165-172, 1993.
Knorre et al., "Photoaffinity Labeling as an Approach to Study Supramolecular Nucleoprotein Complexes." FEBS Letters 433 (1998): 9-14.
Kobertz et al., "An Efficient Synthesis of a Furan-Side Furocoumarin Thymidine Monoadduct." J. Org. Chem. 62.8 (1997) 2630-2632.
Kobertz et al., "Solid-Phase Synthesis of Oligonucleotides Containing a Site-Specific Psoralen Derivative." Journal of American Chemical Society 119 (1997): 5960-5961.
Kobertz et al., "Total Synthesis of a Cis-Syn 2-Carbomethoxypsoralen Furan-Side Thymidine Monoadduct." Journal of American Chemical Society 118 (1996): 7101-7107.
Kolberg et al., "Branched DNA (bDNA) Technology for Direct Quantification of Nucleic Acids: Research and Clinical Applications", pp. 327-338, 1998.
Kosman, et al., "Multiplex Detection of RNA Expression in Drosophila Embryos," Science, 305, p. 846, 2004.
Kumar D, An CI, Yokobayashi Y (2009) Conditional RNA interference mediated by allosteric ribozyme. J Am Chem Soc 131:13906-13907.

(56) References Cited

OTHER PUBLICATIONS

Kumar D, Kim SH, Yokobayashi Y (2011) Combinatorially inducible RNA interference triggered by chemically modified oligonucleotides. J Am Chem Soc 133:2783-2788.
Kurreck, J. Angew. "RNA interference: from basic research to therapeutic applications" Chem., Int. Ed. 2009, 48, 1378-1398.
Kuzuya et al., "Six-Helix and Eight-Helix DNA Nanotubes Assembled from Half-Tubes", Nano Lett., vol. 7, No. 6, pp. 1757-1763, 2007.
Lacenere et al., "Effects of a Modified Dye-Labeled Nucleotide Spacer Arm on Incorporation by Thermophilic DNA Polymerases." Nucleosides, Nucleotides, and Nucleic Acids 25 (2006) 9-15.
Ladiges, et al., "Tissue specific expression of PKR protein kinase in aging B6D2F1 mice," Mechanisms of Ageing and Development, vol. 114, pp. 123-132, (2000).
Lan et al., A simple, reliable, and sensitive method for nonradioactive in situ hybridization: use of microwave heating to improve hybridization efficiency and preserve tissue morphology. J Histochem Cytochem 44(3):281-287. 1996.
Larsson, C. et al., "In situ detection and genotyping of individual mRNA molecules," Nature Methods, vol. 7, pp. 395-397, May 1, 2010.
Larsson, C. et al., "In situ genotyping individual DNA molecules by target-primed rolling-circle amplification of padlock probes," Nature Methods, vol. 1, No. 3, pp. 227-232, Dec. 2004.
Lawley et al., "DNA Adducts from Chemotherapeutic Agents." Mutation Research—Fundamental and Molecular mechanisms of Mutagenesis 355 (1996): 13-40.
Lawrence et al., "Highly Localized Tracks of Specific Transcripts within Interphase Nuclei Visualized by In Situ Hybridication," Cell, 57, pp. 493-502, 1989.
Layzer et al., "In Vivo Activity of Nuclease-Resistant siRNAs." RNA 10 (2004): 766-771.
Le et al., "DNA-Templated Self-Assembly of Metallic Nanocomponent Arrays on a Surface", Nano Lett., vol. 4, No. 12, pp. 2343-2347, 2004.
Lee, J.F., Hesselberth, J.R.; Meyers, L.A.; and Ellington, A.D. "Aptamer database." Nucleic Acids Research, 32: D95-100, 2004.
Lee, S. K.; Kumar, P. "Conditional RNAi: towards a silent gene therapy" Adv. Drug Delivery Rev. 2009, 61, 650-664.
Lee et al., "A self-replicating peptide", Nature, vol. 382, pp. 525-528, Aug. 8, 1996.
Lehmann, R. et al., "In situ hybridization to RNA," Methods in Cell Biology, vol. 44, pp. 575-598, 1994.
Leisinger, B. Viral Load Testing for HIV Beyond the CD4 Count, Laboratory Medicine, vol. 30, No. 2, pp. 102-109, 1999.
Levsky et al., "Single-Cell Gene Expression Profiling," Science 297, pp. 836-840, 2002.
Levy et al., "Exponential growth by cross-catalytic cleavage of deoxyribozymogens", PNAS, vol. 100, No. 11, pp. 6416-6421, May 27, 2003.
Li et al., A new class of homogenous nucleic acid probes based on specific displacement hybridization, Nucleic Acids Research, vol. 30, No. 2e5 (2002), pp. 1-9.
Li, H.; LaBean, T.H.; Kenan, D.J. "Single-chain antibodies against DNA aptamers for use as adapter molecules on DNA tile arrays in nanoscale materials organization." Organic and Biomolecular Chemistry 2006, 3420-3426. 2006.
Li, Z, Trimble, M.J.; Brun, Y.V.; Jensen, G.J. "The structure of FtsZ filaments in vivo suggests a force-generating role in cell division." EMBO J.,26, pp. 4694-4708. 2007.
Lima W.F., Wu H.J., Nichols J.G., Sun H., Murray H.M., Crooke S.T. "Binding and cleavage specificities of human Argonaute2" J Biol Chem 284:26017-26028 (2009).
Lin et al., "DNA Tile Based Self-Assembly: Building Complex Nanoarchitectures", ChemPhysChem, vol. 7, pp. 1641-1647, 2006.
Lin, F. et al., Standardization of Diagnostic Immunohistochemistry Literature Review and Geisinger Experience, Archives of Pathology & Laboratory Medicine, vol. 138, No. 12, pp. 1564-1577, (2014).
Liu et al., "A colorimetric lead biosensor using DNAzyme-directed assembly of gold nanoparticles," J. Am. Chem. Soc., 125(22), pp. 6642-6643, 2003.
Liu et al., "Approaching The Limit: Can One DNA Oligonucleotide Assemble into Large Nanostructures?", Angew. Chem. Int. Ed., vol. 45, pp. 1942-1945, 2006.
Liu et al., "DNA nanotubes self-assembled from triple-crossover tiles as templates for conductive nanowires", PNAS, vol. 101, No. 3, pp. 717-722, Jan. 20, 2004.
Linuma et al., Polyhedra Self-Assembled from DNA Tripods and Characterized with 3D DNA-PAINT, Science, vol. 344, No. 6179, pp. 65-69, 2014.
Macechko et al., "Comparison of Immunologic Amplification vs Enzymatic Deposition of Fluorochrome-conjugated Tyramide as Detection Systems for FISH," J Histochem Cytochem, 45(3), pp. 359-363, 1997.
MacFadden et al., Mechanism and Structural Diversity of Exoribonuclease-Resistant RNA Structures in Flaviviral RNAs. Nat. Commun. 2018, 9 (1), 119. https://doi.org/10.1038/s41467-017-02604-y.
Mahato et al., "Modulation of gene expression by antisense and antigene oligodeoxynucleotides and small interfering RNA", Expert Opin. Drug Deliv., vol. 2, No. 1, pp. 3-28. 2005.
Manche et al., "Interactions between Double-Stranded RNA Regulators and the Protein Kinase DAI", Molecular and Cellular Biology, vol. 12, No. 11, pp. 5238-5248, Nov. 1992.
Manoharan et al., "RNA Interference and Chemically Modified Small Interfering RNAs." Current Opinion in Chemical Biology 8 (2004): 570-579.
Markowitz et al., "The Effect of Commencing Combination Antiretroviral Therapy Soon after Human Immunodeficiency Virus Type 1 Infection on Viral Replication and Antiviral Immune Responses", The Journal of Infectious Diseases, vol. 179, oaaes 525-37, 1999.
Martinot-Peignoux et al., "Assessment of Viral Loads in Patients with Chronic Hepatitis C with Amplicor HCV Monitor Version 1.0, Cobas HCV Monitor Version 2.0, and Quantiplex HCV RNA Version 2.0 Assays", Journal of Clinical Microbiology, vol. 38, No. 7, pp. 2722-2725, Jul. 2000.
Masu, H.; Narita, A ; Tokunaga, T.; Ohashi, M.; Aoyama, Y.; Sando, S. Angew. "An activatable siRNA probe: trigger-RNA-dependent activation of RNAi function" Chem., Int. Ed. 2009, 48, 9481-9483.
Mathews, David H., et al. "22 predicting rna secondary structure." Cold Spring Harbor Monograph Archive 43 (2006): 631-657.
Mathieu et al., "Six-Helix Bundles Designed from DNA", Nano Lett., vol. 5, No. 4, pp. 661-665, 2005.
Matsui, T. et al., "Expression of Unphosphorylated Form of Human Double-Stranded RNA-Activated Protein Kinase in *Escherichia coli*", Biochemical and Biophysical Research Communications, vol. 284, No. 3, pp. 798-807, 2001.
McIntyre, G. J.; Yu, Y. H.; Lomas, M.; Fanning, G. C. "The effects of stem length and core placement on shRNA activity" BMC Mol. Biol. 2011, 12, 34.
McLennan, R. et al., Neural crest migration is driven by a few trailblazer cells with a unique molecular signature narrowly confined to the invasive front, Development, vol. 142, No. 11, pp. 2014-2025, (2015).
Meinhardt et al., "Wavelength-dependent Penetration Depths of Ultraviolet Radiation in Human Skin." Journal of Biomedical Optics 13.4 (Jul./Aug. 2008) 044030-1-044030-5.
Meyer et al., Improving Fold Activation of Small Transcription Activating RNAs (STARs) with Rational RNA Engineering Strategies: Improving Small Transcription Activating RNAs. Biotechnol. Bioeng, 113 (1), 216-225. https://doi.org/10.1002/bit.25693, 2016.
Mitchell et al., "Self-Assembly of Chiral DNA Nanotubes", J. Am. Chem. Soc., vol. 126, pp. 16342-16343, 2004.
Mittelstadt, et al., "Interaction of human tRNA-dihydrouridine synthase-2 with interferon-induced protein kinase PKR," Nucleic Acids Research, vol. 36, No. 3, pp. 998-1008, (2008).
Mohr et al., "Catalytic Enantioselective Decarboxylative Protonation." Journal of American Chemical Society 128.35 (2006): 11348-11349.
Mohr et al., "Natural Products as Inspiration for the Development of Asymmetric Catalysis." Nature 455 (Sep. 18, 2008) 323-332.

(56) References Cited

OTHER PUBLICATIONS

Moon et al., Improving CRISPR Genome Editing by Engineering Guide RNAs. Trends Biotechnol. 2019, 37 (8), 870-881, https://doi.org/10.1016/j.tibtech.2019.01.009.

Nakano et al., "Selection for thermodynamically stable DNA tetraloops using temperature gradient gel electrophoresis reveals four motifs: d(cGNNAg), d(cGNABg), d(cCNNGg), and d(gCNNGc)," Biochemistry, vol. 41, pp. 14281-14292,American Chemical Society, 2002.

Naked Scientists (The): Science Radio & Science Podcasts, "RNA-away cancer cells", Sep. 12, 2010, http://www.thenakedscientists.com/HTML/content/news/news/2051/.

Nargessi et al., "Quantitation of estrogen receptor mRNA in breast carcinoma by branched DNA assay", Breast Cancer Research and Treatment, vol. 50, pp. 47-55, 1998.

Nargessi et al., "Quantitation of progesterone receptor mRNA in breast carcinoma by branched DNA assay", Breast Cancer Research and Treatment, vol. 50, pp. 57-62, 1998.

National Science Foundation, "These Cells Will Self-Destruct in Five . . . Four . . . ", Press Release 10-160, p. 1-3. Sep. 6, 2010.

Nieto, M. et al., "In situ hybridization analysis of chick embryos in whole mount and tissue sections," Methods in Cell Biology, vol. 51, pp. 219-235, 1996.

Nikolakakis, K et al., Use of Hybridization Chain Reaction-Fluorescent In Situ Hybridization To Track Gene Expression by Both Partners during Initiation of Symbiosis, Applied and Environmental Microbiology, vol. 81, No. 14, pp. 4728-4735, (2015).

Noll et al., "Formation and Repair of Interstrand Cross-Links in DNA." Chemical Reviews 106.2 (2006) 277-301.

Noll et al., "Preparation of Interstrand Cross-Linked DNA Oligonucleotide Duplexes." Frontiers in Bioscience 9 (Jan. 1, 2004): 421-437.

Nolte, et al., Branched DNA Signal Amplification For Direct Quantitation Of Nucleic Acid Sequences In Clinical Specimens, Advances in Clinical Chemistry, vol. 33, pp. 201-235, 1998.

Nolte et al., Clinical Comparison of an Enhanced-Sensitivity Branched-DNA Assay and Reverse Transcription-PCR for Quantitation of Human Immunodeficiency Virus Type 1 RNA in Plasma, Journal of Clinical MicrobioloQy, vol. 36, No. 3, pp. 716-720, 1998.

Nutiu et al., "Structure-switching signaling aptamers," J. Am. Chem. Soc., vol. 125, pp. 4771-4778, American Chemical Society, 2003.

Ouporov, Igor V., and Leontis, Necocles B., "Refinement of the Solution Structure of a Branched DNA Three-Way Junction," Biophysical Journal, vol. 68, ppg. 266-274. Jan. 1995.

Opalinska et al., "Nucleic-Acid Therapeutics: Basic Principles and Recent Applications", Nature Reviews Drug Discovery, vol. 1, pp. 503-514, 2002.

Pachl et al., "Rapid and Precise Quantification of HIV-1 RNA in Plasma Using a Branched DNA Signal Amplification Assay", Journal of Acquired Immune Deficiency Syndromes and Human Retrovirology, vol. 8, pp. 446-454, 1995.

Pardee et al., Paper-Based Synthetic Gene Networks. Cell 2014, 159 (4), 940-954. https://doi.org/10.1016/j.cell.2014.10.004.

Pardee et al., Rapid, Low-Cost Detection of Zika Virus Using Programmable Biomolecular Components. Cell 2016, 165 (5), 1255-1266, https://doi.org/10.1016/j.cell.2016.04.059.

Pardi et al., MRNA Vaccines—a New Era in Vaccinology. Nat. Rev. Drug Discov. 2018, 17 (4), 261-279, https://doi.org/10.1038/nrd.2017.243.

Park, S.H.; Yin, P.; Liu, Y.; Reif, J.H.; LaBean, T.H.; Yan, H. "Programmable DNA Self-Assemblies for Nanoscale Organization of Ligands and Proteins." Nano Letters 2005, 5, 729-733.

Park et al., "Rapid Identification of Candida dubliniensis Using a Species-Specific Molecular Beacon", Journal of Clinical Microbiology, vol. 38, No. 8, pp. 2829-2836, 2000.

Park et al., "Three-Helix Bundle DNA Tiles Self-Assemble into 2D Lattice or 1D Templates for Silver Nanowires", Nano Lett., vol. 5, No. 4, pp. 693-696, 2005.

Patel et al., Cancer Biology & Therapy 14: 8, 693-696; Aug. 2013.

Paterson et al., Efficient Translation of Prokaryotic MRNAs in a Eukaryotic Cell-Free System Requires Addition of a Cap Structure. Nature 1979, 27 (5715), 692-696. https://doi.org/10.1038/279692a0.

Patterson, B., Techniques in Quantification and Localization of Gene Expression, Springer Science+Business Media, LLC, @ 2000 Springer Science+Business Media New York, Originally published by Birkhauser Boston in 2000, 157 oaaes.

Paul et al., "A self-replicating ligase ribozyme", PNAS, vol. 99, No. 20, pp. 12733-12740, Oct. 1, 2002.

Pawlotsky et al., "Quantification of hepatitis C virus RNA in serum by branched DNA-based signal amplification assays", Journal of Virological Methods, vol. 79, pp. 227-235, 1999.

Peng et al., Facile SNP detection using bifunctional, cross-linking oligonucleotide probes, Nucleic Acids Research vol. 36 No. 5e31 (2008), pp. 1-7.

Perales et al., "Gene Transfer in vivo: Sustained Expression and Regulation of Genes Introduced into the Liver by Receptor-Targeted Uptake", Proceedings of the National Academy of Sciences of the United States of America, vol. 91, pp. 4086-4090, Apr. 1994.

Pernthaler, A. et al., "Fluorescence in situ hybridization and catalyzed reporter deposition for the identification of marine bacteria," Applied and Environmental Microbiology, vol. 68, No. 6, pp. 3094-3101, Jun. 2002.

Pieles, U. and Englisch, U. Psoralen covalently linked to oligodeoxyribonucleotides: synthesis, sequence specific recognition of DNA and photo-cross-linking to purimidine residues of DNA. Nucleic Acids Research, 1989. 17: p. 285-299.

Piette, D. et al., "An optimized procedure for whole-mount in situ hybridization on mouse embryos and embryoid bodies," Nature Protocols, vol. 3, No. 7, pp. 1194-1201, 2008.

Pijlman et al., A Highly Structured, Nuclease-Resistant, Noncoding RNA Produced by Flaviviruses Is Required for Pathogenicity. Cell Host Microbe 2008, 4 (6), 579-591.

Pinheiro et al., Challenges and Opportunities for Structural DNA Nanotechnology. Nat. Nanotechnol. 2011, 6 (12), 763-772, https://doi.org/Doi 10.1038/Nnano.2011.187.

Piyush K. Jain et al: "Development of Light-Activated CRISPR Using Guide RNAs with Photocleavable Protectors", Angewandte Chemie International Edition, vol. 55, No. 40, Aug. 24, 2016 (Aug. 24, 2016), pp. 12440-12444,XP055736874.

Player et al., "Single-copy Gene Detection Using Branched DNA (bDNA)) In Situ Hybridization," J. Histochem & Cytochem, 49(5), pp. 603-611, 2001.

Player, "An Enhanced-Sensitivity Branched-DNA Assay for Quantification of Human Immunodeficiency Virus Type 1 RNA in Plasma", 2001.

Pouton et al., "Key issues in non-viral gene delivery", Advanced Drug Delivery Reviews, vol. 46, pp. 187-203, 2001.

Piston et al., "Fluorescent protein FRET: the good, the bad and the ugly", Trends Biochem Sci., Sep. 2007, vol. 32, No. 9, pp. 407-414.

Product: Versant HIV-1 Rna 3.0 Assay (bDNA), PMA No. BP000028/0, Approval Date: Sep. 11, 2002.

Provost, P. et al., "Ribonuclease activity and RNA binding of recombinant human Dicer," EMBO J., vol. 21, pp. 5864-5874, 2002.

Qi et al., "Surface Transfer Doping of Diamond (100) by Tetrafluoro-tetracyanoquinodimethane", J. Am. Chem. Soc., vol. 129, pp. 8084-8085, 2007.

Qian et al., "Recent Developments in Signal Amplification Methods for In Situ Hybridization," Diagnostic Molecular Pathology, 12(1), pp. 1-13, 2003.

Qian, X., L. Jin, and R.V. Lloyd, In situ hybridization: basic approaches and recent development. The Journal of Histotechnology, 2004. 27(1): p. 53-67.

Qian et al., Scaling Up Digital Circuit Computation with DNA Strand Displacement Cascades. Science 2011, 332 (6034), 1196-1201. https://doi.org/Doi 10.1126/Science.1200520.

Ravan, H., Isothermal RNA detection through the formation of DNA concatemers containing HRP-mimicking DNAzymes on the surface of gold nanoparticles, Biosensors and Bioelectronics, vol. 80, pp. 67-73, 2016.

(56) References Cited

OTHER PUBLICATIONS

Rachofsky et al., "Probing structure and dynamics of DNA with 2-aminopurine: Effects of local environment on fluorescence," Biochemistry, vol. 40, pp. 946-956, 2001.
Rana et al., Chemical Communications 52 :3524-3527 (Year: 2016).
Raj et al., "Imaging Individual mRNA Molecules Using Multiple Singly Labeled Probes." Nature Methods 5.10 (Oct. 2008): 877-879.
Read et al., "Barriers to Gene Delivery Using Synthetic Vectors", Advances in Genetics, vol. 53, pp. 19-46, 2005.
Reif, J.H.; Sahu, S.; Yin, P. "Compact Error-Resilient Computational DNA tiling Assemblies." In Proc. 10th International Meeting on DNA Computing; 2004.
Reif, J.H.; Sahu, S.; Yin, P. "Complexity of Graph Self-Assembly in Accretive Systems and Self-Destructible Systems." In Proc. 11th International Meeting on DNA Computing; 2005.
Reynolds et al., "Rational siRNA Design for RNA Interference." Nature Biotechnology 22.3 (Mar. 2004) 326-330.
Rosen, B. et al., "Whole-mount in situ hybridization in the mouse embryo: gene expression in three dimensions," Trends in Genetics, vol. 9, Issue 5, pp. 162-167, May 1993.
Rosenthal, A. et al., "Localizing transcripts to single cells suggests an important role of uncultured deltaproteobacteria in the termite gut hydrogen economy," PNAS, vol. 110, No. 40, pp. 16163-16168, Oct. 1, 2013.
Ross et al., Quantitation of hepatitis C virus RNA by third generation branched DNA-based signal amplification assay, Journal of Virological Methods, vol. 101, No. 1-2, pp. 159-168, 2002.
Roth et al., Selective for the Queuosine Precursor PreQ1 Contains an Unusually Small Aptamer Domain. Nat. Struct. Mol. Biol. 2007, 14 (4), 308-317, https://doi.org/10.1038/nsmb1224.
Rothemund, P.; Papadakis, J.; Winfree, E. "Algorithmic Self-Assembly of DNA Sierpinski Triangles." PLoS Biology 2004, 2, 2041-2053.
Rothemund et al., "Design and Characterization of Programmable DNA Nanotubes", J. Am. Chem. Soc., vol. 126, pp. 16344-16352, 2004.
Rothemund, P.W.K., "Folding DNA to creat nanoscale shapes and patterns", Nature, vol. 440, pp. 297-302, 2006.
Rothemund, P.W.K.; Winfree, E. "The Program-size complexity of self-assembled squares (extended abstract)." In Proceedings of the thirty-second annual ACM symposium on Theory of computing; ACM Press: 2000.
Sahin et al., MRNA-Based Therapeutics—Developing a New Class of Drugs. Nat. Rev. Drug Discov. 2014, 13 (10), 759-780, https://doi.org/10.1038/nrd4278.
Sahu et al., "A self-Assembly Model of Time-Dependent Glue Strength." In Proc. 11th International Meeting on DNA Computing; 2005.
Sambrook, J. et al., "Molecular cloning: a laboratory manual," Cold Springs Harbor Press, 1989.
Santalucia J. "A unified view of polymer, dumbbell, and oligonucleotide DNA nearest-neighbor thermodynamics" Proc Natl Acad Sci 95:1460-1465 (1998).
Sander, J. et al., 'CRISPR-Cas systems for editing, regulating and targeting genomes', Nat Biotech, 32: 347-55., (2014).
Saunders et al., "Introduction of DNA into Bacteria." Methods in Microbiology 29 (1999): 3-49.
Schärer et al., "DNA Interstrand Crosslinks: Natural and Drug-Induced DNA Adducts that Induce Unique Cellular Responses." ChemBioChem 6 (2005): 27-32.
Scherer et al., "Approaches for the sequence-specific knockdown of mRNA", Nature Biotechnology, vol. 21, No. 12, pp. 1457-1465, 2003.
Schipani, Vanessa, "A targeted cancer therapy?" The Scientist, Sep. 7, 2010 blog post, http://www.the-scientist.com/blog/display/57674/.
Schulman et al., "Synthesis of crystals with a programmable kinetic barrier to nucleation", PNAS, vol. 104, No. 39, pp. 15236-15241, Sep. 25, 2007.
Schulte-Merker et al., "no tail (ntl) is the zebrafish homologue of the mouse T (Brachyury) gene." Development 120 (1994): 1009-1015.
Schwartz et al., "Cloning and Functional Analysis of Multiply Spliced mRNA Species of Human Immunodeficiency Virus Type 1", Journal of Virology, vol. 64, No. 6, pp. 2519-2529, Jun. 1990.
Schwarzkopf et al., Multiplexed MiRNA Northern Blots via Hybridization Chain Reaction. Nucleic Acids Res. 2016, 44 (15), e129, https://doi.org/10.1093/nar/gkw503.
Schweitzer et al., "Combining nucleic acid amplification and detection," Curr Opin Biotechnol, 12, pp. 21-27, 2001.
Seelig et al., "Catalyzed Relaxation of a Metastable DNA Fuel", Journal American Chemical Society, vol. 128, No. 37, pp. 12211-12220, 2006.
Seelig et al., Enzyme-Free Nucleic Acid Logic Circuits. Science 2006, 314 (5805), 1585-1588.
Seeman, "De Novo Design of Sequences for Nucleic Acid Structural Engineering", Journal of Biomolecular Structure & Dynamics, pp. 573-581, vol. 8, No. 3, 1990.
Seeman, "DNA in a material world", Department of Chemistry, New York University, Nature, vol. 421, pp. 427-431 (Jan. 23, 2003).
Seeman, "Nucleic acid junctions and lattices," J. Theor. Biol., vol. 99, pp. 237-247, Academic Press Inc. (London) Ltd., 1982.
Seeman, "Nucleic acid nanostructures and topology", Angew. Chem. Int. Ed. vol. 37, pp. 3220-3238 (1998).
Seeman, et al., Nucleic Acid Nanostructures: Bottom Up Control of Geometry on the Nanoscale, Reports on Progress in Physics, 68 :237 (2005).
Segondy et al., "Comparison of the Quantiplex HIV-1 RNA 2.0 Assay with the Amplicor HIV-1 Monitor 1.0 Assay for Quantitation of Levels of Human Immunodeficiency Virus Type 1 RNA in Plasma of Patients Receiving Stavudine-Didanosine Combination Therapy", Journal of Clinical Microbiology, vol. 36, No. 11, pp. 3392-3395, Nov. 1998.
Sekulic, A.; Hudson, C.C; Homme, J.L.; Yin, P.; Otterness, D.M.; Karnitz, L.M.; Abraham, R.T. A Direct Linkage between the Phosphoinositide 3-Kinase-AKT Signaling Pathway and the Mammalian Target of Rapamycin in Mitogen-stimulated and Transformed Cells. Cancer Research 2000, 60, 3504-3513.
Serra M.J., Turner D.H., "Predicting thermodynamic properties of RNA" Methods Enzymol 259: 242-261 (1995).
Shah et al., "The Fries Isomerization of Acetyl and Benzoyl Esters of Umbelliferones." J. Org. Chem. 19 (1954): 1681-1685.
Shah, S. et al., "Single-molecule RNA detection at depth via hybridization chain reaction and tissue hydrogel embedding and clearing," Development, 41 pages, Jun. 2016.
Shaner et al., "A guide to choosing fluorescent proteins", Nature Methods, vol. 2, No. 12, pp. 905-909, Dec. 2005.
Sharma, J.; Chhabra, R.; Cheng, a.; Brownell, J.; Liu, Y.; Yan, H. "Control of Self-Assembly of DNA Tubules through Integration of Gold Nanoparticles" Science 2009, 112-116.
Sharma et al., "DNA-Tile-Directed Self-Assembly of Quantum Dots into Two-Dimensional Nanopatterns", Angew. Chem. Int. Ed., vol. 47, pp. 5157-5159, 2008.
Sherman et al., "Quantitative Evaluation of Hepatitis C Virus RNA in Patients with Concurrent Human Immunodeficiency Virus Infections", Journal of Clinical Microbiology, vol. 31, No. 10, pp. 2679-2682, Oct. 1993.
Shih et al., "A 1.7-kilobase single-stranded DNA that folds into a nanoscale octahedron", Nature, vol. 427, pp. 618-621, Feb. 12, 2004.
Shir et al., "Inhibition of glioma growth by tumor-specific activation of double-stranded RNA-dependent protein kinase PKR", Nature Biotechnology, vol. 20, pp. 895-900, Sep. 2002.
Shlyakhtenko et al., "Structure of Three-Way DNA Junctions 1. Non-Planar DNA Geometry" Journal of Biomolecular Structure and Dynamics, vol. 11: pp. 1175-1189, Nov. 6, 1994.
Shlyakhtenko et al., "Structure and Dynamics of Three-Way DNA Junctions: Atomic Force Microscopy Studies." Nucleic Acids Research. 2000. 28(19): 3472-3477.
Silverman et al., "Oligonucleotide Probes for RNA-Targeted Fluorescence In Situ Hybridization." Advances in Clinical Chemistry 43 (2007): 79-115.

(56) References Cited

OTHER PUBLICATIONS

Silverman et al., "Quenched Autoligation Probes Allow Discrimination of Live Bacterial Species by Single Nucleotide Differences in rRNA." Nucleic Acids Research 33.15 (2005): 4978-4986.
Singleton, P. et al., "Dictionary of Microbiology and Molecular Biology," 2nd Edition, J. Wiley & Sons, 1994.
Situma et al., "Immobilized molecular beacons: A new strategy using UV-activated poly(methyl methacrylate) surfaces to provide large fluorescence sensitivities for reporting on molecular association events." Analytical Biochemistry 363 (2007) 35-45.
Siolas et al., "Synthetic shRNAs as Potent RNAi Triggers." Nature Biotechnology 23.2 (Feb. 2005): 227-231.
Smith et al., Determination of Cryptosporidium parvum oocyst viability by fluorescence in situ hybridization using a ribosomal RNA-directed probe. J Appl Microbiol 96(2):409-417, 2004.
Sokol et al., "Real time detection of DNA•RNA hybridization in living cells", Proc. Natl. Acad. Sci. USA, vol. 95, pp. 11538-11543, Sep. 1998.
Stack, E., et al. Multiplexed immunohistochemistry, imaging, and quantitation: A review, with an assessment of Tyramide signal amplification, multispectral imaging and multiplex analysis, . Methods, vol. 70, No. 1, (2014).
Steckelberg et al., Exoribonuclease-Resistant RNAs Exist within Both Coding and Noncoding Subgenomic RNAs. mBio 2018, 9 (6), e02461-18, /mbio/9/6/mBio.02461-18.atom. https://doi.org/10.1128/mBio.02461-18.
Steckelberg et al., A Folded Viral Noncoding RNA Blocks Host Cell Exoribonucleases through a Conformationally Dynamic RNA Structure. Proc. Natl. Acad. Sci. 2018, 115 (25), 6404-6409. https://doi.org/10.1073/pnas.1802429115.
Stemmer, et al., Single Step Assembly of a Gene and Entire Plasmid from Large Numbers of Oligodeoxyribonnucleotides. Gene, vol. 164, pp. 49-53 (1995).
Storhoff et al., "One-pot colorimetric differentiation of polynucleotides with single base imperfections using gold nanoparticles," J. Am. Chem. Soc., 120, pp. 1959-1964, 1998.
Strader et al., "Diagnosis, Management, and Treatment of Hepatitis C", Hepatology, vol. 39, No. 4, pp. 1147-1171, 2004.
Stratagene Catalog. gene characterization kits. Stratagene Catalog, pp. 39, 1988.
Stuheimer, et al. "Global Structure of Three-Way DNA Junctions with and without Additional Unpaired Bases: A Fluorescence Resonance Energy Transfer Analysis". Biochemistry 1997. 35: pp. 13530-13538.
Sun et al., "Side Chain Chemistry Mediates Backbone Fragmentation in Hydrogen Deficient Peptide Radicals." Journal of Proteome Research 8 (2009) 958-966.
Szucs et al., A New Subclass of Exoribonuclease-Resistant RNA Found in Multiple Genera of Flaviviridae. 2020, 11 (5), 15.
Takei et al., "A Small Interfering RNA Targeting Vascular Endothelial Growth Factor as Cancer Therapeutics." Cancer Research 64. (May 15, 2004): 3365-3370.
Tani et al., "Synthesis and Structural Analysis of 2-Quinuclidonium Tetrafluoroborate." Nature 441 (Jun. 8, 2006) 731-734.
Tautz, D. et al., "A non-radioactive in situ hybridization method for the localization of specific RNAs in Drosophila embryos reveals translational control of the segmentation gene hunchback," Chromosoma, vol. 98, Issue 2, pp. 81-85, Aug. 1989.
Tedeschi et al., "Quantification of Hepatitis C Virus (HCV) in Liver Specimens and Sera from Patients with Human Immunodeficiency Virus Coinfection by Using the Versant HCV RNA 3.0 (Branched DNA-Based) DNA Assay", Journal of Clinical MicrobioloaY, vol. 41, No. 7, oaaes 3046-3050, Jul. 2003.
Thisse, B., "Spatial and temporal expression of the zebrafish genome by large-scale in situ hybridization screening," Methods in Cell Biology, vol. 77, pp. 505-519, 2004.
Thisse, C. et al., "High-resolution in situ hybridization to whole-mount zebrafish embryos," Nature Protocols, vol. 3, No. 1, pp. 59-69, Jan. 2008.
Tijsterman et al., "Dicers at RISC: The Mechanism of RNAi", Cell, vol. 117, pp. 1-3, 2004.
Thomas et al., "Photoaffinity Cross-Linking and RNA Structure Analysis." Methods in Enzymology 318 (2000) 136-147.
Thompson, N.L.; Lieto, A.M., and Allen, N.W. "Recent advances in fluorescence correlation spectroscopy." Curr. Opin.Struct. Biol., 12, 2002.
The Naked Scientists: Science Radio & Science Podcasts, "RNA-away cancer cells", Sep. 12, 2010, http://www.thenakedscientists.com/HTML/content/news/news/2051/.
Trail, P., Antibody drug conjugates as cancer therapeutics, Antibodies, vol. 2, No. 1 pp, .113-129, (2013).
Trimoulet et al., Evaluation of the Versant HCV RNA 3.0 Assay for Quantification of Hepatitis C Virus RNA in Serum, Journal of Clinical Microbiology, vol. 40, No. 6, pp. 2031-2036, 2002.
Tsongalis et al., Branched DNA Technology in Molecular Diagnostics, American Journal of Clinical Pathology, vol. 126, No. 3, 448-453, 2006.
Tuerk et al., "Systematic Evolution of Ligands by Exponential Enrichment: RNA Ligands to Bacteriophage T4 DNA Polymerase," Science 249, pp. 505-510, 1990.
Tuleuova, N.; An, C. I.; Ramanculov, E.; Revzin, A ; Yokobayashi, Y. "Modulating endogenous gene expression of mammalian cells via RNA-small molecule interaction" Biochem. Biophys. Res. Commun. 2008, 376, 169-173.
Turberfield, et al., "DNA fuel for free-running nanomachines, "Physical Review Letters, vol. 90, No. 11, pp. 118102-1-118102-4, Mar. 21, 2003.
Turk, Greg and Levoy, Marc. "Zippered polygon meshes from range images." In SIGGRAPH, pp. 311-318, 1994.
Tyagi et al., "Molecular Beacons: Probes that Fluoresce upon Hybridization," Nature Biotechnology 14, pp. 303-308, 1996.
Tyagi, et al., Multicolor Molecular Beacons for Allele Discrimination, Nature Biotechnology vol. 16, pp. 49-53, Jan. 1998.
Urdea et al., "Branched DNA (bONA) Technology", Chapter 33, Bayer Diagnostics, pp. 388-395, 2000.
Urdea, M.S., "Branched DNA Signal Amplification—Does bDNA represent post-PCR amplification technology?", Biotechnology, vol. 12, pp. 926-928, Sep. 1994.
Van De Corput et al., "Sensitive mRNA Detection by Fluorescence In Situ Hybridization Using Horseradish Peroxidase-labeled Oligodeoxynucleotides and Tyramide Signal Amplification," J. Histochem Cytochem, 46(11), pp. 1249-1259, 1998.
Venkataraman et al., "An Autonomous Polymerization Motor Powered by DNA Hybridization." Nature Nanotechnology 2 (Aug. 2007): 490-494.
Venkataraman et al. "Selective Cell Death Mediated By Small Conditional RNAs", Proc Natl Acad Sci USA, early edition, approved Jul. 21, 2010, p. 1-6.
Venkataraman et al. Abstract of "Selective Cell Death Mediated By Small Conditional RNAs", Proc Natl Acad Sci USA, early edition, http://www.pnas.org/content/early/2010/09/01/1006377107.abstract.
Vermeulen et al., "The contributions of dsRNA structure to Dicer specificity and efficiency", RNA, vol. 11, pp. 674-682, 2005.
Versant Bayer, HCV RNA 3.0 Assay (bDNA), 02616244 Rev. A, Apr. 2003.
Vieregg et al., "Selective Nucleic Acid Capture with Shielded Covalent Probes", J. Am. Chem. Soc., 2013, vol. 135, 9691-9699.
Vieregg et al., "Selective Nucleic Acid Capture with Shielded Covalent Probes—Supplemental Materials", J. Am. Chem. Soc., 2013, vol. 135, pp. S1-S52.
Vodovozova et al., "Photoaffinity Labeling and Its Application in Structural Biology." Biochemistry (Moscow) 72.1 (2007): 1-20.
Voigt et al., Detection and Quantification of RNA Decay Intermediates Using XRN1-Resistant Reporter Transcripts. Nat. Protoc. 2019, 14 (5), 1603-1633. https://doi.org/10.1038/s41596-019-0152-8.
Volker, et al., "Conformational energetics of stable and metastable states formed by DNA triple repeat oligonucleotides: implications for triplet expansion diseases,"PNAS, vol. 99, No. 23, pp. 14700-14705, Nov. 12, 2002.

(56) References Cited

OTHER PUBLICATIONS

Von Kiedrowski, "A Self-Replicating Hexadeoxynucleotide", Agnew. Chem. Int. Ed. Engl., vol. 25, No. 10, pp. 932-935, 1986.
Voorhoeve et al., "Knockdown Stands Up.:" Trends in Biotechnology 21.1 (Jan. 2003) 2-4.
Wagner et al., "Transferrin-Polycation Conjugates as Carriers for DNA Uptake into Cells", Proceedings of the National Academy of Sciences of the United States of America, vol. 87, pp. 3410-3414, May 1990.
Wallner, G. et al., "Optimizing fluorescent in situ hybridization with rRNA-targeted oligonucleotide probes for flow cytometric identification of microorganisms," Cytometry, vol. 14, Issue 2, pp. 136-143, 1993.
Wang, F. et al. From Cascaded Catalytic Nucleic Acids to Enzyme-DNA Nanostructures: Controlling Reactivity, Sensing, Logic Operations, and Assembly of Complex Structures. Chemical Reviews, vol. 114 No. 5, pp. 2881-2941, (2014.
Wang, F. et al., "RNAscope: A novel in situ RNA analysis platform for formalin-fixed, paraffin-embedded tissues," The Journal of Molecular Diagnostics, vol. 14, No. 1, pp. 22-29, Jan. 2012.
Wang et al., Signal Amplification Techniques: BONA, Hybrid Capture, Advanced Techniques in Diagnostic Microbiology, pp. 228-242, 2006.
Wassarman et al., "Psoralen Crosslinking of Small RNAs in vitro." Molecular Biology Reports 17 (1993): 143-151.
Weiszmann, R. et al., "Determination of gene expression patterns using high-throughput RNA in situ hybridization to whole-mount Drosophila embryos," Nature Protoc., vol. 4, No. 5, pp. 605-618, 2009.
Weikersheimer, P.B., "Viral Load Testing for HIV Beyond the CD4 Count", Laboratory Medicine, vol. 30, No. 2, Feb. 1999.
White et al., "The Catalytic Asymmetric Total Synthesis of Elatol." Journal of American Chemical Society 130.3 (2008): 810-811.
Wiedorn, K.H. et al., "Comparison of in-situ hybridization, direct and indirect in-situ PCR as well as 484 tyramide signal amplification for the detection of HPV," Histochemistry and Cell Biology, vol. 111, Issue 2, pp. 89-95, Jan. 1999.
Wijen et al., "The in vivo Genetic Activity Profile of the Monofunctional Nitrogen Mustard 2-Chloroethylamine Differs Drastically from its Bifunctional Counterpart Mechlorethamine." Carcinogenesis 21.10 (2000) 1859-1867.
Wilber, J.C., Branched DNA for Quantification of Viral LOAD, Immunological Investigations, vol. 26, Nos. 1-2, pp. 9-13, 1997.
Wilber et al., "Quantification of HCV RNA in Clinical Specimens by Branched DNA (bDNA) Technology", Methods in Molecular Medicine, vol. 19, No. 1543-1894, pp. 71-78, 1998.
Wilkie et al., "Transcribed genes are localized according to chromosomal position within polarized Drosophila embryonic nuclei," Current Biology, 9, pp. 1263-1266, 1999.
Williams, B.R.G., "PKR; a sentinel kinase for cellular stress", Oncogene, vol. 18, pp. 6112-6120, 1999.
Willis, M.C., et al. Photocross-linking of 5-lodouracil-Substituted RNA and DNA to Proteins. Science, 1993. 262: p. 1255-1257.
Winfree et al., "Design and self-assembly of two-dimensional DNA crystals", Nature, vol. 394, pp. 539-544, Aug. 6, 1998.
Winfree, E. Algorithmic Self-Assembly of DNA, Ph.D. thesis. Thesis, California Institute of Technology, 1998.
Winfree, E. "On the computational power of DNA annealing and ligation." Computation and Neural Systems, California Institute of Technology, May 25, 1995.
Wiznerowicz, M.; Szulc, J.; Trono, D. "Tuning silence: conditional systems for RNA interference" Nat. Methods 2006, 3, 682-688.
Wu et al., "A Model for the Double-stranded RNA (dsRNA)-dependent Dimerization and Activation of the dsRNA-activated Protein Kinase PKR", The Journal of Biological Chemistry, vol. 272, No. 2, pp. 1291-1296, 1997.
Wu et al., "Receptor-mediated in Vitro Gene Transformation by a Soluble DNA Carrier System", The Journal of Biological Chemistry, vol. 262, No. 10, pp. 4429-4432, 1987.
Wu et al., Metabolic Burden: Cornerstones in Synthetic Biology and Metabolic Engineering Applications. Trends Biotechnol. 2016, 34 (8), 652-664, https://doi.org/10.1016/j.tibtech.2016.02.010.
Xie, Z.; Liu, S. J.; Bleris, L.; Benenson, Y. "Logic integration of mRNA signals by an RNAi-based molecular computer" Nucleic Acids Res. 2010, 38, 2692-2701.
Yamaguchi, T. et al., In situ {DNA}-hybridization chain reaction (HCR): a facilitated in situ HCR system for the detection of environmental microorganisms, Environmental Microbiology vol. 17, No. 7 2532-2541. 2015.
Yan et al., "DNA-Templated Self-Assembly of Protein Arrays and Highly Conductive Nanowires", Science, vol. 301, pp. 1882-1884, Sep. 26, 2003.
Yin et al., "Programming biomolecular self-assembly pathways", Nature, vol. 451, pp. 318-323, Jan. 17, 2008.
Yin, P.; Hartemink, "Theoretical and practical advances in genome halving." A.K. Bioinformatics 2005, 21, 869-879.
Yin, P.; Hariadi, R.; Sahu, S.; Choi, H.M.T.; Park, S.H.; :LaBean, T.H.; J.H. Reif, "Programming DNA Tube Circumferences." Science 2008, 321, 824-826.
Yin, P.; Yan, H.; Daniell, X.; Turberfield, A.J.; Reif, J. "A Unidirectional DNA Walker that Moves Autonomously along a Track." Angewandte Chemie International Edition 2004, 43, 4906-4911.
Yin, P.; Turberfield, A.J.; Reif, J.H. "Designs of Autonomous Unidirectional Walking DNA Devices." In Proc. 10th International Meeting on DNA computing; 2004.
Ying et al., Activatable CRISPR Transcriptional Circuits Generate Functional RNA for MRNA Sensing and Silencing. Angew. Chem. Int. Ed. 2020, 59, 18599-18604.
Yoshimura et al., "Interstrand Photocrosslinking of DNA via p-carbamoylvinyl Phenol Nucleoside." Bioorganic & Medicinal Chemistry Letters 15 (2005): 1299-1301.
Yurke, et al., "A DNA-fuelled molecular machine made of DNA" Nature, vol. 406, Aug. 10, 2000, pp. 605-608.
Yu et al., "Clinical Evaluation of the Automated Cobas Amplicor HCV Monitor Test Version 2.0 for Quantifying Serum Hepatitis C Virus RNA and Comparison to the Quantiplex HCV Version 2.0 Test", Journal of Clinical Microbiology, vol. 38, No. 8, pp. 2933-2939, Aug. 2000.
Yu et al., "Clinical application of the Quantiplex HCV RNA 2.0 and Amplicor HCV Monitor assays for quantifying serum hepatitis C virus RNA", J Clin Pathol, vol. 52, pp. 807-811, 1999.
Yu et al., RNA Drugs and RNA Targets for Small Molecules: Principles, Progress, and Challenges. Pharmacol. Rev. 2020, 72 (4), 862-898. https://doi.org/10.1124/pr.120.019554.
Zadeh. "Algorithms for nucleic acid sequence design." Doctoral Thesis [online[, orally defended Dec. 8, 2009 (Dec. 8, 2009), published May 25, 2010 (May 25, 2010), [Retrieved on Jun. 7, 2011], pp. 1-85, Retrieved from the Internet: <URL: http://resolver.caltech.edu/CaltechTHESIS:05112010-205335518>.
Zalatan et al., Engineering Complex Synthetic Transcriptional Programs with Crispr RNA Scaffolds. Cell 2015, 160 (1-2), 339-350. https://doi.org/10.1016/j.cell.2014.11.052.
Zhang et al., Conformational flexibility facilitates self-assembly of complex DNA nanostructures, PNAS, vol. 105, No. 31, pp. 10665-10669, 2008.
Zhang, L., Zhou, W., Velculescu, V.E.; Kern, S.E., Hruban, R.H., Hamilton, S.R.; Vogelstein, B.; and Kinzler, K.W. "Gene expression profiles in normal and cancer cells." Science, 276:1268-1272, 1997.
Zhang, D. Y.; Seelig, G. "Dynamic DNA nanotechnology using strand-displacement reactions" Nat. Chem. 2011, 3, 103-113.
Zhang et al., Targeted Gene Silencing by Small Interfering RNA-Based Knock-Down Technology, Current Pharmaceutical Biotechnology, vol. 5, pp. 1-7, 2004.
Zhang, H. et al., DNA-Mediated Homogeneous Binding Assays for Nucleic Acids and Proteins, Chemical Reviews vol. 113, No. 4, pp. 2812-2841, (2013).
Zhang et al., Winfree, E. Control of DNA Strand Displacement Kinetics Using Toehold Exchange. J. Am. Chem. Soc. 2009, 131, 17303-17314.
Zhang et al., Cooperative Hybridization of Oligonucleotides. J Am Chem Soc 2011, 133 (4), 1077-1086. https://doi.org/Doi 10.1021/Ja109089q.

(56) References Cited

OTHER PUBLICATIONS

Zhang et al., Engineering Entropy-Driven Reactions and Networks Catalyzed by DNA. Science 2007, 318 (5853), 1121-1125. https://doi.org/papers://865820FC-FC44-4379A720006E449021CA/Paper/p1718.
Zheng et al., "Activation of the protein kinase PKR by short double-stranded RNAs with single-stranded tails", RNA, vol. 10, pp. 1934-1945, 2004.
Zhou et al., "RNA Interference and Potential Applications", Current Topics in Medicinal Chemistry, vol. 6, pp. 901-911, 2006.
Zhou, H. et al., "Two-color, rolling-circle amplification on antibody microarrays for sensitive, multiplexed serum-protein measurements," Genome Biology, vol. 5, Issue 4, Article R28, pp. R28.1-R28.12, 2004.
Zhong et al., "High hepatitis B virus (HBV) DNA viral load is an important risk factor for HBV reactivation in breast cancer patients undergoing cytotoxic chemotherapy", Journal of Viral Hepatitis, vol. 11, pp. 55-59, 2004.
Zuker et al., "Optimal computer folding of large RNA sequence using thermodynamics and auxiliary information," Nucleic Acids Research, vol. 9, No. 1, pp. 133-147, 1981.
International Search Report and Written Opinion from PCT/US2005/009471, dated Mar. 8, 2006.
International Search Report and Written Opinion from PCT/US2008/055559, dated Sep. 3, 2008.
International Search Report and Written Opinion of the International Searching Authority for PCT/US11/31127, dated Oct. 31, 2011.
International Search Report and Written Opinion dated Nov. 6, 2017 in International Application No. PCT/US2017/49198.
International Search Report and Written Opinion dated Feb. 5, 2018 in International Application No. PCT/US2017/040485.
International Preliminary Report On Patentability in PCT/2021/020919 dated Sep. 15, 2022 in 18 pages.
International Search Report & Written Opinion in PCT/2021/020919 dated Feb. 14, 2022 in 18 pages.
Supplementary European Search Report from PCT/US2005/009471, dated May 6, 2008.
Supplementary European Search Report dated Jan. 29, 2020 received in European application No. 17847401.1.
Office Action dated Aug. 19, 2020 received in European application No. 17824 751.6.
European Office Action dated Oct. 1, 2020 received in European application No. 1784 7401.1.
European Search Opinion dated Dec. 22, 2009 in European Application No. 06 785 111.3.
European Search Opinion dated Aug. 20, 2012 in European Application No. 12 161 252.7.
Extended European Search Report dated Apr. 22, 2010 in European Patent Application No. 06836249.0.
Extended European Search Report from Application No. 08755764.1, dated Nov. 7, 2011.
Extended European Search Report From Application No. 17824751.6 dated Dec. 9, 2019.
Communication Article 94(3) EPC from Application No. 08755764.1, dated Nov. 7, 2012.
International Preliminary Report on Patentability dated Jan. 17, 2019 in International Application No. PCT/US2017/040485.
International Preliminary Report on Patentability dated Mar. 15, 2019 in International Application No. PCT/US2017/49198.
International Search Report and Written Opinion dated Apr. 18, 2019 in International Application No. PCT/US2018/036969.
Letter accompanying subsequently filed items dated Mar. 17, 2014 in European Application No. 12 161 252.7.
Letter accompanying subsequently filed items dated Oct. 28, 2013 in European Application No. 12 161 252.7.
Main Request dated Nov. 9, 2016 in European Application No. 12 161 252.7.
International Preliminary Report on Patentability, dated Dec. 17, 2019, in International Application No. PCT/US2018/036969.
International Preliminary Report, dated Dec. 26, 2019, in International Application No. PCT/US2018/036969.
Extended European Search Report, dated Feb. 7, 2020, in European Application No. EP 17847401.1.
Communication Article 94(3) EPC from Application No. 18817173.0, dated Mar. 30, 2020.
Communication dated Feb. 18, 2014 in European Application No. 06 785 111.3.
Communication dated Jul. 8, 2013 in European Application No. 06 785 111.3.
Extended European Search Report From U.S. Appl. No. 17/824,751 dated Nov. 29, 2019.
Amended Claims dated Mar. 19, 2013 in European Application No. 12 161 252.7.
Communication of EP Publication No. dated Mar. 25, 2020, in EP Application No. 18817173.0.
Decision of the Opposition Division dated Jan. 2, 2017 in European Application No. 12 161 252. 7.
Decision to grant a European patent dated Jul. 17, 2014 in European Application No. 12 161 252. 7.
Notice of opposition dated Apr. 27, 2015 in European Application No. 12 161 252.7.
Response to Noting of Loss Rights pursuant to Rule 112(1) EPC dated Jan. 18, 2011 in European Application No. 06 785 111.3.
Response to Communication pursuant to Article 94(3) EPC dated Jan. 20, 2014 in European Application No. 06 785 111.3.
Response to Communication pursuant to Rule 79(1) EPC and Opponent's Submission dated Dec. 21, 2015 in European Application No. 12 161 252.7.
Summary of Facts and Submissions dated Apr. 14, 2016 in European Application No. 12 161 252.7.
Summons to Attend Oral Proceedings Annex dated May 10, 2021 for EP 17 847 401.1 in 6 pages.
Statement of Opposition dated Apr. 27, 2015 in European Application No. 12 161 252. 7.
Office Action dated Aug. 19, 2020 in EP Application 17824751.6.
Extended European Search Report From Application No. 18817173.0 dated Feb. 5, 2021.
Extended European Search Report From Application No. 21189594.1 dated Nov. 29, 2021.
Chen, et al. 2016. "Nanoscale Imaging of RNA with Expansion Microscopy." Nature Methods 13 (8): 679-84.
Husain, N. 2016. "Mapping MRNA and Protein Expression with High Signal-to-Background in Diverse Organisms." PhD Thesis, California Institute of Technology.
Koos, et al. 2015. "Proximity-Dependent Initiation of Hybridization Chain Reaction." Nature Communications 6: 7294. https://doi.org/ARTN 7294 10.1038/ncomms8294.
Leino, et al., 2019. "Optimization of Proximity-Dependent Initiation of Hybridization Chain Reaction for Improved Performance." Molecular Systems Design & Engineering 4 (5): 1058-65. https://doi.org/10.1039/C9ME00079H.
Lin, et al. 2018. "A Hybridization-Chain-Reaction-Based Method for Amplifying Immunosignals." Nature Methods 15 (4): 275-78. https://doi.org/10.1038/nmeth.4611.
Wang, et al., 2018. "Multiplexed Imaging Using Same Species Primary Antibodies with Signal Amplification." BioRxiv, January, 274456. https://doi.org/10.1101/274456.
Wang, et al., 2020. "Multiplexed in Situ Protein Imaging Using DNA-Barcoded Antibodies with Extended Hybridization Chain Reactions." BioRxiv, January, 274456. https://doi.org/10.1101/274456.
U.S. File History printed Jun. 16, 2009 for U.S. Appl. No. 11/087,937, filed Mar. 22, 2005, entitled "Hybridization Chain Reaction.".
U.S. File History printed Jun. 16, 2009 for U.S. Appl. No. 11/371,346, filed Mar. 7, 2006, entitled "Hybridization Chain Reaction Amplification for In Situ Imaging.".
U.S. File History printed Jun. 16, 2009 for U.S. Appl. No. 11/371,347, filed Mar. 7, 2006, entitled "Colorimetric Readout of Hybridization Chain Reaction.".
U.S. File History printed Jun. 16, 2009 for U.S. Appl. No. 11/544,306, filed Oct. 6, 2006, entitled "PKR Activation Via Hybridization Chain Reaction.".

(56) References Cited

OTHER PUBLICATIONS

U.S. File History printed Jun. 16, 2009 for U.S. Appl. No. 12/040,735, filed Feb. 29, 2008, entitled "Triggered RNAi.".
U.S. File History printed Jun. 16, 2009 for U.S. Appl. No. 12/152,893, filed May 16, 2008, entitled "A Versatile Nucleic Acid Hairpin Motif for Programming Biomolecular Self-Assembly Pathways,".
U.S. File History printed Jun. 4, 2010 for U.S. Appl. No. 12/395,489, filed Feb. 27, 2009, entitled "Triggered RNAi.".
U.S. File History printed Jun. 4, 2010 for U.S. Appl. No. 12/454,743, filed May 22, 2009, entitled "Triggered RNAi.".
U.S. File History printed Jun. 4, 2010 for U.S. Appl. No. 12/454,799, filed May 22, 2009, entitled "Compositions and Methods for Detecting Analytes.".
U.S. File History printed Jun. 4, 2010 for U.S. Appl. No. 12/467,755, filed May 18, 2009, entitled "Shielded Cross-Linking Probes.".
U.S. File History printed Jun. 4, 2010 for U.S. Appl. No. 12/611,875, filed Nov. 3, 2009, entitled "Hybridization Chain Reaction.".
U.S. Appl. No. 11/471,278, filed Jun. 19, 2006.
U.S. Appl. No. 16/294,864, filed Mar. 6, 2019.
U.S. Appl. No. 15/639,100.
U.S. Appl. No. 11/087,937.
U.S. Appl. No. 12/152,893.
U.S. Appl. No. 12/467,755.
U.S. Appl. No. 13/186,228.
U.S. Appl. No. 15/689,786.
U.S. Appl. No. 16/005,445.
U.S. Appl. No. 12/790,379.
U.S. Appl. No. 13/186,331, filed Jul. 19, 2011.
U.S. Appl. No. 14/033,081.
U.S. Appl. No. 13/186,315.
U.S. Appl. No. 14/320,479.
U.S. Appl. No. 14/497,070.
Final Office Action dated Jun. 28, 2013 for U.S. Appl. No. 13/186,228.
Final Office Action dated Jul. 15, 2011 for U.S. Appl. No. 12/040,735.
Final Office Action dated Jul. 25, 2011 for U.S. Appl. No. 12/395,489.
Final Office Action dated Oct. 15, 2010 for U.S. Appl. No. 12/152,893.
Final Office Action dated Sep. 17, 2010 for U.S. Appl. No. 12/467,755.
Final Office Action dated Sep. 20, 2010 for U.S. Appl. No. 12/454,799.
Final Office Action dated May 27, 2010 for U.S. Appl. No. 11/544,306.
Final Office Action dated Mar. 7, 2013 for U.S. Appl. No. 13/016,811.
Final Office Action dated Jan. 22, 2014 for U.S. Appl. No. 13/186,331.
Final Office Action dated Jun. 25, 2014 for U.S. Appl. No. 13/186,315.
Final Office Action dated Jul. 2, 2014 for U.S. Appl. No. 13/154,989.
Final Office Action dated Aug. 1, 2014 for U.S. Appl. No. 12/454,799.
Final Office Action dated Aug. 29, 2014 for U.S. Appl. No. 12/467,755.
Final Office Action dated Oct. 29, 2014 for U.S. Appl. No. 13/186,228.
Office Action dated Apr. 1, 2010 for U.S. Appl. No. 12/467,755.
Office Action dated Apr. 2, 2014 for U.S. Appl. No. 12/467,755.
Office Action dated Apr. 16, 2010 in U.S. Appl. No. 12/454,799.
Office Action dated Nov. 9, 2010 for U.S. Appl. No. 12/040,735.
Office Action dated Oct. 14, 2011 for U.S. Appl. No. 12/454,743.
Office Action dated Dec. 16, 2010 for U.S. Appl. No. 12/395,489.
Office Action dated Feb. 4, 2010 for U.S. Appl. No. 12/152,893.
Office Action dated Jan. 24, 2013 for U.S. Appl. No. 13/186,228.
Office Action dated Mar. 10, 2011 for U.S. Appl. No. 12/454,743.
Office Action dated Mar. 17, 2011 for U.S. Appl. No. 12/611,875.
Office Action dated Aug. 2, 2013 for U.S. Appl. No. 13/186,315.
Office Action dated Aug. 8, 2013 for U.S. Appl. No. 13/186,331.
Notice of Allowance dated Feb. 20, 2013 for U.S. Appl. No. 12/395,489.
Notice of Allowance dated Apr. 4, 2013 for U.S. Appl. No. 13/363,022.
Notice of Allowance dated May 24, 2013 for U.S. Appl. No. 13/016,811.
Office Action dated Jan. 27, 2014 for U.S. Appl. No. 13/186,315.
Office Action dated Feb. 27, 2014 for U.S. Appl. No. 12/454,799.
Office Action dated May 22, 2014 for U.S. Appl. No. 13/186,228.
Notice of Allowance dated Jul. 1, 2014 for U.S. Appl. No. 13/183,331.
Notice of Allowance dated Oct. 8, 2014 for U.S. Appl. No. 13/186,315.
Notice of Allowance dated Oct. 9, 2014 for U.S. Appl. No. 13/154,989.
Office Action dated Oct. 14, 2014 for U.S. Appl. No. 12/152,893.
Office Action dated Oct. 30, 2014 for U.S. Appl. No. 13/896,235.
Office Action dated Jan. 13, 2015 for U.S. Appl. No. 12/467,755.
Final Office Action dated May 8, 2015 for U.S. Appl. No. 12/467,755.
Office Action dated May 5, 2015 for U.S. Appl. No. 12/454,799.
Office Action dated Jul. 2, 2015 for U.S. Appl. No. 13/186,228.
Office Action dated Aug. 27, 2015 in U.S. Appl. No. 12/467,755.
Office Action Dated Jul. 8, 2016 for U.S. Appl. No. 13/186,228.
Notice of Allowance dated Jun. 26, 2015 for U.S. Appl. No. 12/152,893.
Supplemental Notice of Allowance dated Sep. 17, 2015 for U.S. Appl. No. 12/152,893.
Final Office Action dated Feb. 4, 2016 for U.S. Appl. No. 12/467,755.
Final Office Action dated Nov. 25, 2015 for U.S. Appl. No. 12/454,799.
Office Action dated Jun. 22, 2012 for U.S. Appl. No. 13/363,022.
Final Office Action dated Dec. 10, 2012 for U.S. Appl. No. 13/363,022.
Notice of Allowance dated Jan. 15, 2013 for U.S. Appl. No. 13/363,022.
Office Action dated Sep. 20, 2012 for U.S. Appl. No. 13/016,811.
Notice of Allowance dated Oct. 23, 2013 for U.S. Appl. No. 13/016,811.
Office Action dated Jan. 30, 2014 for U.S. Appl. No. 13/154,989.
Notice of Allowance dated Nov. 8, 2016 for U.S. Appl. No. 13/186,228.
Office Action dated Jan. 5, 2017 for U.S. Appl. No. 14/033,081.
Notice of Allowance dated Feb. 5, 2013 for U.S. Appl. No. 13/079,747.
Final Office Action dated Feb. 7, 2017 for U.S. Appl. No. 14/320,479.
Office Action dated Oct. 12, 2016 for U.S. Appl. No. 14/320,479.
Office Action dated Feb. 22, 2017 for U.S. Appl. No. 14/497,070.
Response to Office Action filed on Jan. 12, 2017 in U.S. Appl. No. 14/320,479.
Notice of Allowance dated Apr. 5, 2017 for U.S. Appl. No. 13/186,228.
Office Action dated Jan. 4, 2016 in U.S. Appl. No. 13/186,228.
Restriction Requirement dated Feb. 23, 2006 in U.S. Appl. No. 11/087,937.
Office Action dated Apr. 27, 2006 in U.S. Appl. No. 11/087,937.
Office Action dated Mar. 1, 2007 in U.S. Appl. No. 11/087,937.
Office Action dated Aug. 23, 2007 in U.S. Appl. No. 11/087,937.
Office Action dated Mar. 25, 2008 in U.S. Appl. No. 11/087,937.
Office Action dated Sep. 26, 2008 in U.S. Appl. No. 11/087,937.
Office Action dated Apr. 30, 2008 in U.S. Appl. No. 11/371,347.
Office Action dated Dec. 3, 2008 in U.S. Appl. No. 11/371,347.
Office Action dated Mar. 26, 2008 in U.S. Appl. No. 11/371,346.
Office Action dated Oct. 16, 2008 in U.S. Appl. No. 11/371,346.
Office Action dated Mar. 20, 2009 in U.S. Appl. No. 11/371,346.
Office Action dated Sep. 29, 2009 in U.S. Appl. No. 11/371,346.
Office Action dated Sep. 21, 2011 in U.S. Appl. No. 12/790,379.
Office Action dated Feb. 8, 2008 in U.S. Appl. No. 11/544,306.
Office Action dated Oct. 15, 2008 in U.S. Appl. No. 11/544,306.
Office Action dated Mar. 19, 2009 in U.S. Appl. No. 11/544,306.
Office Action dated Sep. 2, 2009 in U.S. Appl. No. 11/544,306.
Office Action dated Dec. 24, 2009 in U.S. Appl. No. 11/544,306.
Office Action dated Sep. 19, 2012 in U.S. Appl. No. 12/395,489.
Office Action dated Jul. 2, 2012 in U.S. Appl. No. 13/079,747.
Notice of Allowance dated Apr. 25, 2017 in U.S. Appl. No. 14/320,479.
Notice to File Corrected Application Papers dated May 22, 2017 in U.S. Appl. No. 14/320,479.
Notice Regarding IDS dated May 25, 2017 in U.S. Appl. No. 14/320,479.
Interview Summary dated Jun. 21, 2017 in U.S. Appl. No. 14/320,479.
Interview Summary dated Mar. 29, 2017 in U.S. Appl. No. 14/033,081.
Notice of Allowance dated Jul. 31, 2017 for U.S. Appl. No. 13/186,228.
Notice of Allowance dated Aug. 24, 2017 in U.S. Appl. No. 14/320,479.
Office Action dated Nov. 9, 2018 in U.S. Appl. No. 15/689,786.
Office Action dated Jan. 23, 2019 in U.S. Appl. No. 15/639,100.
Office Action dated Mar. 19, 2019 in U.S. Appl. No. 15/689,786.
Office Action dated Jul. 10, 2019 in U.S. Appl. No. 15/639,100.

(56) References Cited

OTHER PUBLICATIONS

Notice of Allowance dated Sep. 5, 2019 in U.S. Appl. No. 15/639,100.
Advisory Action received in U.S. Appl. No. 11/087,937 dated Jun. 16, 2007 in 8 pages.
Advisory Action received in U.S. Appl. No. 11/087,937 dated Jun. 18, 2008 in 4 pages.
Advisory Action received in U.S. Appl. No. 11/544,306 dated Nov. 18, 2009 in 3 pages.
Advisory Action received in U.S. Appl. No. 12/454,799 dated Jan. 18, 2011 in 6 pages.
Advisory Action received in U.S. Appl. No. 12/454,799 dated Oct. 29, 2014 in 3 pages.
Advisory Action Received Sep. 9, 2014 in U.S. Appl. No. 13/186,315 in 6 pages.
Advisory Action Received Mar. 31, 2016 in U.S. Appl. No. 13/186,228 in 8 pages.
Amendment Received in U.S. Appl. No. 11/544,306 dated Jul. 18, 2008 in 2 pages.
Amendment Received in U.S. Appl. No. 11/544,306 dated Dec. 2, 2009 in 12 pages.
Amendment, RCE, and Response to Final Office Action in U.S. Appl. No. 11/544,306 dated Aug. 25, 2010 in 14 pages.
Amendment and Restriction Requirement filed in U.S. Appl. No. 12/152,893 dated Dec. 18, 2009 in 8 pages.
Amendment accompanying Request for Continued Examination filed in U.S. Appl. No. 12/395,489 dated Jan. 12, 2012 in 9 pages.
Amendment After Allowance (37 C.F.R. §1.312) filed in U.S. Appl. No. 12/395,489 dated Apr. 2, 2013 in 4 pages.
Amendment with Request for Continued Examination filed in U.S. Appl. No. 12/454,799 dated Nov. 25, 2014 in 11 pages.
Amendment with Request for Continued Examination filed in U.S. Appl. No. 13/186,228 dated Apr. 6, 2016 in 17 pages.
Amendment with Request for Continued Examination Filed Apr. 22, 2014 in U.S. Appl. No. 13/186,331 in 11 pages.
Comments on Statement of Reasons for Allowance in U.S. Appl. No. 11/544,306 dated Apr. 22, 2011 in 2 pages.
Comments on Reasons for Notice of Allowance and Summary of Interview filed Jul. 13, 2012 in U.S. Appl. No. 12/454,743 in 4 pages.
Comments in Response to Notice of Allowance Filed Sep. 11, 2019 in U.S. Appl. No. 15/639,100 in 6 pages.
Comments On Statements Of Reasons For Allowance Filed Nov. 17, 2017 in U.S. Appl. No. 14/320,479 in 3 pages.
Comments on Reasons for Allowance Filed Jan. 7, 2015 in U.S. Appl. No. 13/186,315 in 2 pages.
Corrected Notice of Allowability received in U.S. Appl. No. 13/186,315 dated Nov. 12, 2014 in 3 pages.
Comments on Reasons for Allowance Filed Sep. 23, 2014 in U.S. Appl. No. 13/186,331 in 2 pages.
Comments on Reasons for Allowance Filed Oct. 23, 2017 in U.S. Appl. No. 13/186,228 in 3 pages.
Final Amendment Response filed in U.S. Appl. No. 11/087,937 dated May 22, 2008 in 17 pages.
Final Office Amendment Response filed in U.S. Appl. No. 11/371,346 dated Dec. 9, 2009 in 5 pages.
Final Office Action received in U.S. Appl. No. 12/395,489 dated Nov. 25, 2011 in 16 pages.
Final Office Action Amendment Response filed in U.S. Appl. No. 12/454,799 dated Dec. 20, 2010 in 12 pages.
Final Office Action Amendment, RCE and Response filed in U.S. Appl. No. 12/454,799 dated May 23, 2011 in 12 pages.
Final Office Action received in U.S. Appl. No. 12/454,799 dated Aug. 8, 2014 in 11 pages.
Final Office Action Amendment Response filed in U.S. Appl. No. 12/454,799 dated Oct. 17, 2014 in 12 pages.
Final Office Action Amendment, RCE and Response filed in U.S. Appl. No. 12/467,755 dated Dec. 16, 2010 in 14 pages.
Final Office Action Amendment Response filed in U.S. Appl. No. 12/467,755 dated Nov. 25, 2014 in 16 pages.
Final Office Action Accompanying Request for Continued Examination Amendment Response filed in U.S. Appl. No. 12/467,755 dated Aug. 7, 2015 in 22 pages.
Final Office Amendment, RCE and Response filed in U.S. Appl. No. 13/186,228 dated Sep. 27, 2013 in 13 pages.
Final Office Action Amendment Response received in U.S. Appl. No. 13/186,228 dated Jan. 28, 2015 in 15 pages.
Final Office Action and Request Under AFCP 2.0 Amendment Response filed in U.S. Appl. No. 13/186,228 dated Mar. 4, 2016 in 19 pages.
Final Office Action and Request Under AFCP 2.0 Amendment Response filed in U.S. Appl. No. 13/186,228 dated Apr. 6, 2016 in 19 pages.
Final Office Action Amendment Response filed in U.S. Appl. No. 13/186,315 dated Aug. 29, 2014 in 15 pages.
Final Office Action and Request Under AFCP 2.0 Amendment Response filed in U.S. Appl. No. 14/320,479 dated Apr. 7, 2017 in 12 pages.
Final Office Action Amendment Response filed in U.S. Appl. No. 15/639,100 dated Aug. 20, 2019 in 6 pages.
Interview Summary in U.S. Appl. No. 11/087,937 dated Jan. 13, 2009 in 2 pages.
Interview Summary in U.S. Appl. No. 11/544,306 dated Jul. 23, 2010 in 3 pages.
Interview Summary in U.S. Appl. No. 11/544,306 dated Oct. 19, 2010 in 3 pages.
Interview Summary in U.S. Appl. No. 11/544,306 dated Oct. 25, 2010 in 3 pages.
Interview Summary in U.S. Appl. No. 12/040,735 dated Apr. 12, 2011 in 3 pages.
Interview Summary in U.S. Appl. No. 12/040,735 dated Oct. 5, 2011 in 3 pages.
Interview Summary U.S. Appl. No. 12/152,893 dated Jan. 22, 2015 in 3 pages.
Interview Summary received in U.S. Appl. No. 12/395,489 dated Oct. 5, 2011 in 3 pages.
Interview Summary U.S. Appl. No. 12/454,799 dated Oct. 19, 2014 in 3 pages.
Interview Summary U.S. Appl. No. 12/467,755 dated Nov. 29, 2010 In 4 pages.
Interview Summary U.S. Appl. No. 12/467,755 dated Jan. 13, 2015 in 29 pages.
Interview Summary U.S. Appl. No. 12/467,755 dated Jul. 31, 2015 in 3 pages.
Interview Summary U.S. Appl. No. 13/186,228 dated Oct. 2, 2015 in 4 pages.
Interview Summary U.S. Appl. No. 14/320,479 dated Nov. 28, 2011 in 3 pages.
Interview Summary U.S. Appl. No. 14/320,479 dated Jan. 17, 2018 in 2 pages.
Non-Compliant Amendment Response filed in U.S. Appl. No. 12/454,799 dated Mar. 12, 2010 in 9 pages.
Non-Final Amendment Response filed in U.S. Appl. No. 11/087,937 dated May 31, 2007 in 12 pages.
Non-Final Office Amendment Response filed in U.S. Appl. No. 11/087,937 dated Dec. 21, 2007 in 14 pages.
Non-Final Office Amendment Response filed in U.S. Appl. No. 11/087,937 dated Feb. 26, 2009 in 15 pages.
Non-Final Office Amendment Response filed in U.S. Appl. No. 12/611,875 dated Aug. 9, 2011 in 9 pages.
Non-Final Office Action received in U.S. Appl. No. 11/371,347 dated Apr. 13, 2008 in 12 pages.
Non-Final Office Amendment filed in U.S. Appl. No. 11/371,347 dated Jul. 29, 2008 in 10 pages.
Non-Final Office Amendment Response filed in U.S. Appl. No. 11/371,346 dated Jun. 25, 2008 in 9 pages.
Non-Final Office Action Terminal Disclosure Response filled in U.S. Appl. No. 11/371,346 dated Jun. 16, 2009 in 12 pages.
Non-Final Office Amendment Response filed in U.S. Appl. No. 12/790,379 dated Oct. 4, 2011 in 6 pages.
Non-Final Office Amendment Response filled in U.S. Appl. No. 11/544,306 dated May 22, 2008 in 11 pages.

(56) References Cited

OTHER PUBLICATIONS

Non-Final Corrected Office Action filed in U.S. Appl. No. 11/544,306 dated Jul. 24, 2008 in 11 pages.
Non-Final Office Amendment Response filed in U.S. Appl. No. 11/544,306 dated Jan. 15, 2009 in 13 pages.
Non-Final Office Amendment Response received in U.S. Appl. No. 11/544,306 dated Jun. 16, 2009 in 16 pages.
Non-Final Amendment Response filed in U.S. Appl. No. 11/544,306 dated Nov. 2, 2009 in 14 pages.
Non-Final Amendment Response filed in U.S. Appl. No. 11/544,306 dated Apr. 23, 2010 in 10 pages.
Non-Final Amendment Response filed in U.S. Appl. No. 12/040,735 dated May 6, 2011 in 10 pages.
Non-Final Office Action filed in U.S. Appl. No. 12/152,893 dated Aug. 3, 2010 in 13 pages.
Non-Final Office Action Response filed in U.S. Appl. No. 12/152,893 dated Feb. 17, 2015 in 12 pages.
Non-Final Amendment Response filed in U.S. Appl. No. 12/395,489 dated May 16, 2011 in 11 pages.
Non-Final Office Action Amendment Response filed in U.S. Appl. No. 12/395,489 dated Dec. 5, 2012 in 7 pages.
Non-Final Office Action Amendment Response filed in U.S. Appl. No. 12/454,799 dated Jun. 25, 2010 in 9 pages.
Non-Final Office Action Amendment Response filed in U.S. Appl. No. 12/454,799 dated May 23, 2014 in 8 pages.
Non-Final Office Action Amendment Response filed in U.S. Appl. No. 12/454,799 dated Sep. 3, 2015 in 13 pages.
Non-Final Office Action Amendment Response filed in U.S. Appl. No. 12/467,755 dated Feb. 3, 2010 in 7 pages.
Non-Final Office Action Amendment Response filed in U.S. Appl. No. 12/467,755 dated Jun. 30, 2010 in 11 pages.
Non-Final Office Action Amendment Response filed in U.S. Appl. No. 12/467,755 dated Jul. 1, 2010 in 13 pages.
Non-Final Office Amendment Response filed in U.S. Appl. No. 12/467,755 dated Jun. 20, 2014 in 11 pages.
Non-Final Office Action Amendment Response filed in U.S. Appl. No. 12/467,755 dated Apr. 10, 2015 in 18 pages.
Non-Final Office Action Amendment Response filed in U.S. Appl. No. 12/467,755 dated Nov. 23, 2015 in 13 pages.
Non-Final Office Action received in U.S. Appl. No. 12/454,743 dated Aug. 23, 2010 in 9 pages.
Non-Final Office Action Amendment Response filed in U.S. Appl. No. 12/454,743 dated Aug. 10, 2011 in 10 pages.
Non-Final Office Amendment Response filed in U.S. Appl. No. 12/454,743 dated Feb. 14, 2012 in 9 pages.
Non-Final Office Action received in U.S. Appl. No. 13/186,228 dated Nov. 6, 2012 in 6 pages.
Non-Final Office Amendment Response filed in U.S. Appl. No. 13/186,228 dated Apr. 22, 2013 in 10 pages.
Non-Final Office Amendment Response filed in U.S. Appl. No. 13/186,228 dated Aug. 21, 2014 in 15 pages.
Non-Final Office Action Amendment Response filed in U.S. Appl. No. 13/186,228 dated Oct. 7, 2016 in 17 pages.
Non-Final Office Action Amendment Response filed in U.S. Appl. No. 13/186,331 dated Nov. 7, 2013 in 14 pages.
Non-Final Office Action Amendment Response filed in U.S. Appl. No. 13/186,315 dated Nov. 1, 2013 in 13 pages.
Non-Final Office Action Amendment Response filed in U.S. Appl. No. 13/186,315 dated Apr. 25, 2014 in 18 pages.
Non-Final Office Action Amendment Response filed in U.S. Appl. No. 14/320,479 dated May 23, 2016 in 7 pages.
Non-Final Office Amendment Response filed in U.S. Appl. No. 15/639,100 dated Apr. 22, 2019 in 9 pages.
Notice of Allowance received in U.S. Appl. No. 12/040,735 dated Aug. 3, 2012 in 15 pages.
Notice of Allowance received in U.S. Appl. No. 11/087,937 dated Jun. 17, 2009 in 6 pages.
Notice of Allowance received in U.S. Appl. No. 11/087,937 dated Aug. 11, 2009 in 7 pages.
Notice of Allowance received in U.S. Appl. No. 12/611,875 dated Sep. 22, 20011 in 10 pages.
Notice of Allowance received in U.S. Appl. No. 11/371,346 dated Jan. 4, 2009 in 10 pages.
Notice of Allowance received in U.S. Appl. No. 12/790,379 dated Nov. 1, 2011 in 21 pages.
Notice of Allowance received in U.S. Appl. No. 12/395,489 dated Jan. 14, 2013 in 5 pages.
Notice of Allowance received in U.S. Appl. No. 12/454,743 dated Apr. 13, 2012 in 29 pages.
Notice of Allowance dated Jun. 23, 2020 in U.S. Appl. No. 15/689,786.
Notice of Non-Compliant Amendment in U.S. Appl. No. 12/454,799 in 2 pages.
Notice of Non-Compliant Amendment in U.S. Appl. No. 12/454,743 in 5 pages.
Notice to File Corrected Application Papers in U.S. Appl. No. 14/320,479 in 3 pages.
Office Action received in U.S. Appl. No. 11/087,937 dated Mar. 26, 2006 in 9 pages.
Preliminary Amendment and RCE received in U.S. Appl. No. 14/320,479 dated Aug. 14, 2017 in 11 pages.
Request for Continued Examination and Response to Advisory Action filed in U.S. Appl. No. 11/087,937 dated Jun. 24, 2008 in 17 pages.
Request for Continuation filed in U.S. Appl. No. 11/371,346 dated Feb. 17, 2009 in 12 pages.
Request for Continuation filed in U.S. Appl. No. 11/544,306 dated Dec. 2, 2009 in 12 pages.
Request for Continuation filed in U.S. Appl. No. 11/544,306 dated Aug. 25, 2010 in 14 pages.
Request for Continued Examination in U.S. Appl. No. 12/454,799 dated May 23, 2011 in 2 pages.
Response to Rule 312 Communication in U.S. Appl. No. 11/544,306 dated Apr. 13, 2011 in 3 pages.
Response to Final Office Action received in U.S. Appl. No. 12/152,893 dated Jan. 18, 2011 in 9 pages.
Response to Rule 312 Communication in U.S. Appl. No. 12/395,489 dated Jul. 8, 2013 in 2 pages.
Response to Notice to File Corrected Application Papers and Amendment After Notice of Allowance Under 37 C.F.R. 1.312 filed in U.S. Appl. No. 14/320,479 dated Jul. 17, 2017 in 14 pages.
Response to 312 Amendment received in U.S. Appl. No. 14/320,479 dated Aug. 2, 2017 in 2 pages.
Response to Notice to File Corrected Application Papers and Amendment After Notice of AllowanceUnder 37 C.F.R. 1.312 filed in U.S. Appl. No. 14/320,479 dated Oct. 9, 2017 in 4 pages.
Response to Notice of Non-Compliant Amendment Filed on Mar. 12, 2010 in U.S. Appl. No. 12/454,799 in 6 pages.
Response to Restriction Requirement Filed Jul. 19, 2016 in U.S. Appl. No. 14/320,479 in 2 pages.
Restriction Requirement received in U.S. Appl. No. 11/371,347 dated Mar. 19, 2008 in 5 pages.
Restriction Requirement Response filed in U.S. Appl. No. 11/371,347 dated Apr. 9, 2008 in 6 pages.
Restriction Requirement received in U.S. Appl. No. 11/371,346 dated Jan. 24, 2017 in 5 pages.
Restriction Requirement Response filed in U.S. Appl. No. 11/371,346 dated Feb. 18, 2008 in 5 pages.
Restriction Requirement received in U.S. Appl. No. 12/790,379 dated Sep. 21, 2010 in 5 pages.
Restriction Requirement Response filed in U.S. Appl. No. 12/790,379 dated Jan. 11, 2011 in 8 pages.
Restriction Requirement received in U.S. Appl. No. 12/790,379 dated Jun. 13, 2011 in 6 pages.
Restriction Requirement Response filed in U.S. Appl. No. 12/790,379 dated Jul. 12, 2011 in 5 pages.
Restriction Requirement received in U.S. Appl. No. 11/544,306 dated Nov. 14, 2007 in 10 pages.
Restriction Requirement received in U.S. Appl. No. 11/544,306 dated Dec. 12, 2007 in 4 pages.
Amendment accompanying Request for Continued Examination filed in U.S. Appl. No. 12/040,735 dated Jan. 12, 2012 in 10 pages.

(56) References Cited

OTHER PUBLICATIONS

Restriction Requirement received in U.S. Appl. No. 12/040,735 dated Apr. 13, 2010 in 11 pages.
Restriction Requirement Response filed in U.S. Appl. No. 12/040,735 dated May 13, 2010 in 6 pages.
Restriction Requirement received in U.S. Appl. No. 12/040,735 dated Aug. 2, 2010 in 6 pages.
Restriction Requirement Response filed in U.S. Appl. No. 12/040,735 dated Aug. 17, 2010 in 6 pages.
Restriction Requirement received in U.S. Appl. No. 12/152,893 dated Nov. 20, 2009 in 10 pages.
Restriction Requirement received in U.S. Appl. No. 12/395,489 dated Sep. 24, 2010 in 8 pages.
Restriction Requirement Response filed in U.S. Appl. No. 12/395,489 dated Oct. 22, 2010 in 6 pages.
Restriction Requirement received in U.S. Appl. No. 12/454,799 dated Feb. 8, 2010 in 6 pages.
Restriction Requirement Response filed in U.S. Appl. No. 12/454,799 dated Feb. 2, 2010 in 7 pages.
Restriction Requirement Response filed in U.S. Appl. No. 12/467,755 dated Feb. 25, 2010 in 2 pages.
Restriction Requirement Response filed in U.S. Appl. No. 12/454,743 dated Sep. 23, 2010 in 9 pages.
Restriction Requirement Response filed in U.S. Appl. No. 12/454,743 dated Jan. 1, 2011 in 11 pages.
Restriction Requirement Response filed in U.S. Appl. No. 13/186,228 dated Dec. 5, 2012 in 1 page.
Restriction Requirement received in U.S. Appl. No. 15/639,100 dated Sep. 27, 2018 in 6 pages.
Restriction Requirement received in U.S. Appl. No. 15/639,100 dated Oct. 15, 2018 in 3 pages.
Restriction Requirement Received May 23, 2016 in U.S. Appl. No. 14/320,479 in 7 pages.
Summary of interview Filed Jan. 7, 2015 in U.S. Appl. No. 13/186,315 in 3 pages.
Summary of interview Filed Feb. 6, 2017 in U.S. Appl. No. 13/186,228 in 2 pages.
Supplemental Amendment received filed in U.S. Appl. No. 12/467,755 dated Aug. 26, 2015 in 4 pages.
Restriction Requirement received in U.S. Appl. No. 16/005,445 dated Mar. 8, 2021 in 7 pages.
Office Action received in U.S. Appl. No. 16/569,510 dated Sep. 9, 2020 in 47 pages.
Final Office Action received in U.S. Appl. No. 16/569,510 dated Feb. 23, 2021 in 8 pages.
Notice of Allowance received in U.S. Appl. No. 16/569,510 dated May 7, 2021 in 7 pages.

* cited by examiner

Standard guide RNA (gRNA) logic and function gRNA structure and interactions

Conditional guide RNA (cgRNA) ON→OFF logic and function

Conditional guide RNA (cgRNA) OFF→ON logic and function

Cell-selective spatiotemporal control of gene silencing

Cell-selective spatiotemporal regulatory control

Independent diagnosis and treatment

"If X then regulate Y"
treat diseased cells leaving healthy cells untouched
(cancer, autoimmune, microbiome, infectious disease,...)

Allosteric ON→OFF terminator switch cgRNA (Mechanism 1A)

Mechanism 1A: Schematic

Allosteric OFF→ON terminator switch cgRNA (Mechanism 1B)

Mechanism 1B: Annotated Schematic

Allosteric ON→OFF splinted switch cgRNA (Mechanism 2A)

Mechanism 2A: Schematic

Allosteric OFF→ON splinted switch cgRNA (Mechanism 2B)

Mechanism 2B: Schematic

OFF State

ON State trigger:inhibitor

Allosteric OFF→ON split-terminator switch cgRNA (Mechanism 4A)

Mechanism 4A: Schematic

Mechanism 4A: Annotated Schematic

OFF State

ON State

**Allosteric ON→OFF split-terminator switch cgRNA
(Mechanisms 4B and 4C)**

---

Mechanism 4B: Schematic

Mechanism 4C: Annotated Schematic

Interactions for allosteric ON→OFF terminator switch cgRNA

ON State
(absence of trigger X)

In the absence of trigger X, the cgRNA mediates Cas activity on target gene Y

OFF State
(presence of trigger X)

cgRNA:trigger
complex

Trigger X inactivates the cgRNA

Interactions for allosteric ON→OFF splinted switch cgRNA

ON State
(absence of trigger X)

In the absence of trigger X, the cgRNA mediates Cas activity on target gene Y

OFF State
(presence of trigger X)

Trigger X inactivates the cgRNA

Interactions for allosteric OFF→ON split-terminator switch cgRNA

OFF State
(absence of Trigger X)

cgRNA

In the absence of trigger X, the cgRNA is inactive

ON State
(presence of Trigger X)

cgRNA     trigger X     Cas9         target gene Y
                        or dCas9
                        or Cas cgRNA:trigger:Cas:target complex Trigger X activates the cgRNA to mediate Cas activity on target gene Y

Allosteric ON→OFF terminator switch cgRNA

| cgRNAs | Sequence |
|---|---|
| cgRNA A | 5'-aactttcagtttagcggtctGTTTTAGAGCTAGAAATAGCA AGTTAAAATAAGGCTAGTCCGATCAAACGGGTAAACAAACAGGA TAATTAAGGAGGCAGTACCCGGGCACCGAGTCGGTGCTTTTTT-3' (SEQ ID NO: 1) |
| cgRNA B | 5'-aactttcagtttagcggtctGTTTTAGAGCTAGAAATAGCA AGTTAAAATAAGGCTAGTCCGTATCATGGGGTTGTGTGTTGTTG TAAGTGTGTGTGTTGCCCCGGCACCGAGTCGGTGCTTTTTT-3' (SEQ ID NO: 2) |
| cgRNA C | 5'-aactttcagtttagcggtctGTTTTAGAGCTAGAAATAGCA AGTTAAAATAAGGCTAGTCCGAATATAGGGGAAGAGAAAGAAGA AGAGAAGAGAAAGATGTCCCCGGCACCGAGTCGGTGCTTTTTT-3' (SEQ ID NO: 3) |
| Triggers | |
| Trigger X$_A$ | 5'-TACTGCCTCCTTAATTATCCTGTTTGTTTACCCGTTTGAT-3' (SEQ ID NO: 4) |
| Trigger X$_B$ | 5'-CAACACACACACACTTACAACAACACACAACCCCATGATA-3' (SEQ ID NO: 5) |
| Trigger X$_C$ | 5'-ACATCTTTCTCTTCTCTTCTTCTTTCTCTTCCCCTATATT-3' (SEQ ID NO: 6) |

FIG. 11F

Allosteric ON→OFF splinted switch cgRNA

| cgRNAs | Sequence |
|---|---|
| cgRNA A | 5'-catctaattcaacaagaattGTTTTAGAGCTACACCTTACG CCGGTTCAATTCCAAGTCCCTTCCAGTAGCAAGTTAAAATAAGG CTAGTCCGTTATCAACTTAACACCCTTTACAAACCTTCCTCTTC CTTTACCCTAAGTGGCACCGAGTCGGTGCTTTTTTT-3' (SEQ ID NO: 7) |
| cgRNA B | 5'-catctaattcaacaagaattGTTTTAGAGCTAGTAATCGAA TCATAGTAAATTTCCCATCGTCATAATAGCAAGTTAAAATAAGG CTAGTCCGTTATCAACTTCATACGGGTCTGAAGTAGTTCATTCT TATACAGTCAAGTGGCACCGAGTCGGTGCTTTTTTT-3' (SEQ ID NO: 8) |
| cgRNA C | 5'-catctaattcaacaagaattGTTTTAGAGCTAGTCGTTACC TTATCAATATCAACCTCCGCATACACTAGCAAGTTAAAATAAGG CTAGTCCGTTATCAACTTGCACATAGGACCCAACATGCCAACAG AGAAGAGTTAAGTGGCACCGAGTCGGTGCTTTTTTT-3' (SEQ ID NO: 9) |
| Triggers | |
| Trigger X$_A$ | 5'-AGGGTAAAGGAAGAGGAAGGTTTGTAAAGGGTGTTCTGGAA GGGACTTGGAATTGAACCGGCGTAAGGTG-3' (SEQ ID NO: 10) |
| Trigger X$_B$ | 5'-GACTGTATAAGAATGAACTACTTCAGACCCGTATGTTATGA CGATGGGAAATTTACTATGATTCGATTAC-3' (SEQ ID NO: 11) |
| Trigger X$_C$ | 5'-AACTCTTCTCTGTTGGCATGTTGGGTCCTATGTGCGTGTAT GCGGAGGTTGATATTGATAAGGTAACGAC-3' (SEQ ID NO: 12) |

FIG. 12F

Allosteric ON→OFF terminator switch cgRNA

ON→OFF logic
"if not X then Y"

| cgRNAs | Sequence |
|---|---|
| cgRNA Q | 5'-gagtcgcgtgtagcgaagcaGTTTAAGAGCTAGAAATAGCA AGTTAAAATAAGGCTAGTCCGATCTTTGCGCGTTAGTTTCGTTC GTATTTCTGTCATGTTTGCGCGGCACCGAGTCGGTGCtttttttt-3' (SEQ ID NO: 13) |
| cgRNA R | 5'-gagtcgcgtgtagcgaagcaGTTTAAGAGCTAGAAATAGCA AGTTAAAATAAGGCTAGTCCGTATCGCCGGGTTCAAGCAGATGT GGCATTTCAGTGTAGTTCCCGGGCACCGAGTCGGTGCtttttttt-3' (SEQ ID NO: 14) |
| cgRNA S | 5'-gagtcgcgtgtagcgaagcaGTTTAAGAGCTAGAAATAGCA AGTTAAAATAAGGCTAGTCCGTCCATTCGGGTTTACTATTACAA TCTTACGTGTTCTCATTCCCGGGCACCGAGTCGGTGCtttttttt-3' (SEQ ID NO: 15) |
| cgRNA T | 5'-gagtcgcgtgtagcgaagcaGTTTAAGAGCTAGAAATAGCA AGTTAAAATAAGGCTAGTCCGGATAAAGGGAAAGATGAAGTGAT GTGAAGATAGAGTTGGATCCCGGCACCGAGTCGGTGCtttttttt-3' (SEQ ID NO: 16) |
| Triggers | |
| Trigger X$_Q$ | 5'-AGTCAGGCCACTTGTGCCACGGTTTGAGCAAACCGTGCTGC CTGTAGCTCCGCCAATAATGGGAGGCGTAAACATGACAGAAATA CGAACGAAACTAACGCGCAAAGATCtttttttt-3' (SEQ ID NO: 17) |
| Trigger X$_R$ | 5'-AGTCAGGCCACTTGTGCCACGGTTTGAGCAAACCGTGCTGC CTGTAGCTCCGCCAATAATGGGAGGCGTAACTACACTGAAATGC CACATCTGCTTGAACCCGGCGATACtttttttt-3' (SEQ ID NO: 18) |
| Trigger X$_S$ | 5'-AGTCAGGCCACTTGTGCCACGGTTTGAGCAAACCGTGCTGC CTGTAGCTCCGCCAATAATGGGAGGCGTAATGAGAACACGTAAG ATTGTAATAGTAAACCCGAATGGACtttttttt-3' (SEQ ID NO: 19) |
| Trigger X$_T$ | 5'-AGTCAGGCCACTTGTGCCACGGTTTGAGCAAACCGTGCTGC CTGTAGCTCCGCCAATAATGGGAGGCGTTCCAACTCTATCTTCA CATCACTTCATCTTTCCCTTTATCCtttttttt-3' (SEQ ID NO: 20) |

FIG. 13H

| Trigger X_Q | |
|---|---|
| 40 nt | 5'-AGTCAGGCCACTTGTGCCACGGTTTGAGCAAACCGTGCTGCCT GTAGCTCCGCCAATAATGGGAGGCGT*AAACATGACAGAAATACGAA CGAAACTAACGCGCAAAGAT*Ctttttttt-3' (SEQ ID NO: 21) |
| 50 nt Triggers | |
| Center | 5'-AGTCAGGCCACTTGTGCCACGGTTTGAGCAAACCGTGCTGCCT GTAGCTCCGCCAATAATGGGAGGCGT*GCCGAAAACATGACAGAAAT ACGAACGAAACTAACGCGCAAAGATTCCAG*Ctttttttt-3' (SEQ ID NO: 22) |
| 40 nt X_Q at 3' | 5'-AGTCAGGCCACTTGTGCCACGGTTTGAGCAAACCGTGCTGCCT GTAGCTCCGCCAATAATGGGAGGCGT*GCCGATCCAGAAACATGACA GAAATACGAACGAAACTAACGCGCAAAGAT*Ctttttttt-3' (SEQ ID NO: 23) |
| 40 nt X_Q at 5' | 5'-AGTCAGGCCACTTGTGCCACGGTTTGAGCAAACCGTGCTGCCT GTAGCTCCGCCAATAATGGGAGGCGT*AAACATGACAGAAATACGAA CGAAACTAACGCGCAAAGATGCCGATCCAG*Ctttttttt-3' (SEQ ID NO: 24) |
| 70 nt Triggers | |
| Center | 5'-AGTCAGGCCACTTGTGCCACGGTTTGAGCAAACCGTGCTGCCT GTAGCTCCGCCAATAATGGGAGGCGT*GCCGAGCCGAGCCGAAAACA TGACAGAAATACGAACGAAACTAACGCGCAAAGATGCCGAGCCGAT CCAG*Ctttttttt-3' (SEQ ID NO: 25) |
| 40 nt X_Q at 3' | 5'-AGTCAGGCCACTTGTGCCACGGTTTGAGCAAACCGTGCTGCCT GTAGCTCCGCCAATAATGGGAGGCGT*GCCGATCCAGGCCGATCCAG GCCGATCCAGAAACATGACAGAAATACGAACGAAACTAACGCGCAA AGAT*Ctttttttt-3' (SEQ ID NO: 26) |
| 40 nt X_Q at 5' | 5'-AGTCAGGCCACTTGTGCCACGGTTTGAGCAAACCGTGCTGCCT GTAGCTCCGCCAATAATGGGAGGCGT*AAACATGACAGAAATACGAA CGAAACTAACGCGCAAAGATGCCGATCCAGGCCGATCCAGGCCGAT CCAG*Ctttttttt-3' (SEQ ID NO: 27) |
| 100 nt Triggers | |
| Center | 5'-AGTCAGGCCACTTGTGCCACGGTTTGAGCAAACCGTGCTGCCT GTAGCTCCGCCAATAATGGGAGGCGT*GCCGATCCAGGCCGATCCAG GCCGATCCAGAAACATGACAGAAATACGAACGAAACTAACGCGCAA AGATGCCGATCCAGGCCGATCCAGGCCGATCCAG*Ctttttttt-3' (SEQ ID NO: 28) |

FIG. 13J

| 100 nt Triggers | |
|---|---|
| 40 nt X$_Q$ at 3' | 5'-AGTCAGGCCACTTGTGCCACGGTTTGAGCAAACCGTGCTGCCT GTAGCTCCGCCAATAATGGGAGGCGT*GCCGATCCAGGCCGATCCAG GCCGATCCAGGCCGATCCAGGCCGATCCAGGCCGATCCAG<u>AAACAT GACAGAAATACGAACGAAACTAACGCGCAAAGAT</u>*Ctttttttt-3' (SEQ ID NO: 29) |
| 40 nt X$_Q$ at 5' | 5'-AGTCAGGCCACTTGTGCCACGGTTTGAGCAAACCGTGCTGCCT GTAGCTCCGCCAATAATGGGAGGCGT<u>*AAACATGACAGAAATACGAA CGAAACTAACGCGCAAAGAT*</u>*GCCGATCCAGGCCGATCCAGGCCGAT CCAGGCCGATCCAGGCCGATCCAGGCCGATCCAG*Ctttttttt-3' (SEQ ID NO: 30) |
| 150 nt Triggers | |
| Center | 5'-AGTCAGGCCACTTGTGCCACGGTTTGAGCAAACCGTGCTGCCT GTAGCTCCGCCAATAATGGGAGGCGT*GCCGATCCAGGCCGATCCAG GCCGAGCCGATCCAGGCCGATCCAGGCCGATCCAG<u>AAACATGACAG AAATACGAACGAAACTAACGCGCAAAGAT</u>GCCGATCCAGGCCGATC CAGGCCGAGCCGATCCAGGCCGATCCAGGCCGATCCAG*Cttttttt -3' (SEQ ID NO: 31) |
| 40 nt X$_Q$ at 3' | 5'-AGTCAGGCCACTTGTGCCACGGTTTGAGCAAACCGTGCTGCCT GTAGCTCCGCCAATAATGGGAGGCGT*GCCGATCCAGGCCGATCCAG GCCGATCCAGGCCGATCCAGGCCGATCCAGGCCGATCCAGGCCGAT CCAGGCCGATCCAGGCCGATCCAGGCCGATCCAGGCCGATCCAG<u>AA ACATGACAGAAATACGAACGAAACTAACGCGCAAAGAT</u>*Cttttttt -3' (SEQ ID NO: 32) |
| 40 nt X$_Q$ at 5' | 5'-AGTCAGGCCACTTGTGCCACGGTTTGAGCAAACCGTGCTGCCT GTAGCTCCGCCAATAATGGGAGGCGT<u>*AAACATGACAGAAATACGAA CGAAACTAACGCGCAAAGAT*</u>*GCCGATCCAGGCCGATCCAGGCCGAT CCAGGCCGATCCAGGCCGATCCAGGCCGATCCAGGCCGATCCAGGC CGATCCAGGCCGATCCAGGCCGATCCAGGCCGATCCAG*Cttttttt -3' (SEQ ID NO: 33) |

FIG. 13J (CONTINUED)

Allosteric OFF→ON terminator switch cgRNA

OFF→ON logic
"if X then Y"

······ No-target gRNA (Ideal OFF state)
--- cgRNA (OFF state)
····· cgRNA + trigger (ON state)
— Standard gRNA (Ideal ON state)

| cgRNAs | Sequence |
|---|---|
| cgRNA M | 5'-gagtcgcgtgtagcgaagcaGTTTAAGAGCTATGCTGGAAACAGCATAGCAAGTTTAAATAAGGCTAGTCCGTTATCA*GCACC*ttttttt-3' (SEQ ID NO: 34) |
| cgRNA N | 5'-gagtcgcgtgtagcgaagcaGTTTAAGAGCTATGCTGGAAACAGCATAGCAAGTTTAAATAAGGCTAGTCCGTTATCA*GGCCC*ttttttt-3' (SEQ ID NO: 35) |
| cgRNA O | 5'-gagtcgcgtgtagcgaagcaGTTTAAGAGCTATGCTGGAAACAGCATAGCAAGTTTAAATAAGGCTAGTCCGTTATCA*CCCAC*ttttttt-3' (SEQ ID NO: 36) |
| Triggers | |
| Trigger X$_M$ | 5'-*GTGC*GGCACCGAGTCGGTGCttttttt-3' (SEQ ID NO: 37) |
| Trigger X$_N$ | 5'-*GGCC*GGCACCGAGTCGGTGCttttttt-3' (SEQ ID NO: 38) |
| Trigger X$_O$ | 5'-*TGGG*GGCACCGAGTCGGTGCttttttt-3' (SEQ ID NO: 39) |

FIG. 14H

| cgRNAs | Sequence |
|---|---|
| cgRNA M | 5'-gagtcgcgtgtagcgaagcaGTTTAAGAGCTATGCTGGAAA CAGCATAGCAAGTTTAAATAAGGCTAGTCCGTTATCA*GCACATC CCAC*tttttttt-3' (SEQ ID NO: 40) |
| cgRNA N | 5'-gagtcgcgtgtagcgaagcaGTTTAAGAGCTATGCTGGAAA CAGCATAGCAAGTTTAAATAAGGCTAGTCCGTTATCA*GGCCAGG TTCC*tttttttt-3' (SEQ ID NO: 41) |
| cgRNA O | 5'-gagtcgcgtgtagcgaagcaGTTTAAGAGCTATGCTGGAAA CAGCATAGCAAGTTTAAATAAGGCTAGTCCGTTATCA*CCCAGAA CACC*tttttttt-3' (SEQ ID NO: 42) |
| Triggers | |
| Trigger X$_M$ | 5'-AGTCAGGCCACTTGTGCCACGGTTTGAGCAAACCGTGCTGC CTGTAGCTCCGCCAATAATGGGAGGCGT*TGGGATGTGC*GCTACC GAGTCGGTGCtttttttt-3' (SEQ ID NO: 43) |
| Trigger X$_N$ | 5'-AGTCAGGCCACTTGTGCCACGGTTTGAGCAAACCGTGCTGC CTGTAGCTCCGCCAATAATGGGAGGCGT*GAACCTGGCC*GCTACC GAGTCGGTGCtttttttt-3' (SEQ ID NO: 44) |
| Trigger X$_O$ | 5'-AGTCAGGCCACTTGTGCCACGGTTTGAGCAAACCGTGCTGC CTGTAGCTCCGCCAATAATGGGAGGCGT*GTGTTCTGGG*GCTACC GAGTCGGTGCtttttttt-3' (SEQ ID NO: 45) |

FIG. 15H

Allosteric OFF→ON terminator switch cgRNAs
with different terminator duplex lengths

|d| ∈ {4, 6, 8, 10} nt

|d| ∈ {10, 20, 30, 40} nt

| cgRNAs and Triggers with |d| = 10 nt | |
|---|---|
| cgRNAs | Sequence |
| cgRNA M | 5'-gagtcgcgtgtagcgaagca GTTAAGAGCTATGCTGGAAA CAGCATAGCAAGTTTAAATAAGGCTAGTCCGTTATCA GCACATC CCActtttttt-3' (SEQ ID NO: 46) |
| cgRNA N | 5'-gagtcgcgtgtagcgaagca GTTAAGAGCTATGCTGGAAA CAGCATAGCAAGTTTAAATAAGGCTAGTCCGTTATCA GGCCAGG TTCCttttttt-3' (SEQ ID NO: 47) |
| cgRNA O | 5'-gagtcgcgtgtagcgaagca GTTAAGAGCTATGCTGGAAA CAGCATAGCAAGTTTAAATAAGGCTAGTCCGTTATCA CCCAGAA CACCttttttt-3' (SEQ ID NO: 48) |
| Triggers | |
| Trigger X$_M$ | 5'-AGTCAGGCCACTTGTGCCACGGTTTGAGCAAACCGTGCTGC CTGTAGCTCCGCCAATAATGGGAGGCGT TGGATGTGC TGCTTCGCTACACGCGACTC ttttttt-3' (SEQ ID NO: 49) |
| Trigger X$_N$ | 5'-AGTCAGGCCACTTGTGCCACGGTTTGAGCAAACCGTGCTGC CTGTAGCTCCGCCAATAATGGGAGGCGT GAACCTGGCC TGCTTCGCTACACGCGACTC ttttttt-3' (SEQ ID NO: 50) |
| Trigger X$_O$ | 5'-AGTCAGGCCACTTGTGCCACGGTTTGAGCAAACCGTGCTGC CTGTAGCTCCGCCAATAATGGGAGGCGT GTGTTCTGGG TGCTTCGCTACACGCGACTC ttttttt-3' (SEQ ID NO: 51) |
| cgRNAs and Triggers with |d| = 8 nt | |
| cgRNAs | Sequence |
| cgRNA M | 5'-gagtcgcgtgtagcgaagca GTTAAGAGCTATGCTGGAAA CAGCATAGCAAGTTTAAATAAGGCTAGTCCGTTATCA GCACATC CCttttttt-3' (SEQ ID NO: 52) |
| cgRNA N | 5'-gagtcgcgtgtagcgaagca GTTAAGAGCTATGCTGGAAA CAGCATAGCAAGTTTAAATAAGGCTAGTCCGTTATCA GGCCAGG TCttttttt-3' (SEQ ID NO: 53) |
| cgRNA O | 5'-gagtcgcgtgtagcgaagca GTTAAGAGCTATGCTGGAAA CAGCATAGCAAGTTTAAATAAGGCTAGTCCGTTATCA CCCAGAA CCttttttt-3' (SEQ ID NO: 54) |
| Triggers | |
| Trigger X$_M$ | 5'-AGTCAGGCCACTTGTGCCACGGTTTGAGCAAACCGTGCTGC CTGTAGCTCCGCCAATAATGGGAGGCGT GGATGTGC TGCTTCGCTACACGCGACTC ttttttt-3' (SEQ ID NO: 55) |
| Trigger X$_N$ | 5'-AGTCAGGCCACTTGTGCCACGGTTTGAGCAAACCGTGCTGC CTGTAGCTCCGCCAATAATGGGAGGCGT ACCTGGCC TGCTTCGCTACACGCGACTC ttttttt-3' (SEQ ID NO: 56) |
| Trigger X$_O$ | 5'-AGTCAGGCCACTTGTGCCACGGTTTGAGCAAACCGTGCTGC CTGTAGCTCCGCCAATAATGGGAGGCGT GTTCTGGG TGCTTCGCTACACGCGACTC ttttttt-3' (SEQ ID NO: 57) |
| cgRNAs and Triggers with |d| = 6 nt | |
| cgRNAs | Sequence |
| cgRNA M | 5'-gagtcgcgtgtagcgaagca GTTAAGAGCTATGCTGGAAA CAGCATAGCAAGTTTAAATAAGGCTAGTCCGTTATCA GCACATC tttttt-3' (SEQ ID NO: 58) |
| cgRNA N | 5'-gagtcgcgtgtagcgaagca GTTAAGAGCTATGCTGGAAA CAGCATAGCAAGTTTAAATAAGGCTAGTCCGTTATCA GGCCAGC tttttt-3' (SEQ ID NO: 59) |
| cgRNA O | 5'-gagtcgcgtgtagcgaagca GTTAAGAGCTATGCTGGAAA CAGCATAGCAAGTTTAAATAAGGCTAGTCCGTTATCA CCCAGAC tttttt-3' (SEQ ID NO: 60) |
| Triggers | |
| Trigger X$_M$ | 5'-AGTCAGGCCACTTGTGCCACGGTTTGAGCAAACCGTGCTGC CTGTAGCTCCGCCAATAATGGGAGGCGT ATGTGC TGCTTCGCTACACGCGACT ttttttt-3' (SEQ ID NO: 61) |
| Trigger X$_N$ | 5'-AGTCAGGCCACTTGTGCCACGGTTTGAGCAAACCGTGCTGC CTGTAGCTCCGCCAATAATGGGAGGCGT CTGGCC TGCTTCGCTACACGCGACT ttttttt-3' (SEQ ID NO: 62) |
| Trigger X$_O$ | 5'-AGTCAGGCCACTTGTGCCACGGTTTGAGCAAACCGTGCTGC CTGTAGCTCCGCCAATAATGGGAGGCGT TCTGGG TGCTTCGCTACACGCGACT ttttttt-3' (SEQ ID NO: 63) |

FIG. 16D

| cgRNAs with \|dl\| = {40, 30, 20, 10} nt | Sequence |
|---|---|
| cgRNA 40 | 5'-agtcgcgtgtagcgaagcaGTTTAAGAGCTATGCTGGAAAC AGCATAGCAAGTTTAAATAAGGCTAGTCCGTTATCA*CATATCCC ATCCACCTCCACCTCCACATTCCCAC*ctttttttt-3' (SEQ ID NO: 64) |
| cgRNA 30 | 5'-agtcgcgtgtagcgaagcaGTTTAAGAGCTATGCTGGAAAC AGCATAGCAAGTTTAAATAAGGCTAGTCCGTTATCA*CATATCCC ATCCACCTCCACCTCCACCTCCC*ttttttt-3' (SEQ ID NO: 65) |
| cgRNA 20 | 5'-agtcgcgtgtagcgaagcaGTTTAAGAGCTATGCTGGAAAC AGCATAGCAAGTTTAAATAAGGCTAGTCCGTTATCA*CATATCCC ATCCACCTCCACC*ttttttt-3' (SEQ ID NO: 66) |
| cgRNA 10 | 5'-agtcgcgtgtagcgaagcaGTTTAAGAGCTATGCTGGAAAC AGCATAGCAAGTTTAAATAAGGCTAGTCCGTTATCA*CATATCCC ATC*ttttttt-3' (SEQ ID NO: 67) |
| Triggers with \|dl\| = {40, 30, 20, 10} nt | |
| Trigger $X_{40}$ | 5'-AGTCAGGCCACTTGTGCCACGGTTTGAGCAAACCGTGCTGC CTGTAGCTCCGCCAATAATGGGAGGCGT*GTGGGAATGTGGAGGT GGAGGTGGAGGTGGATGGGATATG*GGCACCGAGTCGGTGCtttt ttt-3' (SEQ ID NO: 68) |
| Trigger $X_{30}$ | 5'-AGTCAGGCCACTTGTGCCACGGTTTGAGCAAACCGTGCTGC CTGTAGCTCCGCCAATAATGGGAGGCGT*GGAGGTGGAGGTGGAG GTGGATGGGATATG*GGCACCGAGTCGGTGCttttttt-3' (SEQ ID NO: 69) |
| Trigger $X_{20}$ | 5'-AGTCAGGCCACTTGTGCCACGGTTTGAGCAAACCGTGCTGC CTGTAGCTCCGCCAATAATGGGAGGCGT*GTGGAGGTGGATGGGA TATG*GGCACCGAGTCGGTGCttttttt-3' (SEQ ID NO: 70) |
| Trigger $X_{10}$ | 5'-AGTCAGGCCACTTGTGCCACGGTTTGAGCAAACCGTGCTGC CTGTAGCTCCGCCAATAATGGGAGGCGTA*TGGGATATG*GGCACC GAGTCGGTGCttttttt-3' (SEQ ID NO: 71) |

FIG. 16E

| gRNAs | Sequence |
|---|---|
| Standard gRNA | 5'-gagtcgcgtgtagcgaagcaGTTTTAGAGCTAGAAATAGCAAGTTAAAATAAGGCTAGTCCGTTATCAACTTGAAAAAGTGGCACCGAGTCGGTGCtttttttt-3' (SEQ ID NO: 72) |
| No-target gRNA | 5'-GTTTTAGAGCTAGAAATAGCAAGTTAAAATAAGGCTAGTCCGTTATCAACTTGAAAAAGTGGCACCGAGTCGGTGCtttttttt-3' (SEQ ID NO: 73) |
| 8 nt deletion | 5'-gagtcgcgtgtagcgaagcaGTTTTAGAGCTAGAAATAGCAAGTTAAAATAAGGCTAGTCCGTTATCAACTTGAAAAAGTGGCACCGCtttttttt-3' (SEQ ID NO: 74) |
| 23 nt deletion | 5'-gagtcgcgtgtagcgaagcaGTTTTAGAGCTAGAAATAGCAAGTTAAAATAAGGCTAGTCCGTTATCAACTTCtttttttt-3' (SEQ ID NO: 75) |
| 32 nt deletion | 5'-gagtcgcgtgtagcgaagcaGTTTTAGAGCTAGAAATAGCAAGTTAAAATAAGGCTAGTCCGTCtttttttt-3' (SEQ ID NO: 76) |
| 45 nt deletion | 5'-gagtcgcgtgtagcgaagcaGTTTTAGAGCTAGAAATAGCAAGTTAAAATCtttttttt-3' (SEQ ID NO: 77) |

FIG. 17C

Allosteric ON→OFF terminator switch cgRNA with mRNA trigger

| cgRNAs | Sequence |
|---|---|
| cgRNA A | 5'-aactttcagtttagcggtctGTTTTAGAGCTAGAAATAGCA AGTTAAAATAAGGCTAGTCCGATCAAACGGGTAAACAAACAGGA TAATTAAGGAGGCAGTACCCGGCCACCGAGTCGGTGCTTTTTT-3' (SEQ ID NO: 78) |
| cgRNA E | 5'-aactttcagtttagcggtctGTTTTAGAGCTAGAAATAGCA AGTTAAAATAAGGCTAGTCCGACACAAGGGGAAATTAACAACAC AACACACACAACACAGGCCCCGCCACCGAGTCGGTGCTTTTTT-3' (SEQ ID NO: 79) |
| Triggers | |
| Trigger X<sub>A</sub> | 5'-tggctaaagaaagaggagaaaaggtttatggtagcaggtca tgcctctggcagcccgcattcgggaccgcctctcattcgaatt gcgaacatgaagagatccacctcgccggctcgatccagccgcat ggcgcgcttctggtcgtcagcgaacatgatcatcgcgtcatcca ggccagcgccaacgccgcggaatttctgaatctcggaagcgtac tcggcgttccgctcgccgagatcgacggcgatctgttgatcaag atcctgccgcatctcgatcccaccgccgaaggcatgccggtcgc ggtgcgctgccggatcggcaatccctctacggagtactgcggtc tgatgcatcggcctccggaaggcgggctgatcatcgaactcgaa cgtgccggcccgtcgatcgatctgtcaggcacgctggcgccggc gctggagcggatccgcacggcgggttcactgcgcgcgctgtgcg atgacaccgtgctgctgtttcagcagtgcaccggctacgaccgg gtgatggtgtatcgtttcgatgagcaaggccacggcctggtatt ctccgagtgccatgtgcctgggctcgaatcctatttcggcaacc gctatccgtcgtcgactgtcccgcagatggcgcggcagctgtac gtgcggcagcgcgtccgcgtgctggtcgacgtcacctatcagcc ggtgccgctggagccgcggctgtcgccgctgaccgggcgcgatc tcgacatgtcgggctgcttcctgcgctcgatgtcgccgtgccat ctgcagttcctgaaggacatgggcgtgcgcgccaccctggcggt gtcgctggtggtcggcggcaagctgtggggcctggttgtctgtc accattatctgccgcgcttcatccgtttcgagctgcgggcgatc tgcaaacggctcgccgaaaggatcgcgacgcggatcaccgcgct tgagagcgaattcggtggtggtggttctggtggtggtggttcta tgagtgtcaacttagcttcccagttgcgggaagggacgaaaaaa tcccactccatggcggagaacgtcggctttgtcaaatgcttcct caagggcgttgtcgagaaaaattcctaccgtaagctggttggca atctctactttgtctacagtgccatggaagaggaaatggcaaaa tttaaggaccatcccatcctcagccacatttacttccccgaact caaccgcaaacaaagcctagagcaagacctgcaattctattacg gctccaactggcggcaagaagtgaaaatttctgccgctggccaa gcctatgtggaccgagtccggcaagtggccgctacggccccctga attgttggtggcccattcctacacccgttacctggggatctttt ccggcggtcaaattctcaagaaaattgcccaaaatgccatgaat ctccacgatggtggcacagctttctatgaatttgccgacattga tgacgaaaaggcttttaaaaatacctaccgtcaagctatgaatg atctgcccattgaccaagccaccgccgaacggattgtggatgaa gccaatgacgcctttgccatgaacatgaaaatgttcaacgaact gaaggcaacctgatcaaggcgatcggcattatggtgttcaaca gcctcacccgtcgccgcagtcaaggcagcaccgaagttggcctc gccacctccgaaggctagtaaacgtcgactctcgagtgagattg ttgacggtaccgtattttTACTGCCTCCTTAATTATCCTGTTTG TTTACCCGTTTGATcgcaaaaaacccgcttcggcggggttttt tcgc-3' (SEQ ID NO: 80) |

FIG. 18E

| | |
|---|---|
| Trigger X$_E$ | 5'-tggctaaagaaagaggagaaaaggtttatggtagcaggtca tgcctctggcagcccgcattcgggaccgcctctcattcgaatt gcgaacatgaagagatccacctcgccggctcgatccagccgcat ggcgcgcttctggtcgtcagcgaacatgatcatcgcgtcatcca ggccagcgccaacgcgcggaatttctgaatctcggaagcgtac tcggcgttccgctcgccgagatcgacggcgatctgttgatcaag atcctgccgcatctcgatcccaccgccgaaggcatgccggtcgc ggtgcgctgccggatcggcaatccctctacggagtactgcggtc tgatgcatcggcctccggaaggcgggctgatcatcgaactcgaa cgtgccggcccgtcgatcgatctgtcaggcacgctggcgccggc gctggagcggatccgcacggcgggttcactgcgcgcgctgtgcg atgacaccgtgctgctgtttcagcagtgcaccggctacgaccgg gtgatggtgtatcgtttcgatgagcaaggccacggcctggtatt ctccgagtgccatgtgcctgggctcgaatcctatttcggcaacc gctatccgtcgtcgactgtcccgcagatggcgcggcagctgtac gtgcggcagcgcgtccgcgtgctggtcgacgtcacctatcagcc ggtgccgctggagccgcggctgtcgccgctgaccgggcgcgatc tcgacatgtcgggctgcttcctgcgctcgatgtcgccgtgccat ctgcagttcctgaaggacatgggcgtgcgcgccaccctggcggt gtcgctggtggtcggcggcaagctgtggggcctggttgtctgtc accattatctgccgcgcttcatccgtttcgagctgcgggcgatc tgcaaacggctcgccgaaaggatcgcgacgcggatcaccgcgct tgagagcgaattcggtggtggtggttctggtggtggtggttcta tgagtgtcaacttagcttcccagttgcgggaagggacgaaaaaa tcccactccatggcggagaacgtcggctttgtcaaatgcttcct caagggcgttgtcgagaaaaattcctaccgtaagctggttggca atctctactttgtctacagtgccatggaagaggaaatggcaaaa tttaaggaccatcccatcctcagccacatttacttccccgaact caaccgcaaacaaagcctagagcaagacctgcaattctattacg gctccaactggcggcaagaagtgaaaatttctgccgctggccaa gcctatgtggaccgagtccggcaagtggccgctacggccccctga attgttggtggcccattcctacacccgttacctggggatcttt ccggcggtcaaattctcaagaaaattgcccaaaatgccatgaat ctccacgatggtggcacagctttctatgaatttgccgacattga tgacgaaaaggcttttaaaaatacctaccgtcaagctatgaatg atctgcccattgaccaagccaccgccgaacggattgtggatgaa gccaatgacgcctttgccatgaacatgaaaatgttcaacgaact tgaaggcaacctgatcaaggcgatcggcattatggtgttcaaca gcctcacccgtcgccgcagtcaaggcagcaccgaagttggcctc gccacctccgaaggctagtaaacgtcgactctcgagtgagattg ttgacggtaccgtattt*CCTGTGTTGTGTGTTGTGTTGTTA ATTTCCCCTTGTGT*cgcaaaaaacccgcttcggcggggttttt tcgc-3' (SEQ ID NO: 81) |

FIG. 18F

Allosteric ON → OFF terminator switch cgRNA

ON → OFF logic
"if not X then Y"

| cgRNAs | Sequence |
|---|---|
| cgRNA | 5'-gagtcgcgtgtagcgaagcaGTTTTAGAGCTAGAAATAGCAAGTTAAAATAAGGCTAGTCCGTCCATTCGGGTTTACTATTACAATCTTACGTGTTCTCATTCCCGGGCGCCCGAGTCGGGTGCttttttt-3' (SEQ ID NO: 82) |
| Triggers | |
| Non-cognate trigger (X') | 5'-AGTCAGGCCACTTGTGCCACGGTTTGAGCAAACCGTGCTGCCTGTAGCTCCGCCAATAATGGGAGGCGTAAACATGACAGAAATACGAACGAAACTAACGCGCAAAGATCttttttt-3' (SEQ ID NO: 83) |
| Cognate-trigger (X) | 5'-AGTCAGGCCACTTGTGCCACGGTTTGAGCAAACCGTGCTGCCTGTAGCTCCGCCAATAATGGGAGGCGTAATGAGAACACGTAAGATTGTAATAGTAAACCCGAATGGACttttttt-3' (SEQ ID NO: 84) |

FIG. 21E

| cgRNAs | Sequence |
|---|---|
| cgRNA | 5'-gagtcgcgtgtagcgaagcaGTTTAAGAGCTATGCTGGAAA CAGCATAGCAAGTTTAAATAAGGCTAGTCCGTTATCAGGCCAGG TTCCttttttt-3' (SEQ ID NO: 85) |
| Triggers | |
| Non-cognate trigger (X') | 5'-AGTCAGGCCACTTGTGCCACGGTTTGAGCAAACCGTGCTGC CTGTAGCTCCGCCAATAATGGGAGGCGTTGGGATGTGCGGCACC GAGTCGGTGCttttttt-3' (SEQ ID NO: 86) |
| Cognate trigger (X) | 5'-AGTCAGGCCACTTGTGCCACGGTTTGAGCAAACCGTGCTGC CTGTAGCTCCGCCAATAATGGGAGGCGTGAACCTGGCCGGCACC GAGTCGGTGCttttttt-3' (SEQ ID NO: 87) |

FIG. 22E

Allosteric ON→OFF tandem switch cgRNA (Mechanism 3A)

Mechanism 3A: Schematic

Mechanism 3A: Annotated Schematic

Allosteric OFF→ON tandem switch cgRNA (Mechanism 3B)

---

Mechanism 3B: Schematic

OFF State

ON State

Mechanism 3B: Annotated Schematic

Allosteric OFF→ON 5'-inhibited split-terminator switch cgRNA (Mechanism 5)

Mechanism 5: Schematic

OFF State

ON State

Mechanism 5: Annotated Schematic

Allosteric OFF→ON 3'-inhibited split-terminator switch cgRNA
(Mechanism 6)

---

Mechanism 6: Schematic

OFF State

5' fragment
cg5

3' fragment
cg3 a* b* c* d*
RNA trigger X cg5 trigger:cg3 trigger:cg5:cg3

Target gene Y

Mechanism 6: Annotated Schematic

OFF State

ON State

Allosteric OFF→ON 5'- and 3'-inhibited split-terminator switch cgRNA (Mechanism 7)

Mechanism 7: Schematic

Mechanism 7: Annotated Schematic

Allosteric OFF→ON 5'- and 3'-inhibited split-terminator switch cgRNA
(Mechanism 8)

---

Mechanism 8: Schematic

Mechanism 8: Annotated Schematic

OFF State (continued top of next page)

Allosteric OFF→ON 5'- and 3'-inhibited split-terminator switch cgRNA (Mechanism 9)

OFF→ON logic
"if X then regulate Y"

---

Mechanism 29: Schematic

OFF State

ON State

| cgRNAs | Sequence |
|---|---|
| cgRNA M | 5'-catctaattcaacaagaattGTTTAAGAGCTAGAAATAGCAAGTTAAAATAAGGCTAGTCCGTTATCAGCAC-3' (SEQ ID NO: 88) |
| cgRNA N | 5'-catctaattcaacaagaattGTTTAAGAGCTAGAAATAGCAAGTTAAAATAAGGCTAGTCCGTTATCAGGCC-3' (SEQ ID NO: 89) |
| cgRNA O | 5'-catctaattcaacaagaattGTTTAAGAGCTAGAAATAGCAAGTTAAAATAAGGCTAGTCCGTTATCACCCA-3' (SEQ ID NO: 90) |
| Triggers | |
| Trigger X$_M$ | 5'-GTGCGGCACCGAGTCGGTG-3' (SEQ ID NO: 91) |
| Trigger X$_N$ | 5'-GGCCGGCACCGAGTCGGTG-3' (SEQ ID NO: 92) |
| Trigger X$_O$ | 5'-TGGGGGCACCGAGTCGGTG-3' (SEQ ID NO: 93) |

FIG. 30D

Allosteric ON→OFF split-terminator switch cgRNA (Mechanism 4B)

Allosteric ON→OFF split-terminator switch cgRNA (Mechanism 4C)

| Mechanism 4B | |
|---|---|
| cg5 | 5'-gagtcgcgtgtagcgaagcaCTTTTAGAGCTAGAAATAGCAAG TTAAAATAAGGCTAGTCCGTCCCATCGTCCGTCCCATCAATTTCCC tttttttt-3' (SEQ ID NO: 94) |
| cg3 | 5'- AATATAATACGGGACGGACGGCCACCGAGTCGGTGCtttttt t-3' (SEQ ID NO: 95) |
| Trigger | 5'-AGTCAGGCCACTTGTGCCACGGTTTGAGCAAACCGTGCTGCCT GTAGCTCCGCCAATAATGGGAGGCGT*CGTCCGTCCCGTATTATATT* Ctttttttt-3' (SEQ ID NO: 96) |
| Mechanism 4C | |
| cg5 | 5'-gagtcgcgtgtagcgaagcaCTTTTAGAGCTAGAAATAGCAAG TTAAAATAAGGCTAGTCCC*ATATATACAAACACAACACACACAA CAACAAACAC*tttttttt-3' (SEQ ID NO: 97) |
| cg3 | 5'-AGTCAGGCCACTTGTGCCACGGTTTGAGCAAACCGTGCTGCCT GTAGCTCCGCCAATAATGGGAGGCGT*TGTCTAGAATTGTTTGTTGT TGTGTGTGTGTTGTGTTTGT*GGCACCGAGTCGGTGCtttttttt-3' (SEQ ID NO: 98) |
| Trigger | 5'-AGTCAGGCCACTTGTGCCACGGTTTGAGCAAACCGTGCTGCCT GTAGCTCCGCCAATAATGGGAGGCGT*ACAAACACAACACACACACA ACAACAAACAATTCTAGACA*ctttttttt-3' (SEQ ID NO: 99) |

FIG. 31E

Allosteric ON→OFF split-terminator switch cgRNA
(Mechanism 4B)

Allosteric ON→OFF split-terminator switch cgRNA
(Mechanism 4C)

ON→OFF logic
"if not X then not Y"

| cgRNAs | Sequence |
|---|---|
| cg5 | 5'-aactttcagtttagcggtct????????????????????????????????????ATATATACAAACACAACACACACACAACAACAAACACAACCCAACCagagcgcaaaaaaccccgcttcggcggggttttttcgc-3' (SEQ ID NO: 100) |
| cg3 | 5'-TGTCTAGAATTGTTTGTTGTTGTGTGTGTTGTGTTTGTggcaccgagtcggtgcttttttcgcc-3' (SEQ ID NO: 101) |
| Triggers | |
| No-trigger control | 5'-cgcaaaaaaccccgcttcggcggggttttttcgc-3' (SEQ ID NO: 102) |
| Trigger X (Mechanism 4B) | 5'-GGTTGGGTTGTGTTTGTTGTTGTGTGTGTTGTGTTTGTcgcaaaaaaccccgcttcggcggggttttttcgc-3' (SEQ ID NO: 103) |
| Trigger X (Mechanism 4C) | 5'-ACAAACACAACACACACACAACAACAAACAATTCTAGACAcgcaaaaaaccccgcttcggcggggttttttcgc-3' (SEQ ID NO: 104) |

FIG. 32F

Allosteric OFF→ON 5' and 3' inhibited split-terminator switch cgRNA (Mechanism 7)

| cgRNAs | Sequence |
|---|---|
| cg5 | 5'-*TTGTTTAAGGCTATGGTGAG*aactttcagtttagcggtct TTTAGAGCTAGAAATAGCAAGTTAAAATAAGGCTAGTCCG*TAA ATAAAAGCCCACCCTCACCATAG*agagcgcaaaaaacccgctt cggcggggttttttcgc-3' (SEQ ID NO: 105) |
| cg3 | 5'-*CCACCCTCACCATAGGTGCTATGGTGAGGGTGGGCTTT*ggc accgagtcggtgcttttttttcgcaaaaaacccgcttcggcggg gttttttcgc-3' (SEQ ID NO: 106) |
| Triggers | |
| No-trigger control | 5'-cgcaaaaaacccgcttcggcggggttttttcgc-3' (SEQ ID NO: 107) |
| Trigger X | 5'-*CTCACCATAGCCTTGAACAA*cgcaaaaaacccgctt cggcggggttttttcgc-3' (SEQ ID NO: 108) |

FIG. 33D

ALLOSTERIC CONDITIONAL GUIDE RNAS FOR CELL-SELECTIVE REGULATION OF CRISPR/CAS

STATEMENT REGARDING FEDERALLY SPONSORED R&D

This invention was made with government support under Grant No. HR0011-17-2-0008 awarded by DARPA, under Grant No. 7000000323 and Grant No. NNX16AO69A by NASA. The government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING, TABLE, OR COMPUTER PROGRAM LISTING

The present application is being filed along with a Sequence Listing in electronic format. The Sequence Listing is provided as a file entitled CALTE157ASEQLIST.txt created on Jan. 21, 2022 and is 34,841 bytes in size. The information in the electronic format of the Sequence Listing is incorporated herein by reference in its entirety.

BACKGROUND

Programmable guide RNAs (gRNAs) play a central role in the CRISPR revolution sweeping biology and medicine by directing the function of Cas protein effectors to a target gene of choice, providing a versatile programmable platform for engineering diverse modes of synthetic regulation in organisms ranging from bacteria to humans. Wildtype Cas9 and Cas12a allow genome editing[1-4] while mutated catalytically dead Cas9 (dCas9) and nickase variants allow gene editing, silencing, induction,[5-8] binding, epigenome editing,[9] chromatin interaction mapping[10] and regulation,[11] and imaging.[12] Hence, gRNA-mediated CRISPR/Cas combines the rich functional vocabulary of different Cas effectors (edit, silence, induce, bind, etc.) and the programmability of the gRNA. To target a new gene of choice, all that is needed is to change the sequence of the gRNA.

However, it can be challenging to confine gRNA activity to a desired location and time within an organism. Strategies for achieving temporal control include modulation of gRNA activity using antisense RNAs[13] and small-molecule induction of gRNAs[14,15] or Cas9.[16] Spatiotemporal control can be achieved in photo accessible tissues using light to uncage gRNAs,[17,18] cleave antisense DNAs,[19] or regulate Cas9.[20] Alternatively, Cas9 can be regulated using tissue-specific promoters[21,22] or microRNAs.[23] Cas9 tolerates, to varying degrees, a variety of modifications to the standard gRNA structure,[24-26] allowing for introduction of auxiliary domains to provide hooks for regulation by small-molecules,[27-29] protein-bound RNAs,[30] nucleases,[31] or nuclease-recruiting DNAs or miRNAs.[31,32]

SUMMARY OF THE INVENTION

In accordance with some implementations, there is an allosteric conditional guide RNA (cgRNA) comprising a target-binding region and a trigger-binding region, wherein the target-binding region is non-overlapping with the trigger-binding region, wherein the cgRNA is active in the absence of a cognate RNA trigger, wherein the cgRNA is configured to mediate the function of a Cas protein effector on a target gene that binds the target-binding region, and wherein upon hybridization to the cognate RNA trigger, the cgRNA is inactivated, inhibiting further mediation of Cas function on the target gene. In accordance with certain implementations, the allosteric cgRNA may further comprise a Cas handle wherein the target-binding region is 5' of the Cas handle and the trigger-binding region is 3' of the Cas handle. In accordance with certain implementations, the allosteric cgRNA may further comprise a first terminator hairpin with an extended loop comprising 5 or more nucleotides wherein the trigger-binding region comprises zero, one, or more nucleotides of a linker 5'-adjacent to the first terminator hairpin, zero, one, or more nucleotides in a 5' portion of a stem of the first terminator hairpin, and one or more nucleotides in the extended loop of the first terminator hairpin, wherein the cgRNA is inactivated upon hybridization of the cognate RNA trigger to the cgRNA. In accordance with some implementations, the allosteric cgRNA may further comprise a Cas handle with an extended loop wherein the target-binding region is 5' of the Cas handle and the trigger-binding region comprises a portion of the extended loop of the Cas handle and no nucleotides 5' of the Cas handle. In accordance with some implementations, the allosteric cgRNA may further comprise a first terminator hairpin with an extended loop comprising 5 or more nucleotides such that the trigger-binding region comprises one or more nucleotides in the extended loop of the Cas handle, and one or more nucleotides in the extended loop of the first terminator hairpin, wherein upon hybridization of the cognate RNA trigger to the cgRNA, the cgRNA is inactivated. In accordance with some implementations, the allosteric cgRNA may further comprise a first terminator hairpin with an extended loop comprising 5 or more nucleotides wherein the trigger-binding region further comprises zero, one, or more nucleotides of a linker 5'-adjacent to the first terminator hairpin, zero, one, or more nucleotides in a 5' portion of a stem of the first terminator hairpin, and one or more nucleotides in the extended loop of the first terminator hairpin, wherein the cgRNA is inactivated upon hybridization of the cognate RNA trigger to the cgRNA.

In accordance with some implementations, there is an allosteric conditional guide RNA (cgRNA) and an RNA inhibitor strand, wherein the cgRNA comprises a target-binding region and an inhibitor-binding region, and the RNA inhibitor strand comprises a trigger-binding region, wherein the cgRNA is configured to bind to a portion of the trigger-binding region to form a cgRNA:inhibitor complex: wherein the target-binding region is not base-paired to the trigger-binding region in the cgRNA:inhibitor complex; wherein the cgRNA:inhibitor complex is inactive in the absence of a cognate RNA trigger; and wherein upon hybridization of a cognate RNA trigger to the inhibitor, the cgRNA is activated, mediating the function of a Cas protein effector on a target gene that binds the target-binding region. In accordance with some implementations, the cgRNA further comprises a Cas handle wherein the target-binding region is 5' of the Cas handle and the inhibitor-binding region is 3' of the Cas handle. In accordance with some implementations, the inhibitor further comprises a toehold of one or more unpaired nucleotides at one or both ends, the cgRNA further comprising a first terminator hairpin with an extended loop comprising 5 or more nucleotides, the cgRNA further comprising an inhibitor-binding region comprising: zero, one, or more nucleotides of a linker 5'-adjacent to the first terminator hairpin; zero, one, or more nucleotides in a 5' portion of a stem of the first terminator hairpin; and one or more nucleotides in the extended loop of the first terminator hairpin; wherein the cgRNA is inactive in the cgRNA: inhibitor complex, and wherein hybridization of the cognate RNA trigger to the inhibitor displaces the cgRNA from the inhibitor, thereby activating the cgRNA. In accordance with some implementations, the cgRNA further comprises a Cas handle with an extended loop wherein the target-binding region is 5' of the Cas handle, and wherein the inhibitor-binding region comprises a portion of the extended loop of the Cas handle and no nucleotides 5' of the Cas handle. In accordance with some implementations, the inhibitor further comprises a toehold of one or more unpaired nucleotides at one or both ends, the cgRNA further comprising a first terminator hairpin with an extended loop comprising 5 or more nucleotides, and the inhibitor-binding region comprising: one or more nucleotides in the extended loop of the Cas handle; and one or more nucleotides in the extended loop of the first terminator hairpin; wherein the cgRNA is inactive in the cgRNA:inhibitor complex, and wherein hybridization of the cognate RNA trigger to the inhibitor displaces the cgRNA from the inhibitor, thereby activating the cgRNA. In accordance with some implementations, the inhibitor comprises a toehold of one or more unpaired nucleotides at one or both ends, the cgRNA further comprising a first terminator hairpin with an extended loop comprising 5 or more nucleotides, and the inhibitor-binding region comprising: one or more nucleotides in the extended loop of the Cas handle; zero, one, or more nucleotides of a linker 5'-adjacent to the first terminator hairpin; zero, one, or more nucleotides of a 5' portion of a stem of the first terminator hairpin; and one or more nucleotides in the extended loop of the first terminator hairpin; wherein the cgRNA is inactive in the cgRNA:inhibitor complex, and wherein hybridization of the cognate trigger to the inhibitor displaces the cgRNA from the inhibitor, thereby activating the cgRNA.

In accordance with some implementations, there is an allosteric conditional guide RNA (cgRNA) comprising a 5' fragment (cg5) and a 3' fragment (cg3), cg5 comprising a target-binding region and a trigger-binding region, and cg3 comprising a cognate RNA trigger: wherein the target-binding region is non-overlapping with the trigger-binding region; wherein cg5 and cg3 are inactive when not bound to each other; and wherein upon hybridization of cg3 to cg5 to form a cg5:cg3 complex, the cgRNA is activated, mediating the function of a Cas protein effector on a target gene that binds the target-binding region. In accordance with some implementations, the fragment cg5 further comprises a Cas handle wherein the target-binding region is 5' of the Cas handle and the trigger-binding region is 3' of the Cas handle. In accordance with some implementations, the fragment cg5 further comprises a trigger-binding region comprising a 5' portion of a stem of a terminator duplex and the fragment cg3 further comprises a 3' portion of a stem of the terminator duplex, wherein hybridization of cg5 to cg3 forms the terminator duplex, activating the cgRNA.

In accordance with some implementations, there is an allosteric conditional guide RNA (cgRNA) comprising a 5' fragment (cg5) and a 3' fragment (cg3), cg5 comprising a target-binding region and a trigger-binding region, and cg3 configured to bind to a portion of the trigger-binding region to form a cg5:cg3 complex: wherein the target-binding region is non-overlapping with the trigger-binding region; wherein the cg5:cg3 complex is active in the absence of a cognate RNA trigger, mediating the function of a Cas protein effector on a target gene that binds the target-binding region; wherein cg5 and cg3 are inactive when not bound to each other; and wherein hybridization of the cognate RNA trigger to cg5 displaces cg3 from cg5, thereby inhibiting further mediation of Cas function on the target gene. In accordance with some implementations, the fragment cg5 further comprises a Cas handle wherein the target-binding region is 5' of the Cas handle and the trigger-binding region is 3' of the Cas handle. In accordance with some implementations, the fragment cg5 further comprises a trigger-binding region comprising: a 5' portion of a stem of a terminator duplex; zero, one, or more nucleotides of a linker 5'-adjacent to the 5' portion of the stem of the terminator duplex, and a toehold comprising zero, one, or more nucleotides 3'-adjacent to 5' portion of the stem of the terminator duplex, wherein the fragment cg3 further comprises a 3' portion of the stem of the terminator duplex, wherein hybridization of cg5 to cg3 forms the terminator duplex within the cg5:cg3 complex, and wherein hybridization of the trigger to cg5 displaces cg3 from cg5, thereby breaking the terminator duplex and inactivating the cgRNA.

In accordance with some implementations, there is an allosteric conditional guide RNA (cgRNA) comprising: a 5' fragment (cg5) and a 3' fragment (cg3), cg5 comprising a target-binding region; and cg3 comprising a trigger-binding region, wherein cg5 is configured to bind to a portion of the trigger-binding region to form a cg5:cg3 complex: wherein the target-binding region is not base-paired to the trigger-binding region in the cg5:cg3 complex; wherein the cg5:cg3 complex is active in the absence of a cognate RNA trigger, mediating the function of a Cas protein effector on a target gene that binds the target-binding region; wherein cg5 and cg3 are inactive when not bound to each other; and wherein hybridization of the cognate RNA trigger to cg3 displaces cg5 from cg3, thereby inhibiting further mediation of Cas function on the target gene. In accordance with some implementations, the fragment cg5 further comprises a Cas handle wherein the target-binding region is 5' of the Cas handle, and wherein the fragment cg3 binds to cg5 3' of the Cas handle. In accordance with some implementations, the fragment cg3 further comprises a trigger-binding region comprising a 3' portion of a stem of a terminator duplex, and a toehold comprising zero, one, or more nucleotides 5'-adjacent to the 3' portion of the stem of the terminator duplex; the fragment cg5 further comprises a 5' portion of the stem of the terminator duplex; and wherein hybridization of cg5 to cg3 forms the terminator duplex within the cg5:cg3 complex, and wherein hybridization of the cognate RNA trigger to cg3 displaces cg5 from cg3, thereby breaking the terminator duplex and inactivating the cgRNA.

In accordance with some implementations, there is an allosteric conditional guide RNA (cgRNA) comprising a 5' fragment (cg5) and a 3' fragment (cg3): wherein cg5 comprises a Cas handle, a target-binding region 5' of the Cas handle, and a cg3-binding region 3' of the Cas handle, wherein cg3 comprises a cg5-binding region, and wherein either cg5 or cg3 comprises a trigger-binding region: wherein the target-binding region is non-overlapping with the trigger-binding region and is configured not to bind to the trigger-binding region; wherein cg5 and cg3 are inactive when not bound to each other, wherein in the absence of a cognate RNA trigger, cg5 and cg3 are configured to be inhibited from binding to each other, and wherein upon hybridization of the cognate RNA trigger to either cg5 or cg3, cg5 and cg3 hybridize to form a trigger:cg5:cg3 complex that activates the cgRNA, thereby mediating the function of a Cas protein effector on a target gene that binds the target-binding region. In accordance with some implementations, the fragment cg5 further comprises: a trigger-binding region comprising a first inhibitor region, and a second inhibitor region, wherein in the absence of the cognate RNA trigger, the first inhibitor region is configured to bind to the second inhibitor region, thereby inhibiting binding between cg5 and cg3. In accordance with some implementations, the cognate RNA trigger comprises a cg5-binding region; the trigger-binding region further comprises a toehold of one or more unpaired nucleotides at one or both ends; the cg3-binding region of cg5 comprises a 5' portion of a stem of a terminator duplex; and the cg5-binding region of cg3 comprises a 3' portion of the stem of the terminator duplex; wherein upon hybridization of the cognate RNA trigger to cg5, cg5 hybridizes to cg3 to form the terminator duplex, thereby activating the cgRNA. In accordance with some implementations, cg3 further comprises: a trigger-binding region comprising a first inhibitor region, and a second inhibitor region, wherein in the absence of the cognate RNA trigger, the first inhibitor region is configured to bind the second inhibitor region, thereby inhibiting binding between cg5 and cg3. In accordance with some implementations, the cognate RNA trigger comprises a cg3-binding region; the trigger-binding region further comprises a toehold of one or more unpaired nucleotides at one or both ends; the cg5-binding region of cg3 comprises a 3' portion of a stem of a terminator duplex; and the cg3-binding region of cg5 comprises a 5' portion of the stem of the terminator duplex, wherein upon hybridization of the cognate RNA trigger to cg3, cg3 hybridizes to cg5 to form the terminator duplex, thereby activating the cgRNA. In accordance with some implementations, cg5 further comprises: a trigger-binding region comprising a first inhibitor region and a second inhibitor region; and wherein cg3 further comprises a third inhibitor region and a fourth inhibitor region, wherein in the absence of a cognate RNA trigger, the first inhibitor region is configured to bind the second inhibitor region and the third inhibitor region is configured to bind to the fourth inhibitor region, thereby inhibiting binding between cg5 and cg3. In accordance with some implementations, the cognate RNA trigger comprises a cg5-binding region; the trigger-binding region of cg5 further comprises a toehold of one or more unpaired nucleotides at one or both ends; the cg3-binding region of cg5 comprises a 5' portion of a stem of a terminator duplex; and the cg5-binding region of cg3 comprises a 3' portion of the stem of the terminator duplex comprising a toehold of one or more unpaired nucleotides at one or both ends, wherein upon hybridization of the cognate RNA trigger to cg5, cg5 hybridizes to cg3 to form the terminator duplex, thereby activating the cgRNA. In accordance with some implementations, the trigger-binding region of cg5 is 5' of the target-binding region. In accordance with some implementations, cg3 comprises a trigger mimic region having a sequence identical to that of the cg5-binding region of the cognate RNA trigger, wherein upon activation of the cgRNA by the cognate RNA trigger, the trigger mimic region is exposed and capable of serving as the cognate RNA trigger for a new copy of the cgRNA comprising a new copy of the 5' fragment cg5 and a new copy of the 3' fragment cg3. In accordance with some implementations, the trigger-binding region of cg5 is 3' of the Cas handle. In accordance with some implementations, the cgRNA additionally comprises a splint as a third fragment wherein the splint comprises a cg3-binding region comprising a fifth inhibitor region and further comprising a toehold of one or more unpaired nucleotides at one or both ends; and a cg5-binding region comprising a sixth inhibitor region; wherein in the absence of a cognate RNA trigger, the fifth inhibitor region is configured to bind the sixth inhibitor region, inhibiting binding of the splint to cg5 and cg5, and wherein upon activation of the cgRNA by the cognate RNA trigger, cg3 hybridizes to the cg3-binding region of the splint and the cg5-binding region of the splint hybridizes to cg5, displacing the trigger from cg5, and catalytically regenerating the trigger which then serves as the cognate RNA trigger for a new copy of the cgRNA comprising a new copy of the 5' fragment cg5 and a new copy of the 3' fragment cg3. In accordance with some implementations, the catalytically regenerated trigger serves as the cognate RNA trigger for a new copy of the cgRNA which further comprises a new copy of the splint fragment. In accordance with some implementations, cg3 comprises a trigger mimic region having a sequence identical to that of the cg5-binding region of the cognate RNA trigger, wherein upon activation of the cgRNA by the cognate RNA trigger, the trigger mimic region hybridizes to the trigger-binding region of cg5, displacing the trigger from cg5, and catalytically regenerating the trigger which can then serve as the cognate RNA trigger for a new copy of the cgRNA comprising a new copy of the 5' fragment cg5 and a new copy of the 3' fragment cg3.

In accordance with some implementations, there is a method of conditionally inhibiting mediation of Cas function on a target gene, comprising: providing an allosteric conditional guide RNA (cgRNA); and combining the cgRNA with a system comprising a target gene and a Cas protein effector; wherein the cgRNA is active in mediating the function of the Cas protein effector on the target gene in the absence of a cognate RNA trigger, and wherein upon hybridization to the cognate RNA trigger, the cgRNA is inactivated, inhibiting further mediation of Cas function on the target gene.

In accordance with some implementations, there is a method of conditionally mediating the function of a Cas protein effector on a target gene, comprising: providing an allosteric conditional guide RNA (cgRNA) and an RNA inhibitor strand; and combining the cgRNA and RNA inhibitor strand with a system comprising a target gene and a Cas protein effector; wherein in the absence of a cognate RNA trigger, the inhibitor is bound to the cgRNA and the cgRNA is inactive; and wherein upon hybridization of a cognate RNA trigger to the inhibitor, the cgRNA is activated, mediating the function of a Cas protein effector on the target gene.

In accordance with some implementations, there is a method of conditionally mediating the function of a Cas protein effector on a target gene, comprising: providing an allosteric conditional guide RNA (cgRNA) comprising a 5' fragment (cg5) and a 3' fragment (cg3); and combining the cgRNA with a system comprising a target gene and a Cas protein effector; wherein cg5 and cg3 are inactive when not bound to each other; and wherein upon hybridization of cg3 to cg5, the cgRNA is activated, mediating the function of a Cas protein effector on the target gene.

In accordance with some implementations, there is a method of conditionally inhibiting mediation of Cas function on a target gene, comprising: providing an allosteric conditional guide RNA (cgRNA) comprising a 5' fragment (cg5) and a 3' fragment (cg3); and combining the cgRNA with a system comprising a target gene and a Cas protein effector; wherein in the absence of a cognate RNA trigger cg5 is bound to cg3 and the cgRNA is active; and wherein hybridization of the cognate RNA trigger to cg5 displaces cg3 from cg5, thereby inhibiting further mediation of Cas function on the target gene.

In accordance with some implementations, there is a method of conditionally inhibiting mediation of Cas function on a target gene, comprising: providing an allosteric conditional guide RNA (cgRNA) comprising a 5' fragment (cg5) and a 3' fragment (cg3); and combining the cgRNA with a system comprising a target gene and a Cas protein effector; wherein in the absence of a cognate RNA trigger cg5 is bound to cg3 and the cgRNA is active; and wherein hybridization of the cognate RNA trigger to cg3 displaces cg5 from cg3, thereby inhibiting further mediation of Cas function on the target gene.

In accordance with some implementations, there is a method of conditionally mediating the function of a Cas protein effector on a target gene, comprising: providing an allosteric conditional guide RNA (cgRNA) comprising a 5' fragment (cg5) and a 3' fragment (cg3); and combining the cgRNA with a system comprising a target gene and a Cas protein effector; wherein in the absence of a cognate RNA trigger, cg5 and cg3 are inhibited from binding to each other and the cgRNA is inactive; and wherein upon hybridization of the cognate RNA trigger to either cg5 or cg3, cg5 and cg3 hybridize to form a trigger:cg5:cg3 complex that activates the cgRNA, thereby mediating the function of a Cas protein effector on the target gene.

In accordance with some implementations of any of the foregoing, one or more of the following may also be present: the trigger is an RNA; the trigger is or is a subsequence of an mRNA, an rRNA, a lncRNA, a miRNA, or a tRNA; the cgRNA is expressed in a cell; the cgRNA is chemically synthesized; the cgRNA, cgRNA fragment, RNA inhibitor strand, and/or trigger further comprises one or more additional regions at the 5' and/or the 3' end; the cgRNA, cgRNA fragment, RNA inhibitor strand, and/or trigger further comprises one or more chemical modifications that alter one or more of degradation properties, affinity, biological activity, and/or delivery properties of the cgRNA; the cgRNA, cgRNA fragment, RNA inhibitor strand, and/or trigger comprises one or more chemical modifications selected from the group consisting of arabino nucleic acids (ANA), locked nucleic acids (LNA), peptide nucleic acids (PNA), phosphoroamidate DNA analogues, phosphorodiamidate morpholino oligomers (PMO), cyclohexene nucleic acids (CeNA), tricycloDNA (tcDNA), bridged nucleic acids (BNA), phosphorothioate modification, 2'-fluoro (2'-F) modification, 2'-fluoroarabino (2'-FANA) modification, 2'-O-Methyl (2'O-Me) modification, and 2'O-(2-methoxyethyl) (2'O-MOE) modification; and the cgRNA works in conjunction with Cas to mediate cell-selective induction, silencing, editing, or binding of a target gene.

In accordance with some implementations of any of the foregoing, the allosteric cgRNA wherein an RNA trigger, RNA helper, and/or RNA inhibitor further comprises a protective element (PEL), wherein none, some, or all of the PEL sequence is derived from a component of a viral xrRNA sequence, and wherein the PEL reduces degradation of the RNA trigger, RNA helper, and/or RNA inhibitor in a prokaryotic or eukaryotic cell. In accordance with some implementations of any of the foregoing, the allosteric cgRNA further wherein the cgRNA and/or one or more cgRNA fragments further comprise a protective element (PEL), wherein none, some, or all of the PEL sequence is derived from a component of a viral xrRNA, and wherein the PEL reduces degradation of the cgRNA in a prokaryotic or eukaryotic cell.

BRIEF DESCRIPTION OF THE DRAWINGS

FIGS. 11A-11F demonstrate ON→OFF conditional logic in bacteria using allosteric terminator switch cgRNAs.

FIG. 12A-12F demonstrate ON→OFF conditional logic in bacteria using allosteric splinted switch cgRNAs.

FIG. 13A-13J demonstrate ON→OFF conditional logic in human cells using allosteric terminator switch cgRNAs.

FIG. 14A-14H demonstrate OFF→ON conditional logic in human cells using allosteric split-terminator switch cgRNAs with a 4-bp terminator duplex.

FIG. 15A-15H demonstrate OFF→ON conditional logic in human cells using allosteric split-terminator switch cgRNAs with a 10-bp terminator duplex.

FIG. 16A-16E demonstrate OFF→ON conditional logic in human cells using allosteric split-terminator switch cgRNAs with terminator duplexes of different lengths (40, 30, 20, 10, 8, 6, 4 bp).

FIG. 17A-17C demonstrate that 3' truncation of a standard gRNA can lead to complete inactivation, providing the basis for engineering cgRNAs with a clean OFF state.

FIGS. 18A-18F demonstrate ON→OFF conditional logic in bacteria using allosteric terminator switch cgRNAs and mRNA triggers.

FIGS. 21A-21E demonstrate an allosteric ON→OFF cgRNA functioning in a multicellular organism FIGS. 22A-22E demonstrate an allosteric OFF→ON cgRNA functioning in a multicellular organism

FIGS. 30A-30D demonstrate allosteric OFF→ON split-terminator switch cgRNAs functioning in bacteria.

FIGS. 31A-31E demonstrate allosteric ON→OFF split-terminator switch cgRNAs functioning in human cells.

FIGS. 32A-32F demonstrate allosteric ON→OFF split-terminator switch cgRNAs functioning in bacteria.

FIGS. 33A-33D demonstrate allosteric OFF→ON 5'- and 3'-inhibited split-terminator switch cgRNAs functioning in bacteria.

DETAILED DESCRIPTION OF THE PREFERRED EMBODIMENT

Programmable guide RNAs (gRNAs) play a central role in the CRISPR revolution sweeping biology and medicine by directing the function of Cas protein effectors to a target gene of choice (FIG. 1A), providing a versatile programmable platform for engineering diverse modes of synthetic regulation in organisms ranging from bacteria to humans. Wildtype Cas9 and Cas12a allow for genome editing[1-4] while mutated catalytically dead Cas9 (dCas9) and nickase variants allow for gene editing, silencing, induction,[5-8] binding, epigenome editing,[9] chromatin interaction mapping[10] and regulation,[11] and imaging.[12] Hence, gRNA-mediated CRISPR/Cas combines the rich functional vocabulary of different Cas effectors (edit, silence, induce, bind, etc.) and the programmability of the gRNA. To target a new gene of choice, all that is needed is to change the sequence of the gRNA.

However, the fact that gRNAs are constitutively active is a significant limitation, making it challenging to confine gRNA activity to a desired location and time within an organism. Strategies for achieving temporal control include modulation of gRNA activity using antisense RNAs[13] and small-molecule induction of gRNAs[14,15] or Cas9.[16] Spatiotemporal control can be achieved in photoaccessible tissues using light to uncage gRNAs,[17,18] cleave antisense DNAs,[19] or regulate Cas9.[20] Alternatively, Cas9 can be regulated using tissue-specific promoters[21,22] or microRNAs.[23] Cas9 tolerates, to varying degrees, a variety of modifications to the standard gRNA structure (FIG. 1B),[24-26] allowing for introduction of auxiliary domains to provide hooks for regulation by small-molecules,[27-29] protein-bound RNAs,[30] nucleases,[31] or nuclease-recruiting DNAs or miRNAs.[31,32] As appreciated herein, for generality, it can be desirable to control gRNA regulatory scope in a manner that is both conditional and programmable, and for simplicity, to leverage dynamic RNA nanotechnology without relying on the functionality of additional pathways.

Figure 2A:
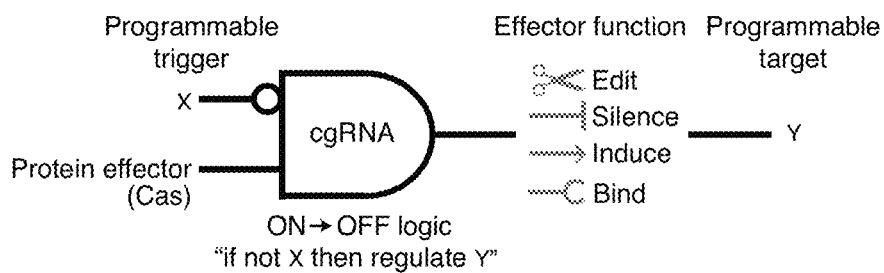
FIGS. 2A-2B depict the logic and function of a conditional guide RNA (cgRNA).
Figure 2B:
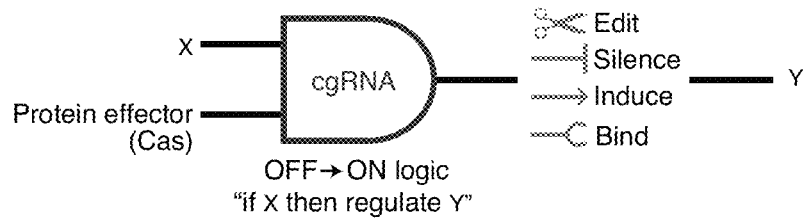

To exert programmable control over the scope of gRNA activity, conditional guide RNAs (cgRNAs) change conformation in response to an RNA trigger X, conditionally directing the function of Cas to a target gene Y (FIG. 2).[26,33,34] Unlike a standard gRNA, a cgRNA is programmable at two levels, with the trigger-binding sequence controlling the scope of cgRNA activity and the target-binding sequence determining the subject of Cas activity. Hybridizing to the trigger changes the cgRNA conformation to perform sequence transduction between X and Y and shape transduction between active/inactive states. The disclosure herein relates to cgRNAs that are allosteric so that the sequence of the target gene Y places no restriction on the sequence of the RNA trigger X, allowing for independent control over the regulatory scope (using X) and the regulatory target (using Y). In some embodiments, cgRNA mechanisms implement ON→OFF logic (conditional inactivation by trigger X; FIG. 2A). In some embodiments, cgRNA mechanisms implement OFF→ON logic (conditional activation by trigger X; FIG. 2B). In some embodiments, cgRNAs work in concert with Cas variants that either edit, silence, induce, or bind the target Y (FIG. 2), creating opportunities for diverse modes of tissue-selective spatiotemporal control over regulation (see for example FIG. 3). In some embodiments, cgRNAs work in concert with Cas variants that mediate induction, silencing, editing, binding, epigenome editing, chromatin interaction mapping and regulation, or imaging of a target gene.

Figure 3A:
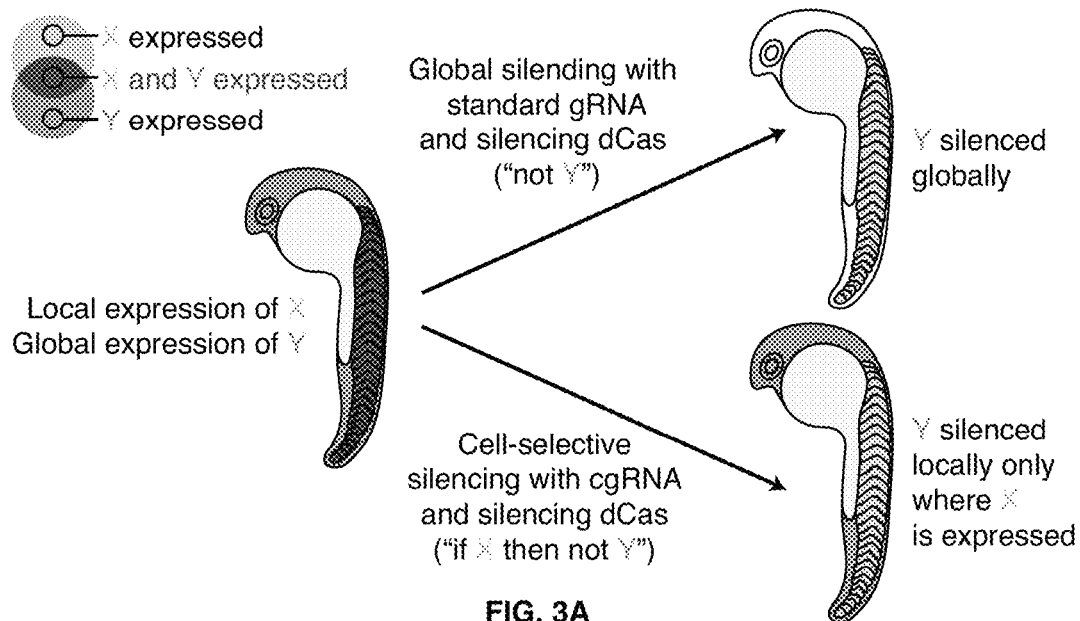
FIGS. 3A-3E depict applications of cell-selection spatiotemporal control of CRISPR/Cas regulation.
Figure 3B:
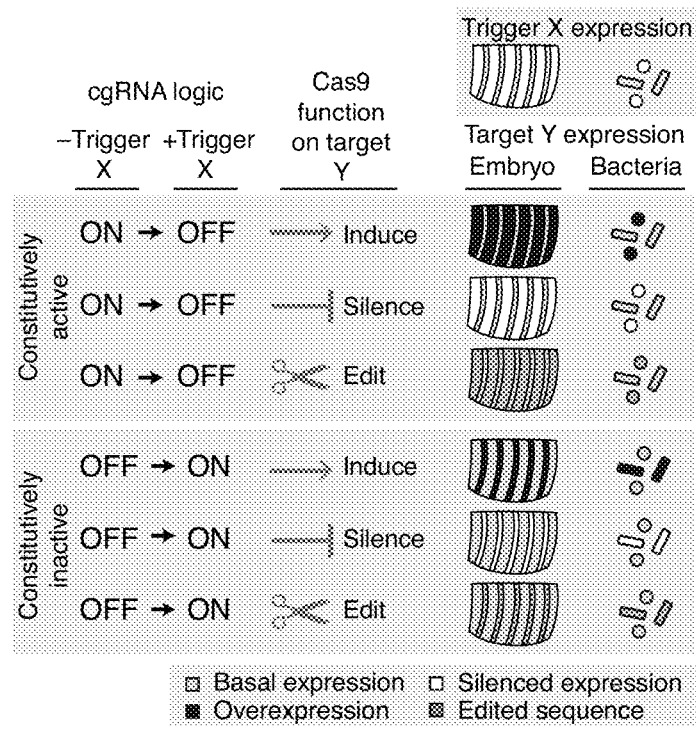
Figure 3C:
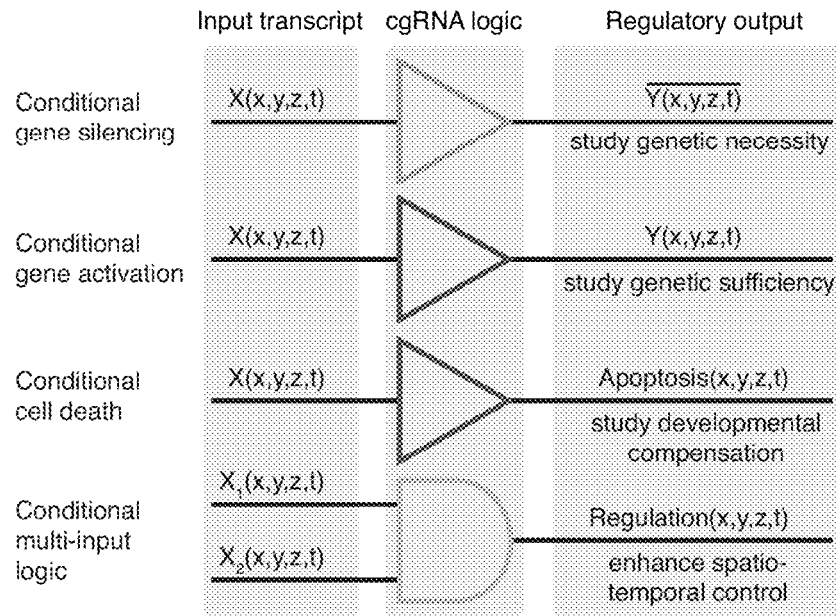
Figure 3D:
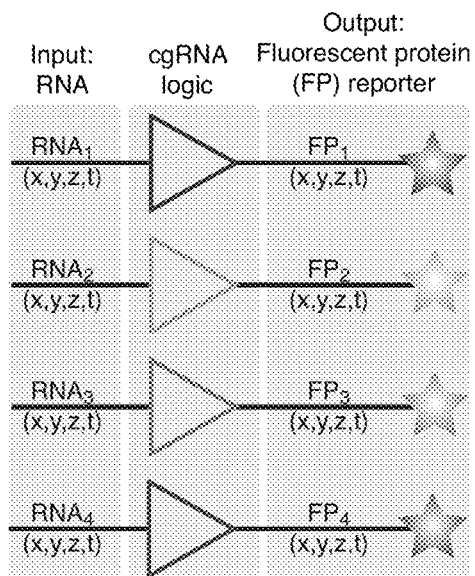
Figure 3E:
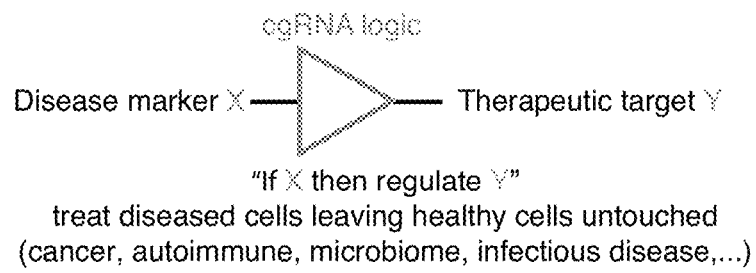

In some embodiments, cgRNAs open the possibility of restricting synthetic regulation to a desired cell type, tissue, or organ. This can be achieved by selecting an endogenous RNA trigger X with the desired spatial and temporal expression profile, allowing for spatiotemporal control over regulation (FIG. 3A). In some embodiments, cgRNAs open the possibility of restricting synthetic regulation to a desired cell type, tissue, or organ without engineering the organism. FIG. 3B illustrates a variety of modes of cell-selective spatiotemporal regulatory control that can be implemented by combining the conditionality of cgRNA logic (ON→OFF and OFF→ON) and the functionality of Cas variants (edit, silence, induce, bind, etc.). In some embodiments, cgRNAs can be used as cell-selective and tissue-selective research tools (FIG. 3C): conditional gene silencing would probe genetic necessity, conditional gene induction would probe genetic sufficiency, conditional cell death would probe developmental compensation. In some embodiments, to shift conditional regulation to a different tissue or developmental stage, the sequence of a cgRNA is simply redesigned to recognize a different input X with the desired spatial and temporal expression profile. In some embodiments, cgRNAs can be used to mediate in vivo imaging of a target RNA using the cgRNA to recognize the RNA of interest and mediate expression of a fluorescent protein reporter. In some embodiments, multiple cgRNAs recognizing different target RNAs and inducing spectrally distinct different fluorescent protein reporters can be used for multiplexed in vivo RNA imaging. In some embodiments, in a model organism with N fluorescent proteins integrated into the genome, a set of N target RNAs can be imaged in vivo using a set of N cgRNAs to induce the fluorescent proteins upon detection of the corresponding target RNAs. In some embodiments, to switch to imaging a new set of N target RNAs, no genome engineering is required as this can be achieved simply by using a new set of N cgRNAs. In some embodiments, cgRNAs also provide a framework for conditional chemotherapies ("if X then regulate Y") with X as a programmable disease marker and Y as an independent programmable therapeutic pathway, allowing for selective treatment or killing of diseased cells leaving healthy cells untouched (FIG. 3E).

The repurposing of RNA-guided CRISPR effectors through development of modified guide RNAs (gRNAs) and CRISPR-associated (Cas) proteins has yielded a suite of powerful tools for biological research, synthetic biology, and medicine. Precision genome editing has been achieved in a variety of organisms using gRNAs to direct the nuclease activity of Cas9 and Cas12a (Cpf1) to a target gene of choice.[1-4] Mutation of the nuclease domains to produce a catalytically dead Cas9 (dCas9) has allowed for silencing of genetic expression via inhibition of transcriptional elongation,[5,6] or induction (or silencing) of genetic expression using dCas9 fusions that incorporate transcriptional regulatory domains.[7] Other dCas9 fusions have mediated target-binding to allow for visualization of genomic loci,[35,36] epigenetic modification,[37] and single-base editing at a specific genomic locus,[4,38] chromatin interaction mapping[10] and regulation,[11] and imaging.[12] Hence, gRNA:effector complexes combine the benefits of the rich functional vocabulary of the protein effector (edit, silence, induce, bind) and the programmability of the gRNA in targeting effector activity to a gene of choice.

Because gRNAs are constitutively active, additional measures are needed to restrict effector activity to a desired location and time. Temporal control can be achieved by small-molecule induction of gRNAs[14,15] or Cas9,[16] but this comes with limitations in terms of multiplexing and spatial control. In some settings, spatiotemporal control can be achieved by regulation of Cas9 via photoactivation[20] or via tissue-specific promoters[21,22] or microRNAs,[23] which comes with the unwelcome restriction that all gRNAs are subject to the same regulatory scope. Cas9 activity is tolerant to significant modifications to the standard gRNA structure.[24-26] The introduction of auxiliary domains can allow for conditional control of gRNA activity via structural changes induced by small-molecules,[27-29] protein-bound RNAs,[30] nucleases,[31] or nuclease-recruiting DNAs.[31] Alternatively, the activity of standard gRNAs can be modulated by antisense RNAs[13] or by photolysis of antisense DNAs incorporating photocleavable groups.[19]

For generality, it is useful to control the regulatory scope of a gRNA in a manner that is both conditional and programmable. Conditional guide RNAs (cgRNAs) achieve this goal by changing conformation in response to an RNA trigger X to conditionally direct the function of a Cas effector to a target gene Y.[26,33,34,39] Unlike a standard gRNA, a cgRNA is programmable at two levels, with the trigger-binding sequence controlling the scope of cgRNA activity and the target-binding sequence determining the subject of effector activity. Functionally, the cgRNA performs sequence transduction between X and Y as well as shape transduction between active/inactive conformations. cgRNA activity can be engineered to toggle either ON→OFF or OFF→ON in response to a cognate RNA trigger X; this conditional control can be exerted over Cas (for example, Cas9 or dCas9) variants that either, for example, edit, silence, induce, or bind the target Y (FIG. 2). For example, by selecting an endogenous transcript X with a desired spatiotemporal expression profile during development, the downstream regulatory effect on target Y could be restricted to a desired tissue and developmental stage within a model organism (FIGS. 3A and 3B). Alternatively, in a therapeutic context, X can be a disease marker and Y an independent therapeutic target, allowing for selective treatment or killing of diseased cells leaving healthy cells untouched (FIG. 3E).

Figure 1A:
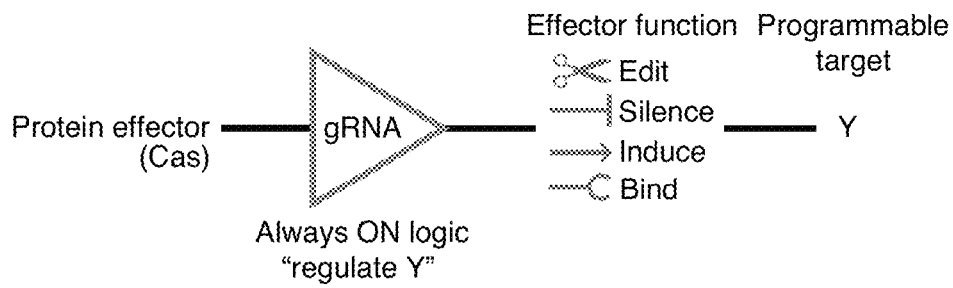
FIGS. 1A-1B depict the logic, function, structure, and interactions of a standard guide RNA (gRNA).

FIG. 1A depicts the logic and function of a standard guide RNA (gRNA). A standard gRNA is always ON, unconditionally directing the activity of a protein effector to a target Y; different Cas9, dCas9, and/or Cas variants implement different functions (for example, edit, silence, induce, bind).

Figure 1B:
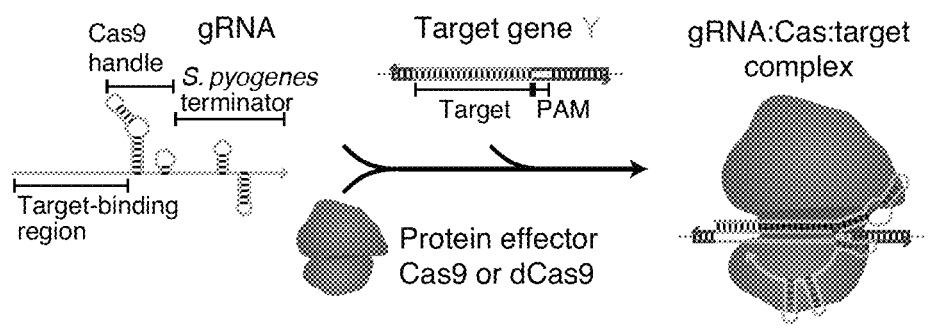

FIG. 1B depicts structure and interactions of a standard gRNA. From 5' to 3', a standard gRNA comprises: a target-binding region, a Cas handle recognized by the protein effector, and a terminator region.

For some embodiments, FIG. 2 depicts the logic and function of a conditional guide RNA (cgRNA). For some embodiments, a cgRNA changes conformation in response to a programmable trigger X to conditionally direct the activity of a protein effector to a programmable target Y. For some embodiments, FIG. 2A depicts ON→OFF logic with a constitutively active cgRNA that is conditionally inactivated by X. For some embodiments, FIG. 2B depicts OFF→ON logic with a constitutively inactive cgRNA that is conditionally activated by X.

For some embodiments, FIG. 3 illustrates applications of cell-selective regulation of CRISPR/Cas function using cgRNAs. FIG. 3A contrasts global silencing (top arrow) of target gene Y using silencing dCas9 and a standard gRNA that implements the unconditional logic "silence Y" to cell-selective silencing (bottom arrow) of target gene Y using silencing dCas9 and a conditional cgRNA, such that Y is silenced locally only where X is expressed. For some embodiments, FIG. 3B illustrates diverse modes of cell-selective spatiotemporal regulatory control using cgRNA conditional logic (ON→OFF or OFF→ON) and different Cas9 functional variants (induce, silence, edit, bind, etc.). ON→OFF and OFF→ON cgRNAs produce inverted regulatory patterns on target Y in response to a given pattern for trigger X. For some embodiments, FIG. 3C illustrates cell-selective and tissue-selective tools. For example, conditional gene silencing ("if gene X is transcribed, silence independent gene Y") can be used to probe genetic necessity, conditional gene activation ("if gene X is transcribed, activate independent gene Y") can be used to probe genetic sufficiency, and conditional cell death ("if gene X is transcribed, induce apoptosis") can be used to probe developmental compensation. In each case, conditional regulation is mediated by a cgRNA whose activity is toggled by a programmable trigger X. For some embodiments, by selecting a trigger X with the desired spatial and temporal expression profiles, the regulatory function is restricted to a desired cell type, tissue, or organ within an organism, mixture of cells, or ecosystem. For some embodiments, to shift conditional regulation to a different tissue type or time point, the cgRNAs can be programmed to recognize a different trigger X. For some embodiments, to enhance cell-selective spatiotemporal control in multi-cellular settings (e.g., within embryos or bacterial mixtures), multi-input conditional logic (operating on two or more inputs $X_1$, $X_2$, . . . ) using AND gates can be used to narrow the scope of regulation on Y; alternatively, OR gates can be used to broaden the scope of regulation on Y. In some embodiments, AND logic is implemented using split-cgRNAs that are functional only in the presence of both $X_1$ and $X_2$. In some embodiments, OR logic is executed using multiple cgRNA variants that accept different inputs ($X_1$, $X_2$, . . . ) but target the same output Y. FIG. 3D illustrates cgRNA-mediated cell-selective reporter regulation for multiplexed in vivo RNA imaging. In some embodiments, 4 cgRNAs each detect a different mRNA input ($mRNA_1$, $mRNA_2$, $mRNA_3$, $mRNA_4$) that serves as an RNA trigger, activating the corresponding cgRNA to induce the corresponding spectrally distinct FP reporter ($FP_1$, $FP_2$, $FP_3$, $FP_4$). In some embodiments, after once optimizing a plasmid-based reporter system expressing inducing dCas9, the 4 FP reporters, and the 4 cgRNAs, imaging a new set of mRNAs requires only updating the sequences of the cgRNAs to accept new mRNAs as triggers. In some embodiments, this cgRNA approach offers important conceptual advantages relative to FP fusion methods, which have revolutionized the study of genetic expression, 43-4 but have the well-known drawbacks that a new fusion must be engineered for each gene of interest, that it is difficult to determine whether fusions affect the expression or function of target proteins, and that fusion methods are not applicable to imaging non-protein gene products such as coding and non-coding RNAs. In some embodiments, cgRNAs eliminate these issues by replacing the conventional physical link of FP fusion approaches with a logical link executed by cgRNAs that execute conditional gene induction, allowing for spatiotemporal monitoring of gene expression levels in living chick embryos without the need to modify the imaged molecules ($mRNA_1$, $mRNA_2$, $mRNA_3$, $mRNA_4$) in any way. FIG. 3E depicts the conditional logic using cgRNAs as conditional chemotherapies: "if disease marker X then regulate therapeutic target Y". In some embodiments, X is a programmable disease marker and Y is an independent therapeutic target, allowing for selective treatment or killing of diseased cells (the subset of cells containing X) while leaving healthy cells untouched (the subset of cells lacking X). In some embodiments, cgRNAs allow for independent diagnosis (detection of disease marker X) and treatment (regulation or editing of independent therapeutic target Y).

For some embodiments, FIG. 10 depicts interactions between allosteric cgRNAs, RNA triggers, and Cas9, dCas9 or Cas. For some embodiments, FIG. 10A depicts interactions for an allosteric ON→OFF terminator switch cgRNA. In the ON state, the terminator switch cgRNA is constitutively active, directing the function of protein effector Cas9, dCas9, or Cas to a target gene Y in the absence of trigger. The extended loop and modified sequence domains in the terminator region are intended not to interfere with the activity of the cgRNA:Cas complex. In the OFF state, in the presence of RNA trigger X, hybridization of the trigger forms a structure incompatible with cgRNA mediation of Cas9, dCas9, and/or Cas function. For some embodiments, FIG. 10B depicts interactions for an allosteric ON→OFF splinted switch cgRNA. In the ON state, the splinted switch cgRNA is constitutively active, directing the function of protein effector Cas9, dCas9, or Cas to a target gene Y in the absence of trigger. The extended loops in the Cas9 handle and terminator region are intended not to interfere with the activity of the cgRNA:Cas complex. In the OFF state, in the presence of RNA trigger X, hybridization of the trigger forms a splint that is structurally incompatible with cgRNA mediation of Cas9, dCas9, and/or Cas function. For some embodiments, FIG. 10C depicts interactions for an allosteric OFF→ON split-terminator switch cgRNA. In the OFF state, the split-terminator switch cgRNA is constitutively inactive. In the absence of RNA trigger X, the cgRNA is incapable of directing the function of the protein effector Cas9, dCas9, and/or Cas. In the ON state, the complex of cgRNA and trigger X mediates the function of the protein effector Cas9, dCas9, or Cas on the target gene Y. The modified sequence domains in the terminator duplex do not to interfere with the activity of the cgRNA:trigger:Cas complex.

Definitions

"Nucleic acids" as used herein includes oligomers of RNA, DNA, 2'OMe-RNA, LNA, PNA, XNA, chemically modifications thereof, synthetic analogs of RNA or DNA, any other material capable of base-pairing, one or more chemical linkers not capable of base-pairing, or any combination thereof. Nucleic acids may include analogs of DNA or RNA having modifications to either the bases or the backbone. For example, nucleic acid, as used herein, includes the use of peptide nucleic acids (PNA). The term "nucleic acids" also includes chimeric molecules. The phrase includes artificial constructs as well as derivatives etc. The phrase includes, for example, any one or more of DNA, RNA, 2'OMe-RNA, LNA, XNA, synthetic nucleic acid analogs, and PNA. The phrase also includes oligomers of RNA, DNA, 2'OMe-RNA, LNA, PNA, XNA and/or other nucleic acid analogs with or without chemical linkers between nucleic acid segments.

Figure 4A:
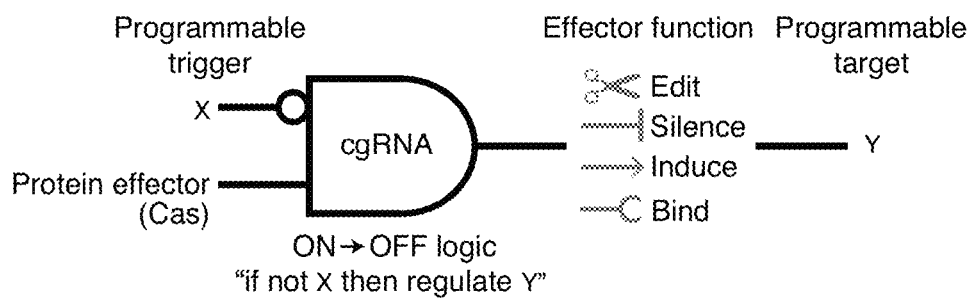
FIGS. 4A-4C depict the logic, function, and mechanism of allosteric ON→OFF terminator switch cgRNAs (Mechanism 1A).

A "nucleic acid strand" refers to an oligomer of nucleotides (typically listed from 5' to 3'). In diagrams, a nucleic acid strand is depicted with an arrowhead at the 3' end. A nucleic acid strand may comprise one or more "regions" and/or "sequence domains" (equivalently "domains"). For example, FIG. 4C depicts a nucleic acid strand (labeled "Allosteric cgRNA") containing a "target-binding region" comprising domain "u", a "Cas handle" region, a "trigger binding region" comprising domains "d", "e", and "f", and other regions and domains. A "secondary structure" of a nucleic acid strand is defined by a set of base pairs (for example, Watson-Crick base pairs [A-U or C-G] or wobble base pairs [G-U] for RNA).

Two "complementary" sequence domains can base-pair to each other (i.e., hybridize) to form a "duplex" or "stem", representing one or more consecutive base pairs between two regions (or equivalently, one or more consecutive base pairs between two sequence domains). For example, in FIG. 4C, domain "e*" is complementary to sequence domain "e", allowing for hybridization to form a "duplex" or "stem". In some settings it is convenient to designate complementary sequence domains using matching domain names with and without an asterisk (for example, domain "e*" complementary to domain "e"). Complementarity may also be specified independent of the sequence domain names. For example, domain "b" may be specified as complementary to domain "c". The complementarity between two complementary sequence domains may be partial, such that when they base-pair to each other to form a duplex (or stem), the base pairs within the duplex (or stem) may have one or more mismatches interspersed between them (i.e., one or more unpaired bases interspersed between the base pairs within the duplex). In some embodiments, a duplex (or stem) comprises, consists, or consists essentially of 1, 2, 3, 4, 5, 6, 7, 8, 9, 10, 11, 12, 13, 14, 15, 16, 17, 18, 19, 20, or more consecutive base pairs between two segments. In some embodiments a duplex (or stem) comprises, consists, or consists essentially of 5, 10, 15, 20, 25, 30, 35, 40, 45, or 50 consecutive base pairs (or any integer number of consecutive base pairs in between any of these values) between two segments. In some embodiments a duplex (or stem) comprises, consists, or consists essentially of 10, 20, 30, 40, 50, 60, 70, 80, 90, or 100 consecutive base pairs (or any integer number of consecutive base pairs in between any of these values) between two segments). In some embodiments a duplex (or stem) comprises, consists, or consists essentially of 100, 200, 300, 400, or 500 consecutive base pairs (or any integer number of consecutive base pairs in between any of these values) between two segments. In some embodiments, a duplex (or stem) comprises, consists, or consists essentially of 2, 3, 4, 5, 6, 7, 8, 9, 10, 11, 12, 13, 14, 15, 16, 17, 18, 19, 20, or more base pairs between two segments wherein 1, 2, 3, 4, 5, 6, 7, 8, 9, 10, 11, 12, 13, 14, 15, 16, 17, 18, 19, 20, or more unpaired bases are interspersed at one or more locations between the base pairs. In some embodiments a duplex (or stem) comprises, consists, or consists essentially of 5, 10, 15, 20, 25, 30, 35, 40, 45, or 50 base pairs (or any integer number of base pairs in between any of these values) between two segments wherein 1, 5, 10, 15, 20, 25, 30, 35, 40, 45, or 40 unpaired bases (or any integer number of unpaired bases between any of these values) are interspersed at one or more locations between the base pairs. In some embodiments a duplex (or stem) comprises, consists, or consists essentially of 10, 20, 30, 40, 50, 60, 70, 80, 90, or 100 base pairs (or any integer number of base pairs in between any of these values) between two segments wherein 1, 10, 20, 30, 40, 50, 60, 70, 80, 90, or 100 unpaired bases (or any integer number of unpaired bases between any of these values) are interspersed at one or more locations between the base pairs. In some embodiments a duplex (or stem) comprises, consists, or consists essentially of 100, 200, 300, 400, or 500 base pairs (or any integer number of base pairs in between any of these values) between two segments wherein 1, 100, 200, 300, 400, or 500 unpaired bases (or any integer number of unpaired bases between any of these values) are interspersed at one or more locations between the base pairs. In some embodiments, a duplex (or stem) comprising N base pairs between 2 segments further comprises 1, 2, 3, 4, 5, 6, 7, 8, 9, 10 or more mismatches corresponding to bases that are unpaired. In some embodiments, a duplex (or stem) comprising N base pairs between 2 segments further comprises 0% N, 1% N, 2% N, 5% N, 10% N, 20% N, 50% N, 100% N, or 200% N or more mismatches (or any percentage of N mismatches intermediate to the stated values) corresponding to bases that are unpaired.

A "hairpin" is a nucleic acid secondary structure comprising from 5' to 3': a 5' portion of a stem, an unpaired (single-stranded) loop, and a 3' portion of the stem, wherein the 5' portion of the stem is base-paired to the 3' portion of the stem.

Within a nucleic acid secondary structure, a "toehold" is a region or domain comprising one or more unpaired nucleotides, wherein the toehold serves as a nucleation site for binding another nucleic acid strand.

A "Cas handle" is a binding site for a Cas protein effector.

A "conditional guide RNA (cgRNA)" conditionally mediates the function of a Cas protein effector on a target gene depending on the presence/absence of a cognate RNA trigger. In some embodiments, cgRNAs implement ON→OFF logic (conditional inactivation by a cognate RNA trigger; for example FIG. 2A). In some embodiments, cgRNAs implement OFF→ON logic (conditional activation by a cognate RNA trigger; for example FIG. 2B). In some embodiments, cgRNAs work in concert with Cas variants that either edit, silence, induce, or bind the target gene (for example, FIG. 2).

A cgRNA is termed "allosteric" if the cognate RNA trigger toggles the activity of the cgRNA without interacting with the target-binding site within the cgRNA, allowing for the sequence of the cognate RNA trigger to be selected independently of the sequence of the target gene.

As used herein, "combining" encompasses any act or situation where at least two elements are able to interact, including, for example, adding one to the other, allowing the two elements to interact, exposing the two elements to each other, placing or having arranged the elements in a situation where they can interact, etc.

As used herein, the term "providing" encompasses any way to provide the denoted material, including for example, having, obtaining, creating, causing to be created, suppling, etc. the denoted material. This can be done directly (such as the provision of an RNA molecule itself) or indirectly (such as the provision of an DNA molecule that is to be transcribed into the RNA molecule). In some embodiments, this process can be an independent process (such as by obtaining an RNA segment), or it can be part of another process in the method (such as by providing an DNA sequence that is then transcribed into an RNA sequence).

As used in some embodiments herein, the term "mediating" can include one or more of facilitating, directing, or enabling.

In some embodiments, an "inactive" cgRNA is said to be "activated" by a cognate RNA trigger if the trigger increases the cgRNA-mediated function of a Cas protein effector on a target gene by 20%, 50%, 90%, 100%, 200%, 500%, 1000%, or more, or any percentage intermediate to the stated values. In some embodiments, an "inactive" cgRNA is said to be "activated" by a cognate RNA trigger if the trigger increases the cgRNA-mediated function of a Cas protein effector on a target gene by 1.2-fold, 1.5-fold, 2-fold, 5-fold, 10-fold, 20-fold, 50-fold, 100-fold, 200-fold, 500-fold, 1000-fold, 2000-fold, 5000-fold, 10,000-fold, 100,000-fold or more, or any fold change intermediate to these values.

In some embodiments, an "active" cgRNA is said to be "inactivated" by a cognate RNA trigger if the trigger decreases the cgRNA-mediated function of a Cas protein effector on a target gene by 20%, 50%, 90%, 95%, 99%, 99.9%, 99.99%, 99.999%, or 100%, or any percentage intermediate to the stated values. In some embodiments, an "active" cgRNA is said to be "inactivated" by a cognate RNA trigger if the trigger decreases the cgRNA-mediated function of a Cas protein effector on a target gene by 1.5-fold, 2-fold, 5-fold, 10-fold, 20-fold, 50-fold, 100-fold, 200-fold, 500-fold, 1000-fold, 2000-fold, 5000-fold, 10,000-fold, 100,000-fold or more, or any fold change intermediate to these values.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive. Unless defined otherwise, technical and scientific terms used herein have the same meaning as commonly understood by one of ordinary skill in the art to which this invention belongs. See, for example Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). It is to be understood that both the general description and the detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety. Also, the term "embodiment" as used herein refers to an aspect or an implementation of what is disclosed herein, and embodiments may be combined with one another.

Allosteric ON→OFF Terminator Switch cgRNAs (Mechanism 1A)

Figure 4B:
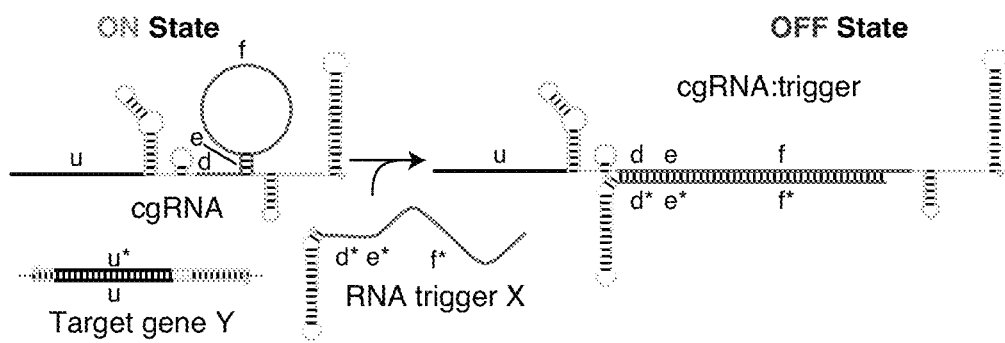
Figure 4C:
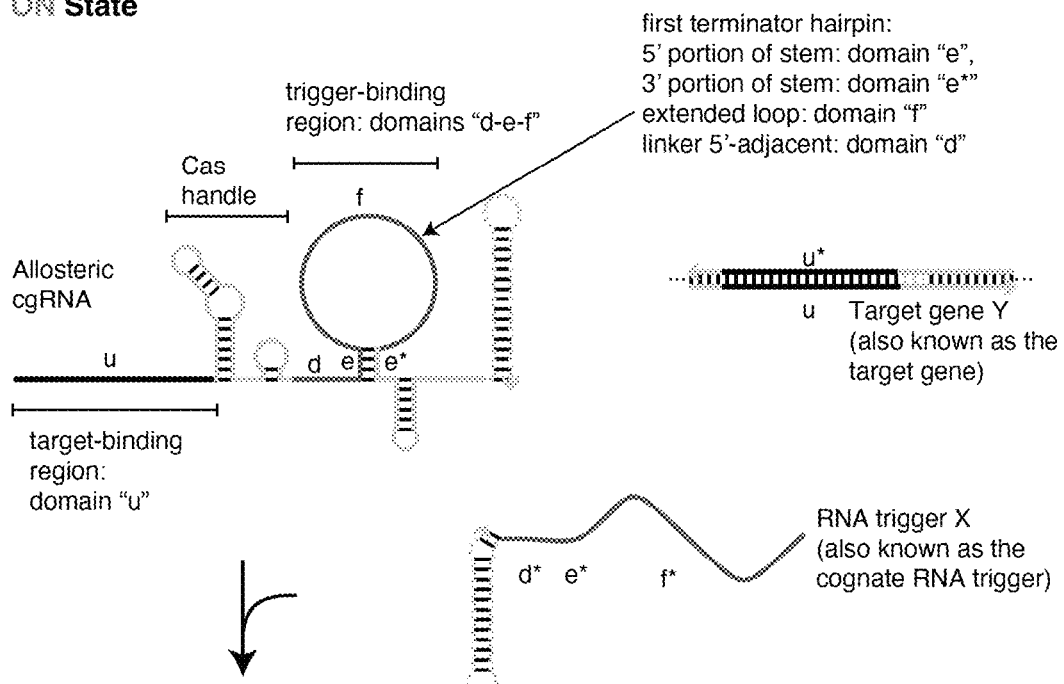
Figure 4C:
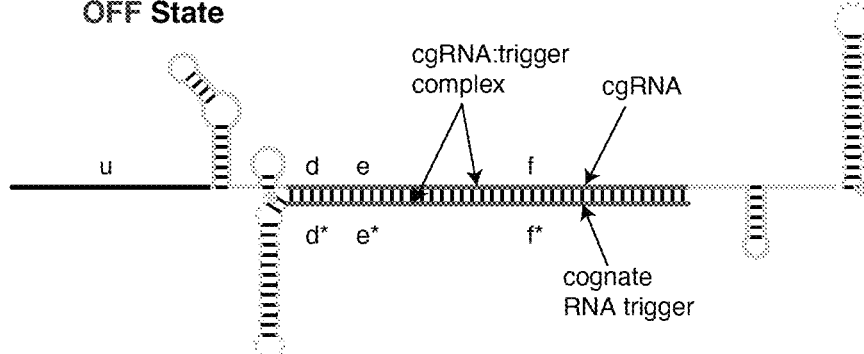
Figure 10A:
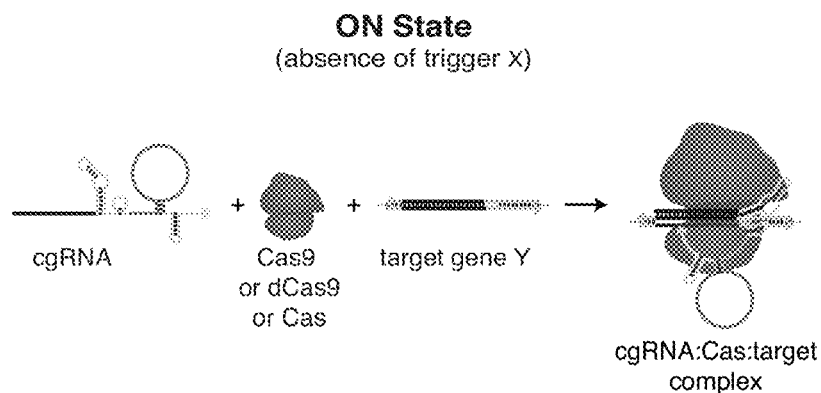
FIGS. 10A-10C depict the interactions between allosteric cgRNAs, triggers, and Cas.
Figure 10A:
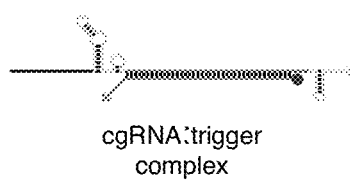

In some embodiments, allosteric ON→OFF cgRNA logic (FIG. 4A) is implemented using an allosteric ON→OFF terminator switch cgRNA mechanism (FIGS. 4B and 4C). The ON→OFF terminator switch cgRNA of FIGS. 4B and 4C is conditionally inactivated by RNA trigger X (the cognate RNA trigger). Compared to a standard gRNA (FIG. 1), in some embodiments the ON→OFF terminator switch cgRNA has a modified terminator region with an extended loop and rationally designed sequence domains "d-e-f". In some embodiments, the cgRNA comprises a target-binding region (domain "u"), a Cas handle, a trigger-binding region (domains "d-e-f"), a first terminator hairpin, and a linker 5'-adjacent to the first terminator hairpin (domain "d"); wherein the first terminator hairpin comprises a 5' portion of the stem (domain "e"), a 3' portion of the stem (domain "e*"), and an extended loop (domain "f"). In some embodiments, to toggle to the OFF state, hybridization of the RNA trigger X (the cognate RNA trigger) to the trigger-binding region of the cgRNA (forming the cgRNA:trigger complex) disrupts the structure of the first terminator hairpin to form a structure incompatible with cgRNA mediation of Cas9, dCas9, and/or Cas function (FIG. 10A). In some embodiments, the mechanism is allosteric because the trigger down-regulates cgRNA:Cas function not by sequestering the target-binding region (domain "u" in FIGS. 4B and 4C), but by hybridizing to the distal trigger-binding region (domains "d-e-f" in FIGS. 4B and 4C). Hence, the sequences of the RNA trigger X and the regulatory target Y (the target gene) are fully independent. In some embodiments, domain "d" in the cgRNA is constrained to a wild-type subsequence of the standard gRNA. In some embodiments, domain "e" in the cgRNA is constrained to a wild-type subsequence of the standard gRNA. In some embodiments, a partial subsequence of domain "f" in the cgRNA is constrained to a wild-type subsequence of the standard gRNA. In some embodiments, domain "d*" in the trigger is optional. In some embodiments, domain "e*" in the trigger is optional. In some embodiments, the extended terminator loop comprises or comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values.

Allosteric OFF→ON Terminator Switch cgRNAs (Mechanism 1B)

Figure 5A:
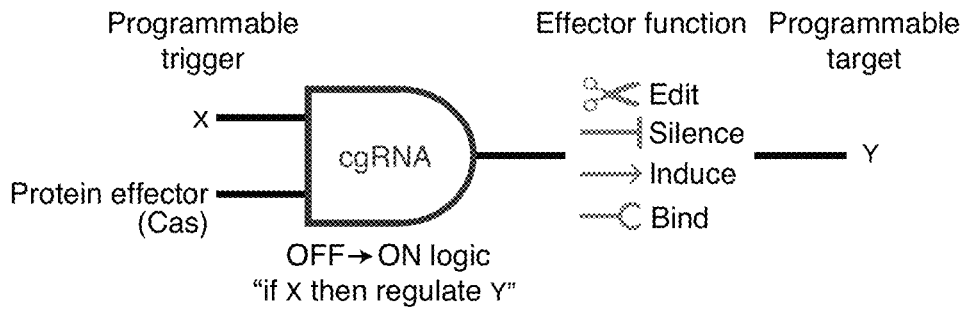
FIGS. 5A-5C depict the logic, function, and mechanism of allosteric OFF→ON terminator switch cgRNAs (Mechanism 1B).
Figure 5B:
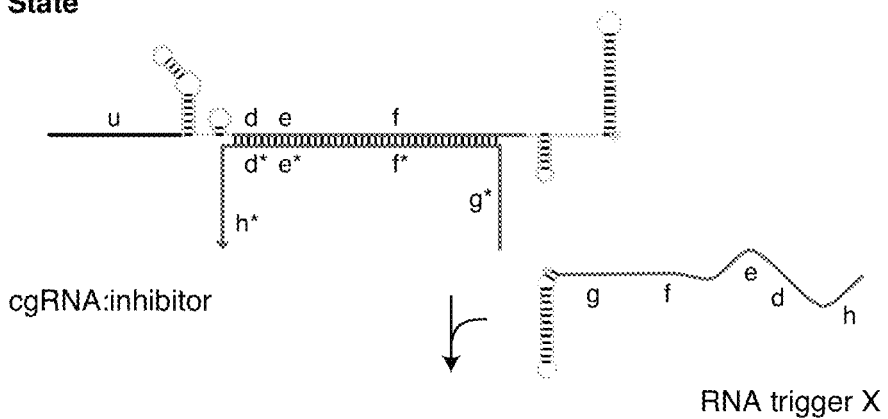
Figure 5B:
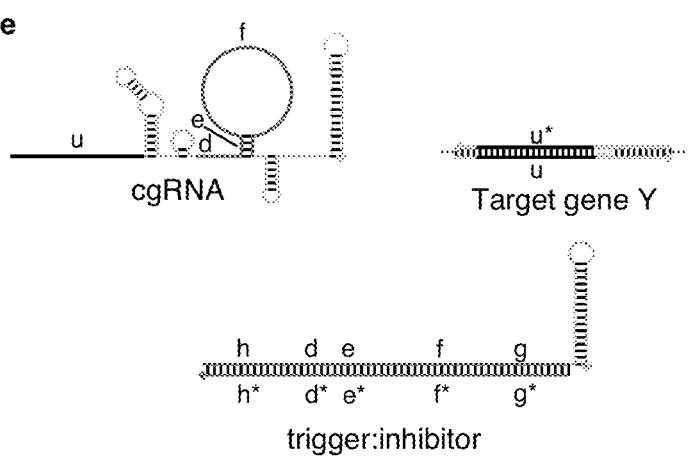
Figure 5C:
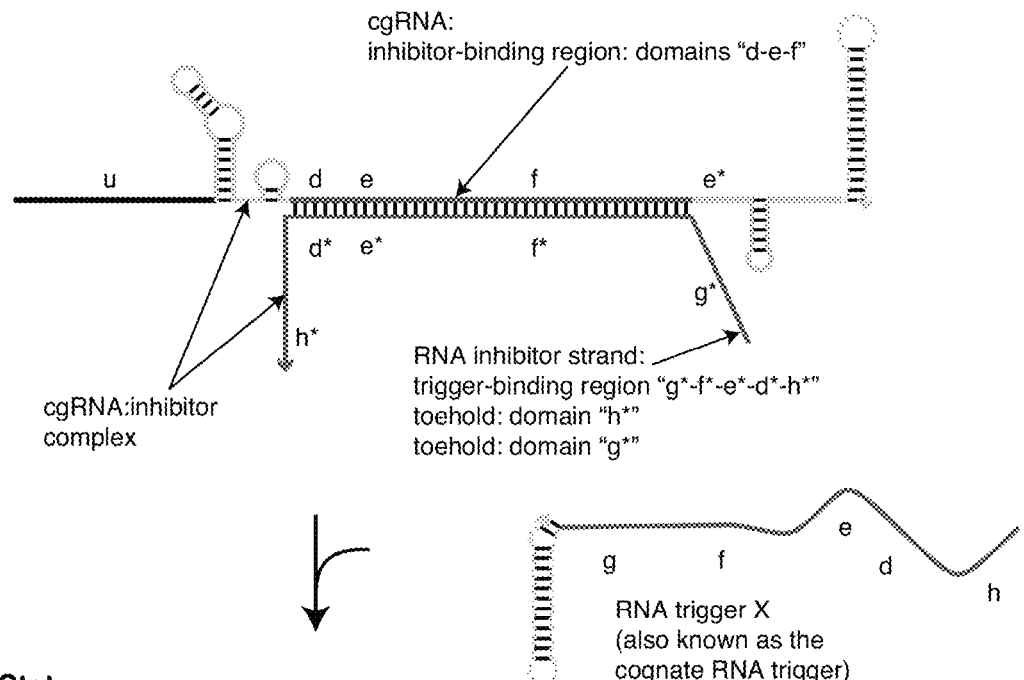
Figure 5C:
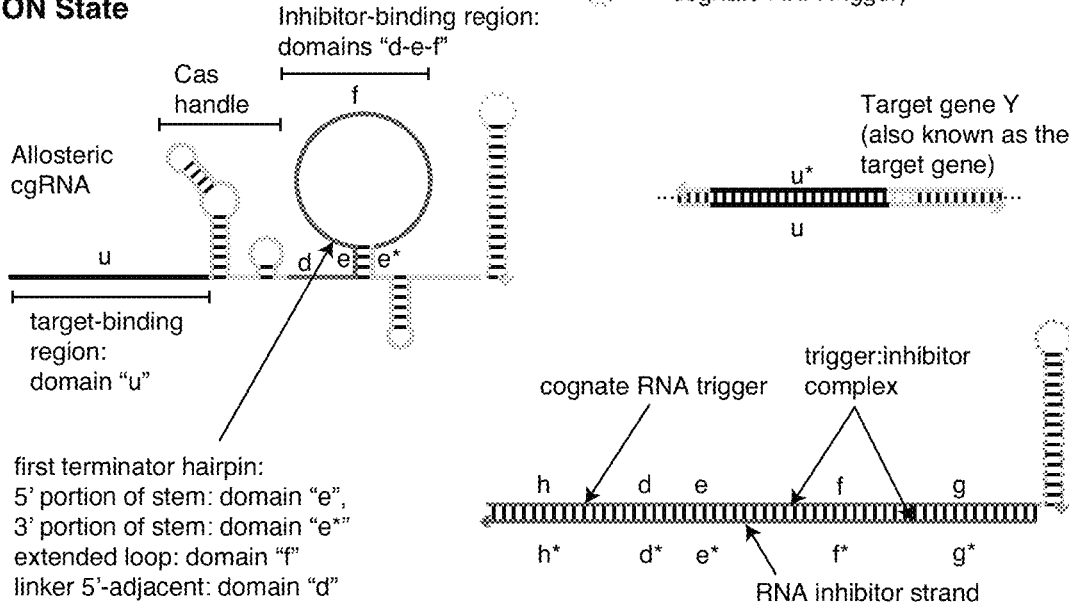

In some embodiments, allosteric OFF→ON cgRNA logic (FIG. 5A) is implemented using an allosteric OFF→ON terminator switch cgRNA mechanism (FIGS. 5B and 5C). The OFF→ON terminator switch cgRNA of FIGS. 5B and 5C is conditionally activated by RNA trigger X (the cognate RNA trigger), which binds to the inhibitor to remove the inhibitor from the cgRNA. Compared to a standard gRNA (FIG. 1), in some embodiments the OFF→ON terminator switch cgRNA has a modified terminator region with an extended loop and rationally designed sequence domains "d-e-f". In some embodiments, the cgRNA comprises a target-binding region (domain "u"), a Cas handle, an inhibitor-binding region (domains "d-e-f"), a first terminator hairpin, and a linker 5'-adjacent to the first terminator hairpin (domain "d"); wherein the first terminator hairpin comprises a 5' portion of the stem (domain "e"), a 3' portion of the stem (domain "e*"), and an extended loop (domain "f"). In some embodiments, the RNA inhibitor strand comprises a trigger-binding region (domains "g*-f*-e*-d*-h*") and a toehold at one or both ends (domains "g*" and/or "h*"). In some embodiments, in the OFF state, the inhibitor is hybridized to the inhibitor-binding region of the cgRNA (forming the cgRNA:inhibitor complex) to disrupt the structure of the first terminator hairpin and form a structure incompatible with cgRNA mediation of Cas9, dCas9, and/or Cas function. In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "g*" on the inhibitor, and then hybridizes to domains "f*-e*-d*-h*" to displace the inhibitor from the cgRNA (forming the trigger:inhibitor complex). In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "h*" on the inhibitor, and then hybridizes to domains "d*", "e*", "f*", and "g*" to displace the inhibitor from the cgRNA (forming the trigger:inhibitor complex). In some embodiments, domain "g" in the trigger is optional. In some embodiments, domain "g*" in the inhibitor is optional. In some embodiments, domain "h" in the trigger is optional. In some embodiments, domain "h*" in the inhibitor is optional. In some embodiments, the mechanism is allosteric because the inhibitor down-regulates cgRNA:Cas function not by sequestering the target-binding region (domain "u" in FIGS. 5B and 5C), but by hybridizing to the distal terminator region comprising domains "d-e-f" in FIGS. 5B and 5C. As a result, the sequence of the RNA trigger X (which binds to the inhibitor to up-regulate cgRNA:Cas function) is independent of domain "u", yielding full sequence independence between trigger X and regulatory target Y (the target gene). In some embodiments, the extended terminator loop comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, a toehold domain comprises, consists, or consists essentially of 4 nt, or 10 nt, or 20 nt, or 30 nt, or 40 nt, or 50 nt, or 100 nt, or 200 nt, or more, or any number of nucleotides intermediate to any of the preceding values.

Allosteric ON→OFF Splinted Switch cgRNAs (Mechanism 2A)

Figure 6A:
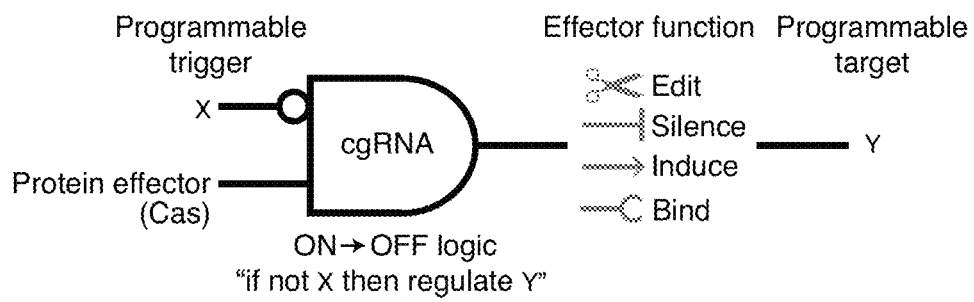
FIGS. 6A-6C depict the logic, function, and mechanism of allosteric ON→OFF splinted switch cgRNAs (Mechanism 2A).
Figure 6B:
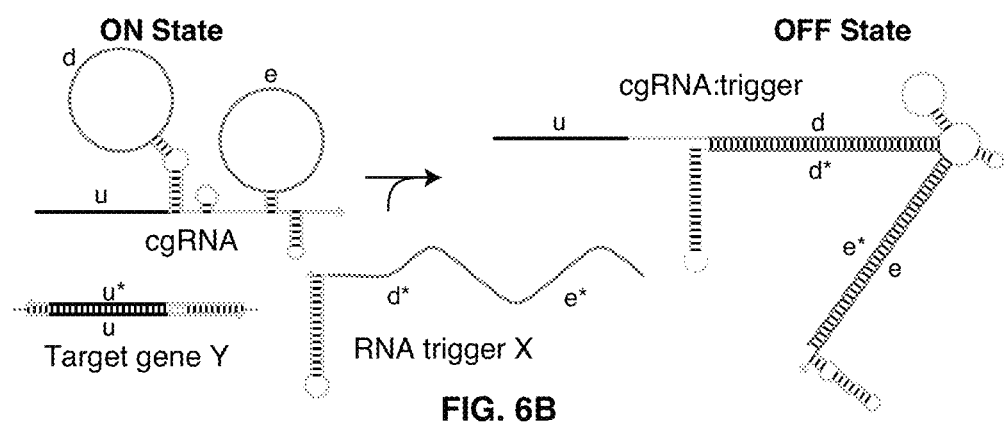
Figure 6C:
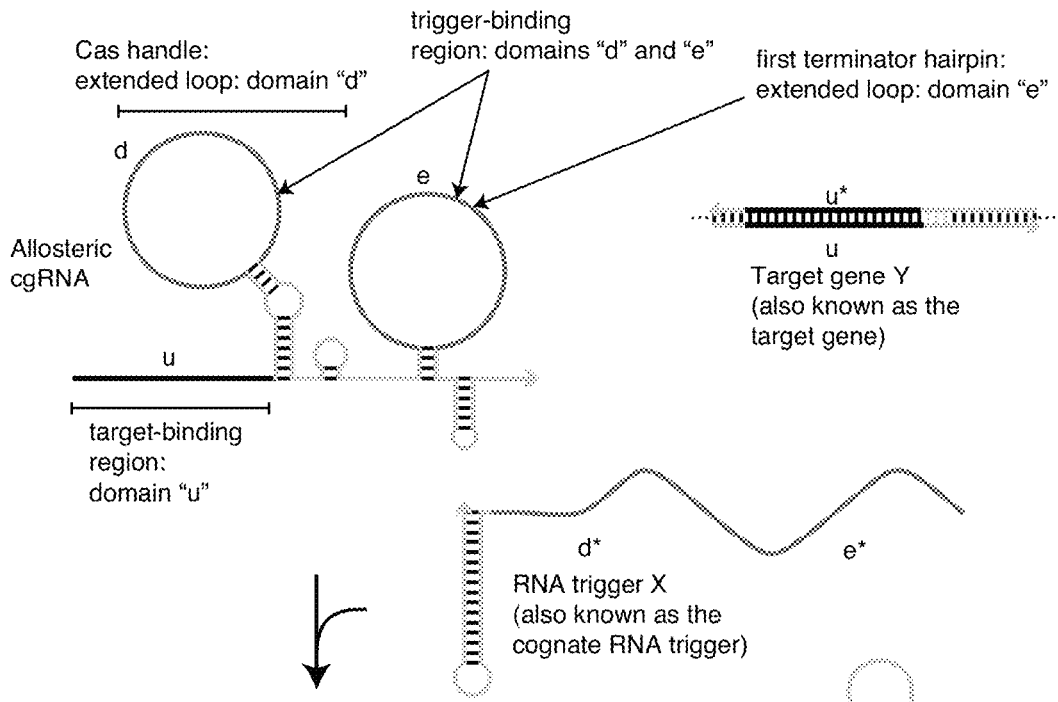
Figure 6C:
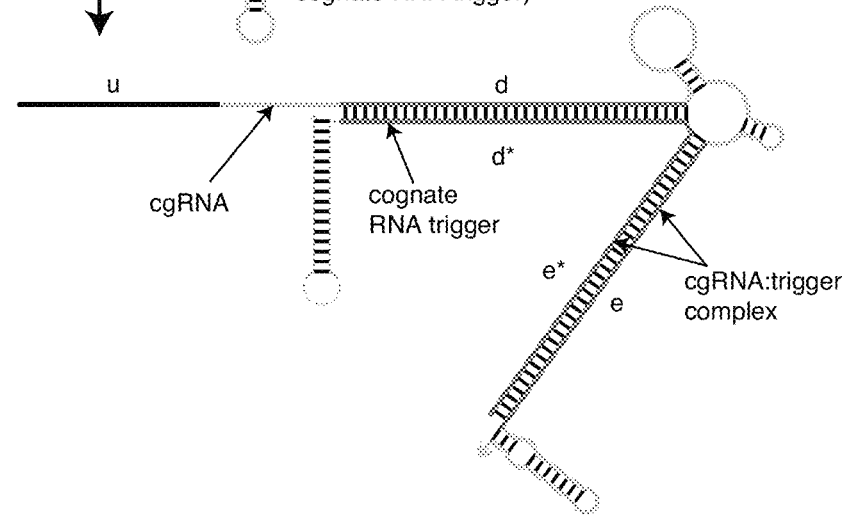
Figure 10B:
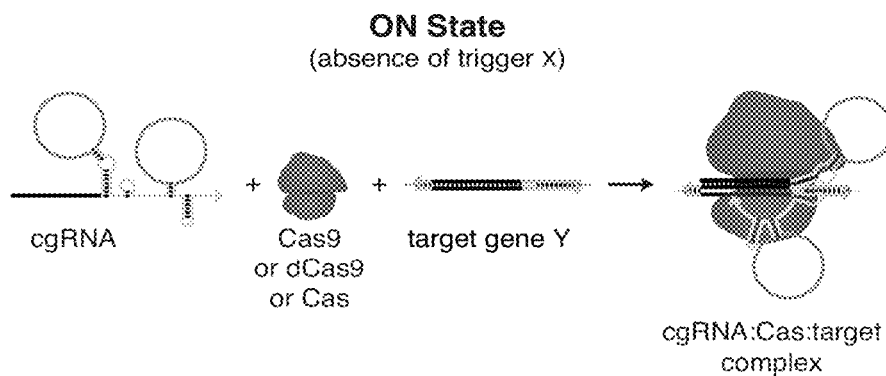
Figure 10B:
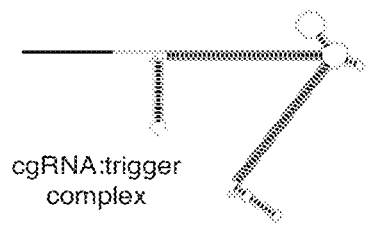

In some embodiments, allosteric ON→OFF cgRNA logic (FIG. 6A) is implemented using an allosteric ON→OFF splinted switch cgRNA mechanism (FIGS. 6B and 6C). The ON→OFF splinted switch cgRNA of FIGS. 6B and 6C is conditionally inactivated by RNA trigger X (the cognate RNA trigger). Compared to a standard gRNA (FIG. 1), in some embodiments the ON→OFF splinted switch cgRNA has extended loops in both the Cas9 handle (domain "d") and terminator (domain "e"). In some embodiments, the cgRNA comprises a target-binding region (domain "u"), a Cas handle with an extended loop (domain "d"), a trigger binding region (domains "d" and "e"), and a first terminator hairpin with an extended loop (domain "e"). In some embodiments, to toggle to the OFF state, hybridization of RNA trigger X (the cognate RNA trigger) to the trigger-binding region of the cgRNA (forming the cgRNA:trigger complex) disrupts the structure of the Cas handle and the first terminator hairpin to form a structure incompatible with cgRNA mediation of Cas9, dCas9, and/or Cas function (FIG. 10B). In some embodiments, the mechanism is allosteric because the trigger down-regulates cgRNA:Cas function by hybridizing to extended loops (domains "d" and "e" in FIGS. 6B and 6C) distal to the target-binding region (domain "u" in FIGS. 6B and 6C). The resulting full sequence independence between RNA trigger X (the cognate RNA trigger) and target gene Y (the target gene) provides the flexibility for X to control regulatory scope (also known as the scope of activity) independent of the choice of Y. In some embodiments, the extended Cas handle comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, the extended terminator loop comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values.

Allosteric OFF→ON Splinted Switch cgRNAs (Mechanism 2B)

Figure 7A:
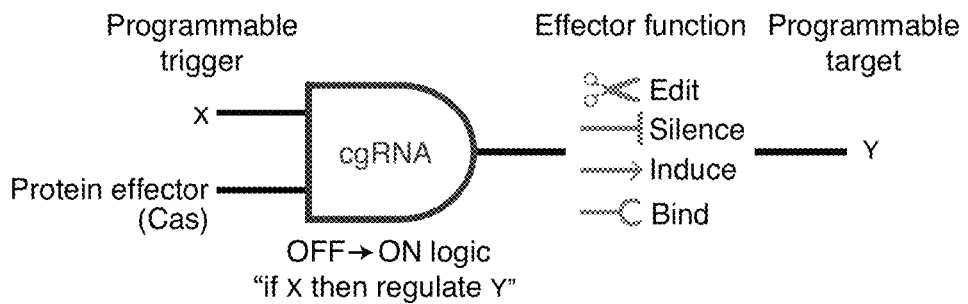
FIGS. 7A-7C depict the logic, function, and mechanism of allosteric OFF→ON splinted switch cgRNAs (Mechanism 2B).
Figure 7B:
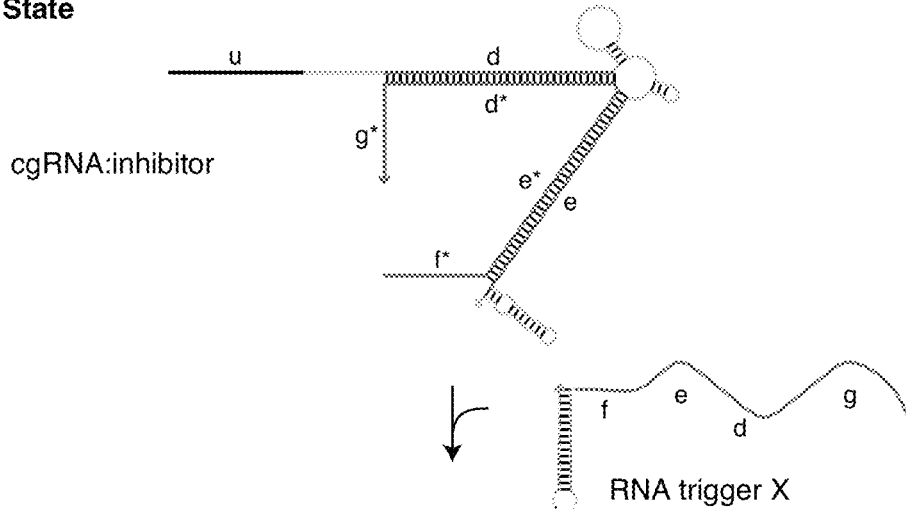
Figure 7B:
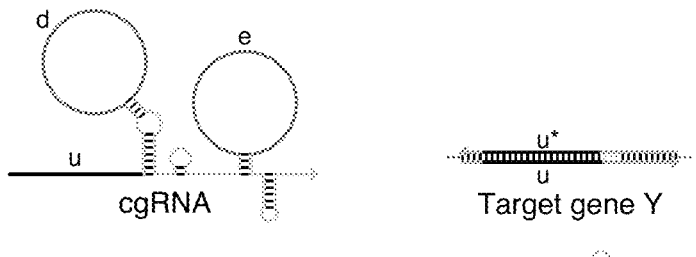
Figure 7B:
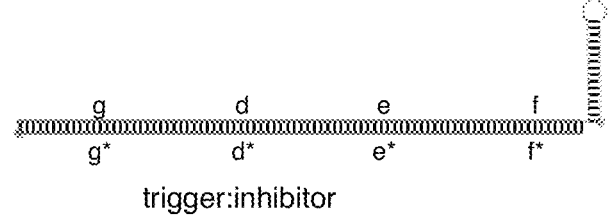
Figure 7C:
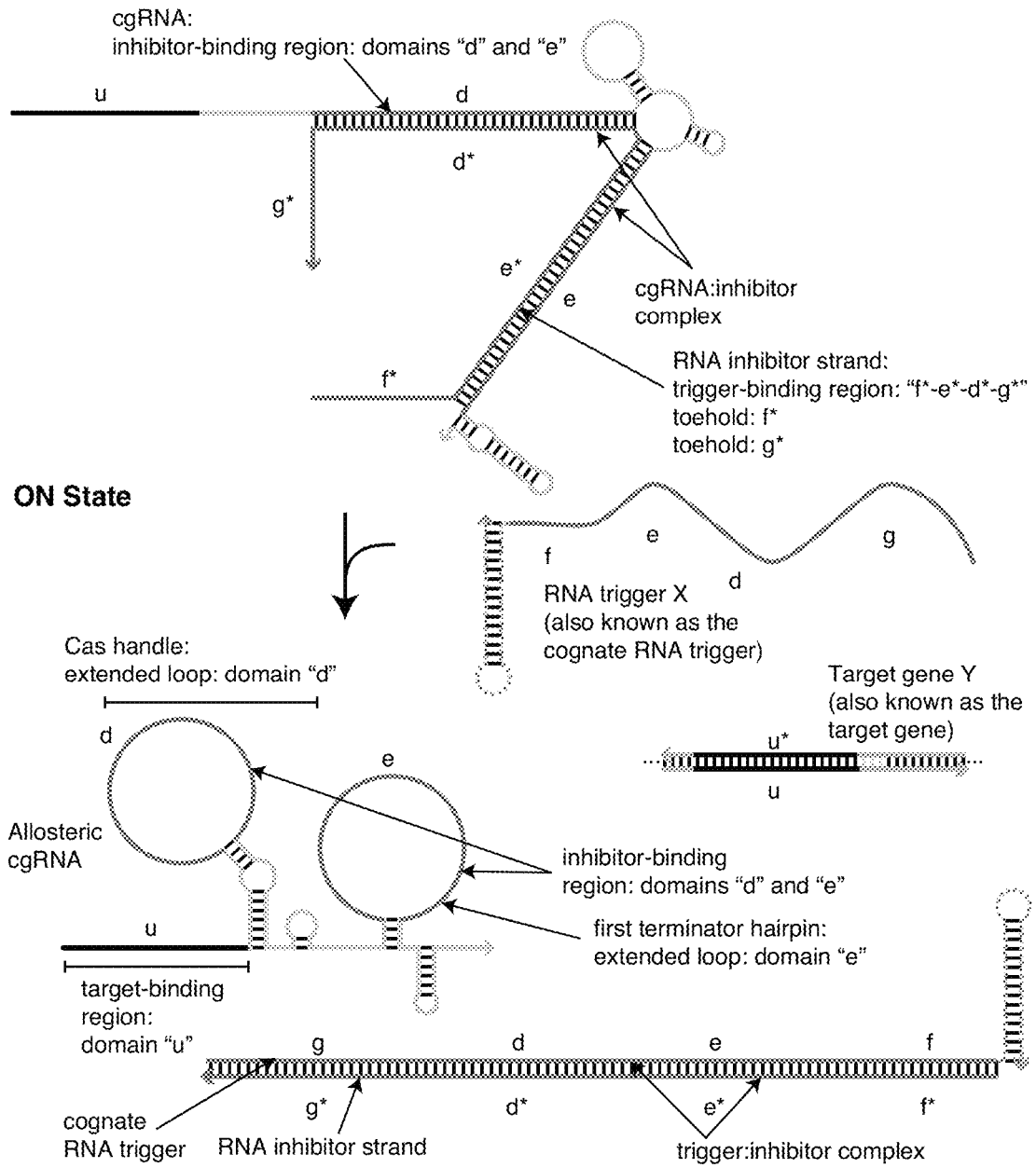

In some embodiments, allosteric OFF→ON cgRNA logic (FIG. 7A) is implemented using an allosteric OFF→ON splinted switch cgRNA mechanism (FIGS. 7B and 7C). The OFF→ON splinted switch cgRNA of FIGS. 7B and 7C is conditionally activated by RNA trigger X (the cognate RNA trigger), which binds to the inhibitor to remove the inhibitor from the cgRNA. Compared to a standard gRNA (FIG. 1), in some embodiments, the OFF→ON splinted switch cgRNA has extended loops in both the Cas9 handle (domain "d") and terminator (domain "e"). In some embodiments, the cgRNA comprises a target-binding region (domain "u"), a Cas handle with an extended loop (domain "d"), an inhibitor-binding region (domains "d" and "e"), and a first terminator hairpin with an extended loop (domain "e"). In some embodiments, the RNA inhibitor strand comprises a trigger-binding region (domains "f*-e*-d*-g*") and a toehold at one or both ends (domains "f*" and/or "g*"). In some embodiments, in the OFF state, the inhibitor is hybridized to the inhibitor-binding region of the cgRNA (forming the cgRNA:inhibitor complex) to disrupt the structure of the Cas handle and the first terminator hairpin and form a structure incompatible with cgRNA mediation of Cas9, dCas9, and/or Cas function. In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "f*" on the inhibitor, and then hybridizes to domains "e*-d*-g*" to displace the inhibitor from the cgRNA (forming the trigger:inhibitor complex). In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "g*" on the inhibitor, and then hybridizes to domains "d*", "e*" and "f*" to displace the inhibitor from the cgRNA (forming the trigger:inhibitor complex). In some embodiments, domain "f" in the trigger is optional. In some embodiments, domain "f*" in the inhibitor is optional. In some embodiments, domain "g" in the trigger is optional. In some embodiments, domain "g*" in the inhibitor is optional. In some embodiments, the mechanism is allosteric because the inhibitor down-regulates cgRNA:Cas function by hybridizing to extended loops (domains "d" and "e" in FIGS. 7B and 7C) distal to the target-binding region (domain "u" in FIGS. 7B and 7C). As a result, the sequence of the RNA trigger X (which binds to the inhibitor to up-regulate cgRNA:Cas function) is independent of domain "u", yielding full sequence independence between trigger X (the cognate RNA trigger) and regulatory target Y (the target gene). In some embodiments, the extended Cas handle comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, the extended terminator loop comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, a toehold domain comprises, consists, or consists essentially of 4 nt, or 10 nt, or 20 nt, or 30 nt, or 40 nt, or 50 nt, or 100 nt, or 200 nt, or more, or any number of nucleotides intermediate to any of the preceding values.

Allosteric ON→OFF Tandem Switch cgRNAs (Mechanism 3A)

Figure 23A:
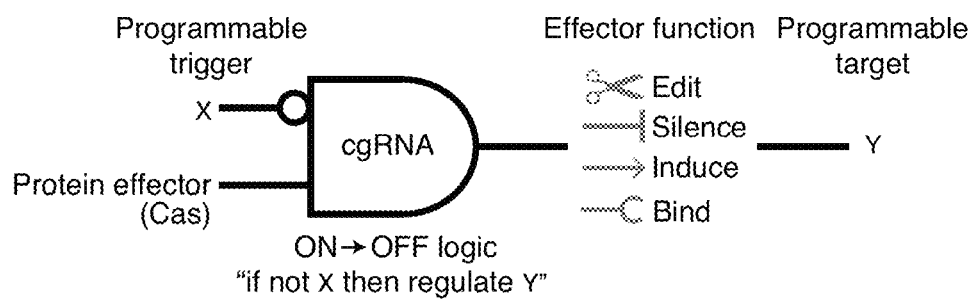
FIGS. 23A-23C depict the logic, function, and mechanism of allosteric ON→OFF tandem switch cgRNAs (Mechanism 3A).
Figure 23B:
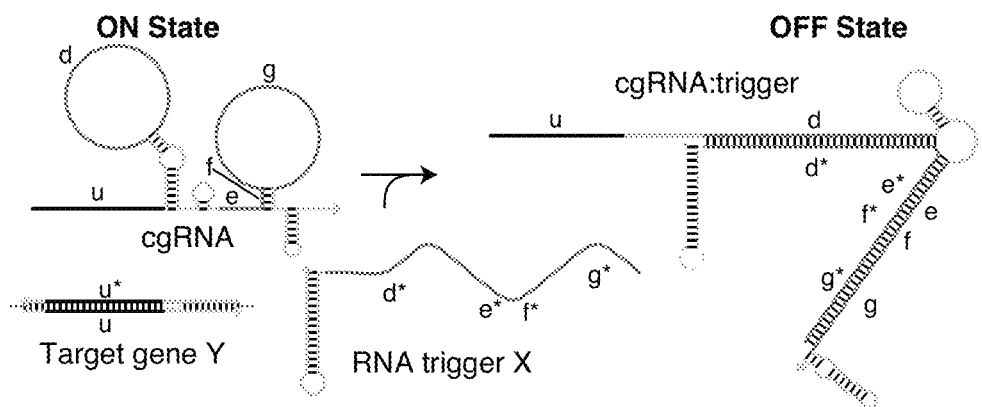
Figure 23C:
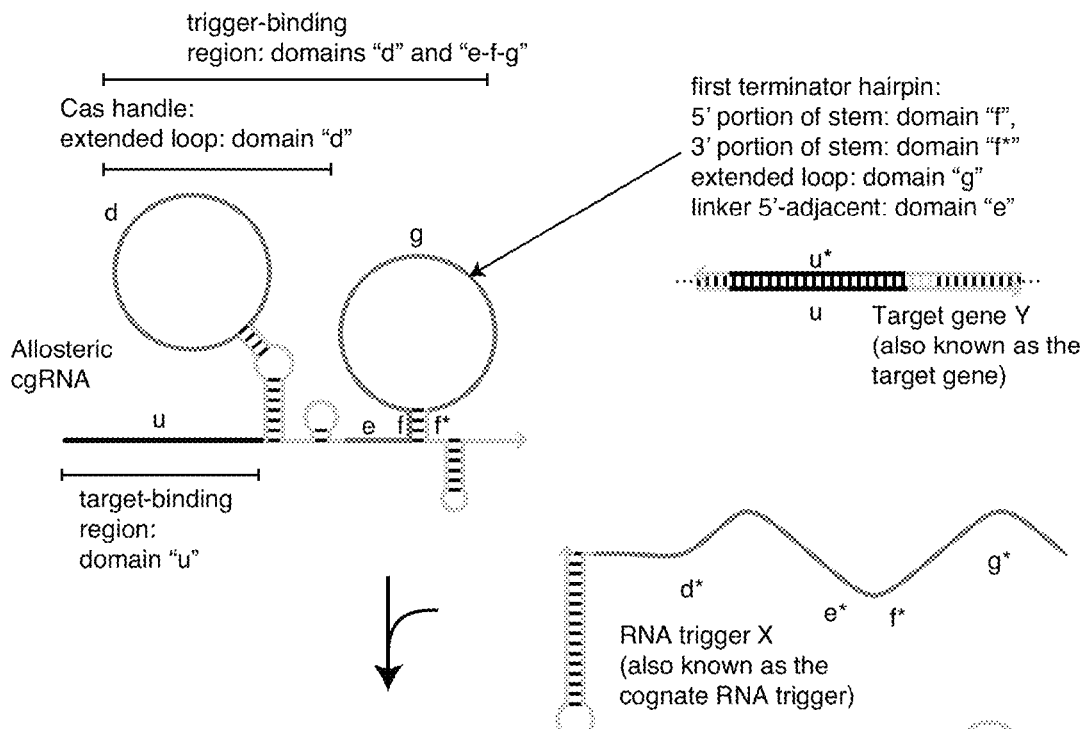
Figure 23C:
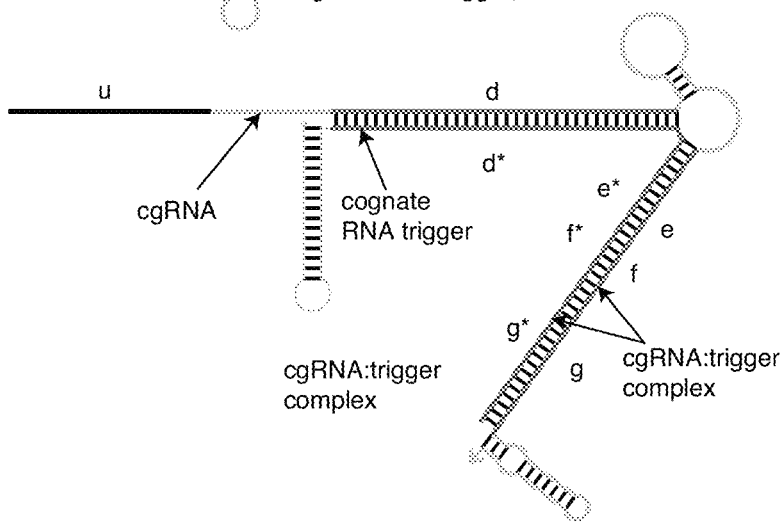

In some embodiments, allosteric ON→OFF cgRNA logic (FIG. 23A) is implemented using an allosteric ON→OFF tandem switch cgRNA mechanism (FIGS. 23B and 23C). The ON→OFF terminator switch cgRNA of FIGS. 23B and 23C is conditionally inactivated by RNA trigger X (the cognate RNA trigger). Compared to a standard gRNA (FIG. 1), in some embodiments the ON→OFF tandem switch cgRNA has an extended loop in the Cas9 handle (domain "d") and a modified terminator region with an extended loop and rationally designed sequence domains "e-f-g". In some embodiments, the cgRNA comprises a target-binding region (domain "u"), a Cas handle with an extended loop (domain "d"), a trigger-binding region (domain "d" and "e-f-g"), a first terminator hairpin, and a linker 5'-adjacent to the first terminator hairpin (domain "e"); wherein the first terminator hairpin comprises a 5' portion of the stem (domain "f"), a 3' portion of the stem (domain "f*"), and an extended loop (domain "g"). In some embodiments, to toggle to the OFF state, hybridization of the RNA trigger X (the cognate RNA trigger) to the trigger-binding region of the cgRNA (forming the cgRNA:trigger complex) disrupts the structure of the Cas handle and the first terminator hairpin to form a structure incompatible with cgRNA mediation of Cas9, dCas9, and/or Cas function. In some embodiments, the mechanism is allosteric because the trigger down-regulates cgRNA:Cas function not by sequestering the target-binding region (domain "u" in FIGS. 23B and 23C), but by hybridizing to the distal trigger-binding region (domain "d" and domains "e-f-g" in FIGS. 23B and 23C). Hence, the sequences of the RNA trigger X (the cognate RNA trigger) and the regulatory target Y (the target gene) are fully independent. In some embodiments, domain "e" in the cgRNA is constrained to a wild-type subsequence of the standard gRNA. In some embodiments, domain "f" in the cgRNA is constrained to a wild-type subsequence of the standard gRNA. In some embodiments, a partial subsequence of domain "g" in the cgRNA is constrained to a wild-type subsequence of the standard gRNA. In some embodiments, a partial subsequence of domain "d" in the cgRNA is constrained to a wild-type subsequence of the standard gRNA. In some embodiments, domain "e*" in the trigger is optional. In some embodiments, domain "f*" in the trigger is optional. In some embodiments, the extended Cas handle comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, the extended terminator loop comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values.

Allosteric OFF→ON Tandem Switch cgRNAs (Mechanism 3B)

Figure 24A:
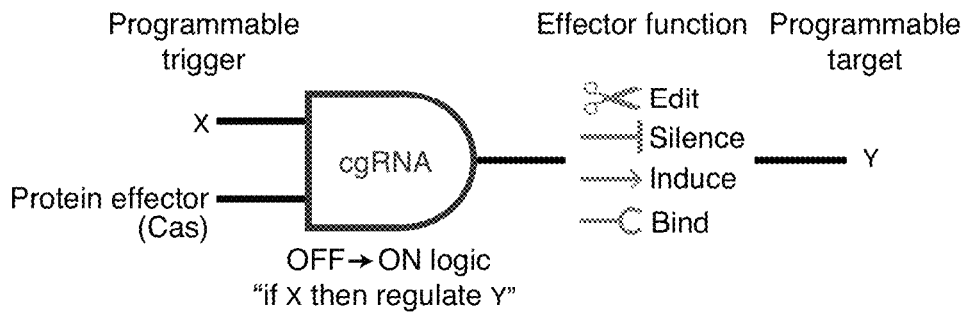
FIGS. 24A-24C depict the logic, function, and mechanism of allosteric OFF→ON tandem switch cgRNAs (Mechanism 3B).
Figure 24B:
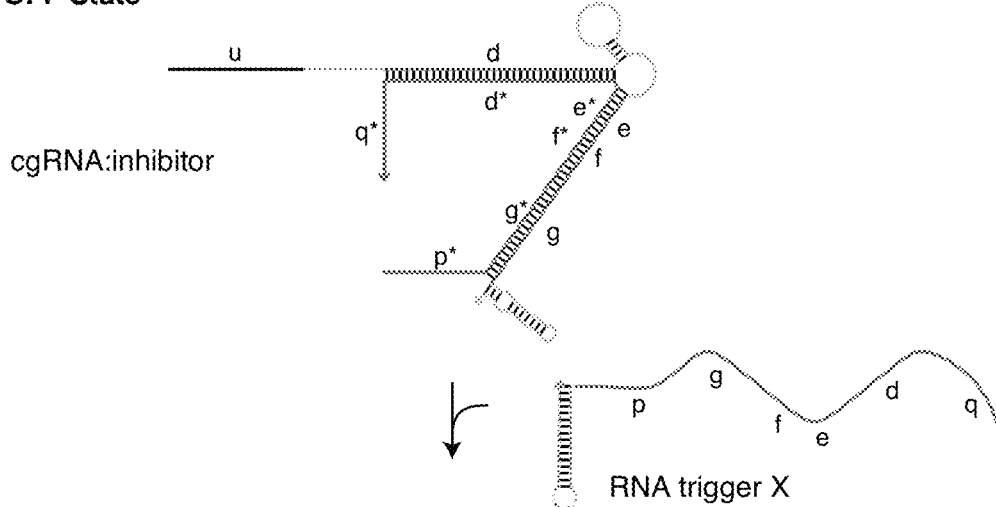
Figure 24B:
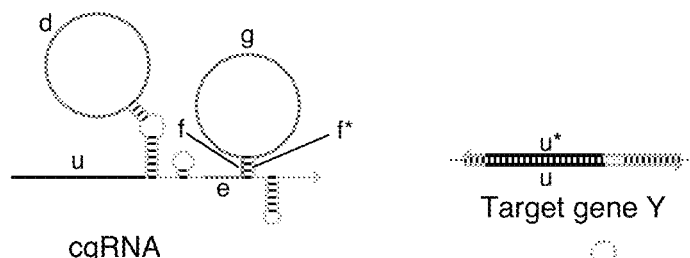
Figure 24B:
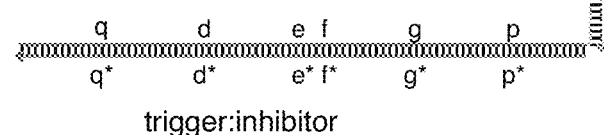
Figure 24C:
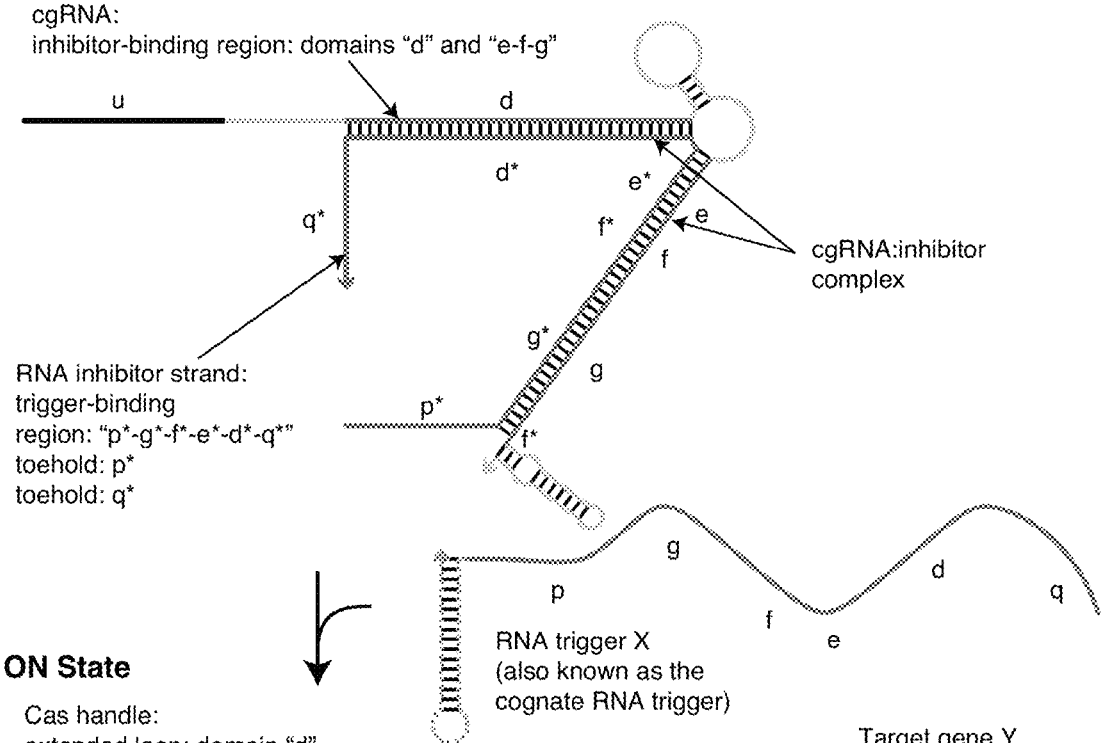
Figure 24C:
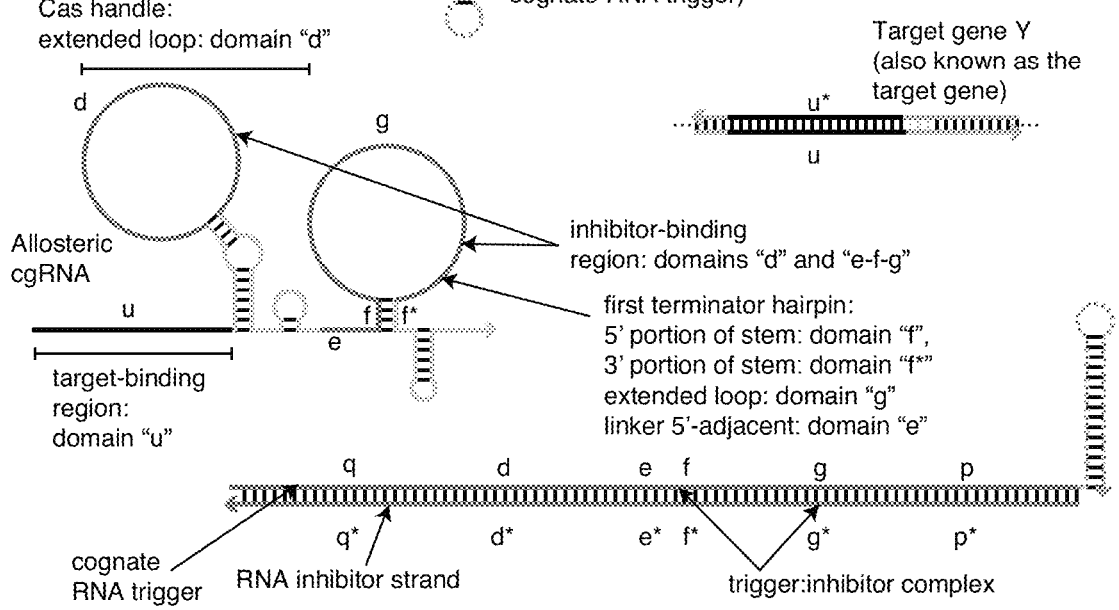

In some embodiments, allosteric OFF→ON cgRNA logic (FIG. 24A) is implemented using an allosteric OFF→ON tandem switch cgRNA mechanism (FIGS. 24B and 24C). The OFF→ON tandem switch cgRNA of FIGS. 24B and 24C is conditionally activated by RNA trigger X (the cognate RNA trigger), which binds to the inhibitor to remove the inhibitor from the cgRNA. Compared to a standard gRNA (FIG. 1), in some embodiments the OFF→ON tandem switch cgRNA has an extended loop in the Cas9 handle (domain "d") and a modified terminator region with an extended loop and rationally designed sequence domains "e-f-g". In some embodiments, the cgRNA comprises a target-binding region (domain "u"), a Cas handle with an extended loop (domain "d"), an inhibitor-binding region (domains "d" and "e-f-g"), a first terminator hairpin, and a linker 5'-adjacent to the first terminator hairpin (domain "e"); wherein the first terminator hairpin comprises a 5' portion of the stem (domain "f"), a 3' portion of the stem (domain "f*"), and an extended loop (domain "g"). In some embodiments, the RNA inhibitor strand comprises a trigger-binding region (domains "p*-g*-f*-e*-d*-q*") with a toehold at one or both ends (domains "p*" and/or "q*"). In the OFF state, the inhibitor is hybridized to the inhibitor-binding region of the cgRNA (forming the cgRNA:inhibitor complex) to disrupt the structure of the Cas handle and the first terminator hairpin and form a structure incompatible with cgRNA mediation of Cas9, dCas9, and/or Cas function. In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "p*" on the inhibitor, and then hybridizes to domains "g*-f*-e*-d*-q*" to displace the inhibitor from the cgRNA (forming the trigger:inhibitor complex). In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "q*" on the inhibitor, and then hybridizes to domains "d*", "e*", "f*", "g*", and "p*" to displace the inhibitor from the cgRNA (forming the trigger:inhibitor complex). In some embodiments, domain "p" in the trigger is optional. In some embodiments, domain "p*" in the inhibitor is optional. In some embodiments, domain "q" in the trigger is optional. In some embodiments, domain "q*" in the inhibitor is optional. In some embodiments, the mechanism is allosteric because the inhibitor down-regulates cgRNA:Cas function not by sequestering the target-binding region (domain "u" in FIGS. 24B and 24C), but by hybridizing to the distal terminator region comprising domains "d" and "e-f-g" in FIGS. 24B and 24C. As a result, the sequence of the RNA trigger X (which binds to the inhibitor to up-regulate cgRNA:Cas function) is independent of domain "u", yielding full sequence independence between trigger X (the cognate RNA trigger) and regulatory target Y (the target gene). In some embodiments, the extended Cas handle comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, the extended terminator loop comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, a toehold domain comprises, consists, or consists essentially of 4 nt, or 10 nt, or 20 nt, or 30 nt, or 40 nt, or 50 nt, or 100 nt, or 200 nt, or more, or any number of nucleotides intermediate to any of the preceding values.

Allosteric OFF→ON Split-Terminator Switch cgRNAs (Mechanism 4A)

Figure 8A:
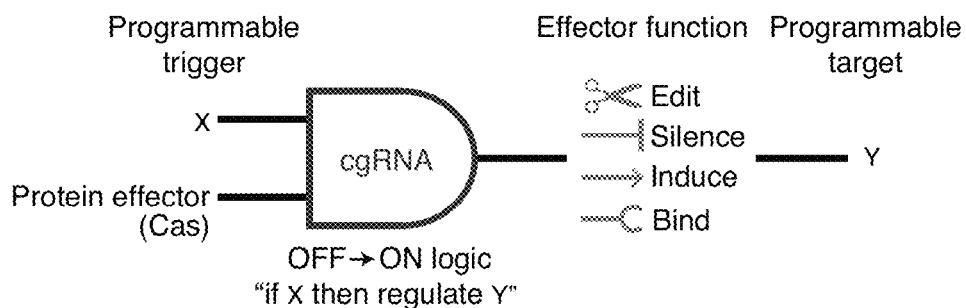
FIGS. 8A-8C depict the logic, function, and mechanism of allosteric OFF→ON split-terminator switch cgRNAs (Mechanism 4A).
Figure 8B:
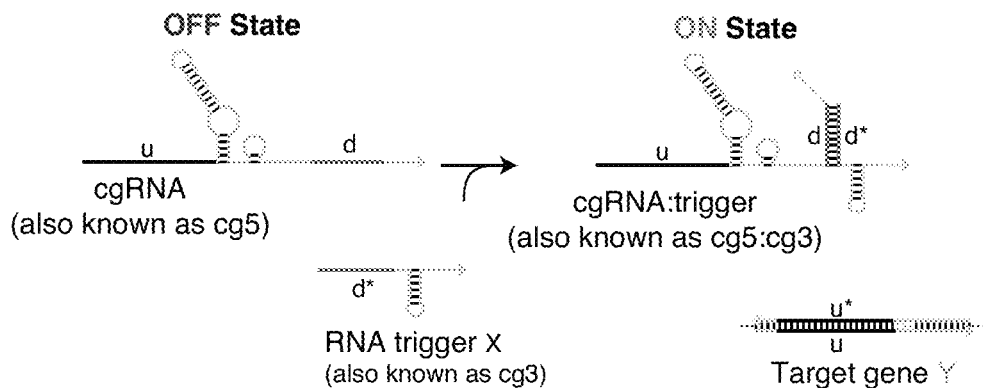
Figure 8C:
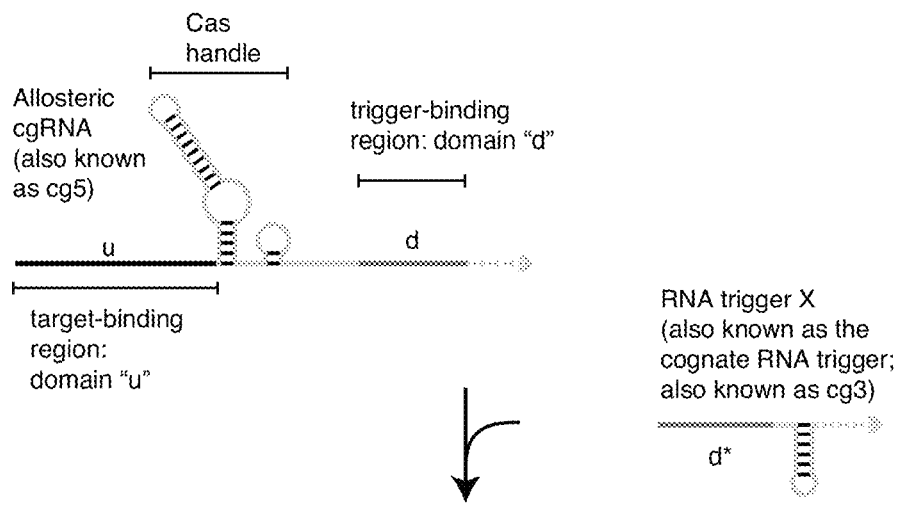
Figure 8C:
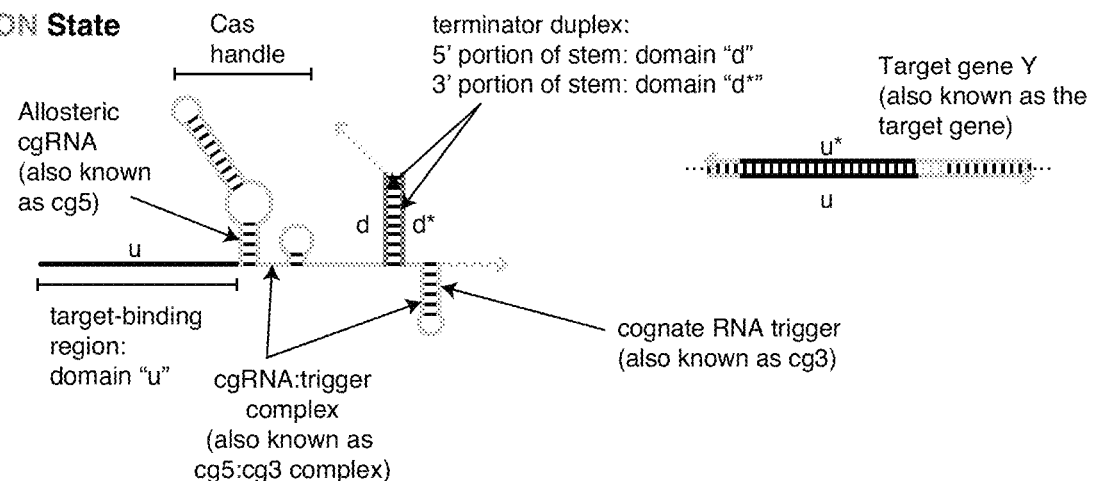
Figure 10C:
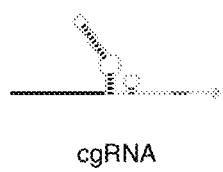
Figure 10C:
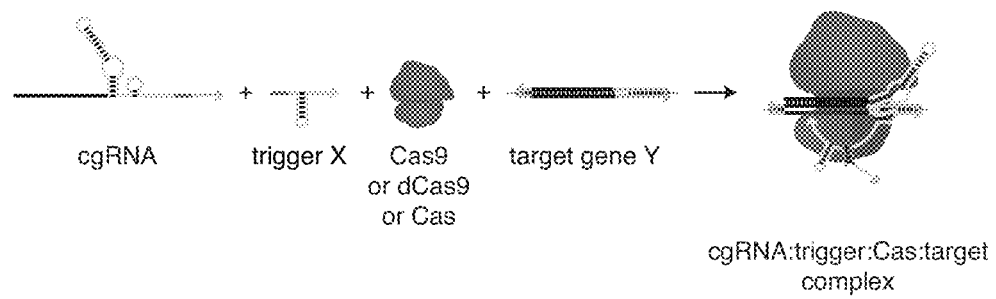

In some embodiments, allosteric OFF→ON cgRNA logic (FIG. 8A) is implemented using an allosteric OFF→ON split-terminator switch cgRNA mechanism (FIGS. 8B and 8C). The OFF→ON split-terminator switch cgRNA of FIGS. 8B and 8C is conditionally activated by RNA trigger X (the cognate RNA trigger). Equivalently, the cgRNA may be interpreted as a 5' fragment (cg5) and the trigger may be interpreted as a 3' fragment (cg3), such that cg5 and cg3 are inactive when not bound to each other, but such that upon binding to each other to form the complex cg5:cg3, this complex constitutes an activated conditional guide RNA capable of mediating Cas9, dCas9, and/or Cas function. Compared to a standard gRNA (FIG. 1), in some embodiments the OFF→ON split-terminator switch cgRNA (also known as cg5) is incomplete, containing only one half of the stem region of the 5' terminator hairpin (sequence domain "d"). In some embodiments, the cgRNA (also known as cg5) comprises a target-binding region (domain "u"), a Cas handle, and a trigger-binding region (domain "d"). In some embodiments, to toggle to the ON state, hybridization of the RNA trigger X (the cognate RNA trigger; also known as cg3) to the trigger-binding region of the cgRNA (also known as cg5) to form the cgRNA:trigger complex (also known as the cg5:cg3 complex) yields a terminator duplex that activates the cgRNA (or equivalently yields a terminator duplex that activates the complex cg5:cg3), allowing for mediation of Cas function (FIG. 10C). In some embodiments, the terminator duplex comprises a 5' portion of the stem (domain "d") and a 3' portion of the stem (domain "d*"). In some embodiments, the mechanism is allosteric because the trigger (also known as cg3) and cgRNA (also known as cg5) interact via a terminator duplex (domains "d" and "d*" in FIGS. 8B and 8C) distal to the target-binding region (domain "u" in FIGS. 8B and 8C). The resulting full sequence independence between RNA trigger X (the cognate RNA trigger; also known as cg3) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, or 6 bp, or 8 bp, or 10 bp, or 20 bp, or 30 bp, or 40 bp, or 50 bp, or 100 bp, or 200 bp, or more, or any number of base pairs intermediate to any of the preceding values.

In some embodiments, the cgRNA (also known as cg5) comprises one or more substrate domains 5'-adjacent to domain "d" and the cognate RNA trigger (also known as cg3) comprises one or more substrate domains 5'-adjacent to domain "d*". In some embodiments, an additional bridge strand hybridizes to a substrate on the cgRNA (also known as cg5) and to a substrate on the helper strand (also known as cg3) for the purpose of holding the cgRNA (also known as cg5) and helper strand (also known as cg3) together in a complex (cg5:cg3:bridge). In some embodiments, an inhibitor strand hybridizes to one or more substrates on the cgRNA (also known as cg5) and one or more substrates on the cognate RNA trigger (also known as cg3) so as to form a junction that disrupts the structure of the terminator duplex, wherein the structure of the cgRNA:trigger:inhibitor complex (also known as the cg5:cg3:inhibitor complex) is incompatible with mediation of Cas9, dCas9, and/or Cas function. In some embodiments, the cgRNA (also known as cg5) can be activated (OFF→ON logic) by the trigger (also known as cg3) and then later inactivated by the inhibitor (ON→OFF logic) corresponding overall to (OFF→ON→OFF) logic. In some embodiments, a cgRNA can be activated and then subsequently inactivated. In some embodiments, the activity of a cgRNA can be repeatedly toggled between the OFF and ON states by successive interactions with a first trigger, a first inhibitor, a second trigger, a second inhibitor, and so on.

Allosteric ON→OFF Split-Terminator Switch cgRNAs (Mechanism 4B)

Figure 9A:
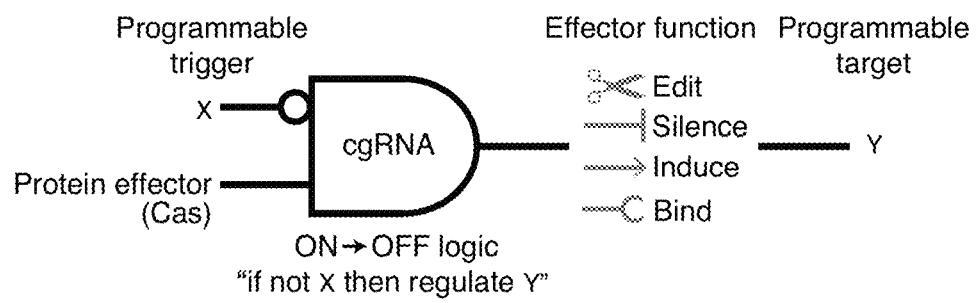
FIGS. 9A-9E depict the logic, function, and mechanism of allosteric ON→OFF split-terminator switch cgRNAs (Mechanisms 4B and 4C).
Figure 9B:
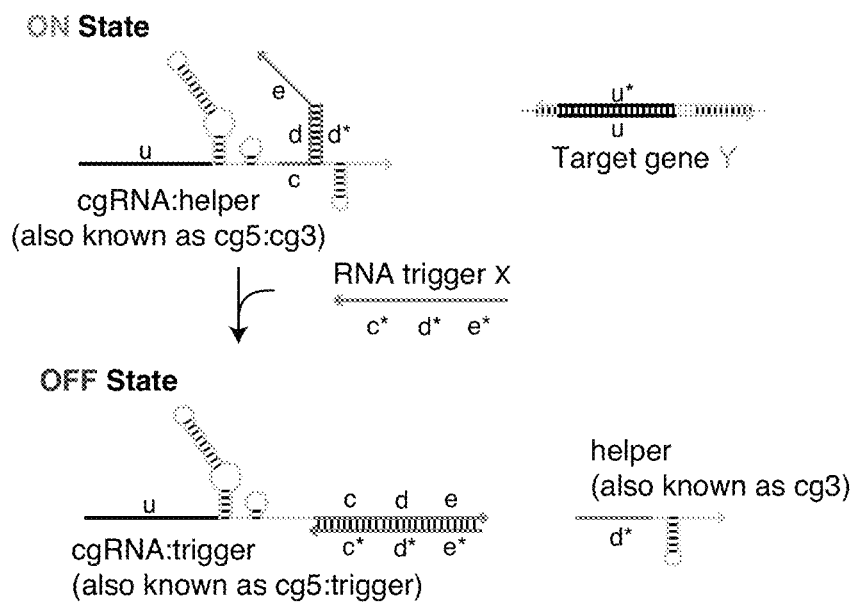
Figure 9C:
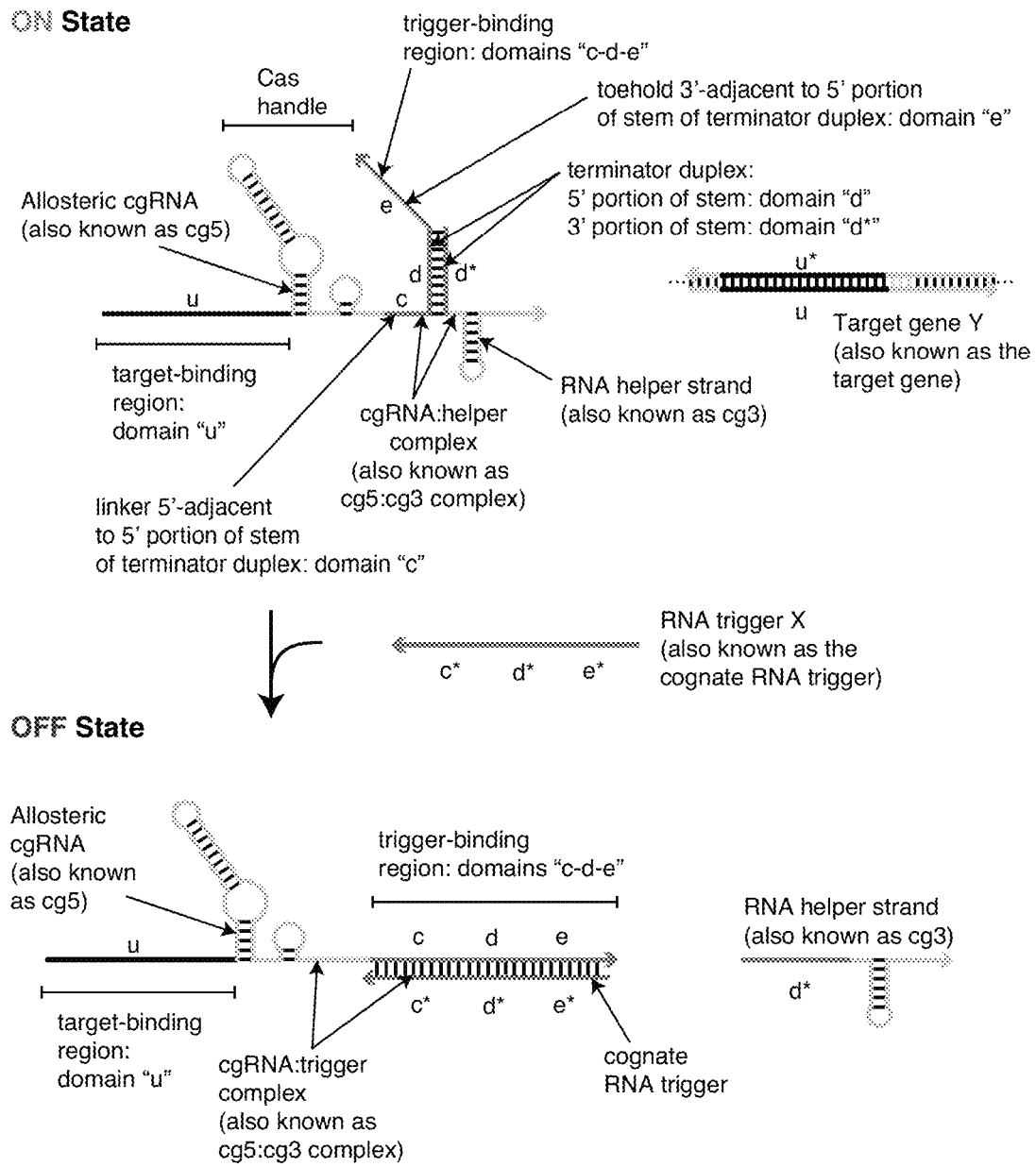

In some embodiments, allosteric ON→OFF cgRNA logic (FIG. 9A) is implemented using an allosteric ON→OFF split-terminator switch cgRNA mechanism (FIGS. 9B and 9C). In some embodiments, the ON→OFF split-terminator switch cgRNA (also known as cg5) of FIGS. 9B and 9C is conditionally inactivated by RNA trigger X (cognate RNA trigger), which binds to the cgRNA to displace the RNA helper strand (also known as cg3) and form a structure incompatible with cgRNA mediation of Cas9, dCas9, and/or Cas function. Equivalently, in some embodiments, the functional conditional guide RNA can be interpreted as a complex of two fragments (complex cg5:cg3 comprising 5'-fragment cg5 and 3'-fragment cg3; FIGS. 9B and 9C) that is conditionally inactivated by RNA trigger X (cognate RNA trigger), which binds to the complex to displace cg3 and form complex cg5:trigger, wherein both cg5:trigger and cg3 are structurally incompatible with mediation of Cas9, dCas9, and/or Cas function. Compared to a standard gRNA (FIG. 1), in some embodiments the ON→OFF split-terminator switch cgRNA (also known as cg5) is incomplete, containing only one half of the stem region of the 5' terminator hairpin (sequence domain "d"). In some embodiments, in the ON state, hybridization of the RNA helper strand (also known as cg3) to domain "d" forms a terminator duplex (domain "d" base-paired to domain "d*") such that the cgRNA:helper complex (also known as the cg5:cg3 complex) is active. In some embodiments, the cgRNA (also known as cg5) comprises a target-binding region (domain "u"), a Cas handle, and a trigger-binding region (domains "c-d-e"); wherein the trigger-binding region comprises a 5' portion of the stem of the terminator duplex (domain "d"), a linker 5'-adjacent to the 5' portion of the stem of the terminator duplex (domain "c"), and a toehold 3'-adjacent to the 5' portion of the stem of the terminator duplex (domain "e"). In some embodiments, the RNA helper strand (also known as cg3) comprises a 3' portion of the stem of the terminator duplex (domain "d*"). In some embodiments, to toggle the cgRNA (also known as cg5) to the OFF state, the RNA trigger X (cognate RNA trigger) displaces the helper (also known as cg3) from the cgRNA (also known as cg5) via toehold-mediated strand displacement in which the trigger first nucleates with the cgRNA (also known as cg5) by binding to the exposed toehold domain "e" on the cgRNA, and then hybridizes to domains "d" and "c" to displace the helper (also known as cg3) from the cgRNA (forming the cgRNA:trigger complex; also known as the cg5:trigger complex), yielding a structure with a disrupted linker (domain "c") and lacking the remainder of the terminator region present in the RNA helper strand (also known as cg3), wherein the structure is incompatible with cgRNA mediation of Cas9, dCas9, and/or Cas function. In some embodiments, to toggle the cgRNA to the OFF state, the RNA trigger X (cognate RNA trigger) displaces the helper (also known as cg3) from the cgRNA (also known as cg5) via toehold-mediated strand displacement in which the trigger first nucleates with the cgRNA (also known as cg5) by binding to the exposed toehold domain "c" (also known as the linker domain "c") on the cgRNA (also known as cg5), and then hybridizes to domains "d" and "e" to displace the helper (also known as cg3) from the cgRNA, yielding a cgRNA:trigger complex (also known as the cg5:trigger complex) that is structurally incompatible with cgRNA mediation of Cas9, dCas9, and/or Cas function. In some embodiments, the mechanism is allosteric because the cgRNA and helper interact via a terminator duplex (domains "d" and "d*" in FIGS. 9B and 9C) distal to the target-binding region (domain "u" in FIGS. 9B and 9C). As a result, the sequence of the RNA trigger X (which binds to the cgRNA domains "c-d-e" to down-regulate Cas function) is also independent of domain "u", yielding full sequence independence between trigger X (the cognate RNA trigger) and regulatory target Y (the target gene). In some embodiments, domain "c*" in the trigger is optional. In some embodiments, domain "e*" in the trigger is optional. In some embodiments, domain "e" in the cgRNA is optional. In some embodiments, domain "c" in the cgRNA is constrained to a wild-type subsequence of the standard gRNA. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values. In some embodiments, a toehold domain comprises, consists, or consists essentially of 4 nt, or 10 nt, or 20 nt, or 30 nt, or 40 nt, or 50 nt, or 100 nt, or 200 nt, or more, or any number of nucleotides intermediate to any of the preceding values.

Allosteric ON→OFF Split-Terminator Switch cgRNAs (Mechanism 4C)

Figure 9D:
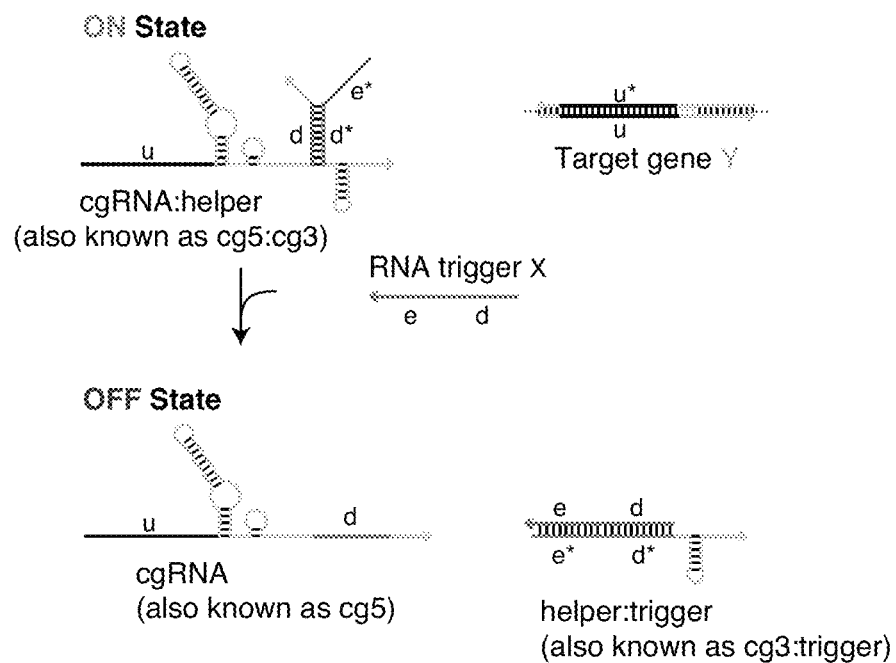
Figure 9E:
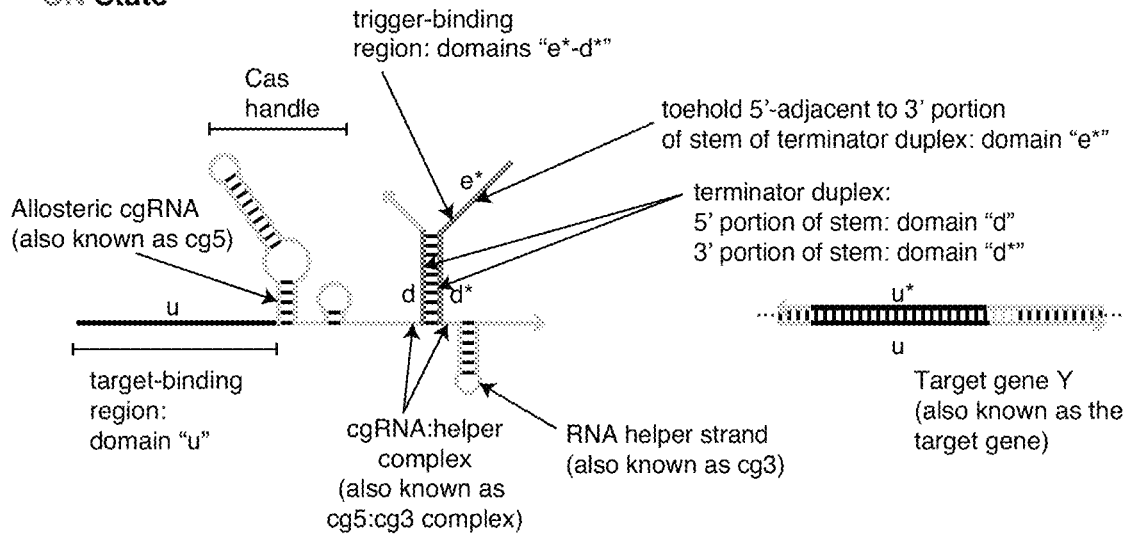
Figure 9E:
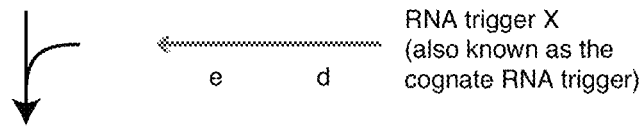
Figure 9E:
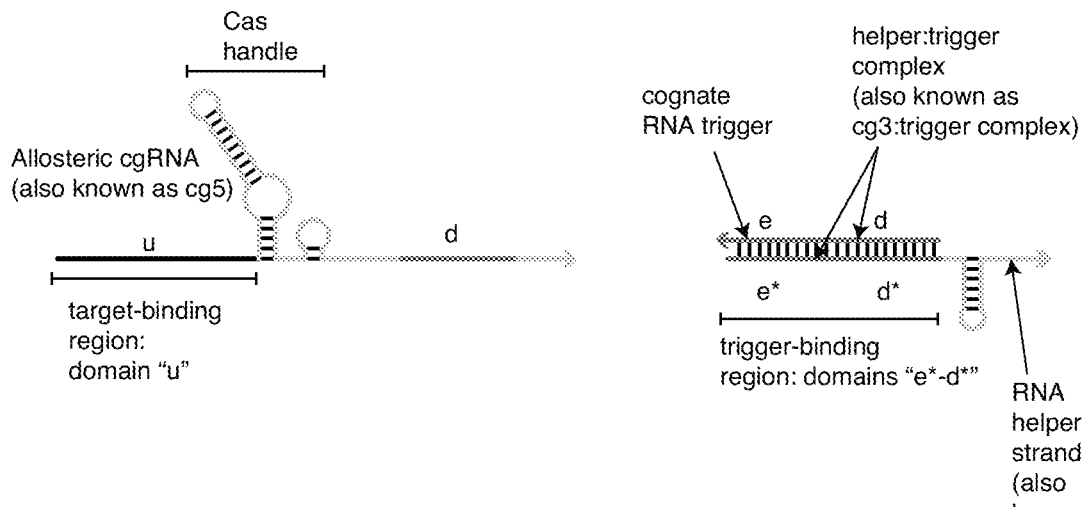

In some embodiments, allosteric ON→OFF cgRNA logic (FIG. 9A) is implemented using an allosteric ON→OFF split-terminator switch cgRNA mechanism (FIGS. 9D and 9E). In some embodiments, the ON→OFF split-terminator switch cgRNA (also known as cg5) of FIGS. 9D and 9E is conditionally inactivated by RNA trigger X (the cognate RNA trigger), which binds to the RNA helper strand (also known as cg3) to remove it from the cgRNA (also known as cg5), which then lacks the terminator duplex and the remainder of the terminator region, yielding a structure incompatible with mediation of Cas9, dCas9, and/or Cas function. Equivalently, in some embodiments, the functional conditional guide RNA can be interpreted as a complex of two fragments (complex cg5:cg3 comprising 5'-fragment cg5 and 3'-fragment cg3; FIGS. 9D and 9E) that is conditionally inactivated by RNA trigger X (cognate RNA trigger), which binds to the complex to displace cg5 and form the cg3:trigger complex, wherein both cg3:trigger and cg5 are structurally incompatible with mediation of Cas9, dCas9, and/or Cas function. Compared to a standard gRNA (FIG. 1), in some embodiments the ON→OFF split-terminator switch cgRNA (also known as cg5) is incomplete, containing only one half of the stem region of the 5' terminator hairpin (sequence domain "d"). In the ON state, hybridization of the RNA helper strand (also known as cg3) to domain "d" forms a terminator duplex (domain "d" base-paired to domain "d*") such that the cgRNA:helper complex (also known as the cg5:cg3 complex) is active. In some embodiments, the cgRNA (also known as cg5) comprises a target-binding region (domain "u"), a Cas handle, and a 5' portion of the stem of the terminator duplex (domain "d"). In some embodiments, the RNA helper strand (also known as cg3) comprises a trigger-binding region (domains "e*-d*"); wherein the trigger-binding region comprises a 3' portion of the stem of the terminator duplex (domain "d*") and a toehold 5'-adjacent to the 3' portion of the stem of the terminator duplex (domain "e*"). In some embodiments, to toggle the cgRNA (also known as cg5) to the OFF state, the RNA trigger X (the cognate RNA trigger) displaces the RNA helper strand (also known as cg3) from the cgRNA (also known as cg5) via toehold-mediated strand displacement in which the trigger first nucleates with the helper (also known as cg3) by binding to the exposed toehold domain "e*" on the helper (also known as cg3), and then hybridizes to domain "d*" to displace the helper (also known as cg3) from the cgRNA (also known as cg5), forming the helper:trigger complex (also known as the cg3:trigger complex). This yields an incomplete cgRNA (also known as cg5) lacking the terminator duplex, wherein the cgRNA (also known as cg5) is structurally incompatible with mediation of Cas9, dCas9, and or Cas function. In some embodiments, the mechanism is allosteric because the cgRNA (also known as cg5) and helper (also known as cg3) interact via a terminator duplex (domains "d" and "d*" in FIGS. 9D and 9E) distal to the target-binding region (domain "u" in FIGS. 9D and 9E). As a result, the sequence of the RNA trigger X (which binds to the helper domains "e*-d*" to down-regulate Cas function) is independent of domain "u", yielding full sequence independence between trigger X (the cognate RNA trigger) and regulatory target Y (the target gene). In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values. In some embodiments, a toehold domain comprises, consists, or consists essentially of 4 nt, or 10 nt, or 20 nt, or 30 nt, or 40 nt, or 50 nt, or 100 nt, or 200 nt, or more, or any number of nucleotides intermediate to any of the preceding values.

In some embodiments, the RNA helper strand (also known as cg3) comprises one or more additional domains 5'-adjacent to domain "d*". In some embodiments, one or more of these additional domains functions as a toehold to nucleate interactions with an auxiliary trigger that hybridizes to the helper strand (also known as cg3) to remove the helper strand (also known as cg3) from the cgRNA (also known as cg5). In some embodiments, one or more of these additional domains functions as a substrate to provide a binding site for an additional strand that hybridizes to both the substrate and to the cgRNA (also known as cg5) for the purpose of holding the cgRNA (also known as cg5) and helper strand (also known as cg3) together in complex (cg5:cg3: additional-strand). In some embodiments, the RNA helper strand (also known as cg3) comprises one or more additional domains 3'-adjacent to domain "d*". In some embodiments, one or more of these additional domains functions as a toehold to nucleate interactions with an auxiliary trigger that hybridizes to the helper strand (also known as cg3) to remove the helper strand (also known as cg3) from the cgRNA (also known as cg5). In some embodiments, the cgRNA (also known as cg5) comprises one or more substrate domains 3'-adjacent to domain "d" and the RNA helper strand (also known as cg3) comprises one or more substrate domains 5'-adjacent to domain "d*". In some embodiments, the trigger hybridizes to one or more substrates on the cgRNA (also known as cg5) and one or more substrates on the helper strand (also known as cg3) so as to form a 3-way junction that disrupts the structure of the terminator duplex, wherein the structure of the cgRNA:helper:trigger complex (also known as the cg5: cg3:trigger complex) is incompatible with mediation of Cas9, dCas9, and/or Cas function.

Allosteric OFF→ON 5'-Inhibited Split-Terminator Switch cgRNAs (Mechanism 5)

Figure 25A:
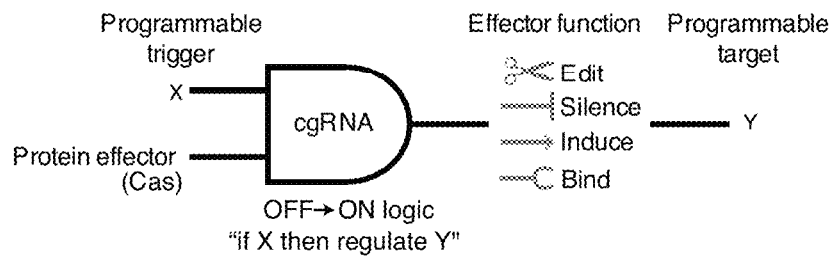
FIGS. 25A-25C depict the logic, function, and mechanism of allosteric OFF→ON 5'-inhibited split-terminator switch cgRNAs (Mechanism 5).
Figure 25B:
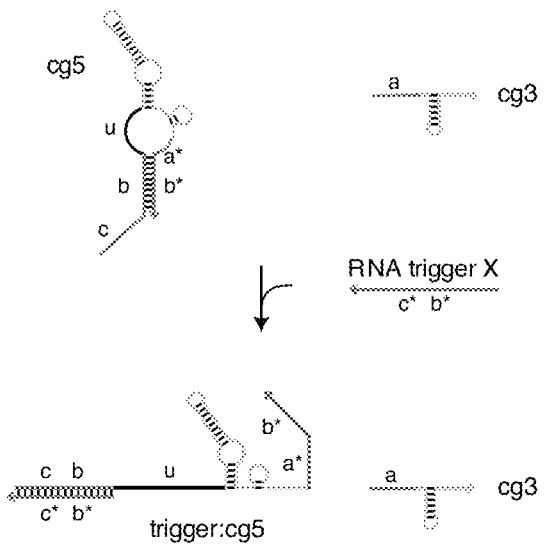
Figure 25B:
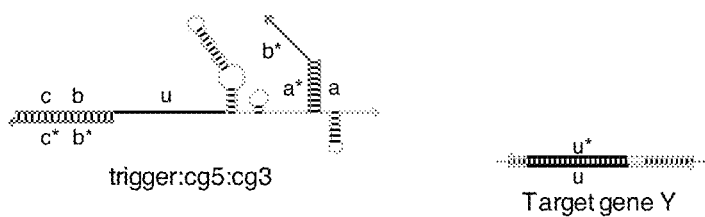
Figure 25C:
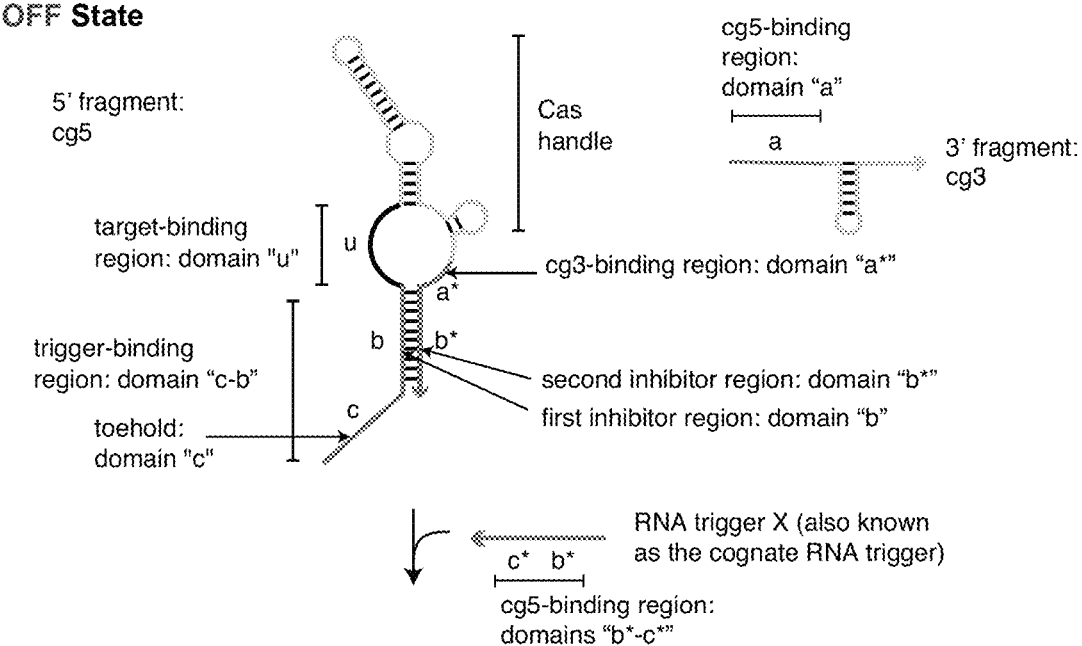
Figure 25C:
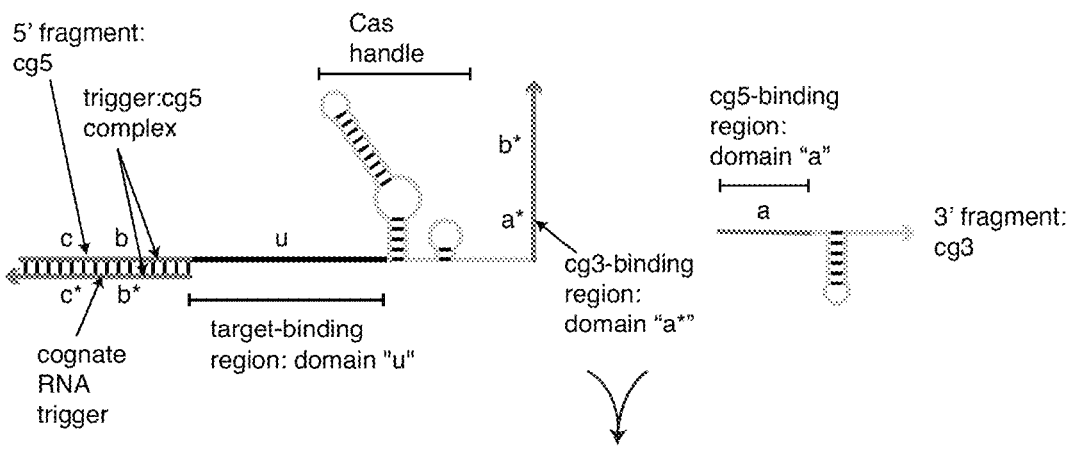
Figure 25C:
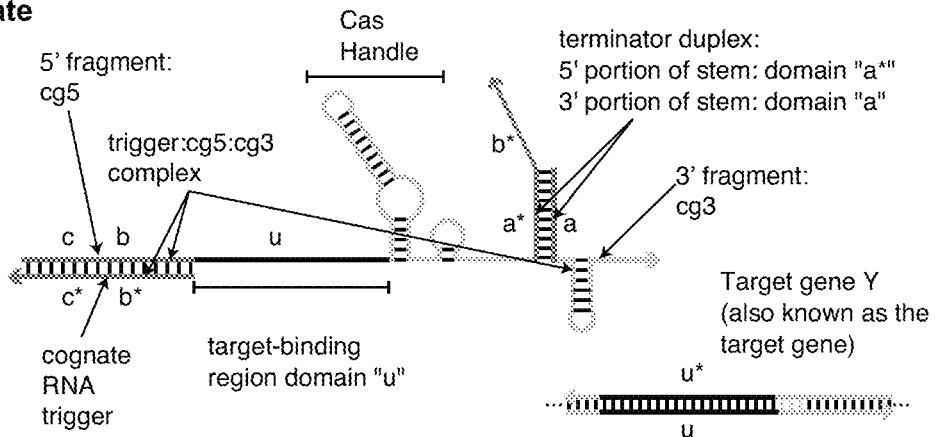

In some embodiments, allosteric OFF→ON cgRNA logic (FIG. 25A) is implemented using an allosteric OFF→ON 5'-inhibited split-terminator switch cgRNA mechanism (FIGS. 25B and 25C). In some embodiments, the OFF→ON 5'-inhibited split-terminator switch cgRNA (FIGS. 25B and 25C) comprises two inactive cgRNA fragments (cg5 and cg3) that are conditionally activated by RNA trigger X (the cognate RNA trigger), which binds to cg5 to allow for formation of the trigger:cg5:cg3 complex that activates the cgRNA, mediating the function of a Cas protein effector on a target gene (Y). In some embodiments, the OFF→ON 5'-sequestered split-terminator switch cgRNA comprises two fragments (FIGS. 25B and 25C), a 5'-fragment (cg5) and a 3'-fragment (cg3), that are inactive when not bound to each other (OFF state). In some embodiments, cg5 comprises a Cas handle, a target-binding region (sequence domain "u") 5' of the Cas handle, and a cg3-binding region (sequence domain "a*") 3' of the Cas handle. In some embodiments, cg3 comprises a cg5-binding region (sequence domain "a"). In some embodiments, cg5 further comprises a trigger-binding region (sequence domains "c-b") comprising a first inhibitor region (sequence domain "b"), and a second inhibitor region (sequence domain "b*"), such that in the absence of the cognate RNA trigger, the first inhibitor region (sequence domain "b") is configured to bind to the second inhibitor region (sequence domain "b*"), inhibiting binding between cg5 and cg3 by sequestering the cg3-binding region of cg5 (sequence domain "a*") in a loop. In some embodiments, the cognate RNA trigger comprises a cg5-binding region (sequence domains "b*-c*"), the trigger-binding region further comprises a toehold of one or more unpaired nucleotides at one or both ends (for example, domain "c"), the cg3-binding region of cg5 comprises the 5' portion of the stem of a terminator duplex (sequence domain "d"), and the cg5-binding region of cg3 comprises the 3' portion of the stem of the terminator duplex (sequence domain "d*"), such that upon hybridization of the cognate RNA trigger to cg5, cg5 hybridizes to cg3 to form the terminator duplex, activating the cgRNA (ON state). In some embodiments, the target-binding region (sequence domain "u") is non-overlapping with the trigger-binding region (sequence domains "c-b") and is configured not to bind to the trigger-binding region, allowing for allosteric signal transduction, in which the sequence of the cognate RNA trigger (X) can be selected independently of the sequence of the target gene (Y). In some embodiments, the cognate RNA trigger comprises additional flanking nucleotides 5' and/or 3' of the cg5-binding region. In some embodiments, to toggle the cgRNA from the OFF state to the ON state, the RNA trigger X (cognate RNA trigger) opens up the sequestering loop in cg5 via toehold-mediated strand displacement in which the trigger first nucleates with cg5 by hybridizing to the exposed toehold "c" on cg5 and then hybridizes to domain "b" to open the loop containing domain "a*", facilitating hybridization between domain "a*" in cg5 and domain "a" in cg3 to form the terminator duplex and activate the cgRNA, allowing for mediation of Cas function on the target gene (FIG. 25C). In some embodiments, the mechanism is allosteric because the trigger and cg5 interact via domains "c-b" in cg5 and "b*-c*" in the trigger (see FIGS. 25B and 25C) that are independent of the target-binding region (domain "u" in FIGS. 25B and 25C). The resulting full sequence independence between RNA trigger X (the cognate RNA trigger) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values.

Allosteric OFF→ON 3'-Inhibited Split-Terminator Switch cgRNAs (Mechanism 6)

Figure 26A:
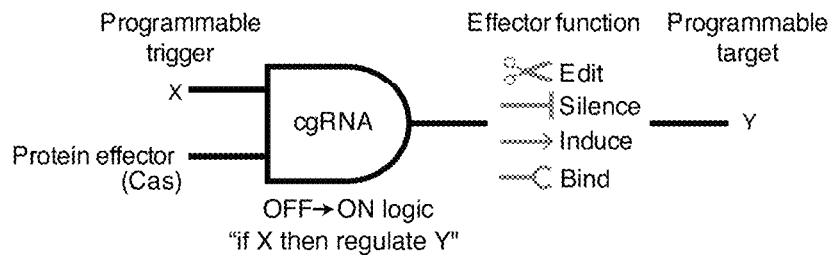
FIGS. 26A-26C depict the logic, function, and mechanism of allosteric OFF→ON 3'-inhibited split-terminator switch cgRNAs (Mechanism 6).
Figure 26B:
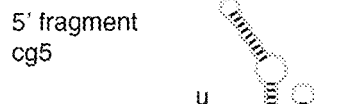
Figure 26B:
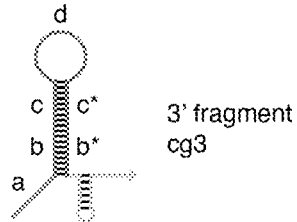
Figure 26B:
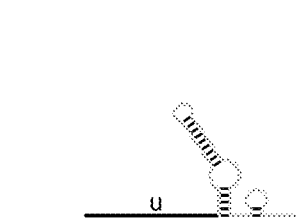
Figure 26B:
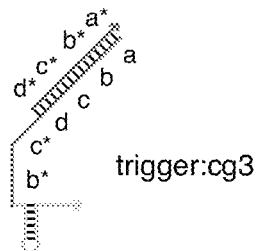
Figure 26B:
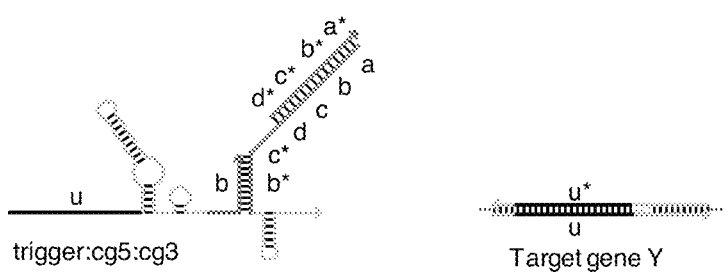
Figure 26C:
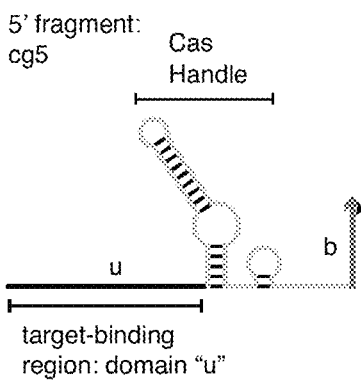
Figure 26C:
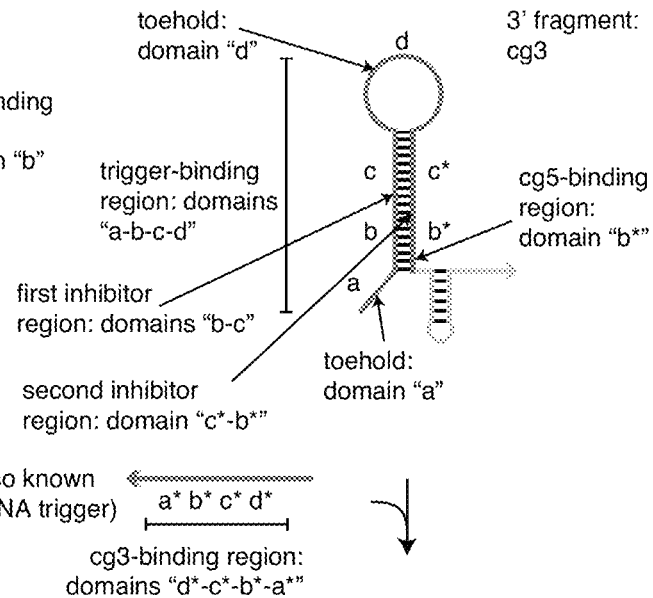
Figure 26C:
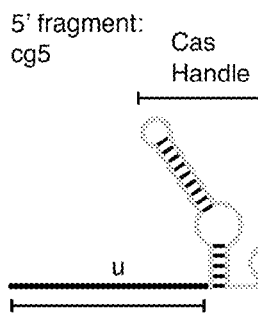
Figure 26C:
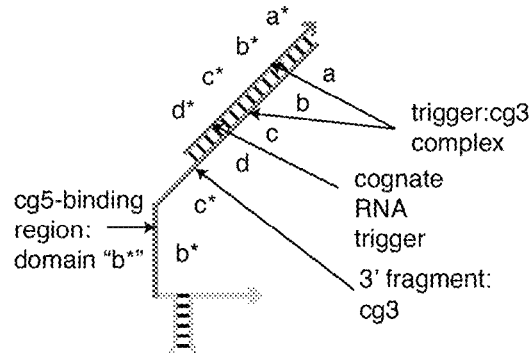
Figure 26C:
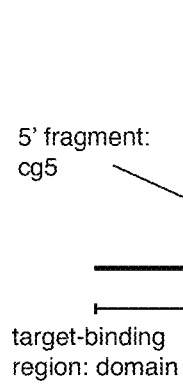
Figure 26C:
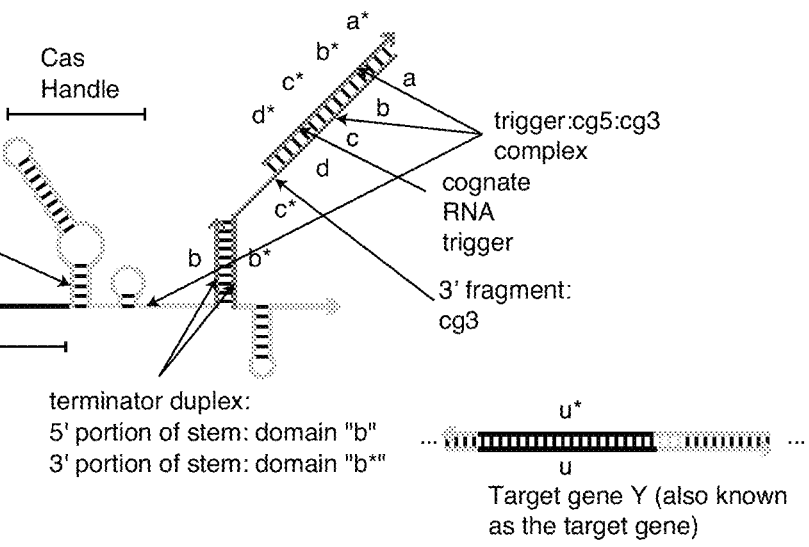

In some embodiments, allosteric OFF→ON cgRNA logic (FIG. 26A) is implemented using an allosteric OFF→ON 3'-inhibited split-terminator switch cgRNA mechanism (FIGS. 26B and 26C). In some embodiments, the OFF→ON 3'-inhibited split-terminator switch cgRNA (FIGS. 26B and 26C) comprises two inactive cgRNA fragments (cg5 and cg3) that are conditionally activated by RNA trigger X (the cognate RNA trigger), which binds to cg3 to allow for formation of the trigger:cg5:cg3 complex that activates the cgRNA, mediating the function of a Cas protein effector on a target gene (Y). In some embodiments, the OFF→ON 3'-sequestered split-terminator switch cgRNA comprises two fragments (FIGS. 26B and 26C), a 5'-fragment (cg5) and a 3'-fragment (cg3), that are inactive when not bound to each other (OFF state). In some embodiments, cg5 comprises a Cas handle, a target-binding region (sequence domain "u") 5' of the Cas handle, and a cg3-binding region (sequence domain "b") 3' of the Cas handle. In some embodiments, cg3 comprises a cg5-binding region (sequence domain "b*"). In some embodiments, cg3 further comprises a trigger-binding region (sequence domains "a-b-c-d") comprising a first inhibitor region (sequence domains "b-c"), and a second inhibitor region (sequence domain "c*-b*"), such that in the absence of the cognate RNA trigger, the first inhibitor region (sequence domains "b-c") is configured to bind to the second inhibitor region (sequence domain "c*-b*"), inhibiting binding between cg3 and cg5 by sequestering the cg5-binding region of cg3 (sequence domain "b*") in a duplex (i.e., the duplex formed by base-pairing between domains "b" and "b*" within cg3). In some embodiments, the cognate RNA trigger comprises a cg3-binding region (sequence domains "d*-c*-b*-a*"), the trigger-binding region further comprises a toehold of one or more unpaired nucleotides at one or both ends (for example, domain "a" and/or domain "d"), the cg3-binding region of cg5 comprises the 5' portion of the stem of a terminator duplex (sequence domain "b"), and the cg5-binding region of cg3 comprises the 3' portion of the stem of the terminator duplex (sequence domain "b*"), such that upon hybridization of the cognate RNA trigger to cg3, cg3 hybridizes to cg5 to form the terminator duplex, activating the cgRNA (ON state). In some embodiments, the target-binding region (sequence domain "u") is non-overlapping with the trigger-binding region (sequence domains "a-b-c-d") and is configured not to bind to the trigger-binding region, allowing for allosteric signal transduction, in which the sequence of the cognate RNA trigger (X) can be selected independently of the sequence of the target gene (Y). In some embodiments, the cognate RNA trigger comprises additional flanking nucleotides 5' and/or 3' of the cg3-binding region. In some embodiments, to toggle the cgRNA from the OFF state to the ON state, the RNA trigger X (cognate RNA trigger) opens up the duplex in cg3 via toehold-mediated strand displacement in which the trigger first nucleates with cg3 by hybridizing to the exposed toehold "a" on cg3 (and/or the exposed toehold "d") and then hybridizes to domains "b-c" to open the duplex sequestering domain "b*", facilitating hybridization between domain "b*" in cg3 and domain "b" in cg5 to form the terminator duplex and activate the cgRNA, allowing for mediation of Cas function on the target gene (FIG. 26C). In some embodiments, the mechanism is allosteric because the trigger and cg3 interact via domains "a-b-c-d" in cg3 and "d*-c*-b*-a*" in the trigger (see FIGS. 26B and 26C) that are independent of the target-binding region (domain "u" in cg5; FIGS. 26B and 26C). The resulting full sequence independence between RNA trigger X (the cognate RNA trigger) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values.

Allosteric OFF→ON 5'- and 3'-Inhibited Split-Terminator Switch cgRNAs (Mechanism 7)

Figure 27A:
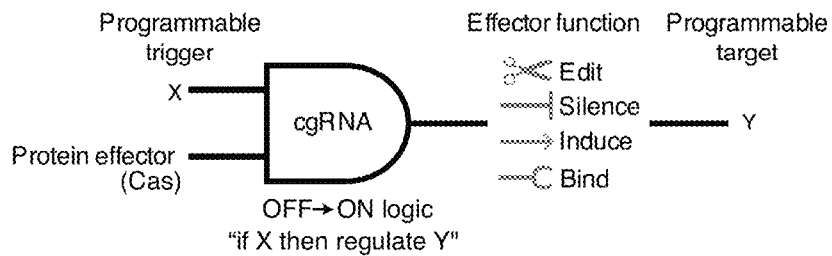
FIGS. 27A-27C depict the logic, function, and mechanism of allosteric OFF→ON 5'- and 3'-inhibited split-terminator switch cgRNAs (Mechanism 7).
Figure 27B:
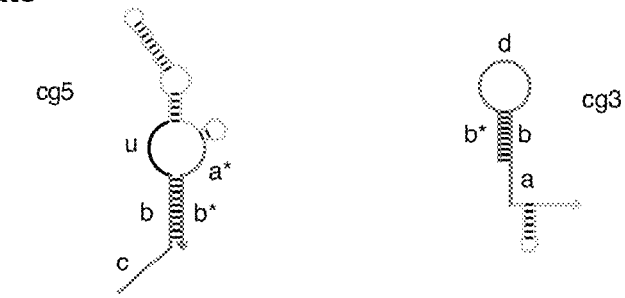
Figure 27B:
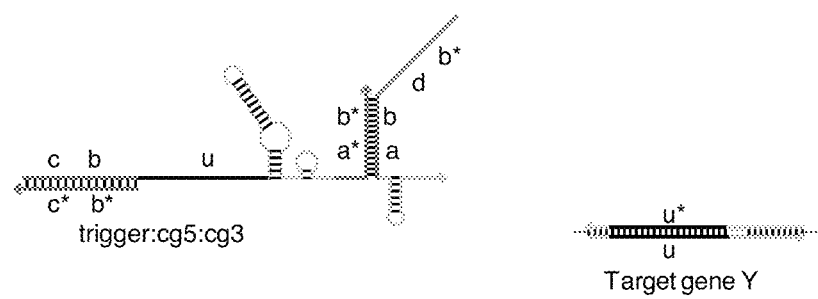
Figure 27C:
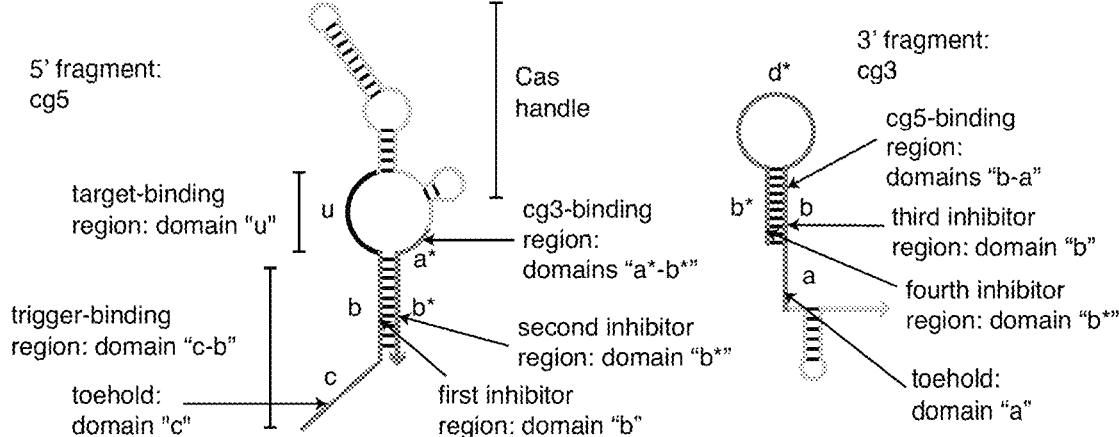
Figure 27C:
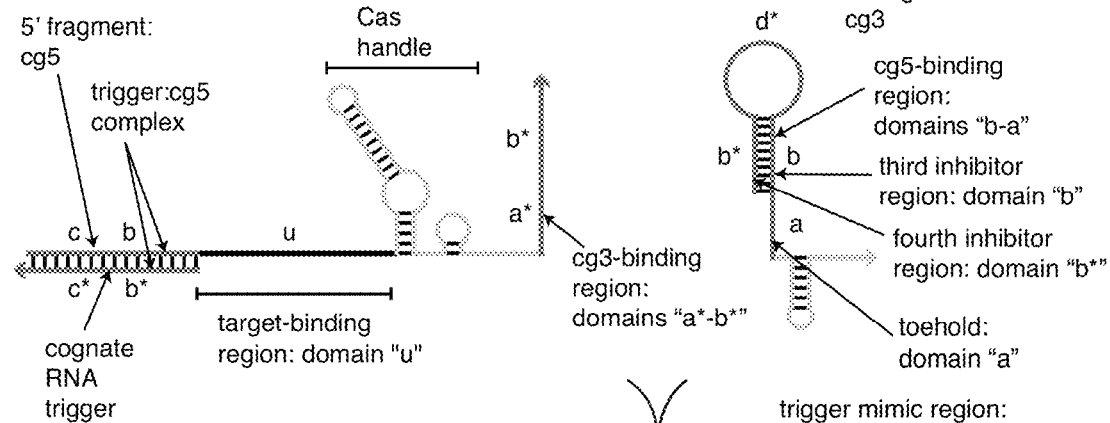
Figure 27C:
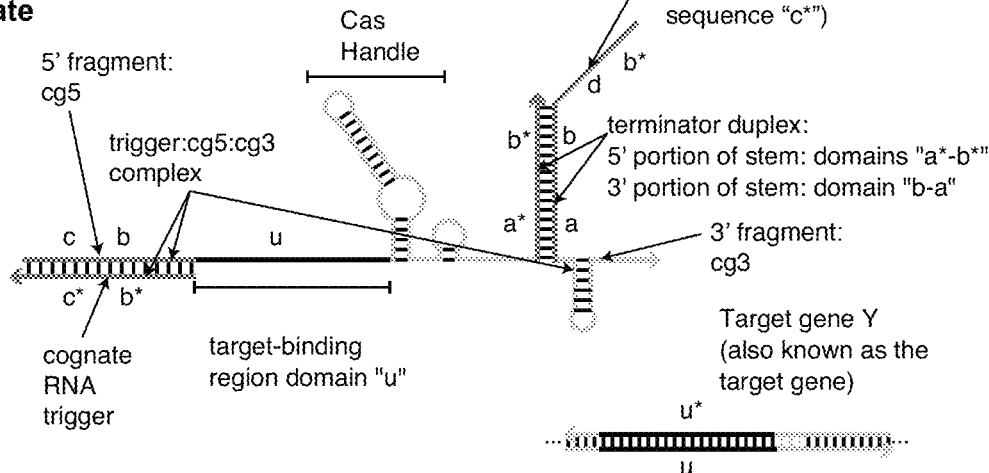

In some embodiments, allosteric OFF→ON cgRNA logic (FIG. 27A) is implemented using an allosteric OFF→ON 5'- and 3'-inhibited split-terminator switch cgRNA mechanism (Mechanism 7; FIGS. 27B and 27C). In some embodiments, the OFF→ON 5'- and 3'-inhibited split-terminator switch cgRNA (Mechanism 7; FIGS. 27B and 27C) comprises two inactive cgRNA fragments (cg5 and cg3) that are conditionally activated by RNA trigger X (the cognate RNA trigger), which binds to cg5 to allow for formation of the trigger:cg5:cg3 complex that activates the cgRNA, mediating the function of a Cas protein effector on a target gene (Y). In some embodiments, the OFF→ON 5'- and 3'-inhibited split-terminator switch cgRNA (Mechanism 7) comprises two fragments (FIGS. 27B and 27C), a 5'-fragment (cg5) and a 3'-fragment (cg3), that are inactive when not bound to each other (OFF state). In some embodiments, cg5 comprises a Cas handle, a target-binding region (sequence domain "u") 5' of the Cas handle, and a cg3-binding region (sequence domains "a*-b*") 3' of the Cas handle. In some embodiments, cg3 comprises a cg5-binding region (sequence domains "b-a"). In some embodiments, cg5 further comprises: 1) a trigger-binding region (sequence domains "c-b") comprising a first inhibitor region (sequence domain "b" in cg5), 2) and a second inhibitor region (sequence domain "b*" in cg5); and cg3 further comprises a third inhibitor region (sequence domain "b" in cg3) and a fourth inhibitor region (sequence domain "b*" in cg3); such that in the absence of the cognate RNA trigger, the first inhibitor region (sequence domain "b" in cg5) is configured to bind to the second inhibitor region (sequence domain "b*" in cg5) and the third inhibitor region (sequence domain "b" in cg3) is configured to bind to the fourth inhibitor region (sequence domain "b*" in cg3), inhibiting binding between cg5 and cg3 by sequestering the cg3-binding region of cg5 (sequence domains "a*-b*") in a loop and duplex ("a*" is sequestered in a loop and "b*" is sequestered in a duplex; FIGS. 27B and 27C) and by sequestering a portion of the cg5-binding region of cg3 (sequence domain "b") in a duplex. In some embodiments, the cognate RNA trigger comprises a cg5-binding region (sequence domains "b*-c*"), the trigger-binding region of cg5 further comprises a toehold of one or more unpaired nucleotides at one or both ends (for example, domain "c"), the cg3-binding region of cg5 comprises the 5' portion of the stem of a terminator duplex (sequence domains "a*-b*"), and the cg5-binding region of cg3 comprises the 3' portion of the stem of the terminator duplex (sequence domain "b-a"), such that upon hybridization of the cognate RNA trigger to cg5, cg5 hybridizes to cg3 to form the terminator duplex, activating the cgRNA (ON state). In some embodiments, the target-binding region (sequence domain "u") is non-overlapping with the trigger-binding region (sequence domains "c-b") and is configured not to bind to the trigger-binding region, allowing for allosteric signal transduction, in which the sequence of the cognate RNA trigger (X) can be selected independently of the sequence of the target gene (Y). In some embodiments, the cognate RNA trigger comprises additional flanking nucleotides 5' and/or 3' of the cg5-binding region. In some embodiments, to toggle the cgRNA from the OFF state to the ON state, the RNA trigger X (cognate RNA trigger) opens up the sequestering loop and duplex in cg5 via toehold-mediated strand displacement in which the trigger first nucleates with cg5 by hybridizing to the exposed toehold "c" on cg5 and then hybridizes to domain "b" to open the loop containing domain "a*" and the duplex containing domain "b*", facilitating hybridization between domains "a*-b*" in cg5 and domains "b-a" in cg3 to form the terminator duplex and activate the cgRNA, allowing for mediation of Cas function on the target gene (FIG. 27C). In some embodiments, once the cognate RNA trigger binds to cg5 to form complex trigger:cg5 and expose domains "a*-b*", cg5 opens up the sequestering duplex in cg3 via toehold-mediated strand displacement in which cg5 first nucleates with cg3 by hybridizing to the exposed toehold "a" on cg3 and then hybridizes to domain "b" to open the duplex containing domain "b*". In some embodiments, the mechanism is allosteric because the trigger and cg5 interact via domains "c-b" in cg5 and "b*-c*" in the trigger (see FIGS. 27B and 27C) that are independent of the target-binding region (domain "u" in FIGS. 27B and 27C). The resulting full sequence independence between RNA trigger X (the cognate RNA trigger) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values.

In some embodiments (Mechanism 7; FIGS. 27B and 27C), cg3 further comprises a trigger mimic region (sequence domains "b*-d") with the same sequence as the cg5-binding region of the cognate RNA trigger (sequence domains "b*-c*") (that is, in some embodiments, the sequence of domain "d" is specified to be the same as the sequence of domain "c*"), such that upon activation of the cgRNA by the cognate RNA trigger, the trigger mimic region (sequence domains "b*-d" with the sequence of domain "d" defined to be the same as the sequence of domain "c*") is exposed. In some embodiments, this exposed trigger mimic region is then capable of serving as the cognate RNA trigger for a new copy of the cgRNA comprising a new copy of the 5' fragment cg5 and a new copy of the 3' fragment cg3. In some embodiments, the original cognate RNA trigger molecule is capable of triggering the ON state of a first cgRNA, which in turn is capable of trigger the ON state of a second cgRNA, which in turn is capable of trigger the ON state of a third cgRNA, and so on; this situation is equivalent to catalytic activation of multiple cgRNAs by a single cognate RNA trigger molecule.

Allosteric OFF→ON 5'- and 3'-Inhibited Split-Terminator Switch cgRNAs (Mechanism 8)

Figure 28A:
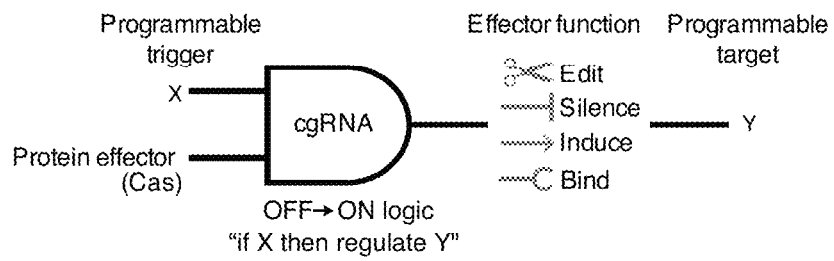
FIGS. 28A-28D depict the logic, function, and mechanism of allosteric OFF→ON 5'- and 3'-inhibited split-terminator switch cgRNAs (Mechanism 8).
Figure 28B:
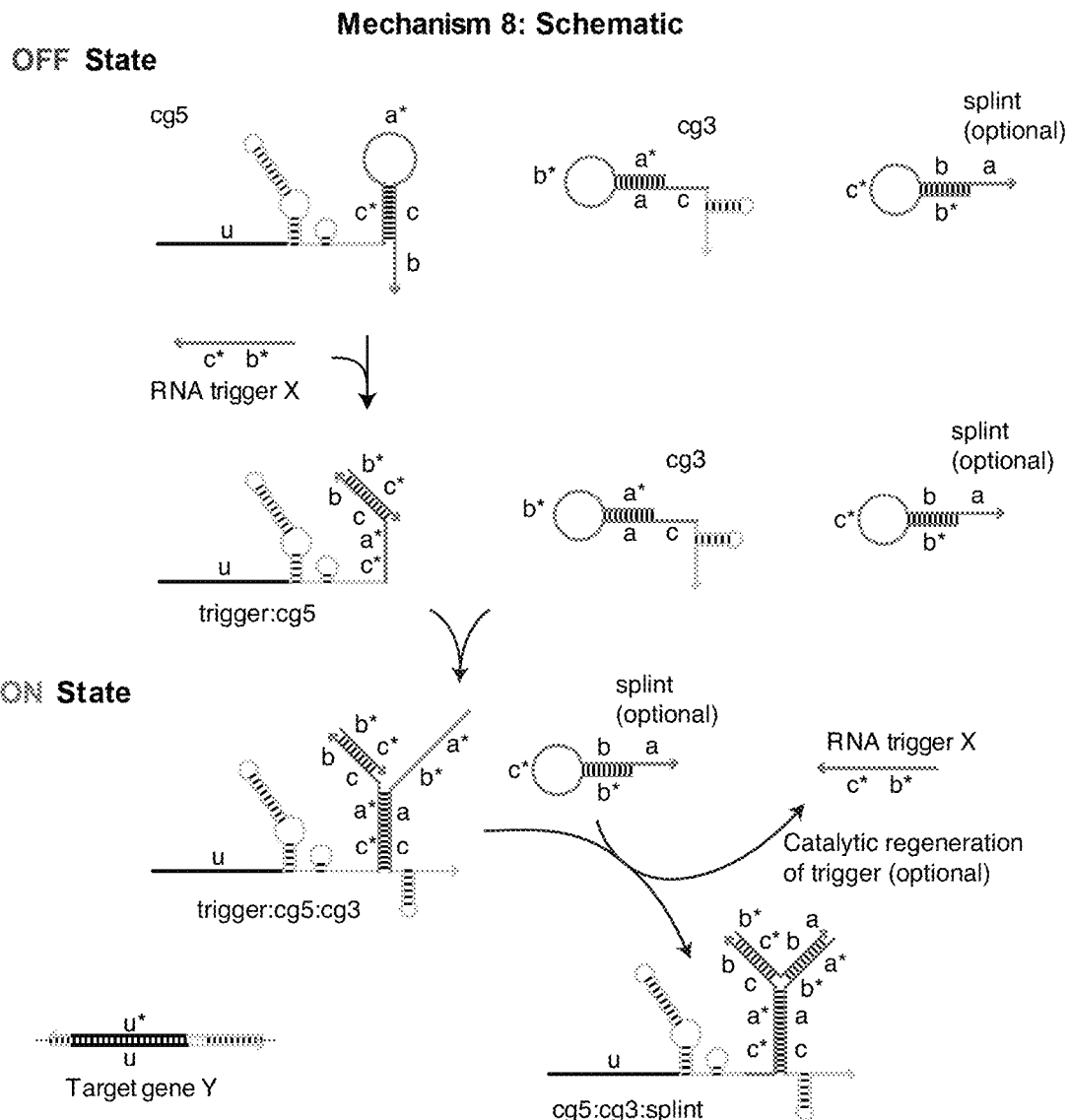
Figure 28C:
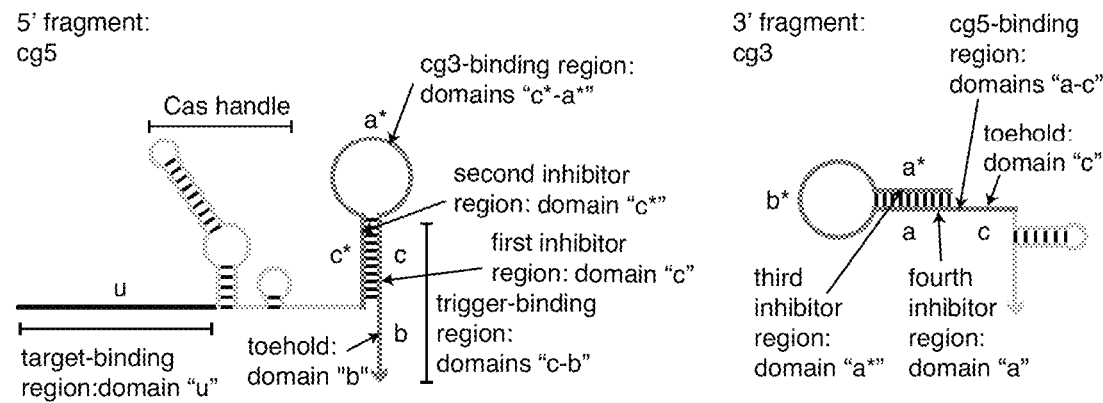
Figure 28C:
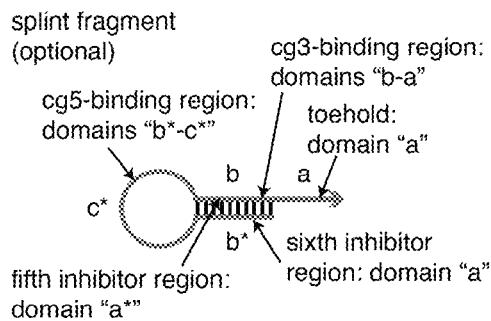
Figure 28C:
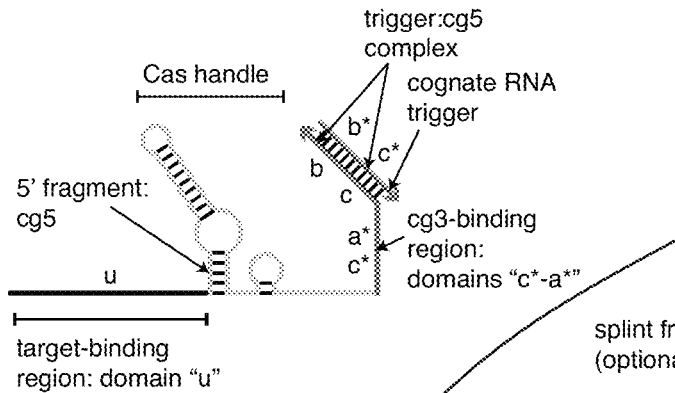
Figure 28C:
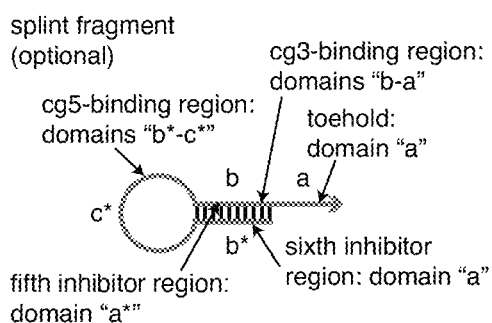

In some embodiments, allosteric OFF→ON cgRNA logic (FIG. 28A) is implemented using an allosteric OFF→ON 5'- and 3'-inhibited split-terminator switch cgRNA mechanism (Mechanism 8; FIGS. 28B, 28C and 28D). In some embodiments, the OFF→ON 5'- and 3'-inhibited split-terminator switch cgRNA (Mechanism 8; FIGS. 28B, 28C and 28D) comprises two inactive cgRNA fragments (cg5 and cg3) that are conditionally activated by RNA trigger X (the cognate RNA trigger), which binds to cg5 to allow for formation of the trigger:cg5:cg3 complex that activates the cgRNA, mediating the function of a Cas protein effector on a target gene (Y). In some embodiments, the OFF→ON 5'- and 3'-inhibited split-terminator switch cgRNA (Mechanism 8) comprises two fragments (FIGS. 28B, 28C and 28D), a 5'-fragment (cg5) and a 3'-fragment (cg3), that are inactive when not bound to each other (OFF state). In some embodiments, cg5 comprises a Cas handle, a target-binding region (sequence domain "u") 5' of the Cas handle, and a cg3-binding region (sequence domains "c*-a*") 3' of the Cas handle. In some embodiments, cg3 comprises a cg5-binding region (sequence domains "a-c"). In some embodiments, cg5 further comprises: 1) a trigger-binding region (sequence domains "c-b") comprising a first inhibitor region (sequence domain "c" in cg5), 2) and a second inhibitor region (sequence domain "c*" in cg5); and cg3 further comprises a third inhibitor region (sequence domain "a*" in cg3) and a fourth inhibitor region (sequence domain "a" in cg3); such that in the absence of the cognate RNA trigger, the first inhibitor region (sequence domain "c" in cg5) is configured to bind to the second inhibitor region (sequence domain "c*" in cg5) and the third inhibitor region (sequence domain "a*" in cg3) is configured to bind to the fourth inhibitor region (sequence domain "a" in cg3), inhibiting binding between cg5 and cg3 by sequestering the cg3-binding region of cg5 (sequence domains "c*-a*") in a loop and duplex ("a*" is sequestered in a loop and "c*" is sequestered in a duplex; FIGS. 28B, 28C and 28D) and by sequestering a portion of the cg5-binding region of cg3 in a duplex (the sequestered portion corresponds to domain "a" which is base paired to domain "a*" in a duplex). In some embodiments, the cognate RNA trigger comprises a cg5-binding region (sequence domains "b*-c*"), the trigger-binding region of cg5 further comprises a toehold of one or more unpaired nucleotides at one or both ends (for example, domain "b"), the cg3-binding region of cg5 comprises the 5' portion of the stem of a terminator duplex (sequence domains "c*-a*"), and the cg5-binding region of cg3 comprises the 3' portion of the stem of the terminator duplex (sequence domain "a-c"), such that upon hybridization of the cognate RNA trigger to cg5, cg5 hybridizes to cg3 to form the terminator duplex, activating the cgRNA (ON state). In some embodiments, the target-binding region (sequence domain "u") is non-overlapping with the trigger-binding region (sequence domains "c-b") and is configured not to bind to the trigger-binding region, allowing for allosteric signal transduction, in which the sequence of the cognate RNA trigger (X) can be selected independently of the sequence of the target gene (Y). In some embodiments, the cognate RNA trigger comprises additional flanking nucleotides 5' and/or 3' of the cg5- binding region. In some embodiments, to toggle the cgRNA from the OFF state to the ON state, the RNA trigger X (cognate RNA trigger) opens up the sequestering loop and duplex in cg5 via toehold-mediated strand displacement in which the trigger first nucleates with cg5 by hybridizing to the exposed toehold "b" on cg5 and then hybridizes to domain "c" to open the loop containing domain "a*" and the duplex containing domain "c*", facilitating hybridization between domains "c*-a*" in cg5 and domains "a-c" in cg3 to form the terminator duplex and activate the cgRNA, allowing for mediation of Cas function on the target gene (FIGS. 28C and 28D). In some embodiments, once the cognate RNA trigger binds to cg5 to form complex trigger: cg5 and expose domains "c*-a*", cg5 opens up the sequestering duplex in cg3 via toehold-mediated strand displacement in which cg5 first nucleates with cg3 by hybridizing to the exposed toehold "c" on cg3 and then hybridizes to domain "a" to open the duplex containing domain "a*". In some embodiments, the mechanism is allosteric because the trigger and cg5 interact via domains "c-b" in cg5 and "b*-c*" in the trigger (see FIGS. 28B, 28C and 28D) that are independent of the target-binding region (domain "u" in FIGS. 28B, 28C and 28D). The resulting full sequence independence between RNA trigger X (the cognate RNA trigger) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values.

In some embodiments (Mechanism 8; FIGS. 28B, 28C and 28D), cg3 additionally comprises a third fragment (known as the splint fragment) comprising a cg3-binding region (sequence domains "b-a") comprising a fifth inhibitor region (sequence domain "b") and a cg5-binding region (sequence domains "b*-c") comprising a sixth inhibitor region (sequence domains "b*") such that in the absence of the cognate RNA trigger, the fifth inhibitor region is configured to bind the sixth inhibitor region, inhibiting binding of the splint to cg5 and cg3, and such that upon activation of the cgRNA by the cognate RNA trigger, cg3 hybridizes to the cg3-binding region of the splint (sequence domains "b-a") and cg5 hybridizes to the cg5-binding region of the splint (sequence domains "b*-c*"), displacing the trigger from cg5, corresponding to catalytic regeneration of the trigger, which can then serve as the cognate RNA trigger for a new copy of the cgRNA comprising a new copy of the 5' fragment cg5, a new copy of the 3' fragment cg3, and a new copy of the splint. In some embodiments, the original cognate RNA trigger molecule is capable of triggering the ON state of a first cgRNA, which in turn is capable of trigger the ON state of a second cgRNA, which in turn is capable of trigger the ON state of a third cgRNA, and so on; this situation corresponds to catalytic activation of multiple cgRNAs by a single cognate RNA trigger molecule. In some embodiments, after the cognate RNA trigger actives the cgRNA, cg3 opens up the sequestering duplex in the splint via toehold-mediated strand displacement in which cg3 first nucleates with the splint by hybridizing to the exposed toehold "a" on the splint and then hybridizes to domain "b" to open the duplex containing domain "b*"; in some embodiments, the exposed cg5-binding region (sequence domains "b*-c*") in the splint then hybridizes to cg5 to displace the cognate RNA trigger.

Allosteric OFF→ON 5'- and 3'-Inhibited Split-Terminator Switch cgRNAs (Mechanism 9)

Figure 29A:
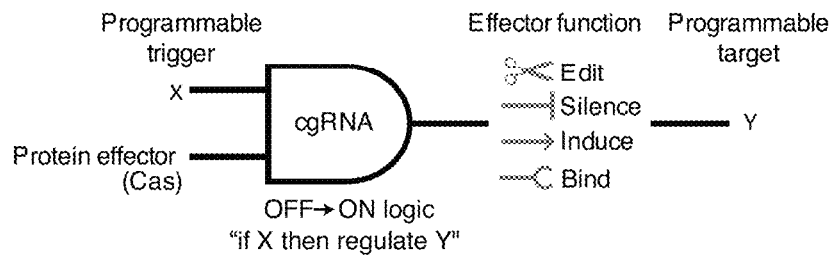
FIGS. 29A-29D depict the logic, function, and mechanism of allosteric OFF→ON 5'- and 3'-inhibited split-terminator switch cgRNAs (Mechanism 9).
Figure 29B:
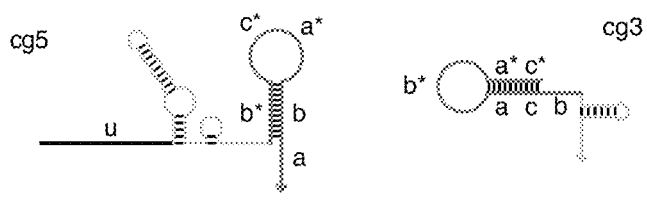
Figure 29B:
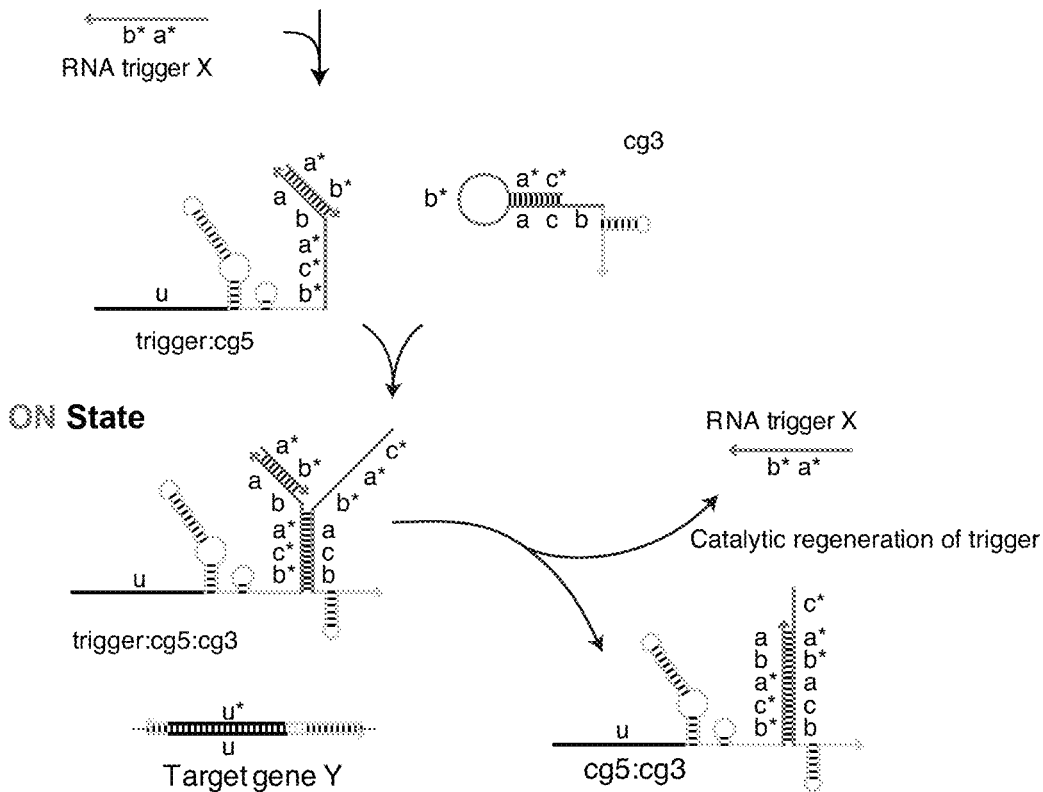
Figure 29C:
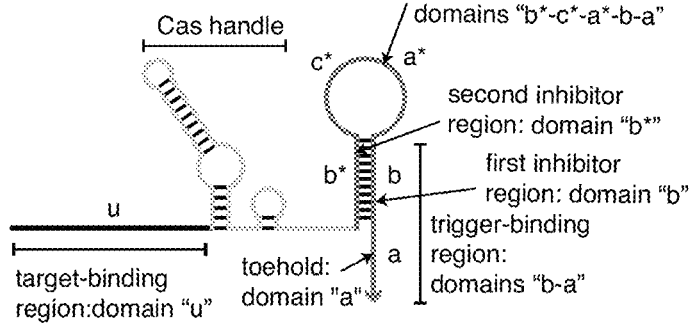
Figure 29C:
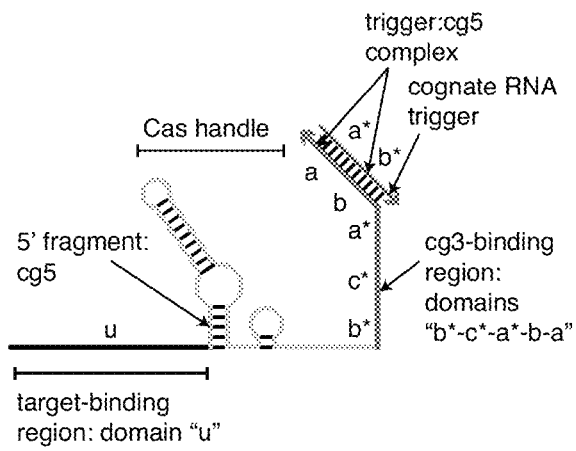
Figure 29D:
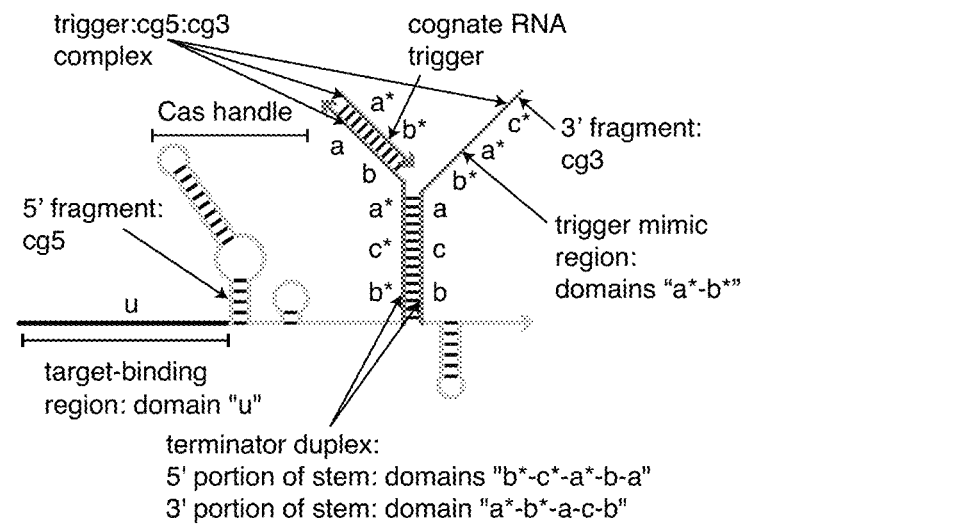
Figure 29D:
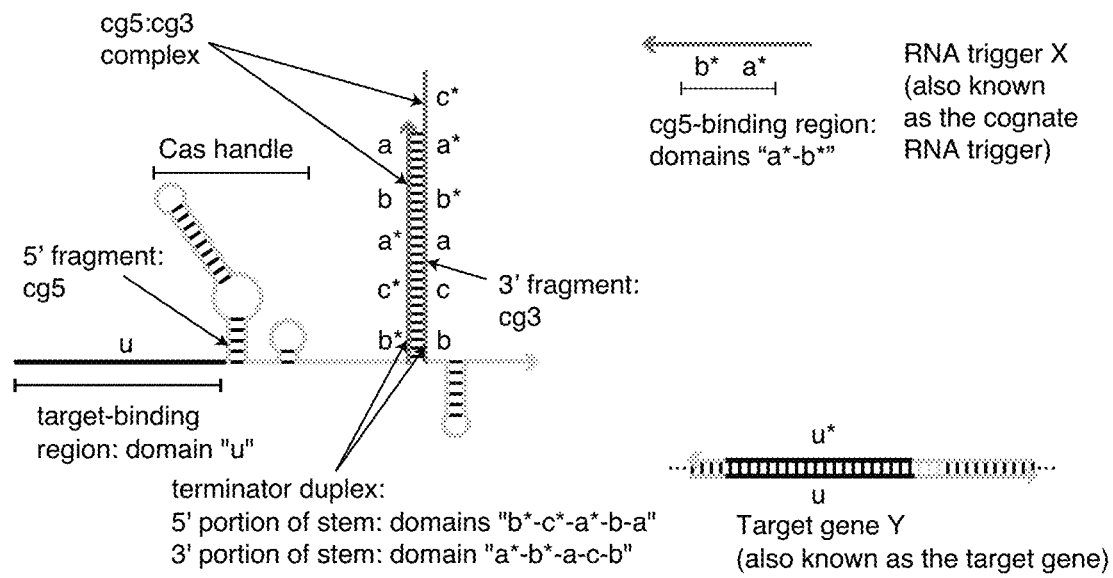

In some embodiments, allosteric OFF→ON cgRNA logic (FIG. 29A) is implemented using an allosteric OFF→ON 5'- and 3'-inhibited split-terminator switch cgRNA mechanism (Mechanism 9; FIGS. 29B, 29C and 29D). In some embodiments, the OFF→ON 5'- and 3'-inhibited split-terminator switch cgRNA (Mechanism 9; FIGS. 29B, 29C and 29D) comprises two inactive cgRNA fragments (cg5 and cg3) that are conditionally activated by RNA trigger X (the cognate RNA trigger), which binds to cg5 to allow for formation of the trigger:cg5:cg3 complex that activates the cgRNA, mediating the function of a Cas protein effector on a target gene (Y). In some embodiments, the OFF→ON 5'- and 3'-inhibited split-terminator switch cgRNA (Mechanism 9) comprises two fragments (FIGS. 29B, 29C and 29D), a 5'-fragment (cg5) and a 3'-fragment (cg3), that are inactive when not bound to each other (OFF state). In some embodiments, cg5 comprises a Cas handle, a target-binding region (sequence domain "u") 5' of the Cas handle, and a cg3-binding region (sequence domains "b*-c*-a*") 3' of the Cas handle. In some embodiments, cg3 comprises a cg5-binding region (sequence domains "a-c-b"). In some embodiments, cg5 further comprises: 1) a trigger-binding region (sequence domains "b-a") comprising a first inhibitor region (sequence domain "b" in cg5), 2) and a second inhibitor region (sequence domain "b*" in cg5); and cg3 further comprises a third inhibitor region (sequence domains "c*-a*" in cg3) and a fourth inhibitor region (sequence domains "a-c" in cg3); such that in the absence of the cognate RNA trigger, the first inhibitor region (sequence domain "b" in cg5) is configured to bind to the second inhibitor region (sequence domain "b*" in cg5) and the third inhibitor region (sequence domains "c*-a*" in cg3) is configured to bind to the fourth inhibitor region (sequence domain "a-c" in cg3), inhibiting binding between cg5 and cg3 by sequestering the cg3-binding region of cg5 (sequence domains "b*-c*-a*") in a loop and duplex ("c*-a*" is sequestered in a loop and "b*" is sequestered in a duplex; FIGS. 29B, 29C and 29D) and by sequestering a portion of the cg5-binding region of cg3 in a duplex (the sequestered portion corresponds to domains "a-c" which are base paired to domain "c*-a*" in a duplex). In some embodiments, the cognate RNA trigger comprises a cg5-binding region (sequence domains "a*-b*"), the trigger-binding region in cg5 further comprises a toehold of one or more unpaired nucleotides at one or both ends (for example, domain "a"), the cg3-binding region of cg5 comprises the 5' portion of the stem of a terminator duplex (sequence domains "b*-c*-a*"), and the cg5-binding region of cg3 comprises the 3' portion of the stem of the terminator duplex (sequence domain "a-c-b"), such that upon hybridization of the cognate RNA trigger to cg5, cg5 hybridizes to cg3 to form the terminator duplex, activating the cgRNA (ON state). In some embodiments, the target-binding region (sequence domain "u") is non-overlapping with the trigger-binding region (sequence domains "b-a") and is configured not to bind to the trigger-binding region, allowing for allosteric signal transduction, in which the sequence of the cognate RNA trigger (X) can be selected independently of the sequence of the target gene (Y). In some embodiments, the cognate RNA trigger comprises additional flanking nucleotides 5' and/or 3' of the cg5-binding region. In some embodiments, to toggle the cgRNA from the OFF state to the ON state, the RNA trigger X (cognate RNA trigger) opens up the sequestering loop and duplex in cg5 via toehold-mediated strand displacement in which the trigger first nucleates with cg5 by hybridizing to the exposed toehold "a"

on cg5 and then hybridizes to domain "b" to open the loop containing domains "c*-a*" and the duplex containing domain "b*", facilitating hybridization between domains "b*-c*-a*" in cg5 and domains "a-c-b" in cg3 to form the terminator duplex and activate the cgRNA, allowing for mediation of Cas function on the target gene (FIGS. 29C and 29D). In some embodiments, once the cognate RNA trigger binds to cg5 to form complex trigger:cg5 and expose domains "b*-c*-a*", cg5 opens up the sequestering duplex in cg3 via toehold-mediated strand displacement in which cg5 first nucleates with cg3 by hybridizing to the exposed toehold "b" on cg3 and then hybridizes to domains "c-a" to open the duplex containing domains "c*-a*". In some embodiments, the mechanism is allosteric because the trigger and cg5 interact via domains "b-a" in cg5 and "a*-b*" in the trigger (see FIGS. 29B, 29C and 29D) that are independent of the target-binding region (domain "u" in FIGS. 29B, 29C and 29D). The resulting full sequence independence between RNA trigger X (the cognate RNA trigger) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values.

In some embodiments, the cg3-binding region of cg5 comprises sequence domains "b*-c*-a*-b-a" and the cg5-binding region of cg3 comprises sequence domains "a*-b*-a-c-b". In some embodiments, the cg3-binding region of cg5 comprises the 5' portion of the stem of a terminator duplex (sequence domains "b*-c*-a*-b-a"), and the cg5-binding region of cg3 comprises the 3' portion of the stem of the terminator duplex (sequence domain "a*-b*-a-c-b"), such that upon hybridization of the cognate RNA trigger to cg5, cg5 hybridizes to cg3 to form the terminator duplex, activating the cgRNA (ON state). In some embodiments (Mechanism 9; FIGS. 29B, 29C and 29D), cg3 comprises a trigger mimic region (sequence domains "a*-b*") with the same sequence as the cg5-binding region of the cognate RNA trigger (sequence domains "a*-b*") such that upon activation of the cgRNA by the cognate RNA trigger, the trigger mimic region (sequence domains "a*-b*") hybridizes to the trigger-binding region of cg5 (sequence domains "b-a"), displacing the trigger from cg5, corresponding to catalytic regeneration of the trigger which can then serve as the cognate RNA trigger for a new copy of the cgRNA comprising a new copy of the 5' fragment cg5 and a new copy of the 3' fragment cg3. In some embodiments, the original cognate RNA trigger molecule is capable of triggering the ON state of a first cgRNA, which in turn is capable of trigger the ON state of a second cgRNA, which in turn is capable of trigger the ON state of a third cgRNA, and so on; this situation corresponds to catalytic activation of multiple cgRNAs by a single cognate RNA trigger molecule. In some embodiments, the sequence of domain "b*" in cg3 is modified to be only partially complementary to domain "b" in cg5 (or to be non-complementary to domain "b" in cg5) so that cg3 does not displace the trigger from cg5 and the trigger is not catalytically regenerated.

Conditional Guide RNAs

In some embodiments, the trigger comprises any of RNA, DNA, PNA, XNA, 2'OMe-RNA, amino acids, artificial amino acids, chemically modified nucleic acids, chemically modified amino acids, synthetic nucleic acid analogs, and/or chemical linkers. In some embodiments, the trigger is a combination of two or more materials. In some embodiments, the trigger molecule contains a trigger domain that is capable of toggling the activity of a cgRNA from ON→OFF or OFF→ON via a binding event. In some embodiments, the trigger molecule is an mRNA and the trigger domain is a subsequence of the mRNA. In some embodiments, the trigger molecule is an mRNA, an rRNA, a lncRNA, a miRNA, a tRNA, or any other type of endogenous or exogenous RNA comprising a subsequence that is a trigger domain capable of toggling the activity of a cgRNA (from ON→OFF or OFF→ON). In some embodiments, the trigger is a DNA molecule comprising a subsequence that is a trigger domain capable of toggling the activity of a cgRNA (from ON→OFF or OFF→ON). In some embodiments, the trigger molecule is a synthetic nucleic acid comprising a subsequence that is a trigger domain capable of toggling the activity of a cgRNA (from ON→OFF or OFF→ON). In some embodiments, the trigger molecule is expressed and comprises a subsequence that is a trigger domain capable of toggling the activity of a cgRNA (from ON→OFF or OFF→ON). In some embodiments, the trigger molecule is chemically synthesized and comprises a subsequence that is a trigger domain capable of toggling the activity of a cgRNA (from ON→OFF or OFF→ON).

In some embodiments one or more of the nucleotides in the cgRNA and/or trigger sequences is rationally designed. In some embodiments, cgRNA and/or trigger sequences are designed using the reaction pathway designer within the NUPACK the software suite,[40,41] another piece of software, or a computational algorithm. In some embodiments, sequence design is formulated as a multistate optimization problem using a set of target test tubes to represent elementary steps in the reaction pathway as well as to model global crosstalk.[41] In some embodiments, each elementary step tube contains a set of desired on-target complexes (each with a target secondary structure and target concentration), corresponding to the on-pathway hybridization products for a given step, and a set of undesired off-target complexes (each with vanishing target concentration), corresponding to on-pathway reactants and off-pathway hybridization crosstalk for a given step;[41] in this scenario, these elementary step tubes promote full conversion of cognate reactants into cognate products and against local hybridization crosstalk between these same reactants. In some embodiments, to simultaneously design N orthogonal systems, elementary step tubes are specified for each orthogonal system. In some embodiments, to design against off-pathway interactions between systems, a single global crosstalk tube is also specified.[41] In some embodiments, in the global crosstalk tube, the on-target complexes correspond to all reactive species generated during all elementary steps for all systems (for example, single-stranded domains). In some embodiments, in the global crosstalk tube, the off-target complexes correspond to noncognate interactions between these reactive species. In some embodiments, the global crosstalk tube ensemble omits the cognate products that the reactive species are intended to form (they appear as neither on-targets nor off-targets); in this scenario, all reactive species in the global crosstalk tube can be forced to either perform no reaction (remaining as desired on-targets) or to undergo a crosstalk reaction (forming undesired off-targets), providing the basis for minimization of global crosstalk during sequence optimization. In some embodiments, sequence design is performed subject to complementarity constraints including any combination of: 1) sequence constraints inherent to the reaction pathway (for example in FIG. 4B, domain "d" complementary to domain "d*", etc.), 2) sequence constraints imposed by the trigger sequence X, 3) sequence constraints imposed by the target Y, 4) sequence constraints imposed by the protein effector (for example, Cas, dCas, Cas9, dCas9, etc.), 5) sequence constraints imposed by a synthetic terminator,[41] other sequence constraints. In some embodiments, sequences are optimized by reducing the ensemble defect quantifying the average fraction of incorrectly paired nucleotides over the multi-tube ensemble.[41] In some embodiments, defect weights are applied within the ensemble defect to prioritize design effort.[41] In some embodiments, optimization of the ensemble defect implements both a positive design paradigm, explicitly design for on-pathway elementary steps, and a negative design paradigm, explicitly design against off-pathway crosstalk.[41]

In some embodiments, the cgRNA and/or trigger sequence is engineered using directed evolution. In some embodiments, the cgRNA and/or trigger sequence is engineered using a combination of rational design and directed evolution. In some embodiments, the cgRNA and/or trigger sequence is engineered using machine learning. In some embodiments, the cgRNA and/or trigger sequence is engineered using machine learning and directed evolution. In some embodiments, the cgRNA and/or trigger sequence is engineered using a combination of rational design, machine learning, and/or directed evolution.

In some embodiments, the cgRNA comprises one or more chemical modifications that alter one or more of degradation properties, affinity, biological activity, and/or delivery properties of the cgRNA, optionally wherein the one or more chemical modifications is selected from the group consisting of arabino nucleic acids (ANA), locked nucleic acids (LNA), peptide nucleic acids (PNA), phosphoroamidate DNA analogues, phosphorodiamidate morpholino oligomers (PMO), cyclohexene nucleic acids (CeNA), tricycloDNA (tcDNA), bridged nucleic acids (BNA), phosphorothioate modification, 2'-fluoro (2'-F) modification, 2'-fluoroarabino (2'-FANA) modification, 2'O-Methyl (2'O-Me) modification, and 2'O-(2-methoxyethyl) (2'O-MOE) modification.

In some embodiments, the trigger comprises one or more chemical modifications that alter one or more of degradation properties, affinity, biological activity, and delivery properties of the trigger, optionally wherein the one or more chemical modifications is selected from the group consisting of arabino nucleic acids (ANA), locked nucleic acids (LNA), peptide nucleic acids (PNA), phosphoroamidate DNA analogues, phosphorodiamidate morpholino oligomers (PMO), cyclohexene nucleic acids (CeNA), tricycloDNA (tcDNA), bridged nucleic acids (BNA), phosphorothioate modification, 2'-fluoro (2'-F) modification, 2'-fluoroarabino (2'-FANA) modification, 2'O-Methyl (2'O-Me) modification, and 2'O-(2-methoxyethyl) (2'O-MOE) modification.

In some embodiments, the sequence of the cgRNA is a subsequence of a longer RNA, DNA, or any polymer capable of base-pairing. In some embodiments, the polymer containing the cgRNA includes chemical linkers that are not capable of base-pairing. In some embodiments, the sequence of the trigger is a subsequence of a longer RNA, DNA, or any polymer capable of base-pairing. In some embodiments, the polymer containing the trigger includes chemical linkers that are not capable of base-pairing.

In some embodiments, one or more duplexes (or stems) formed by complementary or partially complementary domains of the cgRNA, 5' fragment cg5, 3' fragment cg3, cgRNA:inhibitor complex, cgRNA:helper complex, cg5:cg3 complex, trigger:cg5:cg3 complex, cg3:trigger complex, inhibitor:trigger complex, and/or cgRNA:trigger complex (or any of the cgRNA molecules, cgRNA fragments, triggers, inhibitors, helpers and/or complexes thereof) may contain zero, one, or more of mismatches, loops, multiloops, bulge loops, interior loops, or nicks between strands.

In some embodiments, the cgRNA, cgRNA fragments, inhibitor, and/or helper is expressed in the cells, living organisms, or artificial settings in which it interacts with effector, input, and/or target. In some embodiments, the trigger is expressed in the cells, living organisms or artificial settings in which it interacts with effector, input, and/or target. In some embodiments, the cgRNA, inhibitor, and/or helper is artificially synthesized or exogenously expressed and delivered to the cells, living organisms or artificial settings in which it interacts with effector, input, and/or target. In some embodiments, the trigger is artificially synthesized or exogenously expressed and delivered to the cells, living organisms or artificial settings in which it interacts with effector, input, and/or target. In some embodiments, the effector is expressed in the cells, living organisms or artificial settings in which it interacts with cgRNA, input, and/or target. In some embodiments, the effector is artificially synthesized or exogenously expressed and delivered to the cells, living organisms or artificial settings in which it interacts with effector, input, and/or target. In some embodiments, any of the cgRNA, cgRNA fragments, inhibitor, helper, and/or effector are delivered as a plasmid and expressed. In some embodiments, any of the cgRNA, cgRNA fragments, inhibitor, helper, and/or effector are delivered by a virus, by electroporation, by transfection, by lateral gene transfer, by microinjection, or by nanoparticle delivery. In some embodiments, any of the cgRNA, cgRNA fragments, inhibitor, helper, and/or effector are delivered as DNA and expressed.

In some embodiments, one or more of the cgRNA, cgRNA fragments, inhibitor, and/or helper strands is expressed with a self-cleaving ribozyme at one or both ends that cleaves the transcript to create the cgRNA, cgRNA fragments, inhibitor, and/or helper strands.

In some embodiments, one or more of the cgRNA, cgRNA fragments, inhibitor, and/or helper strands contains a protective element (PEL) at one or both ends, or internally, to inhibit degradation of the strand by ribonucleases.

In some embodiments, the target nucleic acid is endogenous RNA, DNA, or another polymer capable of base-pairing, whether the polymer is coding or non-coding. In some embodiments, the target nucleic acid is exogenous RNA, DNA, or another polymer capable of base-pairing, whether the polymer is coding or non-coding.

In some embodiments, the RNA guided effector is selected from the group consisting of Cas9, nickase Cas9, dCas9, silencing dCas9, inducing dCas9, catalytically dead dCas9, Cas12a, Cas13d, protein fusions or derivatives thereof, RNA-guided CRISPR effector protein or protein complex, or any protein from a similar pathway.

In some embodiments, the cgRNA conditionally performs a downstream function on a target nucleic acid in a living organism, ecosystem, tissue extract, cell lysate, and/or artificial system of reconstituted biological components. In some embodiments, the downstream effector function is the downregulation of the expression of a target nucleic acid. In some embodiments, the downstream effector function is the upregulation of the expression of a target nucleic acid. In some embodiments, the downstream effector function is the editing of the sequence of a target nucleic acid without template. In some embodiments, the downstream effector function is the editing of the sequence of a target nucleic acid with template. In some embodiments, the expression of a therapeutic target is conditionally downregulated in diseased cells or tissues. In some embodiments, the expression of a therapeutic target is conditionally upregulated in diseased cells or tissues. In some embodiments, the sequence of a therapeutic target is conditionally edited in diseased cells or tissues. In some embodiments, the regulation and/or editing of a target gene mediated by a cgRNA results in the conditional death of diseased cells or tissues. In some embodiments, the expression of a target gene is conditionally downregulated in selected prokaryotes. In some embodiments, the expression of a target gene is conditionally upregulated in selected prokaryotes. In some embodiments, the sequence of a target gene is conditionally edited in selected prokaryotes. In some embodiments, the regulation and/or editing of a target gene mediated by a cgRNA results in the conditional death of selected prokaryotes. In some embodiments, the expression of a target gene is conditionally downregulated in selected cells within a plant. In some embodiments, the expression of a target gene is conditionally upregulated in selected sells within a plant. In some embodiments, the sequence of a target gene is conditionally edited in selected cells within a plant. In some embodiments, the regulation and/or editing of a target gene mediated by a cgRNA results in the conditional death of selected cells within a plant. In some embodiments, the expression of a target gene is conditionally downregulated in a sample. In some embodiments, the expression of a target gene is conditionally upregulated in a sample. In some embodiments, the sequence of a target gene is conditionally edited in a sample. In some embodiments, the regulation and/or editing of a target gene mediated by a cgRNA results in conditional cell death in a sample. In some embodiments, the expression of a target gene is conditionally downregulated in selected prokaryotes on or within a human, pet, livestock animal, or crop plant. In some embodiments, the expression of a target gene is conditionally upregulated in selected prokaryotes on or within a human, pet, livestock animal, or crop plant. In some embodiments, the sequence of a target gene is conditionally edited in selected prokaryotes on or within a human, pet, livestock animal, or crop plant. In some embodiments, the regulation and/or editing of a target gene mediated by a cgRNA results in the conditional death of selected prokaryotes on or within a human, pet, livestock animal, or crop plant. In some embodiments, the expression of a target gene is conditionally downregulated in selected eukaryotic cells. In some embodiments, the expression of a target gene is conditionally upregulated in selected eukaryotic cells. In some embodiments, the sequence of a target gene is conditionally edited in selected eukaryotic cells. In some embodiments, the regulation and/or editing of a target gene mediated by a cgRNA results in the conditional death of selected eukaryiotic cells.

In schematics depicting allosteric cgRNAs, cgRNA fragments, cognate RNA triggers, target genes, RNA inhibitor strands, and/or RNA helper strands, and/or interactions between any of the above (for example, the schematics of FIGS. 4B, 4C, 5B, 5C, 6B, 6C, 7B, 7C, 8B, 8C, 9B, 9C, 9D, 9E, 10A, 10B, 10C, 23B, 23C, 24B, 24C, 25B, 25C, 26B, 26C, 27B, 27C, 28B, 28C, 28D, 29B, 29C, 29D), the 3' end of each strand is depicted with an arrowhead. In some embodiments, a base-paired region in a schematic depicting allosteric cgRNAs, cognate RNA triggers, target genes, RNA inhibitor strands, and/or RNA helper strands, and/or interactions between any of the above (for example, the schematics of FIGS. 4B, 4C, 5B, 5C, 6B, 6C, 7B, 7C, 8B, 8C, 9B, 9C, 9D, 9E, 10A, 10B, 10C, 23B, 23C, 24B, 24C, 25B, 25C, 26B, 26C, 27B, 27C, 28B, 28C, 28D, 29B, 29C, 29D), comprises 1, 2, or more base pairs. In some embodiments, a base-paired region in a schematic depicting allosteric cgRNAs, cgRNA fragments, cognate RNA triggers, target genes, RNA inhibitor strands, and/or RNA helper strands, and/or interactions between any of the above (for example, the schematics of FIGS. 4B, 4C, 5B, 5C, 6B, 6C, 7B, 7C, 8B, 8C, 9B, 9C, 9D, 9E, 10A, 10B, 10C, 23B, 23C, 24B, 24C, 25B, 25C, 26B, 26C, 27B, 27C, 28B, 28C, 28D, 29B, 29C, 29D), comprises a duplex (or stem) comprising 1, 2, or more base pairs. In some embodiments, a base-paired region in a schematic depicting allosteric cgRNAs, cgRNA fragments, cognate RNA triggers, target genes, RNA inhibitor strands, and/or RNA helper strands, and/or interactions between any of the above (for example, the schematics of FIGS. 4B, 4C, 5B, 5C, 6B, 6C, 7B, 7C, 8B, 8C, 9B, 9C, 9D, 9E, 10A, 10B, 10C, 23B, 23C, 24B, 24C, 25B, 25C, 26B, 26C, 27B, 27C, 28B, 28C, 28D, 29B, 29C, 29D), comprises a duplex (or stem) comprising 1, 2, or more consecutive base pairs. In some embodiments, a base-paired region in a schematic depicting allosteric cgRNAs, cgRNA fragments, cognate RNA triggers, target genes, RNA inhibitor strands, and/or RNA helper strands, and/or interactions between any of the above (for example, the schematics of FIGS. 4B, 4C, 5B, 5C, 6B, 6C, 7B, 7C, 8B, 8C, 9B, 9C, 9D, 9E, 10A, 10B, 10C, 23B, 23C, 24B, 24C, 25B, 25C, 26B, 26C, 27B, 27C, 28B, 28C, 28D, 29B, 29C, 29D) is optional. In some embodiments, any of allosteric cgRNAs, cgRNA fragments, cognate RNA triggers, RNA inhibitor strands, and/or RNA helper strands can be extended at either or both of the 5' or 3' ends (or internally) by zero, one, or more additional domains, wherein any additional domains may be unstructured, may serve as a protective element (PEL) to reduce RNA degradation, may serve as a toehold, may comprise additional base-pairs, or any combination of the above. In some embodiments, the cognate RNA trigger is a subsequence of an endogenous RNA. In some embodiments, any of allosteric cgRNAs, cgRNA fragments, cognate RNA triggers, RNA inhibitor strands, and/or RNA helper strands may include one or more chemically modified nucleotides or synthetic nucleic acid analogs or other materials capable of base-pairing (including but not limited to DNA, XNA, PNA, 2'OMe-RNA) and/or one or more chemical linkers that are not capable of base-pairing. In some embodiments, the Cas9 handle is a modified handle with a different structure and/or sequence relative to a wildtype Cas9 handle (for example, the "flip+extend" (FE)-modified Cas9 handle used in the experimental studies of FIGS. 14-16)[42]. In some embodiments, the structure and/or sequence of the Cas handle is modified relative to a wildtype Cas sequence via rational design, machine learning, directed evolution, or any combination thereof.

In some embodiments, additional regions or sequence domains may be added at either end of any of the depicted regions or sequence domains. In some embodiments, one or more depicted regions (e.g., sequence domains or nucleotides) are optional.

In some embodiments, an inactive cgRNA (for example, Mechanisms 1B, 2B, 3B, 4A, 5, 6, 7, 8, 9) can be activated by a first trigger sequence (OFF→ON logic). In some embodiments, a cgRNA that is activated by a first trigger sequence (OFF→ON logic) can later be inactivated by second trigger sequence (ON→OFF logic). In some embodiments, a cgRNA can be cycled between the ON and OFF states by first and second trigger sequences.

In some embodiments, an active cgRNA (for example, Mechanisms 1A, 2A, 3A, 4B, 4C) can be inactivated by a first trigger sequence (ON→OFF logic). In some embodiments, a cgRNA that is inactivated by a first trigger sequence (OFF→ON logic) can later be activated by second trigger sequence (ON→OFF logic). In some embodiments, a cgRNA can be cycled between the ON and OFF states by first and second trigger sequences.

In some embodiments, a cgRNA can catalytically regenerate the trigger sequence (for example, Mechanisms 7, 8, 9) so that one trigger molecule can toggle the state of multiple copies of the cgRNA.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, any invention herein is not intended to be limited by the recitation of the preferred embodiments, but is instead to be defined by reference to the appended claims. All references cited herein are incorporated by reference in their entirety.

Arrangements

In addition to the foregoing, some embodiments provide the following arrangements:

Arrangement 1: An allosteric conditional guide RNA (cgRNA) comprising a target-binding region and a trigger-binding region: a. wherein the target-binding region is non-overlapping with the trigger-binding region; b. wherein the cgRNA is active in the absence of a cognate RNA trigger, wherein the cgRNA is configured to mediate the function of a Cas protein effector on a target gene that binds the target-binding region; and c. wherein upon hybridization to the cognate RNA trigger, the cgRNA is inactivated, inhibiting further mediation of Cas function on the target gene.

Arrangement 2: The allosteric cgRNA of Arrangement 1, further comprising a Cas handle wherein the target-binding region is 5' of the Cas handle and the trigger-binding region is 3' of the Cas handle.

Arrangement 3: The allosteric cgRNA of Arrangement 1, the cgRNA further comprising a first terminator hairpin with an extended loop comprising 5 or more nucleotides wherein the trigger-binding region comprises: a. zero, one, or more nucleotides of a linker 5'-adjacent to the first terminator hairpin; b. zero, one, or more nucleotides in a 5' portion of a stem of the first terminator hairpin; and c. one or more nucleotides in the extended loop of the first terminator hairpin; wherein the cgRNA is inactivated upon hybridization of the cognate RNA trigger to the cgRNA.

Arrangement 4: The allosteric cgRNA of Arrangement 1, further comprising a Cas handle with an extended loop wherein the target-binding region is 5' of the Cas handle and the trigger-binding region comprises a portion of the extended loop of the Cas handle and no nucleotides 5' of the Cas handle.

Arrangement 5: The allosteric cgRNA of Arrangement 4, further comprising a first terminator hairpin with an extended loop comprising 5 or more nucleotides such that the trigger-binding region comprises: a. one or more nucleotides in the extended loop of the Cas handle; and b. one or more nucleotides in the extended loop of the first terminator hairpin, wherein upon hybridization of the cognate RNA trigger to the cgRNA, the cgRNA is inactivated.

Arrangement 6: The allosteric cgRNA of Arrangement 4, the cgRNA further comprising a first terminator hairpin with an extended loop comprising 5 or more nucleotides wherein the trigger-binding region further comprises: a. zero, one, or more nucleotides of a linker 5'-adjacent to the first terminator hairpin; b. zero, one, or more nucleotides in a 5' portion of a stem of the first terminator hairpin; and c. one or more nucleotides in the extended loop of the first terminator hairpin, wherein the cgRNA is inactivated upon hybridization of the cognate RNA trigger to the cgRNA.

Arrangement 7: An allosteric conditional guide RNA (cgRNA) and an RNA inhibitor strand, wherein the cgRNA comprises a target-binding region and an inhibitor-binding region, and the RNA inhibitor strand comprises a trigger-binding region, wherein the cgRNA is configured to bind to a portion of the trigger-binding region to form a cgRNA:inhibitor complex: a. wherein the target-binding region is not base-paired to the trigger-binding region in the cgRNA:inhibitor complex; b. wherein the cgRNA:inhibitor complex is inactive in the absence of a cognate RNA trigger; and c. wherein upon hybridization of a cognate RNA trigger to the inhibitor, the cgRNA is activated, mediating the function of a Cas protein effector on a target gene that binds the target-binding region.

Arrangement 8: The allosteric cgRNA and RNA inhibitor strand of Arrangement 7, the cgRNA further comprising a Cas handle wherein the target-binding region is 5' of the Cas handle and the inhibitor-binding region is 3' of the Cas handle.

Arrangement 9: The allosteric cgRNA and RNA inhibitor strand of Arrangement 7, the inhibitor further comprising a toehold of one or more unpaired nucleotides at one or both ends, the cgRNA further comprising a first terminator hairpin with an extended loop comprising 5 or more nucleotides, the cgRNA further comprising an inhibitor-binding region comprising: a. zero, one, or more nucleotides of a linker 5'-adjacent to the first terminator hairpin; b. zero, one, or more nucleotides in a 5' portion of a stem of the first terminator hairpin; and c. one or more nucleotides in the extended loop of the first terminator hairpin, wherein the cgRNA is inactive in the cgRNA:inhibitor complex, and wherein hybridization of the cognate RNA trigger to the inhibitor displaces the cgRNA from the inhibitor, thereby activating the cgRNA.

Arrangement 10: The allosteric cgRNA and RNA inhibitor strand of Arrangement 7, the cgRNA further comprising a Cas handle with an extended loop wherein the target-binding region is 5' of the Cas handle, and wherein the inhibitor-binding region comprises a portion of the extended loop of the Cas handle and no nucleotides 5' of the Cas handle.

Arrangement 11: The allosteric cgRNA and RNA inhibitor strand of Arrangement 10, the inhibitor further comprising a toehold of one or more unpaired nucleotides at one or both ends, the cgRNA further comprising a first terminator hairpin with an extended loop comprising 5 or more nucleotides, and the inhibitor-binding region comprising: a. one or more nucleotides in the extended loop of the Cas handle; and b. one or more nucleotides in the extended loop of the first terminator hairpin; wherein the cgRNA is inactive in the cgRNA:inhibitor complex, and wherein hybridization of the cognate RNA trigger to the inhibitor displaces the cgRNA from the inhibitor, thereby activating the cgRNA.

Arrangement 12: The allosteric cgRNA and RNA inhibitor strand of Arrangement 10, the inhibitor further comprising a toehold of one or more unpaired nucleotides at one or both ends, the cgRNA further comprising a first terminator hairpin with an extended loop comprising 5 or more nucleotides, and the inhibitor-binding region comprising: a. one or more nucleotides in the extended loop of the Cas handle; b. zero, one, or more nucleotides of a linker 5'-adjacent to the first terminator hairpin; c. zero, one, or more nucleotides of a 5' portion of a stem of the first terminator hairpin; and d.

one or more nucleotides in the extended loop of the first terminator hairpin; wherein the cgRNA is inactive in the cgRNA:inhibitor complex, and wherein hybridization of the cognate trigger to the inhibitor displaces the cgRNA from the inhibitor, thereby activating the cgRNA.

Arrangement 13: An allosteric conditional guide RNA (cgRNA) comprising a 5' fragment (cg5) and a 3' fragment (cg3), cg5 comprising a target-binding region and a trigger-binding region, and cg3 comprising a cognate RNA trigger: a. wherein the target-binding region is non-overlapping with the trigger-binding region; b. wherein cg5 and cg3 are inactive when not bound to each other; and c. wherein upon hybridization of cg3 to cg5 to form a cg5:cg3 complex, the cgRNA is activated, mediating the function of a Cas protein effector on a target gene that binds the target-binding region.

Arrangement 14: The allosteric cgRNA of Arrangement 13 wherein the fragment cg5 further comprises a Cas handle wherein the target-binding region is 5' of the Cas handle and the trigger-binding region is 3' of the Cas handle.

Arrangement 15: The allosteric cgRNA of Arrangement 13, wherein fragment cg5 further comprises a trigger-binding region comprising a 5' portion of a stem of a terminator duplex; and fragment cg3 further comprises a 3' portion of the stem of the terminator duplex, such that hybridization of cg5 to cg3 forms the terminator duplex, activating the cgRNA.

Arrangement 16: An allosteric conditional guide RNA (cgRNA) comprising a 5' fragment (cg5) and a 3' fragment (cg3), cg5 comprising a target-binding region and a trigger-binding region, and cg3 configured to bind to a portion of the trigger-binding region to form a cg5:cg3 complex: a. wherein the target-binding region is non-overlapping with the trigger-binding region; b. wherein the cg5:cg3 complex is active in the absence of a cognate RNA trigger, mediating the function of a Cas protein effector on a target gene that binds the target-binding region; c. wherein cg5 and cg3 are inactive when not bound to each other; and d. wherein hybridization of the cognate RNA trigger to cg5 displaces cg3 from cg5, thereby inhibiting further mediation of Cas function on the target gene.

Arrangement 17: The allosteric cgRNA of Arrangement 16, wherein the fragment cg5 further comprises a Cas handle wherein the target-binding region is 5' of the Cas handle and the trigger-binding region is 3' of the Cas handle.

Arrangement 18: The allosteric cgRNA of Arrangement 16, wherein the fragment cg5 further comprises a trigger-binding region comprising: a. a 5' portion of a stem of a terminator duplex; b. zero, one, or more nucleotides of a linker 5'-adjacent to the 5' portion of the stem of the terminator duplex; and c. a toehold comprising zero, one, or more nucleotides 3'-adjacent to the 5' portion of the stem of the terminator duplex; wherein the fragment cg3 further comprises a 3' portion of the stem of the terminator duplex, wherein hybridization of cg5 to cg3 forms the terminator duplex within the cg5:cg3 complex, and wherein hybridization of the trigger to cg5 displaces cg3 from cg5, thereby breaking the terminator duplex and inactivating the cgRNA.

Arrangement 19: An allosteric conditional guide RNA (cgRNA) comprising: a 5' fragment (cg5) and a 3' fragment (cg3), cg5 comprising a target-binding region; and cg3 comprising a trigger-binding region, wherein cg5 is configured to bind to a portion of the trigger-binding region to form a cg5:cg3 complex: a. wherein the target-binding region is not base-paired to the trigger-binding region in the cg5:cg3 complex; b. wherein the cg5:cg3 complex is active in the absence of a cognate RNA trigger, mediating the function of a Cas protein effector on a target gene that binds the target-binding region; c. wherein cg5 and cg3 are inactive when not bound to each other; and d. wherein hybridization of the cognate RNA trigger to cg3 displaces cg5 from cg3, thereby inhibiting further mediation of Cas function on the target gene.

Arrangement 20: The allosteric cgRNA of Arrangement 19, wherein the fragment cg5 further comprises a Cas handle wherein the target-binding region is 5' of the Cas handle, and wherein the fragment cg3 binds to cg5 3' of the Cas handle.

Arrangement 21: The allosteric cgRNA of Arrangement 19, wherein: the fragment cg3 further comprises a trigger-binding region comprising: a. a 3' portion of a stem of a terminator duplex, and b. a toehold comprising zero, one, or more nucleotides 5'-adjacent to the 3' portion of the stem of the terminator duplex; the fragment cg5 further comprises a 5' portion of the stem of the terminator duplex; and wherein hybridization of cg5 to cg3 forms the terminator duplex within the cg5:cg3 complex, and wherein hybridization of the cognate RNA trigger to cg3 displaces cg5 from cg3, thereby breaking the terminator duplex and inactivating the cgRNA.

Arrangement 22: An allosteric conditional guide RNA (cgRNA) comprising: a 5' fragment (cg5) and a 3' fragment (cg3), wherein cg5 comprises a Cas handle, a target-binding region 5' of the Cas handle, and a cg3-binding region 3' of the Cas handle, wherein cg3 comprises a cg5-binding region, and wherein either cg5 or cg3 comprises a trigger-binding region: a. wherein the target-binding region is non-overlapping with the trigger-binding region and is configured not to bind to the trigger-binding region; b. wherein cg5 and cg3 are inactive when not bound to each other; c. wherein in the absence of a cognate RNA trigger, cg5 and cg3 are configured to be inhibited from binding to each other; and d. wherein upon hybridization of the cognate RNA trigger to either cg5 or cg3, cg5 and cg3 hybridize to form a trigger:cg5:cg3 complex that activates the cgRNA, thereby mediating the function of a Cas protein effector on a target gene that binds the target-binding region.

Arrangement 23: The allosteric cgRNA of Arrangement 22, wherein the fragment cg5 further comprises: a. a trigger-binding region comprising a first inhibitor region, and b. a second inhibitor region; wherein in the absence of the cognate RNA trigger, the first inhibitor region is configured to bind to the second inhibitor region, thereby inhibiting binding between cg5 and cg3.

Arrangement 24: The allosteric cgRNA of Arrangement 23, wherein: a. the cognate RNA trigger comprises a cg5-binding region; b. the trigger-binding region further comprises a toehold of one or more unpaired nucleotides at one or both ends; c. the cg3-binding region of cg5 comprises a 5' portion of a stem of a terminator duplex; and d. the cg5-binding region of cg3 comprises a 3' portion of the stem of the terminator duplex; wherein upon hybridization of the cognate RNA trigger to cg5, cg5 hybridizes to cg3 to form the terminator duplex, thereby activating the cgRNA.

Arrangement 25: The allosteric cgRNA of Arrangement 22, wherein cg3 further comprises: a. a trigger-binding region comprising a first inhibitor region, and b. a second inhibitor region; wherein in the absence of the cognate RNA trigger, the first inhibitor region is configured to bind the second inhibitor region, thereby inhibiting binding between cg5 and cg3.

Arrangement 26: The allosteric cgRNA of Arrangement 25, wherein: a. the cognate RNA trigger comprises a cg3-binding region; b. the trigger-binding region further comprises a toehold of one or more unpaired nucleotides at one or both ends; c. the cg5-binding region of cg3 comprises a 3' portion of a stem of a terminator duplex; and d. the cg3-binding region of cg5 comprises a 5' portion of the stem of the terminator duplex; wherein upon hybridization of the cognate RNA trigger to cg3, cg3 hybridizes to cg5 to form the terminator duplex, thereby activating the cgRNA.

Arrangement 27: The allosteric cgRNA of Arrangement 22 wherein cg5 further comprises: a. a trigger-binding region comprising a first inhibitor region; and b. a second inhibitor region; and wherein cg3 further comprises: c. a third inhibitor region; and d. a fourth inhibitor region, wherein in the absence of a cognate RNA trigger, the first inhibitor region is configured to bind the second inhibitor region and the third inhibitor region is configured to bind to the fourth inhibitor region, thereby inhibiting binding between cg5 and cg3.

Arrangement 28: The allosteric cgRNA of Arrangement 27, wherein: a. the cognate RNA trigger comprises a cg5-binding region; b. the trigger-binding region of cg5 further comprises a toehold of one or more unpaired nucleotides at one or both ends; c. the cg3-binding region of cg5 comprises a 5' portion of a stem of a terminator duplex; and d. the cg5-binding region of cg3 comprises a 3' portion of the stem of the terminator duplex comprising a toehold of one or more unpaired nucleotides at one or both ends; wherein upon hybridization of the cognate RNA trigger to cg5, cg5 hybridizes to cg3 to form the terminator duplex, thereby activating the cgRNA.

Arrangement 29: The allosteric cgRNA of Arrangement 27 wherein the trigger-binding region of cg5 is 5' of the target-binding region.

Arrangement 30: The allosteric cgRNA of any one of Arrangements 27, 28, and 29, wherein cg3 comprises a trigger mimic region having a sequence identical to that of the cg5-binding region of the cognate RNA trigger, wherein upon activation of the cgRNA by the cognate RNA trigger, the trigger mimic region is exposed and capable of serving as the cognate RNA trigger for a new copy of the cgRNA comprising a new copy of the 5' fragment cg5 and a new copy of the 3' fragment cg3.

Arrangement 31: The allosteric cgRNA of Arrangement 27 wherein the trigger-binding region of cg5 is 3' of the Cas handle.

Arrangement 32: The allosteric cgRNA of any one of Arrangements 27, 28, and 31 wherein the cgRNA additionally comprises a splint as a third fragment wherein the splint comprises: a. a cg3-binding region comprising a fifth inhibitor region and further comprising a toehold of one or more unpaired nucleotides at one or both ends; and b. a cg5-binding region comprising a sixth inhibitor region; wherein in the absence of a cognate RNA trigger, the fifth inhibitor region is configured to bind the sixth inhibitor region, inhibiting binding of the splint to cg5 and cg3, and wherein upon activation of the cgRNA by the cognate RNA trigger, cg3 hybridizes to the cg3-binding region of the splint and the cg5-binding region of the splint hybridizes to cg5, displacing the trigger from cg5, and catalytically regenerating the trigger which then serves as the cognate RNA trigger for a new copy of the cgRNA comprising a new copy of the 5' fragment cg5 and a new copy of the 3' fragment cg3.

Arrangement 33: The allosteric cgRNA of Arrangement 32, wherein the catalytically regenerated trigger serves as the cognate RNA trigger for a new copy of the cgRNA that further comprises a new copy of the splint fragment.

Arrangement 34: The allosteric cgRNA of any one of Arrangements 27, 28, and 31, wherein cg3 comprises a trigger mimic region having a sequence identical to that of the cg5-binding region of the cognate RNA trigger, wherein upon activation of the cgRNA by the cognate RNA trigger, the trigger mimic region hybridizes to the trigger-binding region of cg5, displacing the trigger from cg5, and catalytically regenerating the trigger which can then serve as the cognate RNA trigger for a new copy of the cgRNA comprising a new copy of the 5' fragment cg5 and a new copy of the 3' fragment cg3.

Arrangement 35: The allosteric cgRNA of any one of Arrangements 1 to 34 where the trigger is an RNA.

Arrangement 36: The allosteric cgRNA of any one of Arrangements 1 to 34 where the trigger is or is a subsequence of an mRNA, an rRNA, a lncRNA, a miRNA, or a tRNA.

Arrangement 37: The allosteric cgRNA of any one of Arrangements 1 to 34 where the cgRNA is expressed in a cell.

Arrangement 38: The allosteric cgRNA of any one of Arrangements 1 to 34 where the cgRNA is chemically synthesized.

Arrangement 39: The allosteric cgRNA of any one of the preceding Arrangements, wherein the cgRNA, cgRNA fragment, RNA inhibitor strand, and/or trigger further comprises one or more additional regions at the 5' and/or the 3' end.

Arrangement 40: The allosteric cgRNA of any one of the preceding Arrangements, wherein the cgRNA, cgRNA fragment, RNA inhibitor strand, and/or trigger comprises one or more chemical modifications that alter one or more of degradation properties, affinity, biological activity, and/or delivery properties of the cgRNA.

Arrangement 41: The allosteric cgRNA of any one of the preceding Arrangements, wherein the cgRNA, cgRNA fragment, RNA inhibitor strand, and/or trigger comprises one or more chemical modifications selected from the group consisting of arabino nucleic acids (ANA), locked nucleic acids (LNA), peptide nucleic acids (PNA), phosphoroamidate DNA analogues, phosphorodiamidate morpholino oligomers (PMO), cyclohexene nucleic acids (CeNA), tricycloDNA (tcDNA), bridged nucleic acids (BNA), phosphorothioate modification, 2'-fluoro (2'-F) modification, 2'-fluoroarabino (2'-FANA) modification, 2'O-Methyl (2'O-Me) modification, and 2'O-(2-methoxyethyl) (2'O-MOE) modification.

Arrangement 42: The allosteric cgRNA of any one of the preceding Arrangements, wherein an RNA trigger, RNA helper, and/or RNA inhibitor further comprises a protective element (PEL), wherein none, some, or all of the PEL sequence is derived from a component of a viral xrRNA sequence, and wherein the PEL reduces degradation of the RNA trigger, RNA helper, and/or RNA inhibitor in a prokaryotic or eukaryotic cell.

Arrangement 43: The allosteric cgRNA of any one of the preceding Arrangements, wherein the cgRNA and/or one or more cgRNA fragments further comprise a protective element (PEL), wherein none, some, or all of the PEL sequence is derived from a component of a viral xrRNA, and wherein the PEL reduces degradation of the cgRNA and/or the cgRNA fragments in a prokaryotic or eukaryotic cell.

Arrangement 44: The allosteric cgRNA of any one of the preceding Arrangements, wherein the cgRNA works in conjunction with Cas to mediate cell-selective induction, silencing, editing, or binding of a target gene.

Arrangement 45: A method of conditionally inhibiting mediation of Cas function on a target gene, comprising: providing an allosteric conditional guide RNA (cgRNA) according to any one of Arrangements 1 to 6 and 35-44; and combining the cgRNA with a system comprising a target gene and a Cas protein effector; wherein the cgRNA is active in mediating the function of the Cas protein effector on the target gene in the absence of a cognate RNA trigger, and wherein upon hybridization to the cognate RNA trigger, the cgRNA is inactivated, inhibiting further mediation of Cas function on the target gene.

Arrangement 46: A method of conditionally mediating the function of a Cas protein effector on a target gene, comprising: providing an allosteric conditional guide RNA (cgRNA) and an RNA inhibitor strand according to any one of Arrangements 7 to 12 and 35-44; and combining the cgRNA and RNA inhibitor strand with a system comprising a target gene and a Cas protein effector; wherein in the absence of a cognate RNA trigger, the inhibitor is bound to the cgRNA and the cgRNA is inactive; and wherein upon hybridization of a cognate RNA trigger to the inhibitor, the cgRNA is activated, mediating the function of a Cas protein effector on the target gene.

Arrangement 47: A method of conditionally mediating the function of a Cas protein effector on a target gene, comprising: providing an allosteric conditional guide RNA (cgRNA) comprising a 5' fragment (cg5) and a 3' fragment (cg3) according to any one of Arrangements 13 to 15 and 35-44; and combining the cgRNA with a system comprising a target gene and a Cas protein effector; wherein cg5 and cg3 are inactive when not bound to each other; and wherein upon hybridization of cg3 to cg5, the cgRNA is activated, mediating the function of a Cas protein effector on the target gene.

Arrangement 48: A method of conditionally inhibiting mediation of Cas function on a target gene, comprising: providing an allosteric conditional guide RNA (cgRNA) comprising a 5' fragment (cg5) and a 3' fragment (cg3) according to any one of Arrangements 16 to 18 and 35-44; and combining the cgRNA with a system comprising a target gene and a Cas protein effector; wherein in the absence of a cognate RNA trigger cg5 is bound to cg3 and the cgRNA is active; and wherein hybridization of the cognate RNA trigger to cg5 displaces cg3 from cg5, thereby inhibiting further mediation of Cas function on the target gene.

Arrangement 49: A method of conditionally inhibiting mediation of Cas function on a target gene, comprising: providing an allosteric conditional guide RNA (cgRNA) comprising a 5' fragment (cg5) and a 3' fragment (cg3) according to any one of Arrangements 19 to 21 and 35-44; and combining the cgRNA with a system comprising a target gene and a Cas protein effector; wherein in the absence of a cognate RNA trigger cg5 is bound to cg3 and the cgRNA is active; and wherein hybridization of the cognate RNA trigger to cg3 displaces cg5 from cg3, thereby inhibiting further mediation of Cas function on the target gene.

Arrangement 50: A method of conditionally mediating the function of a Cas protein effector on a target gene, comprising: providing an allosteric conditional guide RNA (cgRNA) comprising a 5' fragment (cg5) and a 3' fragment (cg3) according to any one of Arrangements 22 to 34 and 35-44; and combining the cgRNA with a system comprising a target gene and a Cas protein effector; wherein in the absence of a cognate RNA trigger, cg5 and cg3 are inhibited from binding to each other and the cgRNA is inactive; and wherein upon hybridization of the cognate RNA trigger to either cg5 or cg3, cg5 and cg3 hybridize to form a trigger:cg5:cg3 complex that activates the cgRNA, thereby mediating the function of a Cas protein effector on the target gene.

EXAMPLES

Example—Logic, Function, Structure, and Interactions of a Standard Guide RNA (gRNA)

FIG. 1A depicts the logic and function of a standard guide RNA (gRNA). A standard gRNA is always ON, unconditionally directing the activity of a protein effector to a target Y; different Cas9, dCas9, and/or Cas variants implement different functions (for example, edit, silence, induce, bind). FIG. 1B depicts structure and interactions of a standard gRNA. From 5' to 3', a standard gRNA comprises: a target-binding region, a Cas handle recognized by the protein effector, and a terminator region.

Example—Logic and Function of a Conditional Guide RNA (cgRNA)

FIG. 2 depicts the logic and function of a conditional guide RNA (cgRNA) in which a cgRNA changes conformation in response to a programmable trigger X to conditionally direct the activity of a protein effector to a programmable target Y. FIG. 2A depicts ON→OFF logic with a constitutively active cgRNA that is conditionally inactivated by X. FIG. 2B depicts OFF→ON logic with a constitutively inactive cgRNA that is conditionally activated by X.

Example—Applications of Cell-Selective Control of Regulatory Control with cgRNAs FIG. 3 illustrates applications of cell-selective regulation of CRISPR/Cas function using cgRNAs. FIG. 3A contrasts global silencing (top arrow) of target gene Y using silencing dCas9 and a standard gRNA that implements the unconditional logic "silence Y" to cell-selective silencing (bottom arrow) of target gene Y using silencing dCas9 and a conditional cgRNA, such that Y is silenced locally only where X is expressed. FIG. 3B illustrates diverse modes of cell-selective spatiotemporal regulatory control using cgRNA conditional logic (ON→OFF or OFF→ON) and different Cas9 functional variants (induce, silence, edit, bind, etc.). ON→OFF and OFF→ON cgRNAs produce inverted regulatory patterns on target Y in response to a given pattern for trigger X. FIG. 3C illustrates some cell-selective and tissue-selective tools. For example, conditional gene silencing ("if gene X is transcribed, silence independent gene Y") can be used to probe genetic necessity, conditional gene activation ("if gene X is transcribed, activate independent gene Y") can be used to probe genetic sufficiency, and conditional cell death ("if gene X is transcribed, induce apoptosis") can be used to probe developmental compensation. In each case, conditional regulation is mediated by a cgRNA whose activity is toggled by a programmable trigger X. For some embodiments, by selecting a trigger X with the desired spatial and temporal expression profiles, the regulatory function is restricted to a desired cell type, tissue, or organ within an organism, mixture of cells, or ecosystem. For some embodiments, to shift conditional regulation to a different tissue type or time point, the cgRNAs can be programmed to recognize a different trigger X. For some embodiments, to enhance cell-selective spatiotemporal control in multi-cellular settings (e.g., within embryos or bacterial mixtures), multi-input conditional logic (operating on two or more inputs $X_1$, $X_2$, . . . ) using AND gates can be used to narrow the scope of regulation on Y; alternatively, OR gates can be used to broaden the scope of regulation on Y. In some embodiments, AND logic is implemented using split-cgRNAs that are functional only in the presence of both $X_1$ and $X_2$. In some embodiments, OR logic is executed using multiple cgRNA variants that accept different inputs ($X_1$, $X_2$, . . . ) but target the same output Y. FIG. 3D illustrates one example of cgRNA-mediated cell-selective reporter regulation for multiplexed in vivo RNA imaging. Four cgRNAs each detect a different mRNA input ($mRNA_1$, mRNA$_2$, mRNA$_3$, mRNA$_4$) that serves as an RNA trigger, activating the corresponding cgRNA to induce the corresponding spectrally distinct FP reporter (FP$_1$, FP$_2$, FP$_3$, FP$_4$). After once optimizing a plasmid-based reporter system expressing inducing dCas9, the 4 FP reporters, and the 4 cgRNAs, imaging a new set of mRNAs requires only updating the sequences of the cgRNAs to accept new mRNAs as triggers. This cgRNA approach offers important conceptual advantages relative to FP fusion methods, which have revolutionized the study of genetic expression,[43-45] but have the well-known drawbacks that a new fusion must be engineered for each gene of interest, that it is difficult to determine whether fusions affect the expression or function of target proteins, and that fusion methods are not applicable to imaging non-protein gene products such as coding and non-coding RNAs. cgRNAs can eliminate these issues by replacing the conventional physical link of FP fusion approaches with a logical link executed by cgRNAs that execute conditional gene induction, allowing for spatiotemporal monitoring of gene expression levels in living chick embryos without the need to modify the imaged molecules (mRNA$_1$, mRNA$_2$, mRNA$_3$, mRNA$_4$) in any way. FIG. 3E depicts the conditional logic using cgRNAs as conditional chemotherapies: "if disease marker X then regulate therapeutic target Y". Here, X is a programmable disease marker and Y is an independent therapeutic target, allowing for selective treatment or killing of diseased cells (the subset of cells containing X) while leaving healthy cells untouched (the subset of cells lacking X). In this way, cgRNAs allow for independent diagnosis (detection of disease marker X) and treatment (regulation or editing of independent therapeutic target Y).

Example—Logic, Function, and Mechanism for Allosteric ON→OFF Terminator Switch cgRNAs (Mechanism 1A)

FIG. 4 depicts the logic, function, and mechanism for allosteric ON→OFF terminator switch cgRNAs. FIG. 4A depicts the conditional logic and function of an ON→OFF terminator switch cgRNA used in conjunction with different Cas protein effectors (for example, edit, silence, induce, bind): "if not X then regulate Y" (if trigger X is not detected, then edit, silence, induce, or bind target gene Y). FIGS. 4B and 4C depict a mechanism for an allosteric ON→OFF terminator switch cgRNA: the constitutively active cgRNA is inactivated by hybridization of RNA trigger X. This mechanism offers the flexibility to rationally design sequence domains (as well as their complementary domains) "d" (linker), "e" (stem), and "f" (extended loop) in the cgRNA, independent of the sequence of the target-binding region (domain "u").

Example—Logic, Function, and Mechanism for Allosteric OFF→ON Terminator Switch cgRNAs (Mechanism 1B)

FIG. 5 depicts the logic, function, and mechanism for allosteric OFF→ON terminator switch cgRNAs. FIG. 5A depicts the conditional logic and function of an OFF→ON terminator switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 5B and 5C depict a mechanism for an allosteric OFF→ON terminator switch cgRNA: the cgRNA: inhibitor complex is inactive; hybridization of RNA trigger X to the inhibitor displaces the inhibitor from the cgRNA, activating the cgRNA. This mechanism offers the flexibility to rationally design sequence domains (as well as their complementary domains) "d" (linker), "e" (stem), and "f" (extended loop) in the cgRNA, as well as toehold domains "g" and "h" in the trigger, independent of the sequence of the target-binding region (domain "u").

Example—Logic, Function, and Mechanisms for Allosteric ON→OFF Splinted Switch cgRNAs (Mechanism 2A)

FIG. 6 depicts the logic, function, and mechanism for allosteric ON→OFF splinted switch cgRNAs. FIG. 6A depicts the conditional logic and function of an ON→OFF splinted switch cgRNA used in conjunction with different Cas protein effectors (for example, edit, silence, induce, bind): "if not X then regulate Y" (if trigger X is not detected, then edit, silence, induce, or bind target gene Y depending on the Cas effector). FIGS. 6B and 6C depict a mechanism for an allosteric ON→OFF splinted switch cgRNA: the constitutively active cgRNA is inactivated by hybridization of RNA trigger X. This mechanism offers the flexibility to rationally design sequence domains (as well as their complementary domains) "d" (extended Cas9 handle loop) and "e" (extended terminator hairpin loop) in the cgRNA, independent of the sequence of the target-binding region (domain "u").

Example—Logic, Function, and Mechanisms for Allosteric OFF→ON Splinted Switch cgRNAs (Mechanism 2B)

FIG. 7 depicts the logic, function, and mechanism for allosteric OFF→ON splinted switch cgRNAs. FIG. 7A depicts the conditional logic and function of an OFF→ON splinted switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 7B and 7C depict a mechanism for an allosteric OFF→ON splinted switch cgRNA: the cgRNA: inhibitor complex is inactive; hybridization of RNA trigger X to the inhibitor displaces the inhibitor from the cgRNA, activating the cgRNA. This mechanism offers the flexibility to rationally design sequence domains (as well as their complementary domains) "d" (extended Cas9 handle loop) and "e" (extended terminator hairpin loop) in the cgRNA, as well as toehold domains "f" and "g" in the trigger, independent of the sequence of the target-binding region (domain "u").

Example—Logic, Function, and Mechanism for Allosteric ON→OFF Tandem Switch cgRNAs (Mechanism 3A)

FIG. 23 depicts the logic, function, and mechanism for allosteric ON→OFF tandem switch cgRNAs. FIG. 23A depicts the conditional logic and function of an ON→OFF tandem switch cgRNA used in conjunction with different Cas protein effectors (for example, edit, silence, induce, bind): "if not X then regulate Y" (if trigger X is not detected, then edit, silence, induce, or bind target gene Y). FIGS. 23B and 23C depict a mechanism for an allosteric ON→OFF tandem switch cgRNA: the constitutively active cgRNA is inactivated by hybridization of RNA trigger X. This mechanism offers the flexibility to rationally design sequence domains (as well as their complementary domains) "d" (extended Cas9 handle loop), "e" (linker), "f" (stem), and "g" (extended terminator hairpin loop) in the cgRNA, independent of the sequence of the target-binding region (domain "u").

Example—Logic, Function, and Mechanism for Allosteric OFF→ON Tandem Switch cgRNAs (Mechanism 3B)

FIG. 24 depicts the logic, function, and mechanism for allosteric OFF→ON tandem switch cgRNAs. FIG. 24A depicts the conditional logic and function of an OFF→ON tandem switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 24B and 24C depict a mechanism for an allosteric OFF→ON tandem switch cgRNA: the cgRNA: inhibitor complex is inactive; hybridization of RNA trigger X to the inhibitor displaces the inhibitor from the cgRNA, activating the cgRNA. This mechanism offers the flexibility to rationally design sequence domains (as well as their complementary domains) "d" (extended Cas9 handle loop), "e" (linker), "f" (stem), and "g" (extended terminator hairpin loop) in the cgRNA, as well as toehold domains "p" and "q" in the trigger, independent of the sequence of the target-binding region (domain "u").

Example—Logic, Function, and Mechanism for Allosteric OFF→ON Split-Terminator Switch cgRNAs (Mechanism 4A)

FIG. 8 depicts the logic, function, and mechanism for allosteric OFF→ON split-terminator switch cgRNAs. FIG. 8A depicts the conditional logic and function for an OFF→ON split-terminator switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 8B and 8C depict a mechanism for an allosteric OFF→ON split-terminator switch cgRNA: the constitutively inactive cgRNA is activated by hybridization of RNA trigger X. Equivalently, the cgRNA may be interpreted as a 5' fragment (cg5) and the trigger may be interpreted as a 3' fragment (cg3), such that cg5 and cg3 are inactive when not bound to each other, but such that upon binding to each other to form the complex cg5:cg3, this complex constitutes an activated conditional guide RNA capable of mediating Cas9 or dCas9 function. This mechanism offers the flexibility to rationally design the sequence of the terminator duplex (cgRNA domain "d" and trigger domain "d*"), independent of the sequence of the target-binding region (domain "u").

Example—Logic, Function, and Mechanisms for Allosteric ON→OFF Split-Terminator Switch cgRNA (Mechanisms 4B and 4C)

FIG. 9 depicts the logic, function, and mechanism for allosteric ON→OFF split-terminator switch cgRNAs. FIG. 9A depicts the conditional logic and function for an ON→OFF split-terminator switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 9B and 9C depict one mechanism for an allosteric ON→OFF split-terminator switch cgRNA (Mechanism 4B): the cgRNA:helper complex is active; hybridization of RNA trigger X to the cgRNA displaces the helper, inactivating the cgRNA. This mechanism offers the flexibility to rationally design the domains (as well as their complementary domains) "c" (linker), "d" (stem), and "e" (toehold) of the cgRNA. FIGS. 9D and 9E depict a second mechanism for an allosteric ON→OFF split-terminator switch cgRNA (Mechanism 4C): the cgRNA:helper complex is active; hybridization of RNA trigger X to the helper displaces the cgRNA, inactivating the cgRNA. This mechanism offers the flexibility to rationally design the terminator duplex (cgRNA domain "d" and RNA helper strand domains "d*") as well as toehold domain "e*" on the RNA helper strand), independent of the sequence of the target-binding region (domain "u").

Example—Logic, Function, and Mechanism for Allosteric OFF→ON 5'-Inhibited Split-terminator Switch cgRNAs (Mechanism 5)

FIG. 25 depicts the logic, function, and mechanism for allosteric OFF→ON 5'-inhibited split-terminator switch cgRNAs. FIG. 25A depicts the conditional logic and function for an OFF→ON 5'-inhibited split-terminator switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 25B and 25C depict a mechanism for an allosteric OFF→ON 5'-inhibited split-terminator switch cgRNA: in some embodiments, the constitutively inactive cgRNA comprises a 5' fragment (cg5) and a 3' fragment (cg3):

1. such that cg5 and cg3 are inactive when not bound to each other,
2. such that in the absence of a cognate RNA trigger, cg5 and cg3 are configured to be inhibited from binding to each other,
3. and such that upon hybridization of the cognate RNA trigger to cg5, cg5 and cg3 hybridize to form a trigger: cg5:cg3 complex that activates the cgRNA, mediating the function of a Cas protein effector on a target gene.

This mechanism offers the flexibility to rationally design sequence domains (as well as their complementary domains) "a", "b", and "c", independent of the sequence of the target-binding region (domain "u").

Example—Logic, Function, and Mechanism for Allosteric OFF→ON 3'-Inhibited Split-Terminator Switch cgRNAs (Mechanism 6)

FIG. 26 depicts the logic, function, and mechanism for allosteric OFF→ON 3'-inhibited split-terminator switch cgRNAs. FIG. 26A depicts the conditional logic and function for an OFF→ON 3'-inhibited split-terminator switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 26B and 26C depict a mechanism for an allosteric OFF→ON 3'-inhibited split-terminator switch cgRNA: in some embodiments, the constitutively inactive cgRNA comprises a 5' fragment (cg5) and a 3' fragment (cg3):

1. such that cg5 and cg3 are inactive when not bound to each other,
2. such that in the absence of a cognate RNA trigger, cg5 and cg3 are configured to be inhibited from binding to each other,
3. and such that upon hybridization of the cognate RNA trigger to cg3, cg5 and cg3 hybridize to form a trigger: cg5:cg3 complex that activates the cgRNA, mediating the function of a Cas protein effector on a target gene.

This mechanism offers the flexibility to rationally design sequence domains (as well as their complementary domains) "a", "b", "c", and "d", independent of the sequence of the target-binding region (domain "u").

Example—Logic, Function, and Mechanism for Allosteric OFF→ON 5'- and 3'-Inhibited Split-Terminator Switch cgRNAs (Mechanism 7)

FIG. 27 depicts the logic, function, and mechanism for allosteric OFF→ON 5'- and 3'-inhibited split-terminator switch cgRNAs (Mechanism 7). FIG. 27A depicts the conditional logic and function for an OFF→ON 5'- and 3'-inhibited split-terminator switch cgRNA (Mechanism 7) used in conjunction with different Cas protein effectors (for example, edit, silence, induce, bind): "if X then regulate Y" (if trigger X is detected, then edit, silence, induce, or bind target gene Y depending on the Cas effector). FIGS. 27B and 27C depict a mechanism for an allosteric OFF→ON 5'- and 3'-inhibited split-terminator switch cgRNA (Mechanism 7): in some embodiments, the constitutively inactive cgRNA comprises a 5' fragment (cg5) and a 3' fragment (cg3):
1. such that cg5 and cg3 are inactive when not bound to each other,
2. such that in the absence of a cognate RNA trigger, cg5 and cg3 are configured to be inhibited from binding to each other,
3. and such that upon hybridization of the cognate RNA trigger to cg5, cg5 and cg3 hybridize to form a trigger: cg5:cg3 complex that activates the cgRNA, mediating the function of a Cas protein effector on a target gene.

In some embodiments, cg3 comprises a trigger mimic region with the same sequence as the cg5-binding region of the cognate RNA trigger, such that upon activation of the cgRNA by the cognate RNA trigger, the trigger mimic region is exposed and capable of serving as the cognate RNA trigger for a new copy of the cgRNA comprising a new copy of the 5' fragment cg5 and a new copy of the 3' fragment cg3. This mechanism offers the flexibility to rationally design sequence domains (as well as their complementary domains) "a", "b", "c", and "d", independent of the sequence of the target-binding region (domain "u").

Example—Logic, Function, and Mechanism for Allosteric OFF→ON 5'- and 3'-Inhibited Split-Terminator Switch cgRNAs (Mechanism 8)

Figure 28:
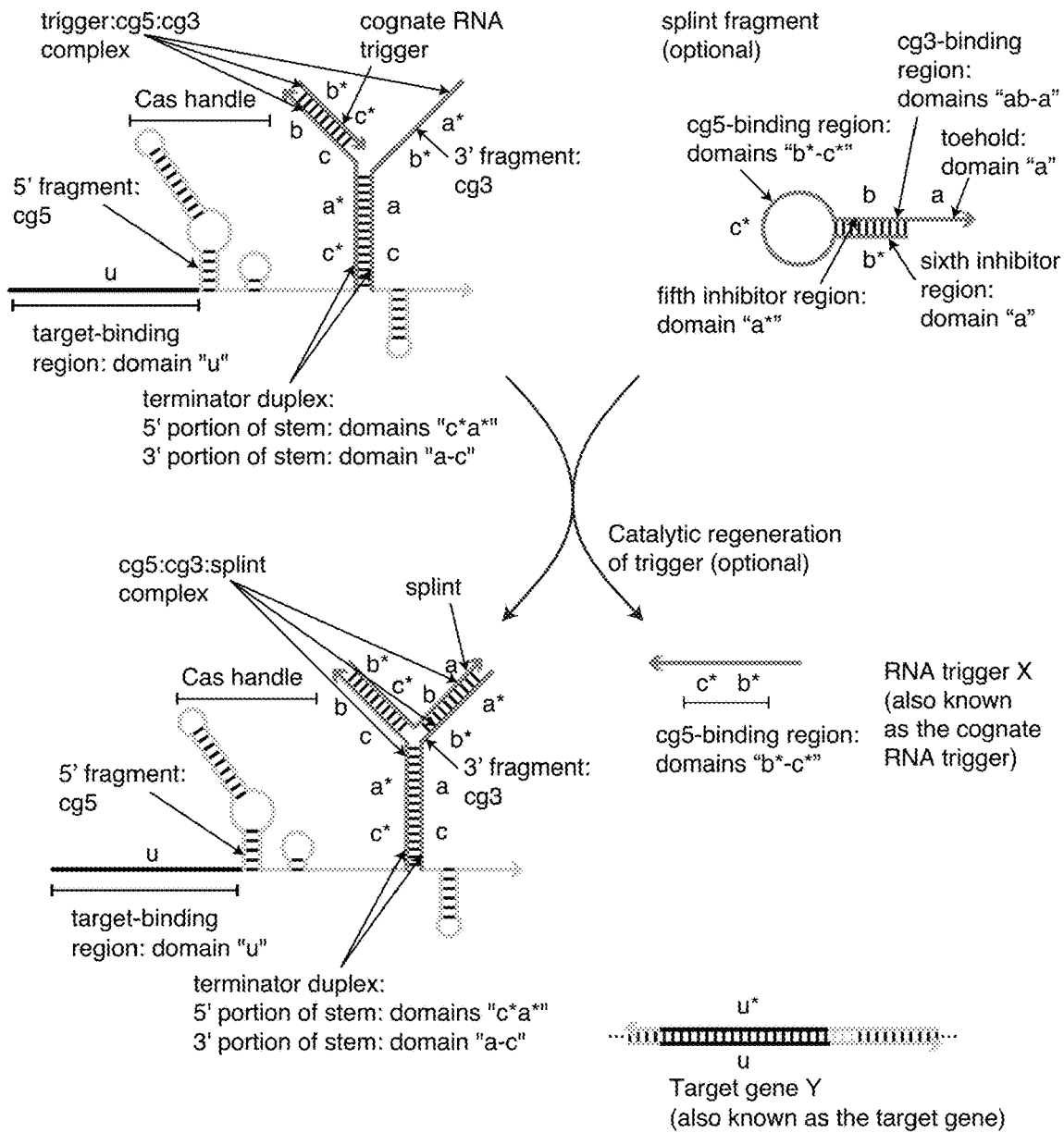

FIG. 28 depicts the logic, function, and mechanism for allosteric OFF→ON 5'- and 3'-inhibited split-terminator switch cgRNAs (Mechanism 8). FIG. 28A depicts the conditional logic and function for an OFF→ON 5'- and 3'-inhibited split-terminator switch cgRNA (Mechanism 8) used in conjunction with different Cas protein effectors (for example, edit, silence, induce, bind): "if X then regulate Y" (if trigger X is detected, then edit, silence, induce, or bind target gene Y depending on the Cas effector). FIGS. 28B, 28C, and 28D depict a mechanism for an allosteric OFF→ON 5'- and 3'-inhibited split-terminator switch cgRNA (Mechanism 8): in some embodiments, the constitutively inactive cgRNA comprises a 5' fragment (cg5) and a 3' fragment (cg3):
1. such that cg5 and cg3 are inactive when not bound to each other,
2. such that in the absence of a cognate RNA trigger, cg5 and cg3 are configured to be inhibited from binding to each other,
and such that upon hybridization of the cognate RNA trigger to cg5, cg5 and cg3 hybridize to form a trigger:cg5: cg3 complex that activates the cgRNA, mediating the function of a Cas protein effector on a target gene.

In some embodiments, the cgRNA additionally comprises a splint fragment such that in the absence of the cognate RNA trigger the splint fragment is configured to be inhibited from binding cg5 and cg3, and such that upon activation of the cgRNA by the cognate RNA trigger, cg3 hybridizes to the split fragment which then hybridizes to cg5, displacing the trigger from cg5 to catalytically regenerate the trigger which can then serve as the cognate RNA trigger for a new copy of the cgRNA comprising a new copy of the 5' fragment cg5, a new copy of the 3' fragment cg3, and a new copy of the splint fragment. This mechanism offers the flexibility to rationally design sequence domains (as well as their complementary domains) "a", "b", and "c", independent of the sequence of the target-binding region (domain "u").

Example—Logic, Function, and Mechanism for Allosteric OFF→ON 5'- and 3'-Inhibited Split-Terminator Switch cgRNAs (Mechanism 9)

FIG. 29 depicts the logic, function, and mechanism for allosteric OFF→ON 5'- and 3'-inhibited split-terminator switch cgRNAs (Mechanism 9). FIG. 29A depicts the conditional logic and function for an OFF→ON 5'- and 3'-inhibited split-terminator switch cgRNA (Mechanism 9) used in conjunction with different Cas protein effectors (for example, edit, silence, induce, bind): "if X then regulate Y" (if trigger X is detected, then edit, silence, induce, or bind target gene Y depending on the Cas effector). FIGS. 29B, 29C, and 29D depict a mechanism for an allosteric OFF→ON 5'- and 3'-inhibited split-terminator switch cgRNA (Mechanism 9): in some embodiments, the constitutively inactive cgRNA comprises a 5' fragment (cg5) and a 3' fragment (cg3):
1. such that cg5 and cg3 are inactive when not bound to each other,
2. such that in the absence of a cognate RNA trigger, cg5 and cg3 are configured to be inhibited from binding to each other,
and such that upon hybridization of the cognate RNA trigger to cg5, cg5 and cg3 are hybridize to form a trigger: cg5:cg3 complex that activates the cgRNA, mediating the function of a Cas protein effector on a target gene.

In some embodiments, cg3 additionally comprises a trigger mimic region such that upon activation of the cgRNA by the cognate RNA trigger, the trigger mimic region hybridizes to cg5 to displace the trigger, catalytically regenerating the trigger which can then serve as the cognate RNA trigger for a new copy of the cgRNA comprising a new copy of the 5' fragment cg5 and a new copy of the 3' fragment cg3. This mechanism offers the flexibility to rationally design sequence domains (as well as their complementary domains)

"a", "b", and "c", independent of the sequence of the target-binding region (domain "u").

Example—Depictions of Interactions Between Allosteric cgRNAs, RNA Triggers, and Cas9 or dCas9

FIG. 10 depicts interactions between allosteric cgRNAs, RNA triggers, and Cas9, dCas9 or Cas. FIG. 10A depicts interactions for an allosteric ON→OFF terminator switch cgRNA. In the ON state, the terminator switch cgRNA is constitutively active, directing the function of protein effector Cas9, dCas9, or Cas to a target gene Y in the absence of trigger. The extended loop and modified sequence domains in the terminator region are intended not to interfere with the activity of the cgRNA:Cas complex. In the OFF state, in the presence of RNA trigger X, hybridization of the trigger forms a structure incompatible with cgRNA mediation of Cas9, dCas9, and/or Cas function. FIG. 10B depicts interactions for an allosteric ON→OFF splinted switch cgRNA. In the ON state, the splinted switch cgRNA is constitutively active, directing the function of protein effector Cas9, dCas9, or Cas to a target gene Y in the absence of trigger. The extended loops in the Cas9 handle and terminator region are intended not to interfere with the activity of the cgRNA:Cas complex. In the OFF state, in the presence of RNA trigger X, hybridization of the trigger forms a splint that is structurally incompatible with cgRNA mediation of Cas9, dCas9, and/or Cas function. FIG. 10C depicts interactions for an allosteric OFF→ON split-terminator switch cgRNA. In the OFF state, the split-terminator switch cgRNA is constitutively inactive. In the absence of RNA trigger X, the cgRNA is incapable of directing the function of the protein effector Cas9, dCas9, and/or Cas. In the ON state, the complex of cgRNA and trigger X mediates the function of the protein effector Cas9, dCas9, or Cas on the target gene Y. The modified sequence domains in the terminator duplex do not to interfere with the activity of the cgRNA:trigger:Cas complex.

Example—Demonstration of Allosteric ON→OFF Terminator Switch cgRNAs in Bacteria FIG. 11 demonstrates allosteric ON→OFF terminator switch cgRNAs performing conditional logic in *E. coli*. FIG. 11A depicts the mechanism for an allosteric ON→OFF terminator switch cgRNA: the constitutively active cgRNA is inactivated by hybridization of RNA trigger X. Rational sequence design of cgRNA terminator region (domains "d-e-f" comprising 6 nt linker, 4 nt stem, 30 nt loop) and complementary trigger region (domains "f*-e*-d*"). FIG. 11B depicts the conditional logic for an ON→OFF terminator switch cgRNA used in conjunction with silencing dCas9: "if not X then not Y" (if trigger X is not detected, then silence target gene Y). FIG. 11C demonstrates that expression of RNA trigger X (40 nt unstructured+synthetic terminator hairpin) toggles the cgRNA from ON→OFF, leading to an increase in fluorescence. Single-cell fluorescence intensities via flow cytometry. Induced expression (aTc) of silencing dCas9 and constitutive expression of mRFP target gene Y and either: standard gRNA (ideal ON state), cgRNA (ON state), cgRNA+RNA trigger X (OFF state; trigger expression is IPTG-induced), no-target gRNA that lacks target-binding region (ideal OFF state). Autofluorescence (AF): cells with no mRFP. FIGS. 11D and 11E demonstrate programmable conditional regulation using 3 orthogonal cgRNAs (A, B, C) and their corresponding cognate triggers ($X_A$, $X_B$, $X_C$). In FIG. 11D, raw fluorescence depicts ON→OFF conditional response to cognate trigger. Fold change=OFF/ON=[cognate trigger−AF]/[no trigger−AF]). In FIG. 11E, normalized fluorescence depicts orthogonality between non-cognate cgRNA/trigger pairs. Crosstalk=[non-cognate trigger−no trigger]/[cognate trigger−no trigger]). Bar graphs depict mean estimated standard error calculated based on the mean single-cell fluorescence over 20,000 cells for each of N=3 replicate wells (OFF:ON ratio and crosstalk calculated with uncertainty propagation). FIG. 11F depicts the sequences of cgRNAs A, B, C, and the sequences of triggers $X_A$, $X_B$, $X_C$. Nucleotides that are lower case italic are constrained by the target gene. Nucleotides shaded gray are constrained by dCas9. Nucleotides that are upper case italic are designed. Sequences are presented as DNA sequences; the corresponding RNA sequence is the same as the DNA sequence except that "U" replaces "T").

Figure 11A:
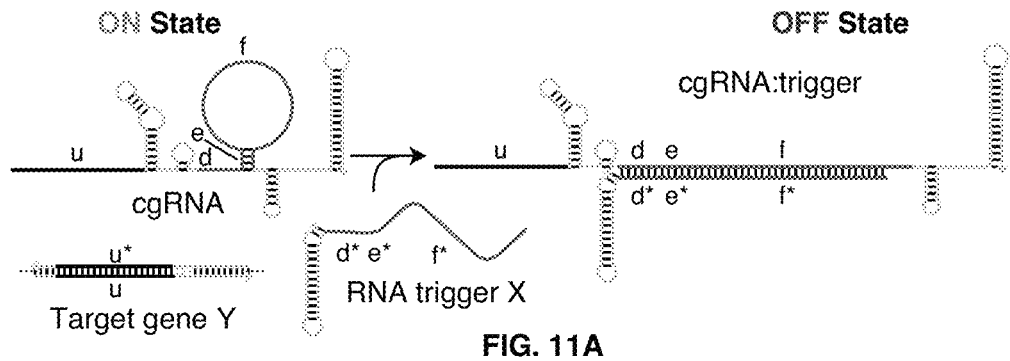
Figure 11B:
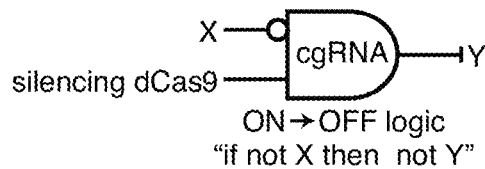
Figure 11C:
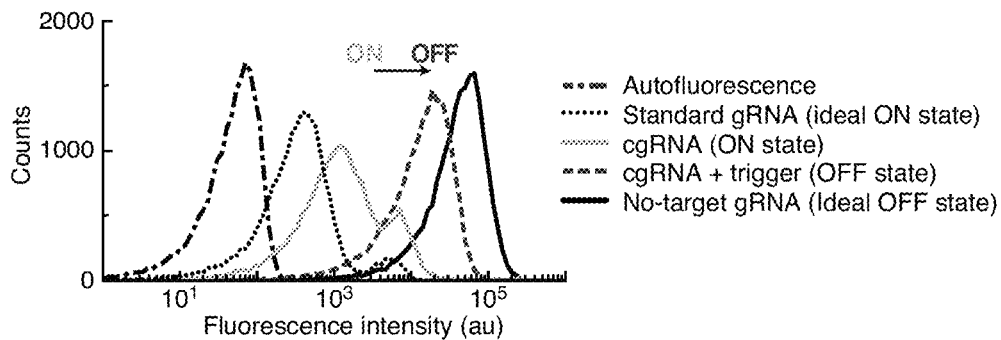
Figure 11D:
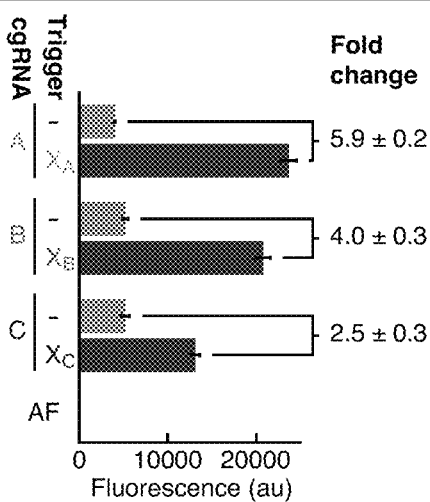
Figure 11E:
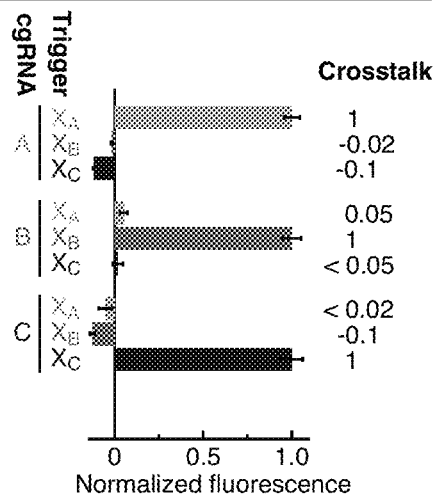

In *E. coli* expressing an allosteric ON→OFF terminator switch (FIG. 11A), silencing dCas9 and a fluorescent protein reporter (mRFP) as the target gene Y (conditional logic: "if not X then not Y'"; FIG. 11B), the cgRNA exhibits a strong conditional response to expression of RNA trigger X (FIG. 11C). FIG. 11D displays raw fluorescence data for a library of three orthogonal ON→OFF splinted switch cgRNAs with and without their cognate triggers. For this library of three cgRNA/trigger pairs, the median fold-change is approximately 4× for the ON→OFF conditional response to expression of the cognate trigger (FIG. 11D) and the median crosstalk between non-cognate/trigger pairs is approximately 2% (FIG. 11E).

Orthogonal cgRNA/trigger pairs were designed using NUPACK.[40,41] cgRNA/trigger plasmids were transformed into a modified *E. coli* MG1655 strain expressing genomically incorporated mRFP and sfGFP4.[5] Strains were grown overnight in EZ-RDM (Teknova), then diluted and grown to midlog phase (approximately 4 h). Cell density was normalized with fresh medium containing aTc for induction of silencing dCas9 expression and IPTG. Induced cells were grown for 12 h, with end-point fluorescence measured via flow cytometry.

Example—Demonstration of Allosteric ON→OFF Splinted Switch cgRNAs in Bacteria FIG. 12 demonstrates allosteric ON→OFF splinted switch cgRNAs performing conditional logic in *E. coli*. FIG. 12A depicts the mechanism for an allosteric ON→OFF splinted switch cgRNA: the constitutively active cgRNA is inactivated by hybridization of RNA trigger X. Rational sequence design of the 35 nt Cas9 handle loop (domain "d") and an extended 35 nt terminator hairpin loop (domain "e"). FIG. 12B depicts the conditional logic for an ON→OFF splinted switch cgRNA used in conjunction with silencing dCas9: "if not X then not Y" (if trigger X is not detected, then silence target gene Y). FIG. 12C demonstrates that expression of RNA trigger X (70 nt unstructured+synthetic terminator hairpin) toggles the cgRNA from ON→OFF, leading to an increase in fluorescence. Single-cell fluorescence intensities via flow cytometry. Induced expression (aTc) of silencing dCas9 and constitutive expression of sfGFP target gene Y and either: standard gRNA (ideal ON state), cgRNA (ON state), cgRNA+RNA trigger X (OFF state), no-target gRNA that lacks target-binding region (ideal OFF state). Autofluorescence (AF): cells with no sfGFP. FIGS. 12D and 12E demonstrate programmable conditional regulation using 3 orthogonal cgRNAs (A, B, C) and their corresponding cognate triggers ($X_A$, $X_B$, $X_C$). In FIG. 12D, raw fluorescence depicts ON→OFF conditional response to cognate trigger. Fold change=OFF/ON=[cognate trigger−AF]/[no trigger−AF]). In FIG. 12E, normalized fluorescence depicts orthogonality between non-cognate cgRNA/trigger pairs. Crosstalk=[non-cognate trigger−no trigger]/[cognate trigger−no trigger]). Bar graphs depict mean±estimated standard error calculated based on the mean single-cell fluorescence over 20,000 cells for each of N=3 replicate wells (OFF:ON ratio and crosstalk calculated with uncertainty propagation). FIG. 12F depicts the sequences of cgRNAs A, B, C, and the sequences of triggers $X_A$, $X_B$, $X_C$. Nucleotides that are lower case italic are constrained by the target gene. Nucleotides shaded gray are constrained by dCas9. Nucleotides that are upper case italic are designed. Sequences are presented as DNA sequences; the corresponding RNA sequence is the same as the DNA sequence except that "U" replaces "T").

Figure 12A:
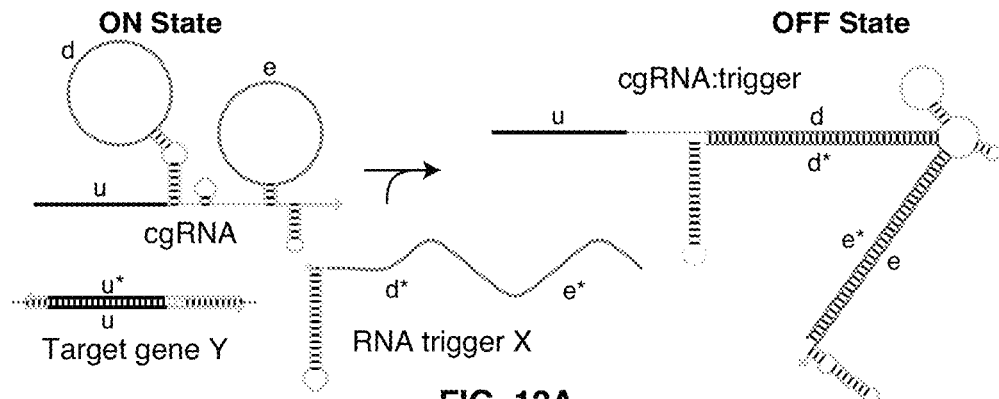
Figure 12B:
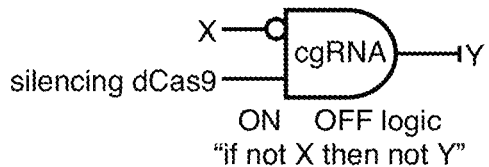
Figure 12C:
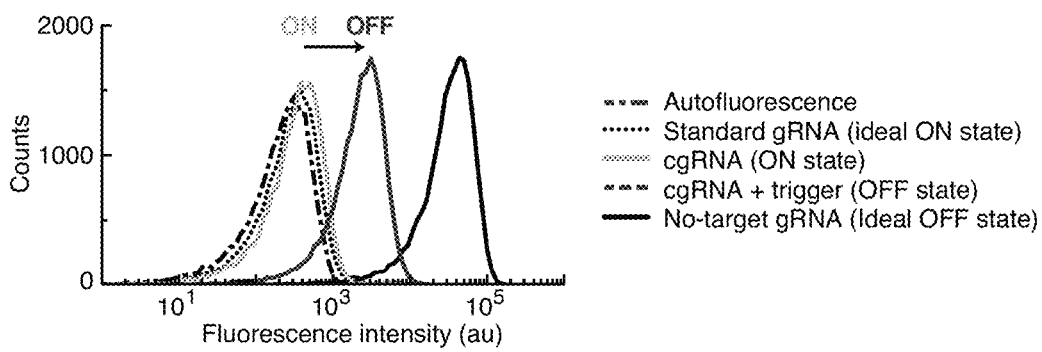
Figure 12D:
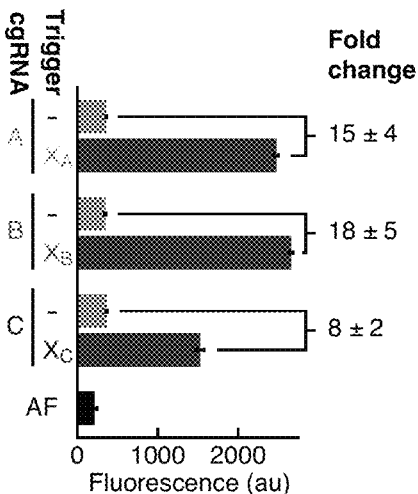
Figure 12E:
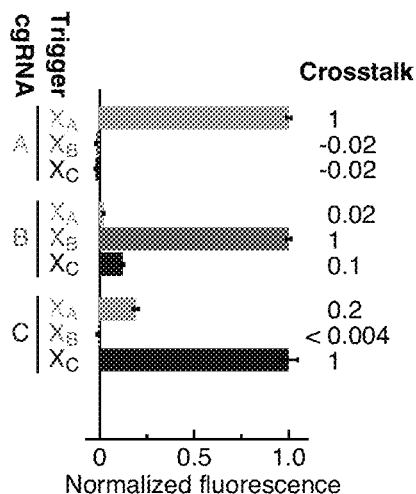

In E. coli expressing an allosteric ON→OFF splinted switch (FIG. 12A), silencing dCas9 and a fluorescent protein reporter (sfGFP) as the target gene Y (conditional logic: "if not X then not Y'"; FIG. 12B), the cgRNA exhibits a strong conditional response to expression of RNA trigger X (FIG. 12C). The ON state approaches the ideal ON state of a standard unconditional gRNA. FIG. 12D displays raw fluorescence data for a library of three orthogonal ON→OFF splinted switch cgRNAs with and without their cognate triggers. For this library of three cgRNA/trigger pairs, the median fold-change is approximately 15× for the ON→OFF conditional response to expression of the cognate trigger (FIG. 12D) and the median crosstalk between non-cognate/trigger pairs is approximately 2% (FIG. 12E).

Orthogonal cgRNA/trigger pairs were designed using NUPACK.[40,41] cgRNA/trigger plasmids were transformed into a modified E. coli MG1655 strain expressing genomically incorporated mRFP and sfGFP4.[5] Strains were grown overnight in EZ-RDM (Teknova), then diluted and grown to midlog phase (approximately 4 h). Cell density was normalized with fresh medium containing aTc for induction of silencing dCas9 expression. Induced cells were grown for 12 h, with end-point fluorescence measured via flow cytometry.

Example—Demonstration of Allosteric ON→OFF Terminator Switch cgRNAs in Human Cells FIG. 13 demonstrates allosteric ON→OFF terminator switch cgRNAs performing conditional logic in HEK 293T cells. FIG. 13A depicts the mechanism for an allosteric ON→OFF terminator switch cgRNA: the constitutively active cgRNA is inactivated by hybridization of RNA trigger X. Rational design of cgRNA terminator region (domains "d-e-f": 6 nt linker, 4 nt stem, 30 nt loop for FIGS. 13C-13H; 6 nt linker, 4 nt stem, 30 nt, 40 nt, 60 nt, 90 nt, or 140 nt loop for FIGS. 13I-13J) and complementary trigger region (domains "f*-e*-d*"). FIG. 13B depicts the conditional logic for an ON→OFF terminator switch cgRNA used in conjunction with inducing dCas9: "if not X then Y" (if trigger X is not detected, induce target gene Y). FIG. 13C demonstrates that expression of RNA trigger X (PEL+40 nt unstructured+hU6 terminator) toggles the cgRNA from ON→OFF, leading to a decrease in fluorescence. Single-cell fluorescence intensities via flow cytometry. Transfection of plasmids expressing inducing dCas9-VPR, Phi-YFP target gene Y, and either: standard gRNA+no-trigger control (ideal ON state), cgRNA+no-trigger control (ON state), cgRNA+ RNA trigger X (OFF state), no-target gRNA that lacks target-binding region+no-trigger control (ideal OFF state). The no-trigger control uses a random pool of triggers to provide a sequence-generic approximation of the metabolic load of trigger expression. FIGS. 13D-13G demonstrate programmable conditional regulation using a library of 4 orthogonal cgRNAs (Q, R, S, T) and their corresponding cognate triggers ($X_Q$, $X_R$, $X_S$, $X_T$). In FIG. 13D, raw fluorescence depicts ON→OFF conditional response to cognate trigger. In FIG. 13E, fold change=ON/OFF. In FIG. 13F, fractional dynamic range=(ON−OFF)/(ideal ON−ideal OFF). In FIG. 13G, crosstalk=(ON−OFF')/(ON−OFF) where OFF' corresponds to cgRNA+non-cognate trigger. Bar graphs depict mean±estimated standard error of the mean (with uncertainty propagation) calculated based on the mean single-cell fluorescence over 1545-3970 cells for each of N=3 replicate wells.

Figure 13A:
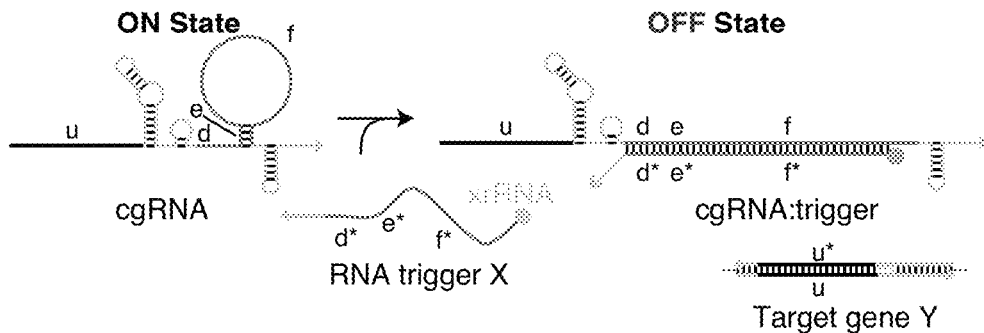
Figure 13B:
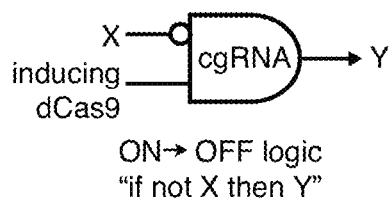
Figure 13C:
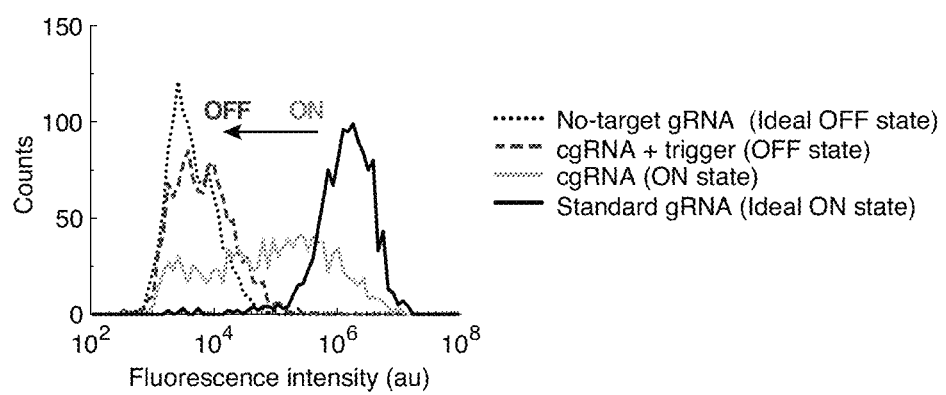
Figure 13D:
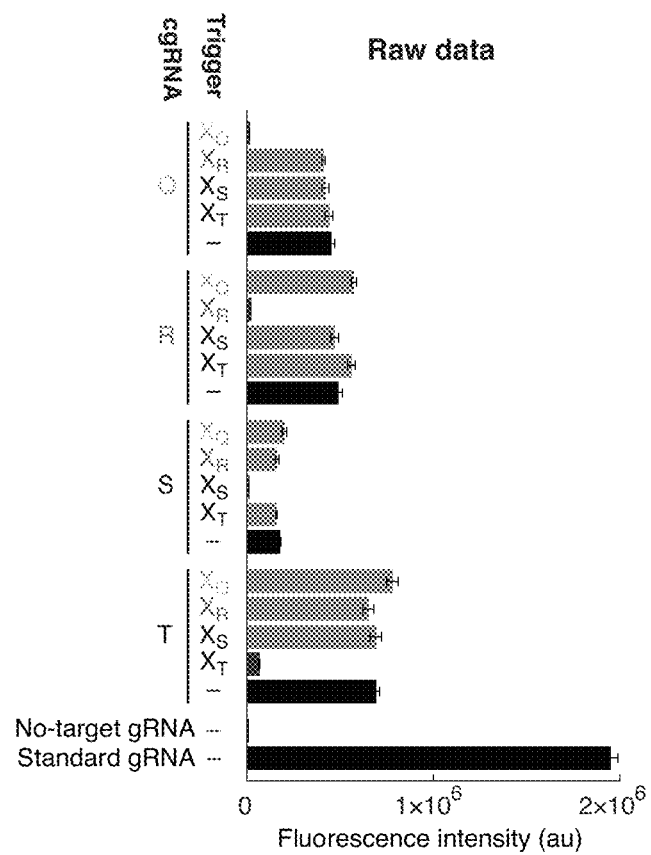
Figure 13E:
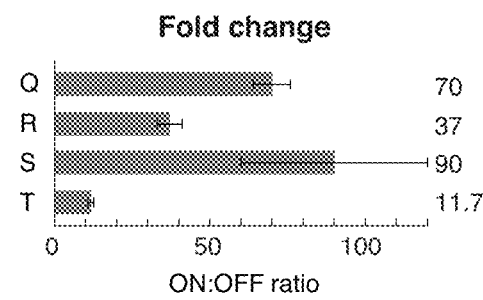
Figure 13F:
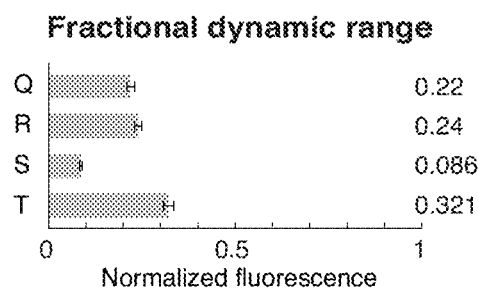
Figure 13G:
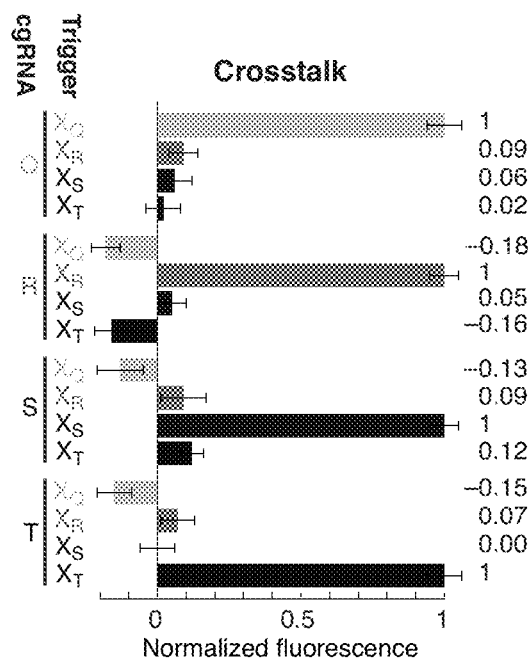
Figure 13I:
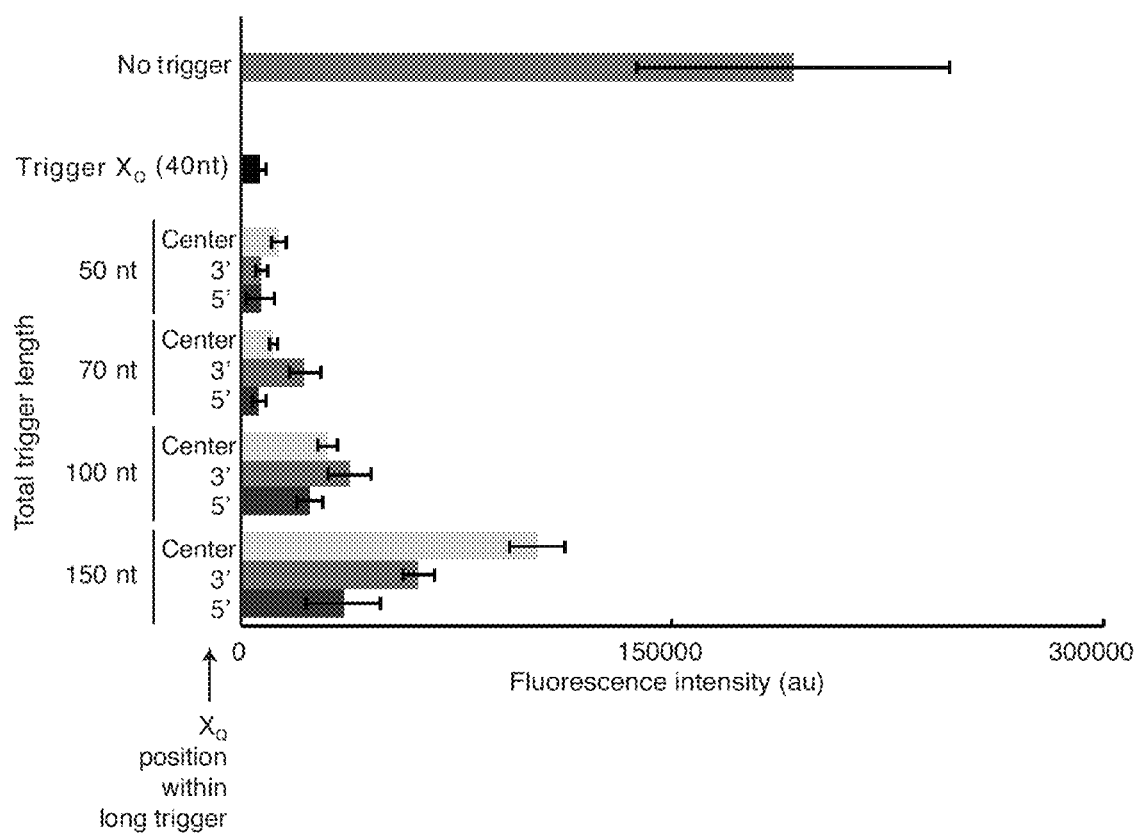

FIG. 13I demonstrates a conditional ON→OFF cgRNA response to RNA triggers of varying lengths. Expression of RNA trigger X (PEL+[40 nt, 50 nt, 70 nt, 100 nt, or 150 nt unstructured]+hU6 terminator) toggles the cgRNA Q from ON→OFF, leading to a decrease in fluorescence. For these studies, the 40 nt trigger sequence $X_Q$ is expressed at either the 5' end, 3'end, or in the middle of a 50 nt, 70 nt, 100 nt, or 150 nt sequence designed to have minimal structure. Bar graphs depict mean±estimated standard error of the mean (with uncertainty propagation) calculated based on the mean single-cell fluorescence over 1993-20393 cells for each of N=4 replicate wells.

FIG. 13H depicts the sequences of cgRNAs Q, R, S, T, and the sequences of triggers $X_Q$, $X_R$, $X_S$, $X_T$ for the studies of FIGS. 13C-13G; FIG. 13J depicts the sequences of the long triggers that incorporate $X_Q$ for the studies of FIG. 13I. Nucleotides that are lower case italic are constrained by the target binding site on the reporter plasmid. Nucleotides shaded gray are constrained by dCas9. Nucleotides that are upper case italic are designed. In FIG. 13I, underlined nucleotides depict the location of the $X_Q$ sequence within the context of the longer trigger sequence. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1)[47]. Sequences are presented as DNA sequences; the corresponding RNA sequence is the same as the DNA sequence except that "U" replaces "T").

In HEK 293T cells expressing an allosteric ON→OFF terminator switch cgRNA (FIG. 13A), inducing dCas9-VPR as the protein effector,[48] and a fluorescent protein reporter (Phi-YFP)[49,50] as the target gene Y (conditional logic: "if not X then Y"; FIG. 13B), the cgRNA exhibits a strong conditional response to expression of the RNA trigger X (FIG. 13C). The OFF state approaches the ideal OFF state of a no-target gRNA lacking the target-binding region. FIG. 13D displays raw fluorescence data for a library of four orthogonal ON→OFF terminator switch cgRNAs with each of four triggers. For each of four cgRNAs, the cognate trigger yields low fluorescence (OFF state) comparable to the ideal OFF state using a no-target gRNA lacking the target-binding region, while each of three non-cognate triggers yields high fluorescence (ON state) comparable to a no-trigger control. For this library of four cgRNA/trigger pairs, the median fold-change is approximately 50× for the ON→OFF conditional response to expression of the cognate trigger (FIG. 13E); the median fractional dynamic range is approximately 20% (FIG. 13F); the median crosstalk between non-cognate/trigger pairs is approximately 4%, and the median crosstalk modulus is approximately 9%.

To optimize fold-change, the goal is to maximize the ON→OFF or OFF→ON conditional response ratio with/ without the cognate RNA trigger (higher is better). To optimize fractional dynamic range, the goal is to maximize the difference between conditional ON and OFF states as a fraction of the unconditional regulatory dynamic range of CRISPR/Cas using standard gRNAs (higher is better). To optimize crosstalk, the goal is to minimize sequence (and metabolic) interactions between cgRNAs and non-cognate triggers including the transcriptome (lower is better). The orthogonal cgRNA/trigger pairs were designed using NUPACK[40,41]. A cgRNA expression plasmid and a trigger expression plasmid were co-transfected with a plasmid expressing an inducing dCas9-VPR fusion[48] and a reporter plasmid containing a gRNA binding site upstream of a minimal CMV promoter for Phi-YFP expression.[51,52] The four plasmids were transiently transfected into HEK 293T cells with Lipofectamine 2000 and grown for 24 h, with end-point fluorescence measured via flow cytometry. Data analysis was performed on cells expressing high levels of both cgRNA and trigger fluorescent protein transfection controls.

Example—Demonstration of Allosteric OFF→ON Split-Terminator Switch cgRNAs in Human Cells FIG. 14 demonstrates allosteric OFF→ON split-terminator switch cgRNAs performing conditional logic in HEK 293T cells. FIG. 14A depicts the mechanism for an allosteric OFF→ON split-terminator switch cgRNA: the constitutively inactive cgRNA is activated by hybridization of RNA trigger X. Rational design of 4 bp terminator duplex (cgRNA domain "d" and trigger domain "d*"). FIG. 14B depicts the conditional logic for an OFF→ON split-terminator switch cgRNA used in conjunction with inducing dCas9: "if X then Y" (if trigger X is detected, induce target gene Y). FIG. 14C demonstrates that expression of RNA trigger X (4 nt+terminator hairpin) toggles the cgRNA from OFF→ON, leading to an increase in fluorescence. Single-cell fluorescence intensities via flow cytometry. Transfection of plasmids expressing inducing dCas9-VPR, Phi-YFP target gene Y, and either: no-target gRNA that lacks target-binding region+no-trigger control (ideal OFF state), cgRNA+no-trigger control (OFF state), cgRNA+RNA trigger X (ON state), standard gRNA+no-trigger control (ideal ON state). FIGS. 14D-14G demonstrate programmable conditional regulation using a library of 3 orthogonal cgRNAs (M,N,O) and their corresponding cognate triggers ($X_M$, $X_N$, $X_O$). In FIG. 14D, raw fluorescence depicts OFF→ON conditional response to cognate trigger. In FIG. 14E, fold change=ON/OFF. In FIG. 14F, fractional dynamic range= (ON−OFF)/(ideal ON−ideal OFF). In FIG. 14G, crosstalk= (ON'−OFF)/(ON−OFF) where ON' corresponds to cgRNA+ non-cognate trigger. Bar graphs depict mean±estimated standard error of the mean (with uncertainty propagation) calculated based on the mean single-cell fluorescence over 1017-2394 cells for each of N=3 replicate wells. FIG. 14H depicts the sequences of cgRNAs M,N,O, and the sequences of triggers $X_M$, $X_N$, $X_O$. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Sequences are presented as DNA sequences; the corresponding RNA sequence is the same as the DNA sequence except that "U" replaces "T"). The orthogonal cgRNA/trigger pairs were designed using NUPACK[40,41].

In HEK 293T cells expressing an allosteric OFF→ON split-terminator switch cgRNA (FIG. 14A), inducing dCas9-VPR as the protein effector,[48] and a fluorescent protein reporter (Phi-YFP)[49,50] as the target gene Y (conditional logic "if X then Y"; FIG. 14B), the cgRNA exhibits a strong conditional OFF→ON response to expression of the RNA trigger X (FIG. 14C). The OFF state approaches the ideal OFF state of a no-target gRNA lacking the target-binding region. FIG. 14D displays raw fluorescence data for a library of three orthogonal OFF→ON split-terminator switch cgRNAs with each of three triggers. The three cgRNAs have clean OFF states (low fluorescence) in the absence of trigger and strong ON states (high fluorescence) in response to expression of the cognate trigger. For this library of three cgRNA/trigger pairs, the median fold-change is approximately 150× for the conditional OFF→ON response to expression of the cognate trigger (FIG. 14E); the median fractional dynamic range is approximately 50% (FIG. 14F); the median crosstalk is approximately 4% (FIG. 14G).

To optimize fold-change, the goal is to maximize the ON→OFF or OFF→ON conditional response ratio with/ without the cognate RNA trigger (higher is better). To optimize fractional dynamic range, the goal is to maximize the difference between conditional ON and OFF states as a fraction of the unconditional regulatory dynamic range of CRISPR/Cas using standard gRNAs (higher is better). To optimize crosstalk, the goal is to minimize sequence (and metabolic) interactions between cgRNAs and non-cognate triggers including the transcriptome (lower is better). The orthogonal cgRNA/trigger pairs were designed using NUPACK[40,41]. A cgRNA expression plasmid and a trigger expression plasmid were co-transfected with a plasmid expressing an inducing dCas9-VPR fusion[48] and a reporter plasmid containing a gRNA binding site upstream of a minimal CMV promoter for Phi-YFP expression.[51,52] The four plasmids were transiently transfected into HEK 293T cells with Lipofectamine 2000 and grown for 24 h, with end-point fluorescence measured via flow cytometry. Data analysis was performed on cells expressing high levels of both cgRNA and trigger fluorescent protein transfection controls.

Figure 14A:
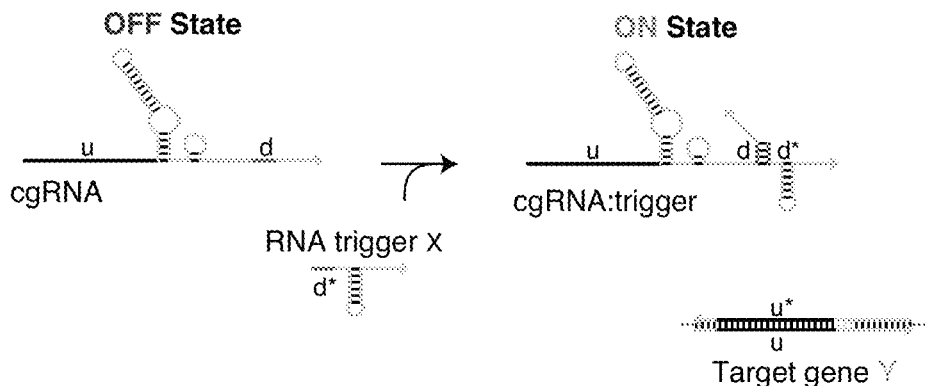
Figure 14B:
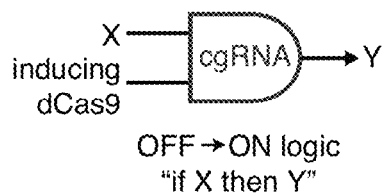
Figure 14C:
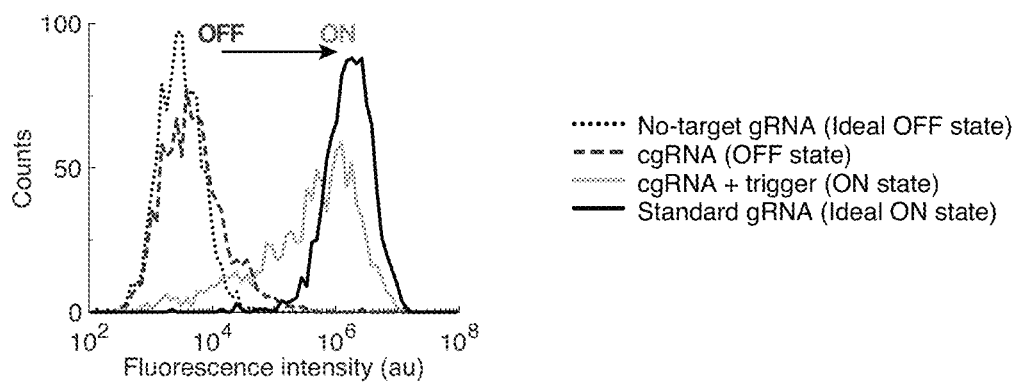
Figure 14D:
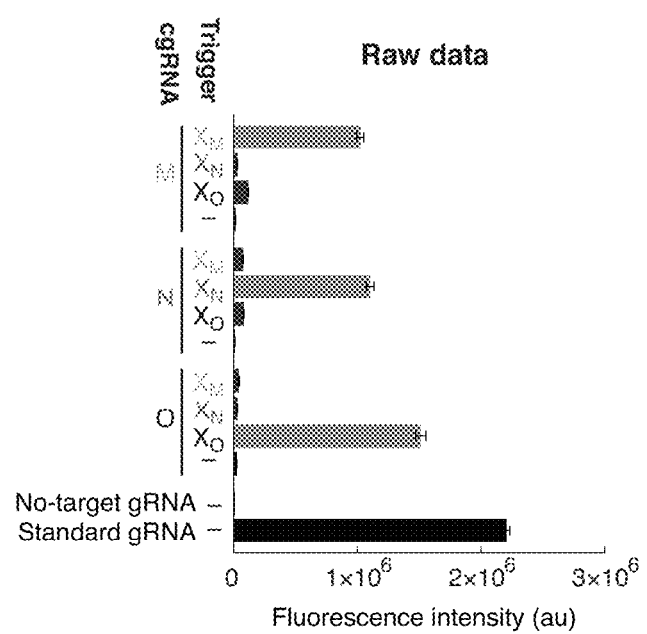
Figure 14E:
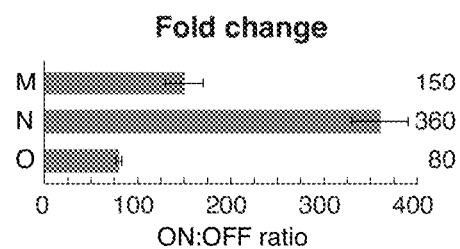
Figure 14F:
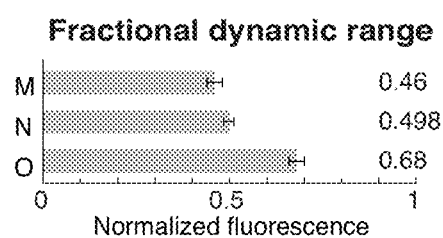
Figure 14G:
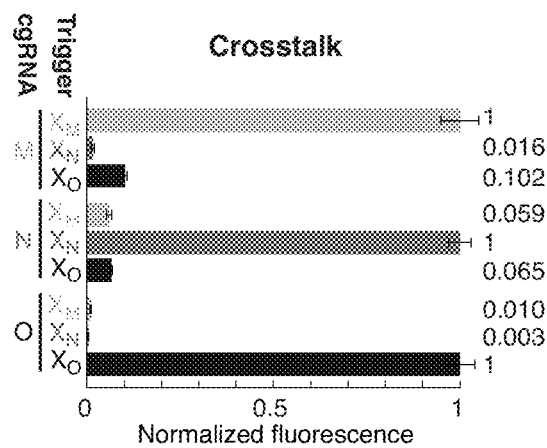

FIG. 14A-14H described above demonstrate split-terminator switch cgRNAs functioning in human cells using a 4 bp terminator duplex (formed via hybridization between domain "d" of the cgRNA and the reverse complementary domain "d*" in the trigger; see the mechanism schematic of FIG. 14A with domain lengths |d|=|d*|=4 nt). FIG. 15A-15H demonstrate that mechanism functioning using a 10 bp terminator duplex (see the mechanism schematic of FIG. 15A with domain lengths |d|=|d*|=10 nt).

Figure 15A:
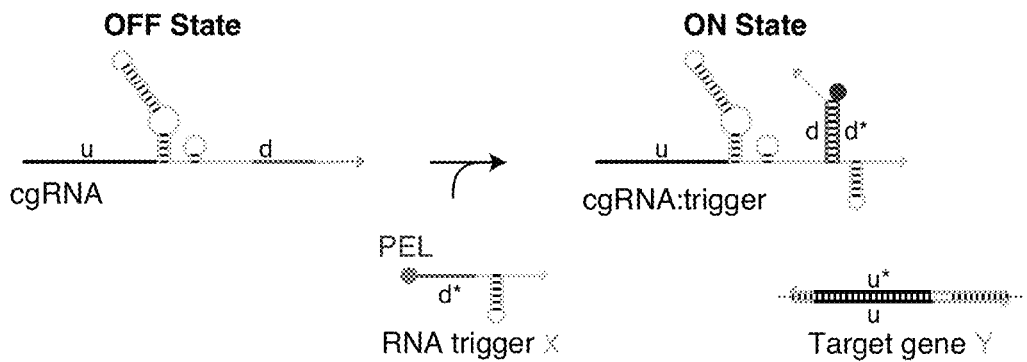
Figure 15B:
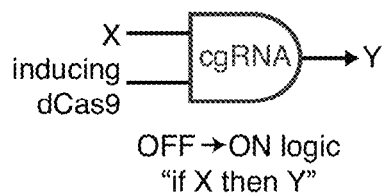
Figure 15C:
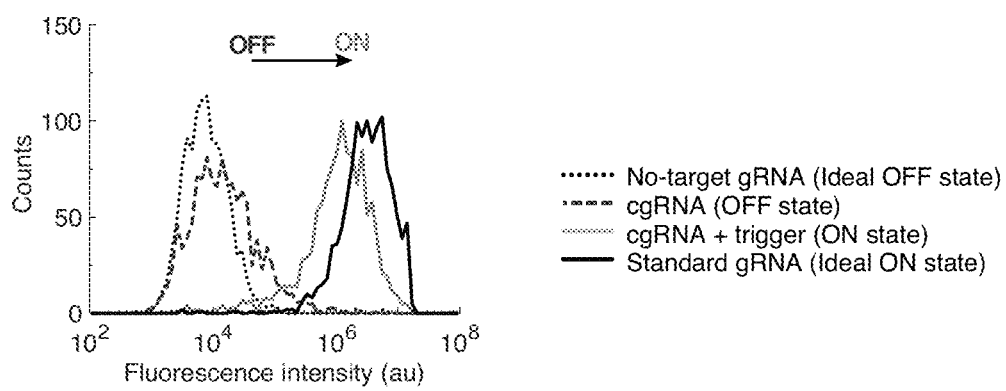
Figure 15D:
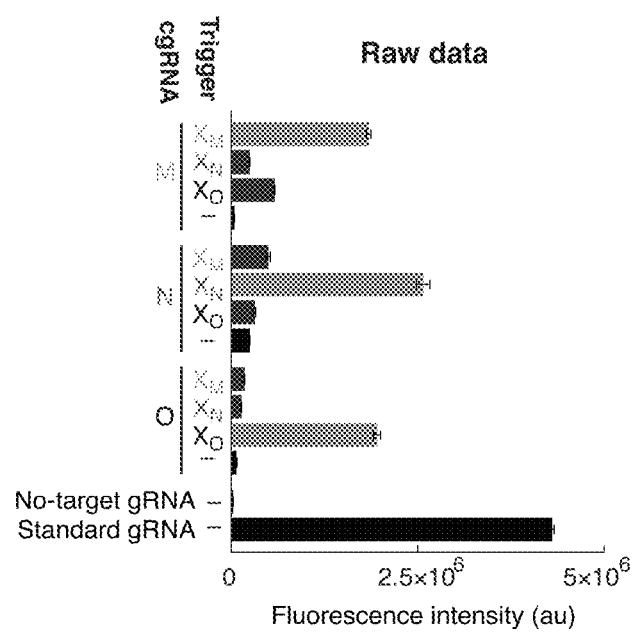
Figure 15E:
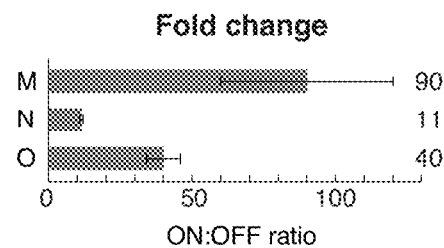
Figure 15F:
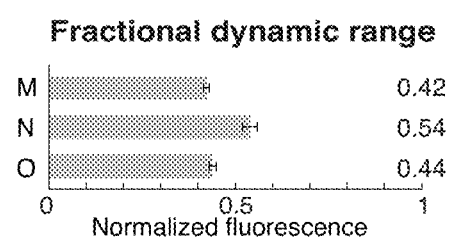
Figure 15G:
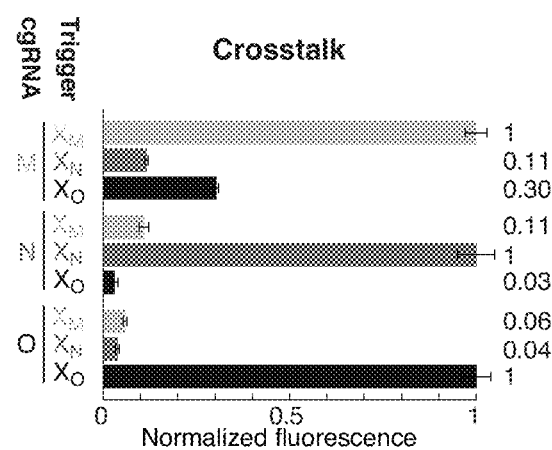

FIG. 15A depicts the mechanism for an allosteric OFF→ON split-terminator switch cgRNA: the constitutively inactive cgRNA is activated by hybridization of RNA trigger X. Rational design of 10 bp terminator duplex (cgRNA domain "d" and trigger domain "d*"). FIG. 15B depicts the conditional logic for an OFF→ON split-terminator switch cgRNA using in conjunction with inducing dCas9: "if X then Y" (if trigger X is detected, induce target gene Y). FIG. 15C demonstrates that expression of RNA trigger X (PEL+10 nt+terminator hairpin) toggles the cgRNA from OFF→ON, leading to an increase in fluorescence. Single-cell fluorescence intensities via flow cytometry. Transfection of plasmids expressing inducing dCas9-VPR, Phi-YFP target gene Y, and either: no-target gRNA that lacks target-binding region+no-trigger control (ideal OFF state), cgRNA+no-trigger control (OFF state), cgRNA+RNA trigger X (ON state), standard gRNA+no-trigger control (ideal ON state). FIGS. 15D-15G demonstrate programmable conditional regulation using a library of 3 orthogonal cgRNAs (M,N,O) and their corresponding cognate triggers ($X_M$, $X_N$, $X_O$). In FIG. 15D, raw fluorescence depicts OFF→ON conditional response to cognate trigger. In FIG. 15E, fold change=ON/OFF. In FIG. 15F, fractional dynamic range=(ON−OFF)/(ideal ON−ideal OFF). In FIG. 15G, crosstalk=(ON'−OFF)/(ON−OFF) where ON' corresponds to cgRNA+non-cognate trigger. Bar graphs depict mean±estimated standard error of the mean (with uncertainty propagation) calculated based on the mean single-cell fluorescence over 1244-2313 cells for each of N=3 replicate wells. FIG. 15H depicts the sequences of cgRNAs M,N,O, and the sequences of triggers $X_M$, $X_N$, $X_O$. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1)[47]. Sequences are presented as DNA sequences; the corresponding RNA sequence is the same as the DNA sequence except that "U" replaces "T"). The orthogonal cgRNA/trigger pairs were designed using NUPACK[40,41]. A cgRNA expression plasmid and a trigger expression plasmid were co-transfected with a plasmid expressing an inducing dCas9-VPR fusion[48] and a reporter plasmid containing a gRNA binding site upstream of a minimal CMV promoter for Phi-YFP expression.[51,52] The four plasmids were transiently transfected into HEK 293T cells with Lipofectamine 2000 and grown for 24 h, with end-point fluorescence measured via flow cytometry. Data analysis was performed on cells expressing high levels of both cgRNA and trigger fluorescent protein transfection controls.

Figure 16A:
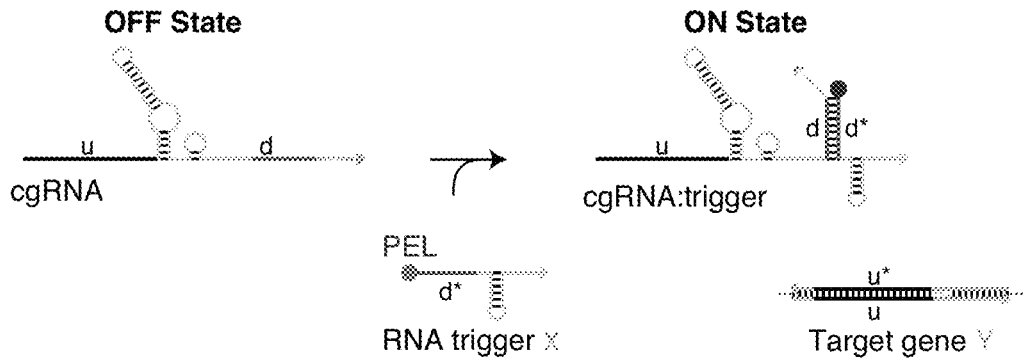
Figure 16B:
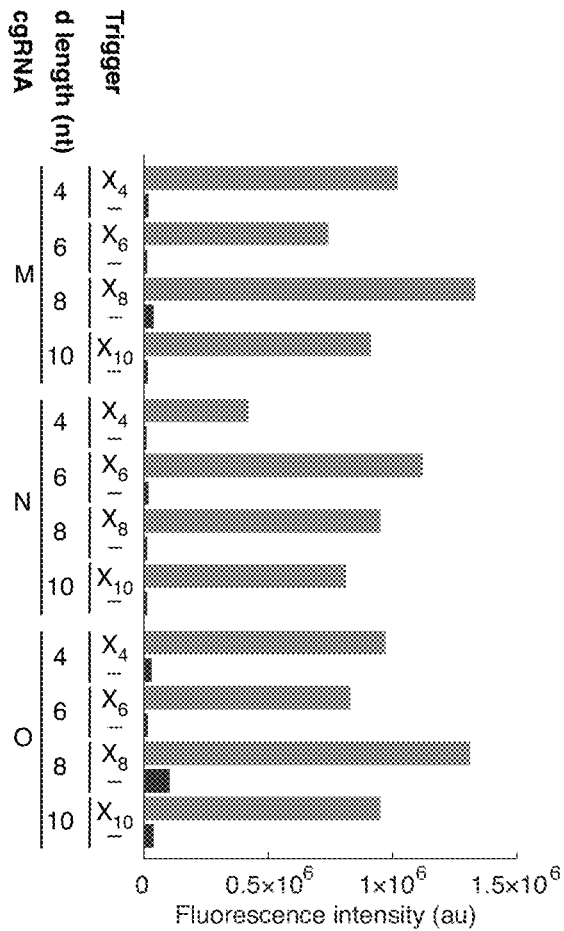
Figure 16C:
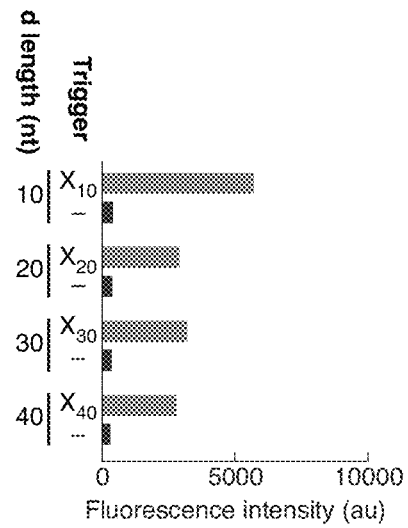

FIG. 16 demonstrates split-terminator switch cgRNAs functioning in HEK293T cells using terminator duplexes of different lengths ranging from |d|=40 nt to |d|=4 nt. FIG. 16A depicts the mechanism for an allosteric OFF→ON split-terminator switch cgRNA and trigger (depicted for a 10 bp terminator duplex with domain lengths |d|=|d*|=10 nt). For terminator duplexes of length 4, 6, 8, or 10 bp (with domain length |d|=4, 6, 8, or 10 nt), FIG. 16B demonstrates that expression of RNA trigger X (PEL+{4, 6, 8, 10} nt+terminator hairpin) toggles the cgRNA from OFF→ON in human cells, leading to an increase in fluorescence. For terminator duplexes of length 10, 20, 30, 40 bp (with domain length |d|=10, 20, 30, 40 nt), FIG. 16C demonstrates that expression of RNA trigger X (PEL+{10, 20, 30, 40} nt+terminator hairpin) toggles the cgRNA from OFF→ON in human cells, leading to an increase in fluorescence. Transfection of plasmids expressing inducing dCas9-VPR, Phi-YFP target gene Y, and either: cgRNA+no-trigger control (OFF state), cgRNA+RNA trigger X (ON state). For each set of conditions, 50,000 cells were collected from a single well, which was gated for live cells, single cells, and highly-transfected cells based on the cgRNA plasmid transfection control (miRFP670+), yielding approximately 2% of the cells. Bar graph depicts mean single-cell fluorescence over approximately 1000 cells for one well. FIG. 16D depicts the sequences of cgRNAs and triggers for the studies of FIG. 16B with terminator duplexes of 6, 8, or 10 bp (cgRNA and trigger sequences with 4 bp terminator duplexes are displayed in FIG. 14H). FIG. 16E depicts the sequences of cgRNAs and triggers for the studies of FIG. 16B with terminator duplexes of 10, 20, 30, or 40 bp. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1)[47]. Sequences are presented as DNA sequences; the corresponding RNA sequence is the same as the DNA sequence except that "U" replaces "T").

Figure 17A:
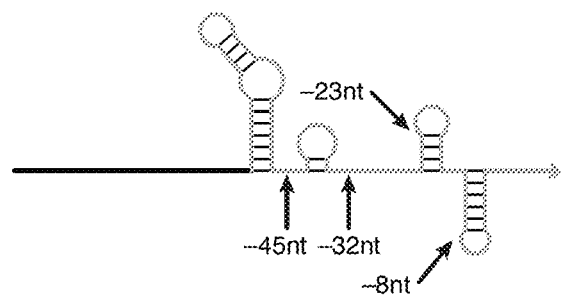
Figure 17B:
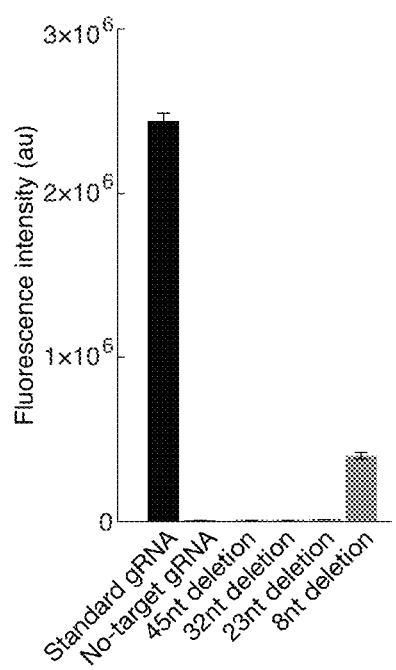
Figure 18A:
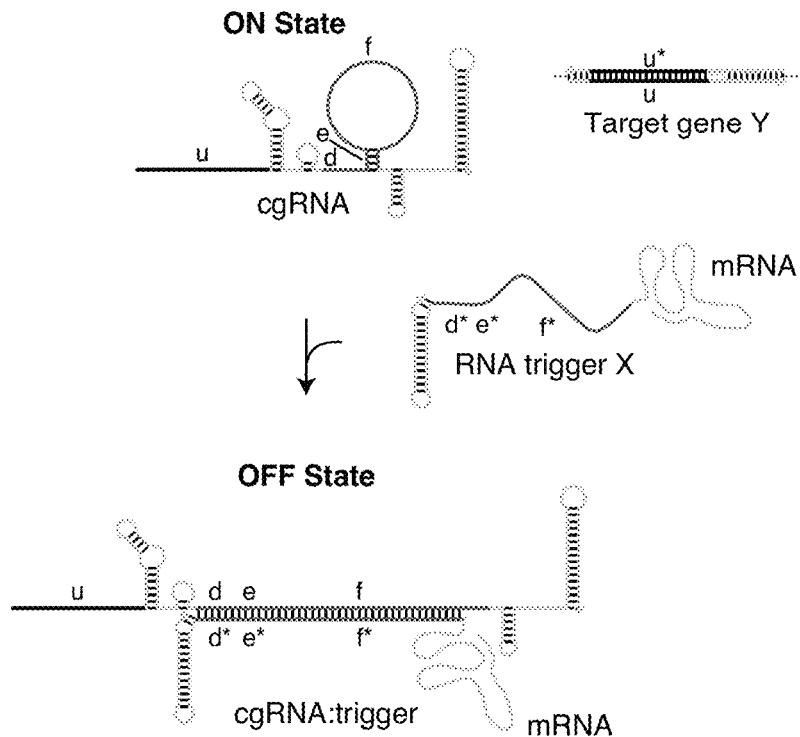
Figure 18B:
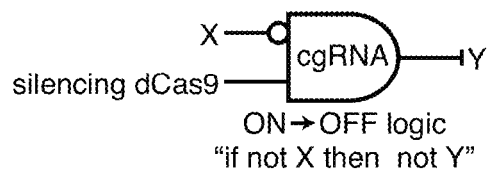
Figure 18C:
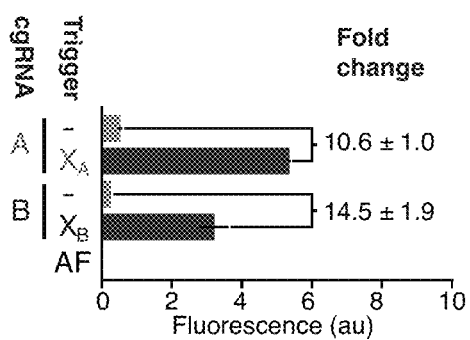
Figure 18D:
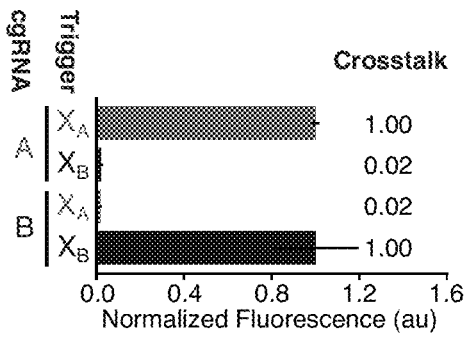

Example—Demonstration of Inactivation of a gRNA in Human Cells Via Truncation from the 3' End FIG. 17 demonstrates inactivation of a standard gRNA in BEK 293T cells by truncation of the gRNA from the 3' end, providing the basis for generating a clean OFF state for split-terminator switch cgRNAs. FIG. 17A depicts four truncation locations: 3' of the Cas9 handle (45 nt deletion), 3' of the nexus hairpin (32 nt deletion), in the loop of terminator hairpin 1 (23 nt deletion), and in the loop of terminator hairpin 2 (8 nt deletion). FIG. 18C demonstrates that all four truncation locations reduce the activity of the gRNA, with the 45 nt, 32 nt, and 23 nt truncations resulting in no detectable activity. Transfection of plasmids expressing inducing dCas9-VPR, Phi-YFP target gene Y, and either: standard gRNA+no-trigger control (ideal ON state), no-target gRNA that lacks target-binding region+no-trigger control (ideal OFF state), the 5' portion of a truncated gRNA+no-trigger control. Bar graphs depict mean±estimated standard error of the mean calculated based on the mean single-cell fluorescence over 2114-3085 cells for each of N=3 replicate wells. FIG. 17C depicts the sequences used in FIG. 17B. Nucleotides that are lower case italic are constrained by the target binding site on the reporter plasmid. Nucleotides shaded gray are constrained by dCas9. Lower case plain nucleotides are constrained by the hU6 terminator sequence[46]. Sequences are presented as DNA sequences; the corresponding RNA sequence is the same as the DNA sequence except that "U" replaces "T").

Figure 30A:
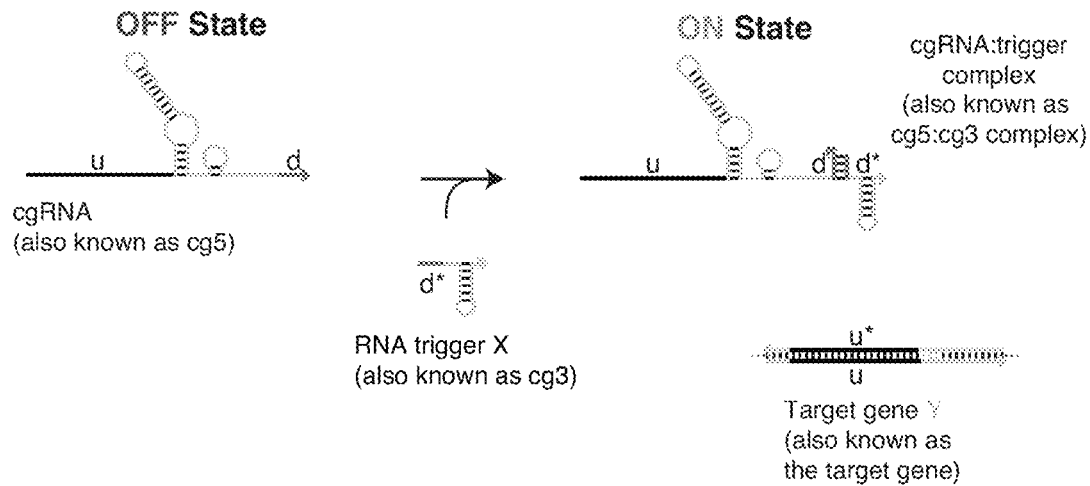
Figure 30B:
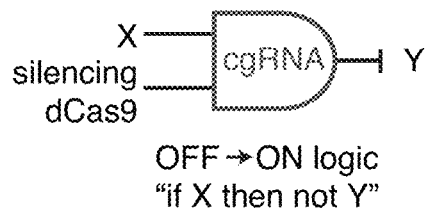
Figure 30C:
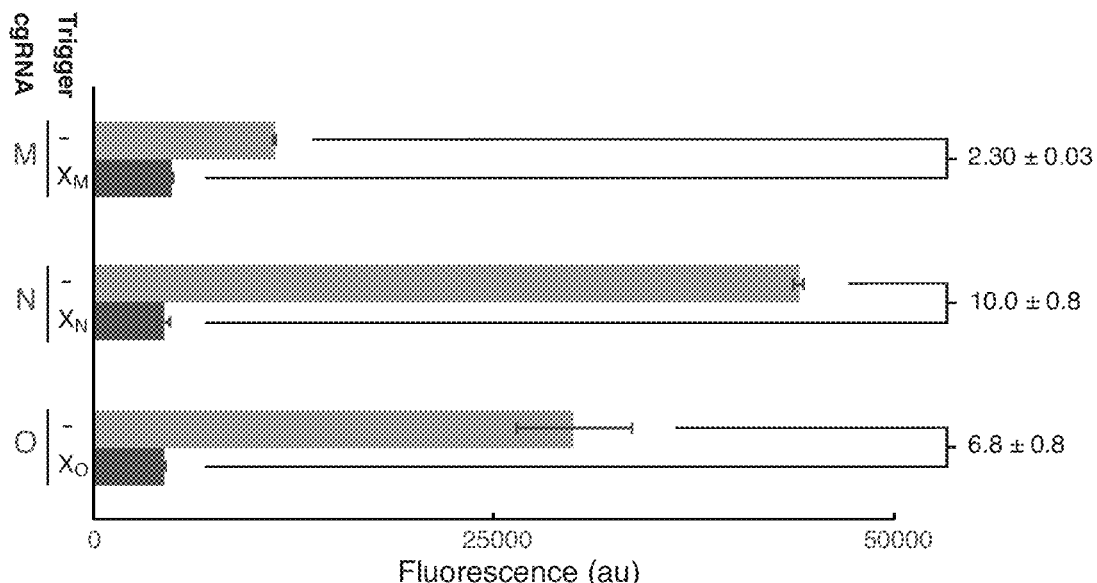

Example—Demonstration of Allosteric OFF→ON Split-Terminator Switch cgRNAs in Bacteria FIG. 30 demonstrates allosteric OFF→ON split-terminator switch cgRNAs performing conditional logic in *E. coli*. FIG. 30A depicts the mechanism for an allosteric OFF→ON split-terminator switch cgRNA: the constitutively inactive cgRNA is activated by hybridization of RNA trigger X. Rational design of 4 bp terminator duplex (cgRNA domain "d" and trigger domain "d*"). FIG. 30B depicts the conditional logic for an OFF→ON split-terminator switch cgRNA used in conjunction with silencing dCas9: "if X then not Y" (if trigger X is detected, then silence target gene Y). FIG. 30C demonstrates that expression of RNA trigger X (4 nt+terminator hairpin) toggles the activity of the cgRNA from OFF→ON (leading to a decrease in fluorescence) for each of three cgRNAs (M, N, O) with their corresponding cognate triggers ($X_M$, $X_N$, $X_O$). Induced expression (aTc) of silencing dCas9 and constitutive expression of sfGFP target gene Y and either: cgRNA (OFF state), cgRNA+RNA trigger X (ON state). In FIG. 30C, raw fluorescence depicts OFF→ON conditional response to cognate trigger. Fold change=OFF/ON=[no trigger]/[cognate trigger]. Bar graphs depict mean±estimated standard error calculated based on the mean single-cell fluorescence over 20,000 cells for each of N=2 replicate wells (OFF:ON ratio calculated with uncertainty propagation). FIG. 30D depicts the sequences of cgRNAs M, N, O, and the sequences of triggers $X_M$, $X_N$, $X_O$. Nucleotides that are lower case italic are constrained by the target gene. Nucleotides shaded gray are constrained by dCas9. Nucleotides that are upper case italic are designed. Sequences are presented as DNA sequences; the corresponding RNA sequence is the same as the DNA sequence except that "U" replaces "T").

In *E. coli* expressing an allosteric OFF→ON split terminator switch (FIG. 30A), silencing dCas9 and a fluorescent protein reporter (sfGFP) as the target gene Y (conditional logic: "if X then Y"; FIG. 30B), the cgRNA exhibits a strong conditional response to expression of RNA trigger X (FIG. 30C). FIG. 30C displays raw fluorescence data for a library of three orthogonal OFF→ON split terminator switch cgRNAs with and without their cognate triggers. For this library of three cgRNA/trigger pairs, the median fold-change is approximately 7× for the OFF→ON conditional response to expression of the cognate trigger (FIG. 30C).

cgRNA/trigger pairs were designed using NUPACK.[40,41] cgRNA/trigger plasmids were transformed into a modified *E. coli* MG1655 strain expressing genomically incorporated mRFP and sfGFP4.[5] Strains were grown overnight in EZ-RDM (Teknova), then diluted 500 fold with fresh medium containing aTc for induction of silencing dCas9 expression. Induced cells were grown for 12 h, with end-point fluorescence measured via flow cytometry.

Example—Demonstration of Allosteric ON→OFF Split-Terminator Switch cgRNAs in Human Cells FIG. 31 demonstrates allosteric ON→OFF split-terminator switch cgRNAs performing conditional logic in BEK 293T cells. FIG. 31A depicts the mechanism for an allosteric ON→OFF split-terminator switch cgRNAs (Mechanism 4B): the constitutively active cgRNA (comprising 5' fragment cg5 [also known as cgRNA] and 3' fragment cg3 [also known as helper]) is inactivated by hybridization of RNA trigger X (also known as the cognate RNA trigger) to cg5, displacing cg3 from cg5 to inactivate the cgRNA. FIG. 31B depicts the mechanism for an allosteric ON→OFF split-terminator switch cgRNAs (Mechanism 4C): the constitutively active cgRNA (comprising 5' fragment cg5 [also known as cgRNA] and 3' fragment cg3 [also known as helper]) is inactivated by hybridization of RNA trigger X (also known as the cognate RNA trigger) to cg3, displacing cg5 from cg3 to inactivate the cgRNA. Rational sequence design of domains "a", "b", "c", "a*", "b*", and "c*". FIG. 31C depicts the conditional logic for an ON→OFF split-terminator switch cgRNA used in conjunction with inducing dCas9: "if not X then Y" (if trigger X is not detected, induce target gene Y).

Figure 31A:
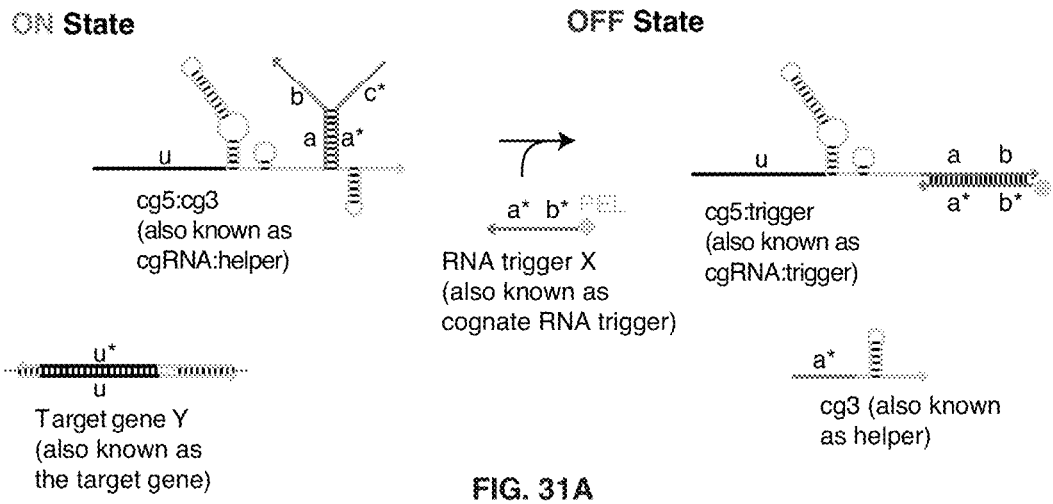
Figure 31B:
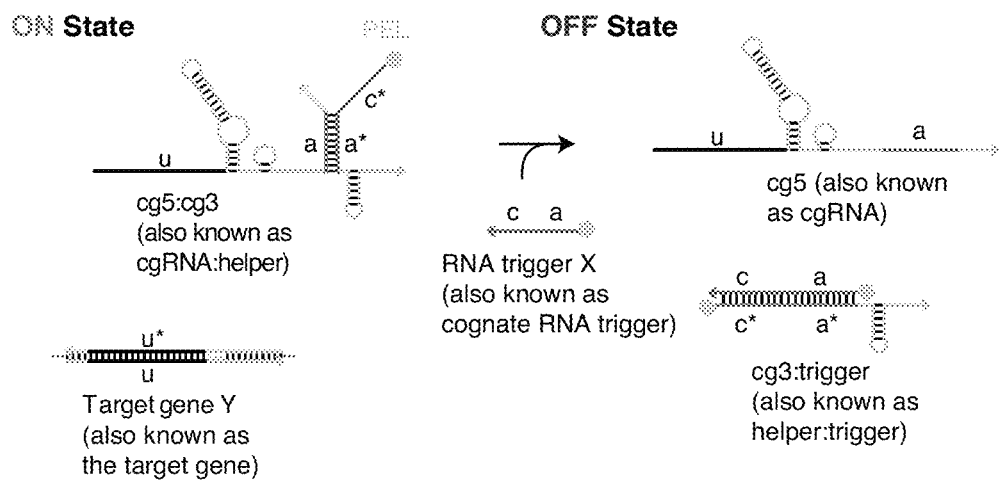
Figure 31C:
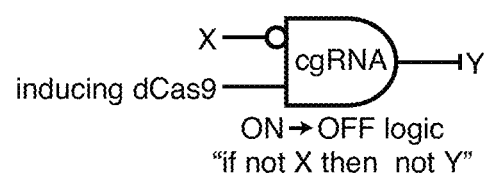
Figure 31D:
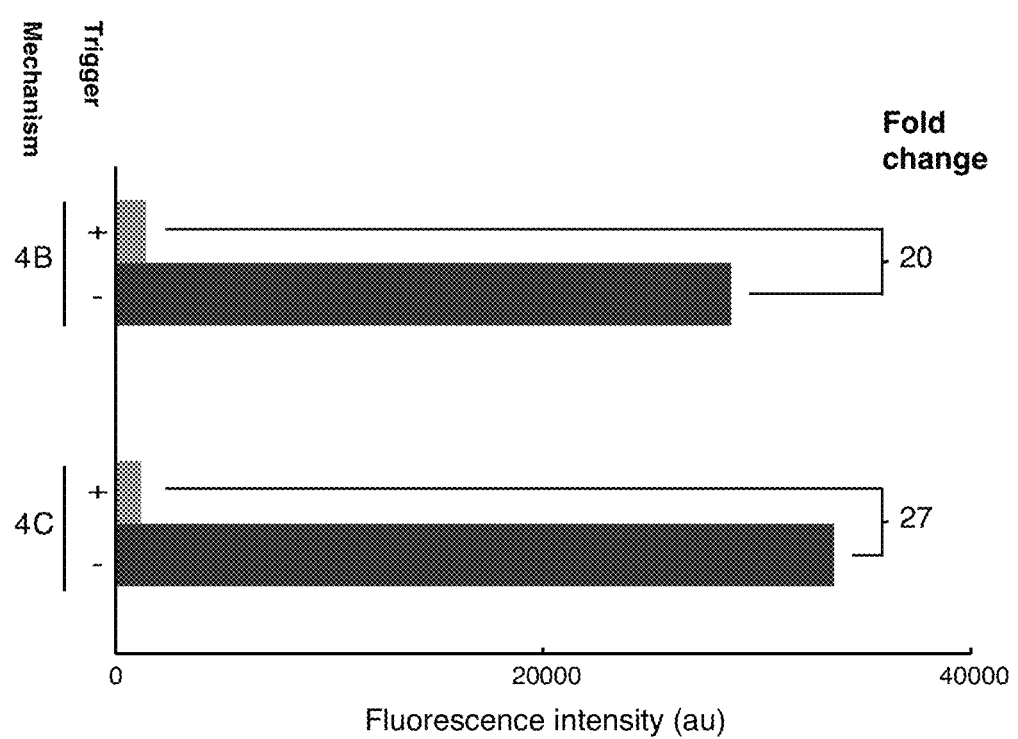
Figure 32A:
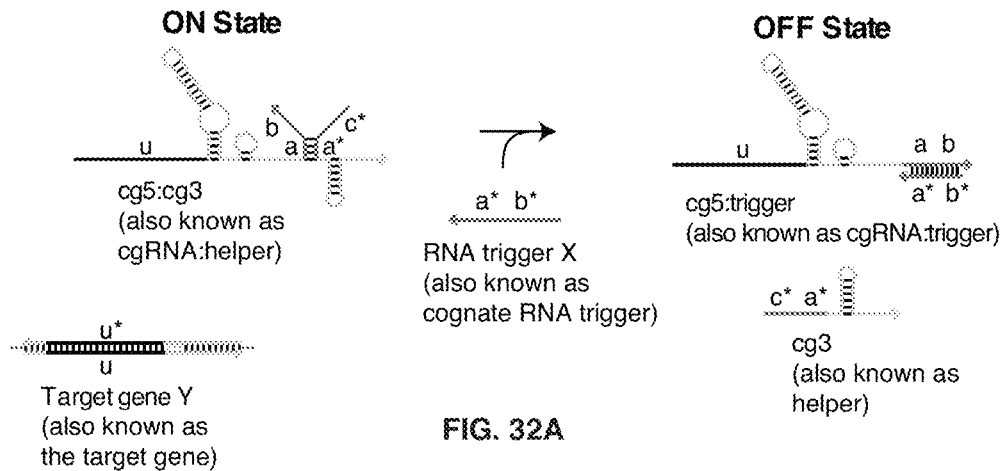
Figure 32B:
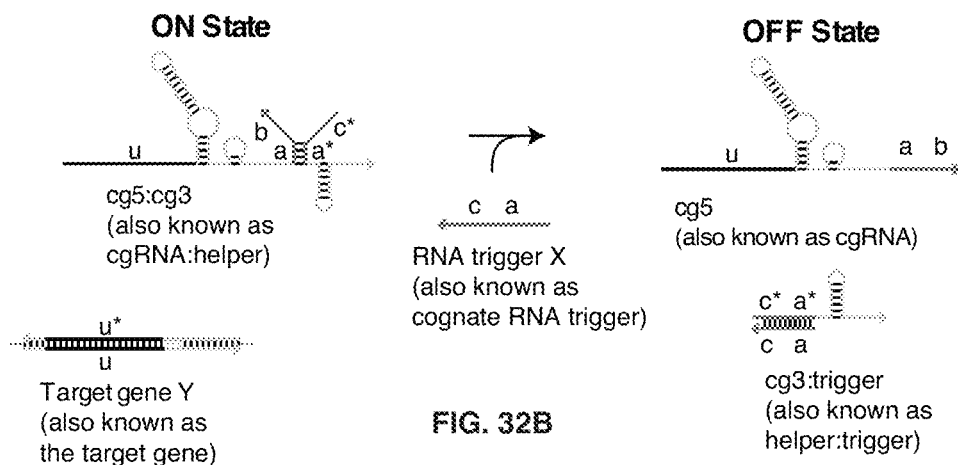
Figure 32C:
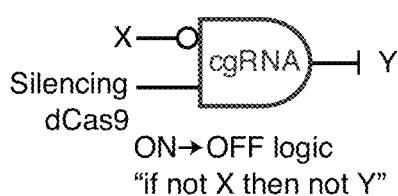
Figure 32D:
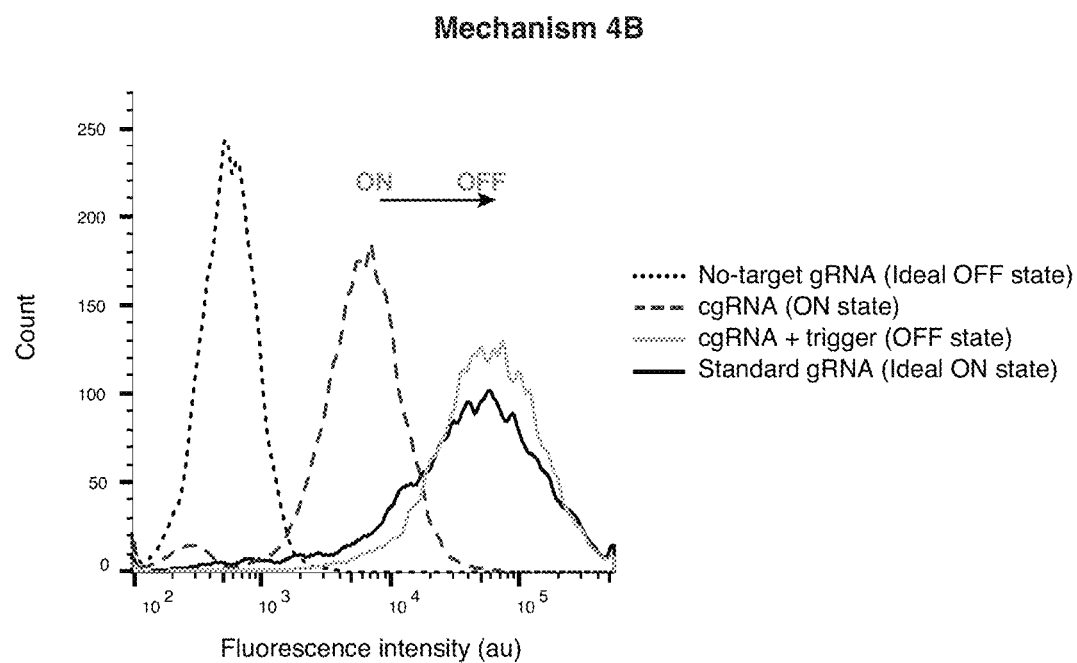
Figure 32E:
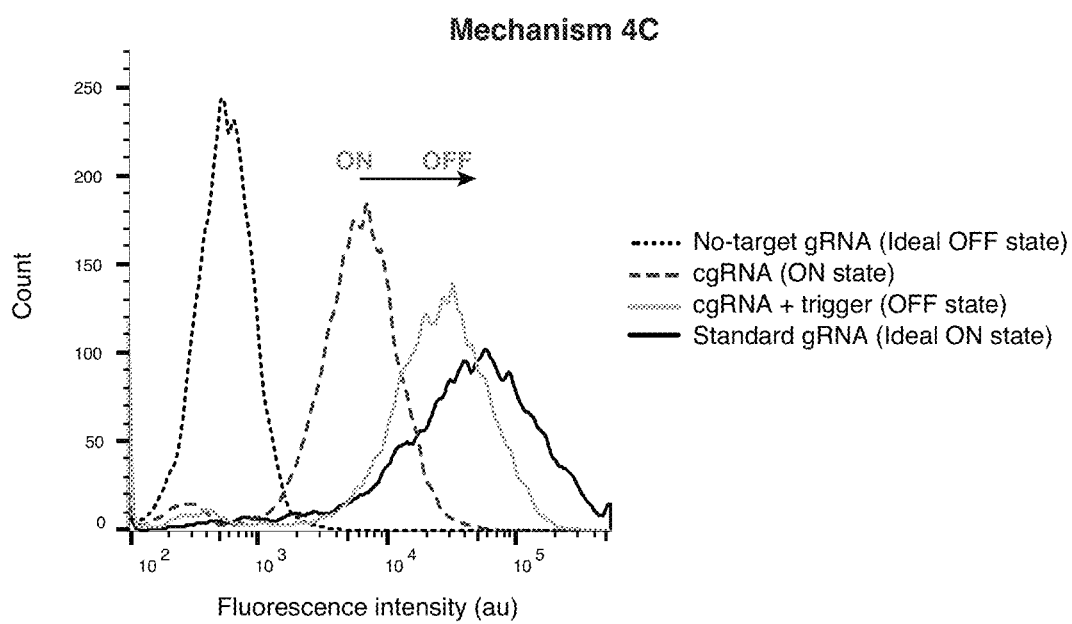

FIG. 31D demonstrates that expression of RNA trigger X (PEL+20 nt unstructured+hU6 terminator for Mechanism 4B; PEL+40 nt unstructured+hU6 terminator for Mechanism 4C) toggles the cgRNA from ON→OFF, leading to a decrease in fluorescence. Transfection of plasmids expressing inducing dCas9-VPR, Phi-YFP target gene Y, and either: cgRNA+no-trigger control (ON state), or cgRNA+RNA trigger X (OFF state). The no-trigger control uses a random pool of triggers to provide a sequence-generic approximation of the metabolic load of trigger expression. Background subtracted fluorescence by no-target gRNA that lacks target-binding region depicts ON→OFF conditional response to cognate trigger. Fold change=ON/OFF. Bar graphs depict the mean single-cell fluorescence over 1989-2305 cells for N=1 well. FIG. 31E depicts the sequences of cg5, cg3, and trigger for Mechanism 4B and 4C. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1)[47]. Sequences are presented as DNA sequences; the corresponding RNA sequence is the same as the DNA sequence except that "U" replaces "T").

In HEK 293T cells expressing an allosteric ON→OFF split-terminator switch cgRNA (Mechanism 4B in FIG. 31A; Mechanism 4C in FIG. 31B), inducing dCas9-VPR as the protein effector,[48] and a fluorescent protein reporter (Phi-YFP)[49,50] as the target gene Y (conditional logic: "if not X then Y"; FIG. 31C), the cgRNA (comprising fragments cg5 and cg3) exhibits a strong conditional response to expression of the RNA trigger X (FIG. 31D).

To optimize fold-change, the goal is to maximize the ON→OFF or OFF→ON conditional response ratio with/without the cognate RNA trigger (higher is better). The cgRNA/trigger pairs were designed using NUPACK[40,41]. A cg5 and cg3 expression plasmid and a trigger expression plasmid were co-transfected with a plasmid expressing an inducing dCas9-VPR fusion[48] and a reporter plasmid containing a gRNA binding site upstream of a minimal CMV promoter for Phi-YFP expression.[51,52] The four plasmids were transiently transfected into BEK 293T cells with Lipofectamine 2000 and grown for 24 h, with end-point fluorescence measured via flow cytometry. Data analysis was performed on cells expressing high levels of both cgRNA and trigger fluorescent protein transfection controls.

Example—Demonstration of Allosteric ON 4 OFF Split-Terminator Switch cgRNAs in Bacteria FIG. 32 demonstrates allosteric ON→OFF split-terminator switch cgRNAs performing conditional logic in *E. coli*. FIG. 32A depicts the mechanism for an allosteric ON→OFF split-terminator switch cgRNAs (Mechanism 4B): the constitutively active cgRNA (comprising 5' fragment cg5 [also known as cgRNA] and 3' fragment cg3 [also known as helper]) is inactivated by hybridization of RNA trigger X (also known as the cognate RNA trigger) to cg5, displacing cg3 from cg5 to inactivate the cgRNA. FIG. 32B depicts the mechanism for an allosteric ON→OFF split-terminator switch cgRNAs (Mechanism 4C): the constitutively active cgRNA (comprising 5' fragment cg5 [also known as cgRNA] and 3' fragment cg3 [also known as helper]) is inactivated by hybridization of RNA trigger X (also known as the cognate RNA trigger) to cg3, displacing cg5 from cg3 to inactivate the cgRNA. FIG. 32C depicts the conditional logic for an ON→OFF split-terminator switch cgRNA used in conjunction with silencing dCas9: "if not X then not Y" (if trigger X is not detected, then silence target gene Y). FIGS. 32D (Mechanism 4B) and 32E (Mechanism 4C) demonstrate that expression of RNA trigger X (40 nt unstructured+synthetic terminator hairpin) toggles the cgRNA from ON→OFF, leading to an increase in single-cell fluorescence intensities via flow cytometry. Induced expression (aTc) of silencing dCas9 and constitutive expression of mRFP target gene Y and either: standard gRNA+no-trigger control (ideal ON state), cgRNA+no-trigger control (ON state), cgRNA+RNA trigger X (OFF state; trigger expression is Salicylate-induced), no-target gRNA that lacks target-binding region+no-trigger control (ideal OFF state). FIG. 32F depicts the sequences of cg5, cg3, trigger X (Mechanism 4B), trigger X (Mechanism 4C), and the no-trigger control. Nucleotides that are lower case italic are constrained by the target gene. Nucleotides shaded gray are constrained by dCas9. Nucleotides that are upper case italic are designed. Sequences are presented as DNA sequences; the corresponding RNA sequence is the same as the DNA sequence except that "U" replaces "T").

Orthogonal cgRNA/trigger pairs were designed using NUPACK.[40,41] cgRNA/trigger plasmids were transformed into E. coli.[5] Strains were grown overnight in EZ-RDM (Teknova), then diluted and seeded into the assay plate. Cells were grown in fresh medium containing aTc, IPTG, and Salicylate for induction of silencing dCas9 expression, cgRNA, and trigger RNA. Induced cells were grown for 12 h, with end-point fluorescence measured via flow cytometry.

Figure 33A:
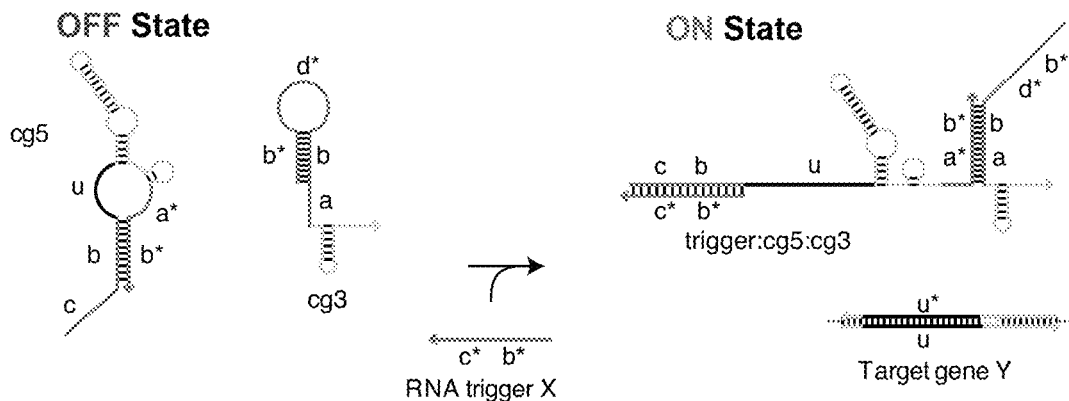
Figure 33B:
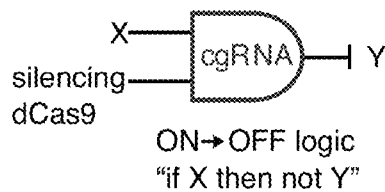
Figure 33C:
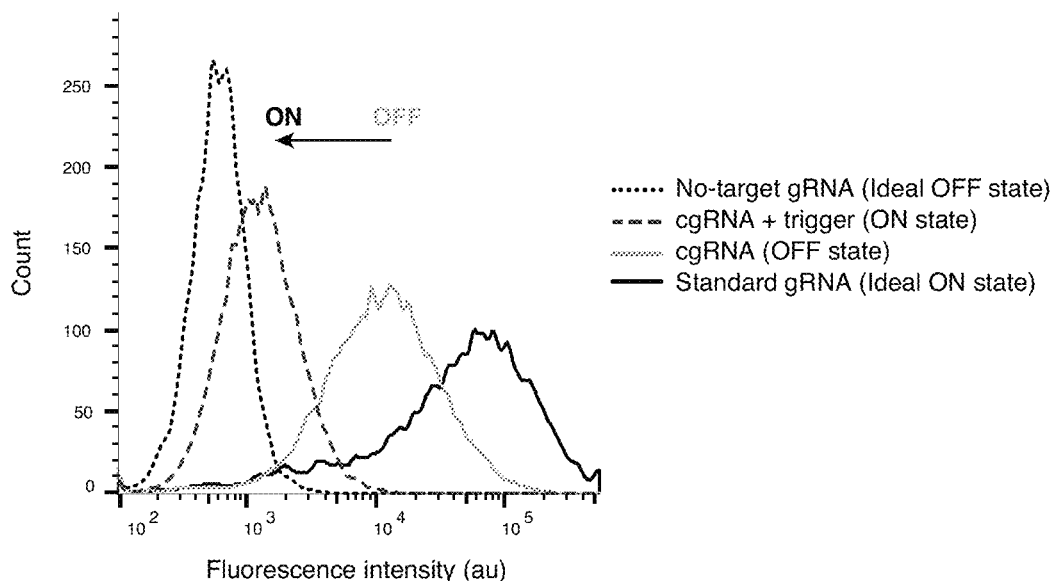

Example—Demonstration of Allosteric OFF→ON 5'- and 3'-Inhibited Split-Terminator Switch cgRNAs in Bacteria FIG. 33 demonstrates allosteric OFF→ON 5'- and 3'-inhibited split-terminator switch cgRNAs (Mechanism 7) performing conditional logic in E. coli. FIG. 33A depicts the mechanism for an allosteric OFF→ON 5'- and 3'-inhibited split-terminator switch cgRNA (Mechanism 7): the constitutively inactive cgRNA comprising 5' fragment cg5 and 3' fragment cg3 is activated by hybridization of RNA trigger X to cg5, allowing for cg5 to bind to cg3 and activate the cgRNA. FIG. 33B depicts the conditional logic for an OFF→ON 5'- and 3'-inhibited split-terminator switch cgRNA used in conjunction with silencing dCas9: "if X then not Y" (if trigger X is detected, then silence target gene Y). FIG. 33C demonstrates that expression of RNA trigger X (20 nt unstructured+synthetic terminator hairpin) toggles the cgRNA from OFF→ON, leading to a decrease in single-cell fluorescence intensities via flow cytometry. Induced expression (aTc) of silencing dCas9 and constitutive expression of mRFP target gene Y and either: standard gRNA+no-trigger control (ideal ON state), cgRNA+no-trigger control (ON state), cgRNA+RNA trigger X (OFF state; trigger expression is Salicylate-induced), no-target gRNA that lacks target-binding region+no-trigger control (ideal OFF state). FIG. 32F depicts the sequences of cg5, cg3, trigger X (Mechanism 4B), trigger X (Mechanism 4C), and the no-trigger control. Nucleotides that are lower case italic are constrained by the target gene. Nucleotides shaded gray are constrained by dCas9. Nucleotides that are upper case italic are designed. Sequences are presented as DNA sequences; the corresponding RNA sequence is the same as the DNA sequence except that "U" replaces "T").

Orthogonal cgRNA/trigger pairs were designed using NUPACK.40,41 cgRNA/trigger plasmids were transformed into E. coli.5 Strains were grown overnight in EZ-RDM (Teknova), then diluted and seeded into the assay plate. Cells were grown in fresh medium containing aTc, IPTG, and Salicylate for induction of silencing dCas9 expression, cgRNA, and trigger RNA. Induced cells were grown for 12 h, with end-point fluorescence measured via flow cytometry.

Example—Demonstration of Allosteric cgRNAs Performing Conditional Logic in Response to mRNA Triggers FIG. 18 demonstrates allosteric cgRNAs performing conditional logic in response to detection of long RNA triggers in E. coli. FIG. 18A depicts the mechanism for an allosteric ON→OFF terminator switch cgRNA: the constitutively active cgRNA is inactivated by hybridization of RNA trigger X (which is a full-length mRNA trigger molecule containing subsequence "f*-e*-d*" that serves as the trigger domain). FIG. 18B depicts the conditional logic for an ON→OFF terminator switch cgRNA used in conjunction with silencing dCas9: "if not X then not Y" (if trigger X is not detected, then silence target gene Y). FIG. 18C demonstrates that expression of RNA trigger X (full-length mRNA) toggles the cgRNA from ON→OFF, leading to an increase in fluorescence. 18C and 18D demonstrate programmable conditional regulation using 2 orthogonal cgRNAs (A, B) and their corresponding cognate triggers (XA, XB). Induced expression (aTc) of silencing dCas9 and constitutive expression of mRFP target gene Y and either: cgRNA(ON state), cgRNA+RNA trigger X (OFF state; trigger expression is IPTG-induced). Autofluorescence (AF): cells with no mRFP. In FIG. 18C, raw fluorescence depicts ON→OFF conditional response to cognate trigger. Fold change=OFF/ON= [cognate trigger–AF]/[no trigger–AF]). In FIG. 18D, normalized fluorescence depicts orthogonality between non-cognate cgRNA/trigger pairs. Crosstalk=[non-cognate trigger—no trigger]/[cognate trigger—no trigger]). Bar graphs depict mean±estimated standard error calculated based on the mean single-cell fluorescence over 20,000 cells for each of N=3 replicate wells (OFF:ON ratio and crosstalk calculated with uncertainty propagation). FIGS. 18E-18F depict the sequences of cgRNAs A, B and the sequences of mRNA trigger molecules XA, XB. Nucleotides that are lower case italic are constrained by the target gene. Nucleotides shaded gray are constrained by dCas9. Nucleotides in a cgRNA that are upper case bold are complementary to the trigger domain of the corresponding trigger molecule. Nucleotides in an mRNA trigger molecule are lower case except for the trigger domain which is upper case bold. Sequences are presented as DNA sequences; the corresponding RNA sequence is the same as the DNA sequence except that "U" replaces "T").

Example—Computational Sequence Design of Orthogonal cgRNA/Trigger Pairs

Figure 19A:
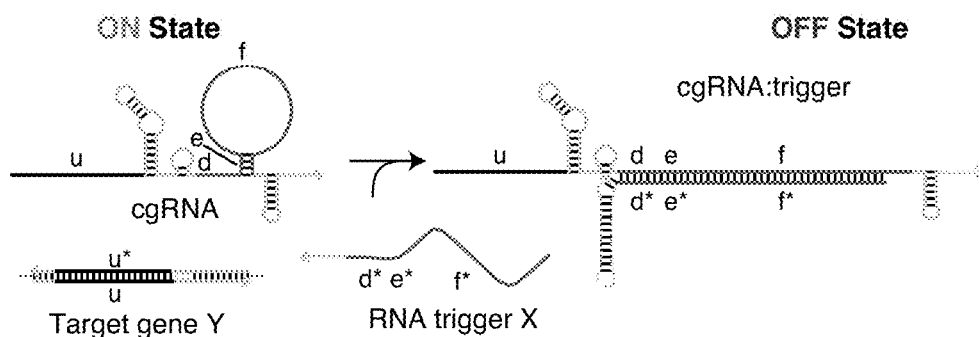
FIGS. 19A-19B depict the mechanism and target test tubes for computational sequence design of a library of orthogonal ON→OFF terminator switch cgRNAs/triggers.
Figure 19B:
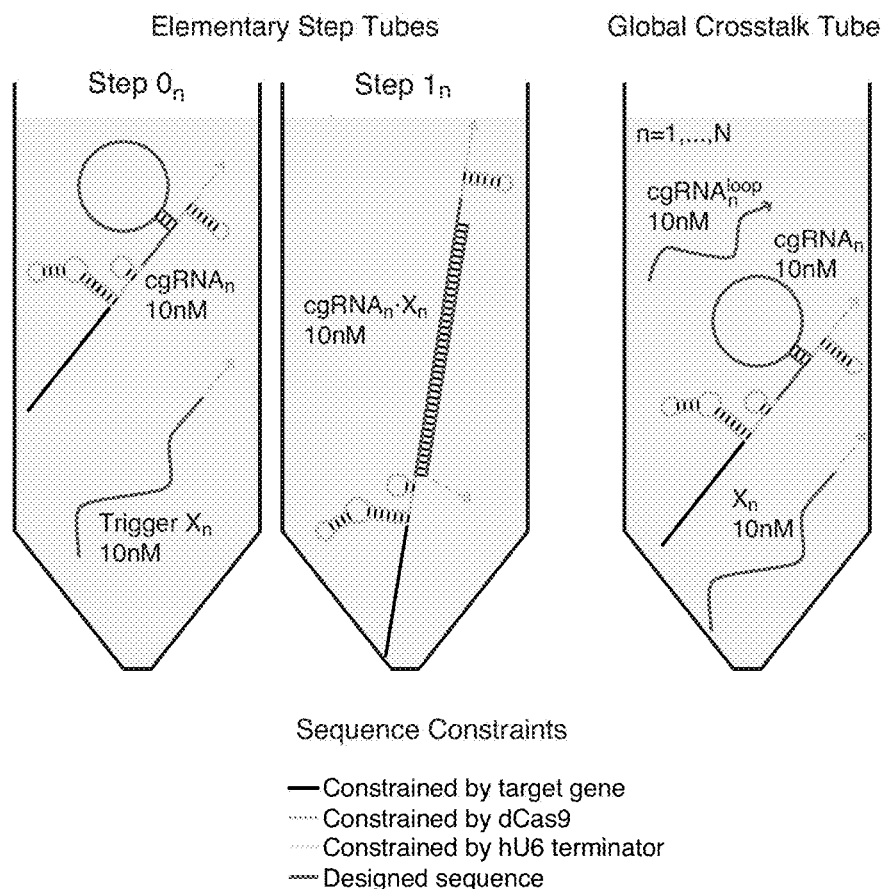
Figure 20A:
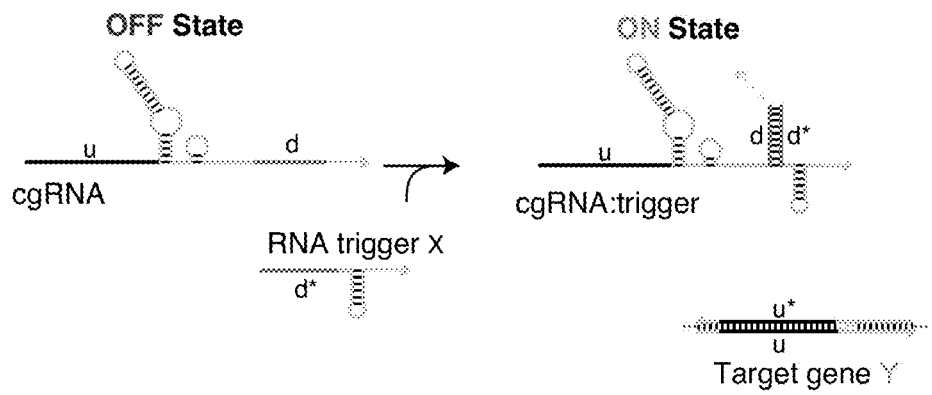
FIGS. 20A-20B depict the mechanism and target test tubes for computational sequence design of a library of orthogonal OFF→ON split-terminator switch cgRNAs/triggers.
Figure 20B:
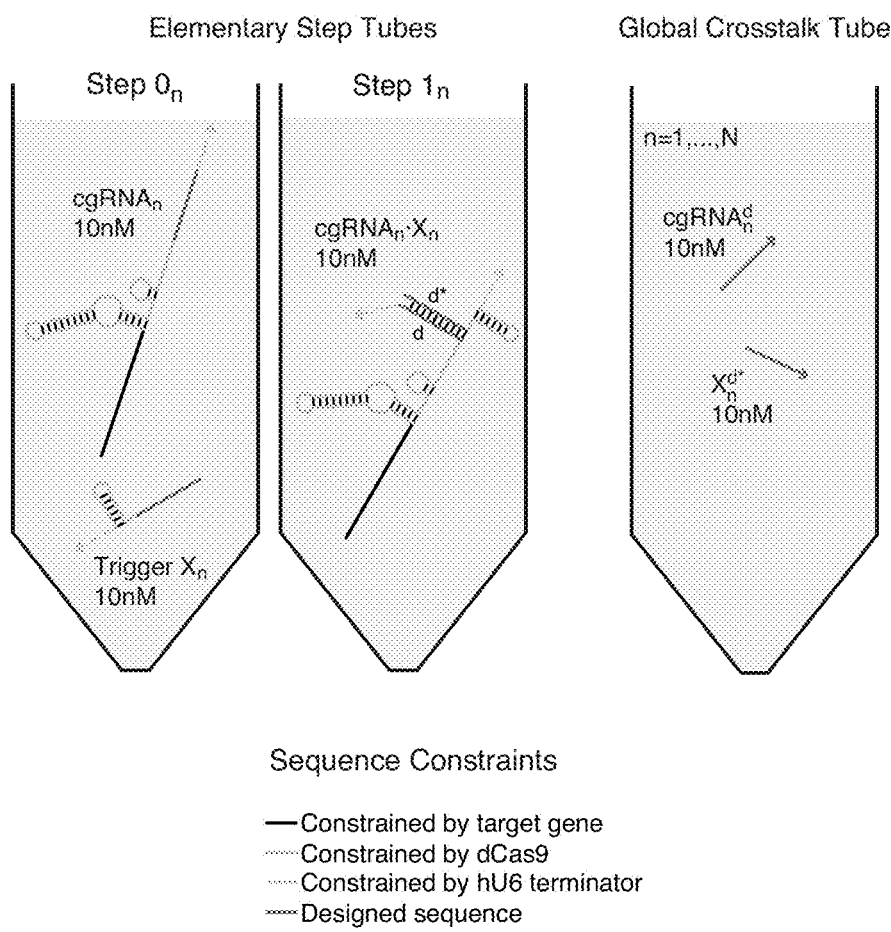

FIG. 19B displays target test tubes for the design of N orthogonal cgRNA/trigger pairs for the ON→OFF terminator switch mechanism (FIG. 19A). FIG. 20B displays target test tubes for the design of N orthogonal cgRNA/trigger pairs for the OFF→ON split-terminator switch mechanism (FIG. 20A). To design N orthogonal cgRNA/trigger pairs (systems), there are two elementary step tubes for each system (n=1, . . . , N): 1) A Reactants tube (Step 0n) containing cgRNAn and the corresponding trigger Xn; 2) A Products tube (Step 1n) containing the complex cgRNAn: Xn. Each target test tube contains a set of desired "on-target" complexes (each with the depicted target secondary structure and target concentration (10 nM in this example)) corresponding to the on-pathway hybridization products for a given step and a set of undesired "off-target" complexes (in this example, all complexes of up to 2 strands, each with a target concentration of 0 nM; not depicted) corresponding to on-pathway reactants and off-pathway hybridization crosstalk for a given step; these elementary step tubes are designed for full conversion of cognate reactants into cognate products and against local hybridization crosstalk between these same reactants. To design N orthogonal systems, there is a single global crosstalk tube containing a set of on-targets and off-targets for each system. The global crosstalk tube contains the depicted on-target complexes corresponding to reactive species generated during Steps 0 and 1 (each with the depicted target secondary structure and target concentration (10 nM in this example) as well as off-target complexes (for this example, all complexes of up to 2 strands, each with a target concentration of 0 nM; not depicted) corresponding to off-pathway interactions between these reactive species. Crucially, the global crosstalk tube ensemble omits the cognate products that the reactive species are intended to form (they appear as neither on-targets nor off-targets). Hence, all reactive species in the global crosstalk tube are forced to either perform no reaction (remaining as desired on-targets) or undergo a crosstalk reaction (forming undesired off-targets), providing the basis for minimization of global crosstalk during sequence optimization. To design a library of N orthogonal cgRNA/trigger pairs, all N cgRNAs have the same on-target structure, and all N triggers have the same on-target structure; within a library, the only difference between cgRNA/trigger pairs is the designed sequence; there are a total of 2N elementary step tubes plus 1 global crosstalk tube. For this example, sequence design was performed subject to complementarity constraints inherent to the reaction pathway (FIGS. 19A and 20A; domain "d" complementary to "d*", etc.), as well as to biological sequence constraints imposed by the the silencing target Y, the protein effector (dCas9), and the terminator; see the constraint shading in FIGS. 19B and 20B. The sequence was optimized by reducing the ensemble defect quantifying the average fraction of incorrectly paired nucleotides over the multi-tube ensemble.[41, 53, 54] Within the ensemble defect, defect weights were applied to prioritize design effort.[41] Optimization of the ensemble defect implemented both a positive design paradigm (explicitly designing for on-pathway elementary steps) and a negative-design paradigm (explicitly designing against off-pathway crosstalk).[41]

Example—Demonstration of Allosteric ON→OFF and OFF→ON cgRNAs Functioning in Multi-Cellular Organisms FIGS. 21 and 22 demonstrate allosteric cgRNAs functioning in developing chicken embryos.

FIG. 21 demonstrates an allosteric ON→OFF terminator switch cgRNA performing conditional logic in a chicken embryo (mechanism of FIG. 13A). FIG. 21A depicts the conditional logic for an ON→OFF terminator switch cgRNA used in conjunction with inducing dCas9: "if not X then Y" (if trigger X is not detected, induce target gene Y). For the experimental demonstration, five plasmids are electroporated into the left side and right side (independently for each side) of a developing chicken embryo (plasmids transfected into both sides: RFP transfection control, inducing dCas9, cgRNA, d2eGFP as the target gene Y; plasmid transfected into the left side only: non-cognate trigger X', plasmid transfected into the right side only: cognate trigger X). FIG. 21B displays RFP fluorescence for the transfection control on both sides of the embryo, demonstrating transfection into both sides of the embryo. FIG. 21C displays GFP fluorescence of the target gene Y, exhibiting high fluorescence on the left side of the embryo (ON state; non-cognate trigger) and low fluorescence on the right side of the embryo (OFF state; cognate trigger). The cognate trigger toggles the cgRNA from the ON state to the OFF state, leading to a large reduction in GFP fluorescence, corresponding to reduced expression of the target gene Y. FIG. 21D displays normalized fluorescence for representative regions in replicate embryos (one dot per embryo) for experiments with transfection of either: no trigger (ON state), non-cognate trigger (ON state), or cognate trigger (OFF state). Error bars represent standard error of the mean over replicate embryos. FIG. 21E depicts the sequences of cgRNAs, the cognate trigger X, and the non-cognate trigger X'. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1)[47]. Sequences are presented as DNA sequences; the corresponding RNA sequence is the same as the DNA sequence except that "U" replaces "T").

Figure 21A:
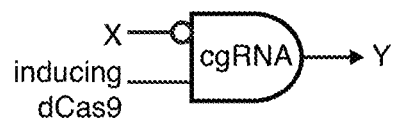
Figure 21B:
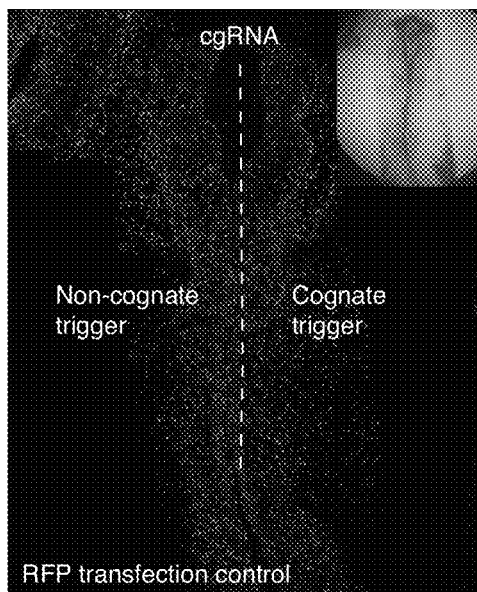
Figure 21C:
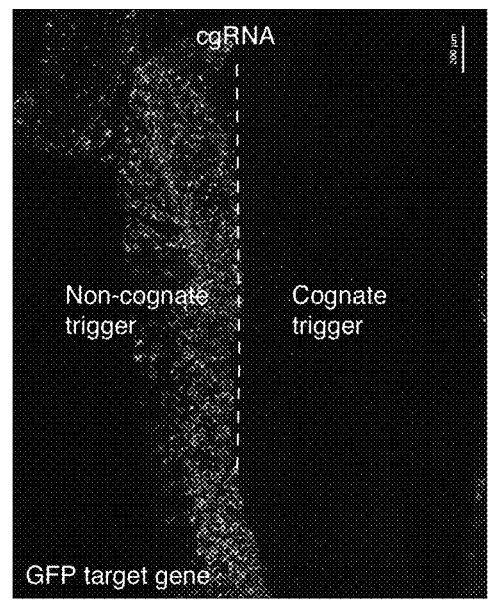
Figure 21D:
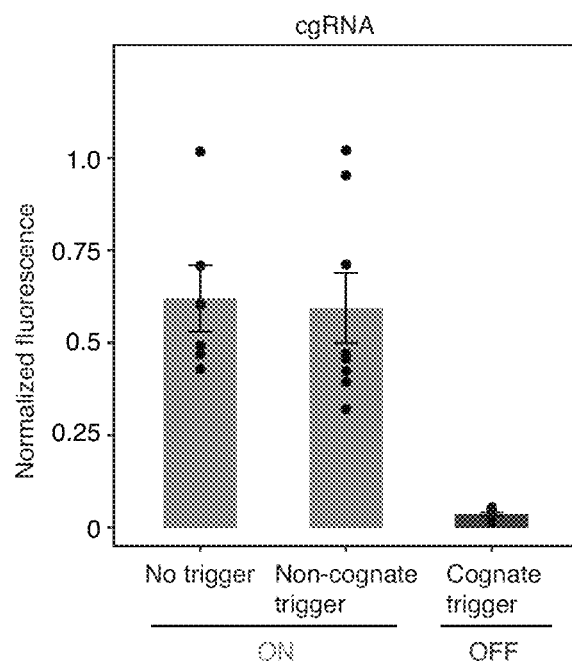
Figure 22A:
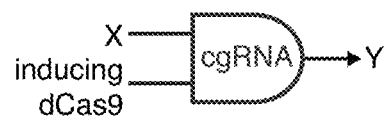
Figure 22B:
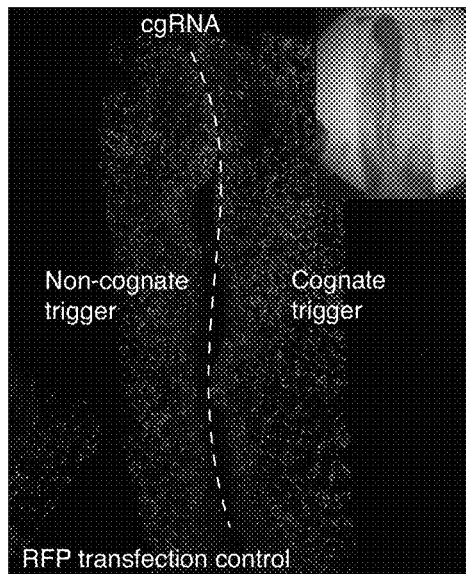
Figure 22C:
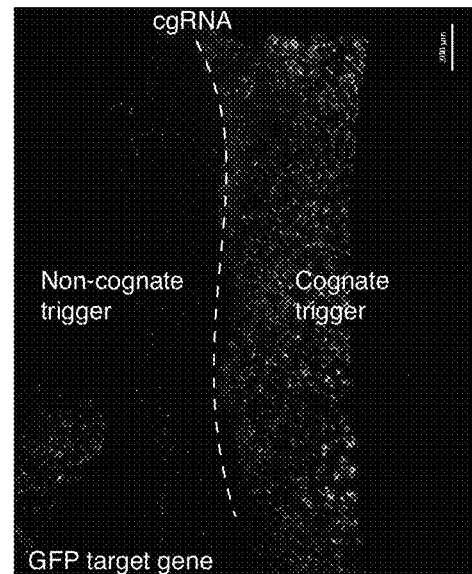
Figure 22D:
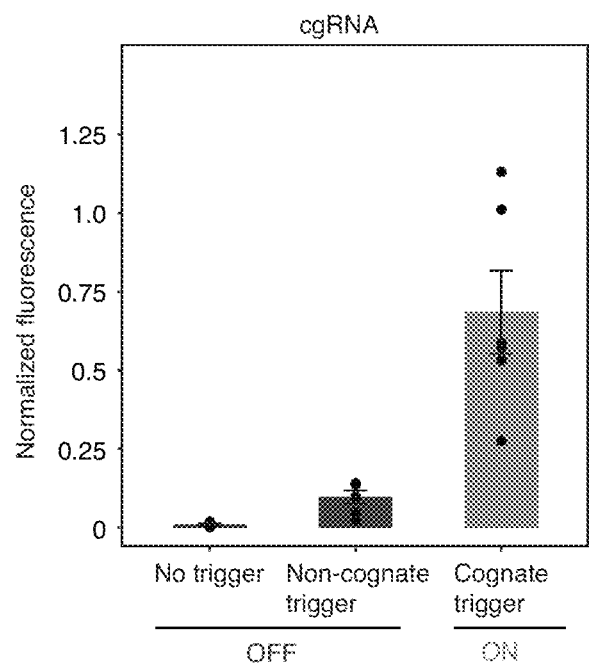

FIG. 22 demonstrates an allosteric OFF→ON split-terminator switch cgRNA performing conditional logic in a chicken embryo (mechanism of FIG. 15A). FIG. 22A depicts the conditional logic for an OFF→ON split-terminator switch cgRNA used in conjunction with inducing dCas9: "if X then Y" (if trigger X is detected, induce target gene Y). For the experimental demonstration, five plasmids are electroporated into the left side and right side (independently for each side) of a developing chicken embryo (plasmids transfected into both sides: RFP transfection control, inducing dCas9, cgRNA, d2eGFP as the target gene Y; plasmid transfected into the left side only: non-cognate trigger X', plasmid transfected into the right side only: cognate trigger X). FIG. 22B displays RFP fluorescence for the transfection control on both sides of the embryo, demonstrating transfection into both sides of the embryo. FIG. 22C displays GFP fluorescence of the target gene Y, exhibiting low fluorescence on the left side of the embryo (OFF state; non-cognate trigger) and high fluorescence on the right side of the embryo (ON state; cognate trigger). The cognate trigger toggles the cgRNA from the OFF to the ON state, leading to a large increase in GFP fluorescence, corresponding to increased expression of the target gene Y. FIG. 21D displays normalized fluorescence for representative regions in replicate embryos (one dot per embryo) for experiments with transfection of either: no trigger (OFF state), non-cognate trigger (OFF state), or cognate trigger (ON state). Error bars represent standard error of the mean over replicate embryos. FIG. 22E depicts the sequences of cgRNAs, the cognate trigger X, and the non-cognate trigger X'. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1). 47 Sequences are presented as DNA sequences; the corresponding RNA sequence is the same as the DNA sequence except that "U" replaces "T").

REFERENCES (1) Cong, L.; Ran, F. A.; Cox, D.; Lin, S.; Barretto, R.; Habib, N.; Hsu, P. D.; Wu, X.; Jiang, W.; Marraffini, L. A.; Zhang, F. Multiplex Genome Engineering Using CRISPR/Cas Systems. *Science* 2013, 339 (6121), 819-823.

(2) Mali, P.; Yang, L.; Esvelt, K. M.; Aach, J.; Guell, M.; DiCarlo, J. E.; Norville, J. E.; Church, G. M. RNA-Guided Human Genome Engineering via Cas9. *Science* 2013, 339 (6121), 823.

(3) Zetsche, B.; Heidenreich, M.; Mohanraju, P.; Fedorova, I.; Kneppers, J.; DeGennaro, E. M.; Winblad, N.; Choudhury, S. R.; Abudayyeh, O. O.; Gootenberg, J. S.; Wu, W. Y.; Scott, D. A.; Severinov, K.; van der Oost, J.; Zhang, F. Multiplex Gene Editing by CRISPR-Cpf1 Using a Single CrRNA Array. *Nat Biotechnol* 2016, 35, 31-34.

(4) Knott, G. J.; Doudna, J. A. CRISPR-Cas Guides the Future of Genetic Engineering. *Science* 2018, 361 (6405), 866-869.

(5) Qi, L. S.; Larson, M. H.; Gilbert, L. A.; Doudna, J. A.; Weissman, J. S.; Arkin, A. P.; Lim, W. A. Repurposing CRISPR as an RNA-Guided Platform for Sequence-Specific Control of Gene Expression. *Cell* 2013, 152 (5), 1173-1183.

(6) Larson, M. H.; Gilbert, L. A.; Wang, X.; Lim, W. A.; Weissman, J. S.; Qi, L. S. CRISPR Interference (CRISPRi) for Sequence-Specific Control of Gene Expression. *Nat Protoc* 2013, 8, 2180-2196.

(7) Gilbert, L. A.; Larson, M. H.; Morsut, L.; Liu, Z.; Brar, G. A.; Torres, S. E.; Stern-Ginossar, N.; Brandman, O.; Whitehead, E. H.; Doudna, J. A.; Lim, W. A.; Weissman, J. S.; Qi, L. S. CRISPR-Mediated Modular RNA-Guided Regulation of Transcription in Eukaryotes. *Cell* 2013, 154 (2), 442-451.

(8) Anzalone, A. V.; Randolph, P. B.; Davis, J. R.; Sousa, A. A.; Koblan, L. W.; Levy, J. M.; Chen, P. J.; Wilson, C.; Newby, G. A.; Raguram, A.; Liu, D. R. Search-and-Replace Genome Editing without Double-Strand Breaks or Donor DNA. *Nature* 2019, 576 (7785), 149-157.

(9) Liu, X. S.; Wu, H.; Krzisch, M.; Wu, X.; Graef, J.; Muffat, J.; Hnisz, D.; Li, C. H.; Yuan, B.; Xu, C.; Li, Y.; Vershkov, D.; Cacace, A.; Young, R. A.; Jaenisch, R. Rescue of Fragile X Syndrome Neurons by DNA Methylation Editing of the FMR1 Gene. *Cell* 2018, 172 (5), 979-992.e6.

(10) Myers, S. A.; Wright, J.; Peckner, R.; Kalish, B. T.; Zhang, F.; Carr, S. A. Discovery of Proteins Associated with a Predefined Genomic Locus via DCas9-APEX-Mediated Proximity Labeling. *Nat. Methods* 2018, 15 (6), 437-439.

(11) Morgan, S. L.; Mariano, N. C.; Bermudez, A.; Arruda, N. L.; Wu, F.; Luo, Y.; Shankar, G.; Jia, L.; Chen, H.; Hu, J.-F.; Hoffman, A. R.; Huang, C.-C.; Pitteri, S. J.; Wang, K. C. Manipulation of Nuclear Architecture through CRISPR-Mediated Chromosomal Looping. *Nat. Commun.* 2017, 8 (1), 15993.

(12) Ma, H.; Tu, L.-C.; Naseri, A.; Huisman, M.; Zhang, S.; Grunwald, D.; Pederson, T. Multiplexed Labeling of Genomic Loci with DCas9 and Engineered SgRNAs Using CRISPRainbow. *Nat. Biotechnol.* 2016, 34 (5), 528-530.

(13) Mückl, A.; Schwarz-Schilling, M.; Fischer, K.; Simmel, F. C. Filamentation and Restoration of Normal Growth in *Escherichia Coli* Using a Combined CRISPRi SgRNA/Antisense RNA Approach. *PLoS One* 2018, 13 (9), e0198058.

(14) Aubrey, B. J.; Kelly, G. L.; Kueh, A. J.; Brennan, M. S.; O'Connor, L.; Milla, L.; Wilcox, S.; Tai, L.; Strasser, A.; Herold, M. J. An Inducible Lentiviral Guide RNA Platform Enables the Identification of Tumor-Essential Genes and Tumor-Promoting Mutations in Vivo. *Cell Rep.* 2015, 10 (8), 1422-1432.

(15) Bertero, A.; Pawlowski, M.; Ortmann, D.; Snijders, K.; Yiangou, L.; Cardoso de Brito, M.; Brown, S.; Bernard, W. G.; Cooper, J. D.; Giacomelli, E.; Gambardella, L.; Hannan, N. R. F.; Iyer, D.; Sampaziotis, F.; Serrano, F.; Zonneveld, M. C. F.; Sinha, S.; Kotter, M.; Vallier, L. Optimized Inducible ShRNA and CRISPR/Cas9 Platforms for in Vitro Studies of Human Development Using HPSCs. *Development* 2016, 143 (23), 4405.

(16) Chen, T.; Gao, D.; Zhang, R.; Zeng, G.; Yan, H.; Lim, E.; Liang, F. Chemically Controlled Epigenome Editing through an Inducible DCas9 System. *J. Am. Chem. Soc.* 2017, 139 (33), 11337-11340.

(17) Moroz-Omori, E. V.; Satyapertiwi, D.; Ramel, M.-C.; Høgset, H.; Sunyovszki, I. K.; Liu, Z.; Wojciechowski, J. P.; Zhang, Y.; Grigsby, C. L.; Brito, L.; Bugeon, L.; Dallman, M. J.; Stevens, M. M. Photoswitchable GRNAs for Spatiotemporally Controlled CRISPR-Cas-Based Genomic Regulation. *ACS Cent. Sci.* 2020, 6 (5), 695-703.

(18) Liu, Y.; Zou, R. S.; He, S.; Nihongaki, Y.; Li, X.; Razavi, S.; Wu, B.; Ha, T. Very Fast CRISPR on Demand. *Science* 2020, 368 (6496), 1265-1269.

(19) Jain, P. K.; Ramanan, V.; Schepers, A. G.; Dalvie, N. S.; Panda, A.; Fleming, H. E.; Bhatia, S. N. Development of Light-Activated CRISPR Using Guide RNAs with Photocleavable Protectors. *Angew. Chem. Int. Ed.* 2016, 55 (40), 12440-12444.

(20) Nihongaki, Y.; Otabe, T.; Sato, M. Emerging Approaches for Spatiotemporal Control of Targeted Genome with Inducible CRISPR-Cas9. *Anal Chem* 2018, 90 (1), 429-439.

(21) Shen, Z.; Zhang, X.; Chai, Y.; Zhu, Z.; Yi, P.; Feng, G.; Li, W.; Ou, G. Conditional Knockouts Generated by Engineered CRISPR-Cas9 Endonuclease Reveal the Roles of Coronin in C. *Elegans* Neural Development. *Dev. Cell* 2014, 30 (5), 625-636.

(22) Ablain, J.; Durand, E. M.; Yang, S.; Zhou, Y.; Zon, L. I. A CRISPR/Cas9 Vector System for Tissue-Specific Gene Disruption in Zebrafish. *Dev. Cell* 2015, 32 (6), 756-764.

(23) Hirosawa, M.; Fujita, Y.; Parr, C. J. C.; Hayashi, K.; Kashida, S.; Hotta, A.; Woltjen, K.; Saito, H. Cell-Type-Specific Genome Editing with a MicroRNA-Responsive CRISPR-Cas9 Switch. *Nucleic Acids Res* 2017, 45 (13), e118.

(24) Briner, A. E.; Donohoue, P. D.; Gomaa, A. A.; Selle, K.; Slorach, E. M.; Nye, C. H.; Haurwitz, R. E.; Beisel, C. L.; May, A. P.; Barrangou, R. Guide RNA Functional Modules Direct Cas9 Activity and Orthogonality. *Mol Cell* 2014, 56 (2), 333-339.

(25) Nowak, C. M.; Lawson, S.; Zerez, M.; Bleris, L. Guide RNA Engineering for Versatile Cas9 Functionality. *Nucleic Acids Res* 2016, 44 (20), 9555-9564.

(26) Hanewich-Hollatz, M. H.; Chen, Z.; Hochrein, L. M.; Huang, J.; Pierce, N. A. Conditional Guide RNAs: Programmable Conditional Regulation of CRISPR/Cas Function in Bacterial and Mammalian Cells via Dynamic RNA Nanotechnology. *ACS Cent. Sci.* 2019, 5 (7), 1241-1249.

(27) Liu, Y.; Zhan, Y.; Chen, Z.; He, A.; Li, J.; Wu, H.; Liu, L.; Zhuang, C.; Lin, J.; Guo, X.; Zhang, Q.; Huang, W.; Cai, Z. Directing Cellular Information Flow via CRISPR Signal Conductors. *Nat Methods* 2016, 13, 938-944.

(28) Tang, W.; Hu, J. H.; Liu, D. R. Aptazyme-Embedded Guide RNAs Enable Ligand-Responsive Genome Editing and Transcriptional Activation. *Nat Commun* 2017, 8, 15939.

(29) Kundert, K.; Lucas, J. E.; Watters, K. E.; Fellmann, C.; Ng, A. H.; Heineike, B. M.; Fitzsimmons, C. M.; Oakes, B. L.; Qu, J.; Prasad, N.; Rosenberg, O. S.; Savage, D. F.; El-Samad, H.; Doudna, J. A.; Kortemme, T. Controlling CRISPR-Cas9 with Ligand-Activated and Ligand-Deactivated SgRNAs. *Nat Commun* 2019, 10 (1), 2127.

(30) Lee, Y. J.; Hoynes-O'Connor, A.; Leong, M. C.; Moon, T. S. Programmable Control of Bacterial Gene Expression with the Combined CRISPR and Antisense RNA System. *Nucleic Acids Res.* 2016, 44 (5), 2462-2473.

(31) Ferry, Q. R. V.; Lyutova, R.; Fulga, T. A. Rational Design of Inducible CRISPR Guide RNAs for de Novo Assembly of Transcriptional Programs. *Nat Commun* 2017, 8, 2109.

(32) Wang, X.-W.; Hu, L.-F.; Hao, J.; Liao, L.-Q.; Chiu, Y.-T.; Shi, M.; Wang, Y. A MicroRNA-Inducible CRISPR-Cas9 Platform Serves as a MicroRNA Sensor and Cell-Type-Specific Genome Regulation Tool. *Nat. Cell Biol.* 2019, 21 (4), 522-530.

(33) Siu, K.-H.; Chen, W. Riboregulated Toehold-Gated GRNA for Programmable CRISPR-Cas9 Function. *Nat. Chem. Biol.* 2019, 15 (3), 217-220.

(34) Oesinghaus, L.; Simmel, F. C. Switching the Activity of Cas12a Using Guide RNA Strand Displacement Circuits. *Nat. Commun.* 2019, 10 (1), 1-11.

(35) Chen, B.; Gilbert, L. A.; Cimini, B. A.; Schnitzbauer, J.; Zhang, W.; Li, G.-W.; Park, J.; Blackburn, E. H.; Weissman, J. S.; Qi, L. S.; Huang, B. Dynamic Imaging of Genomic Loci in Living Human Cells by an Optimized CRISPR/Cas System. *Cell* 2013, 155 (7), 1479-1491.

(36) Knight, S. C.; Tjian, R.; Doudna, J. A. Genomes in Focus: Development and Applications of CRISPR-Cas9 Imaging Technologies. *Angew Chem Int Ed* 2018, 57 (16), 4329-4337.

(37) Hilton, I. B.; D'Ippolito, A. M.; Vockley, C. M.; Thakore, P. I.; Crawford, G. E.; Reddy, T. E.; Gersbach, C. A. Epigenome Editing by a CRISPR-Cas9-Based Acetyltransferase Activates Genes from Promoters and Enhancers. *Nat Biotechnol* 2015, 33, 510.

(38) Gaudelli, N. M.; Komor, A. C.; Rees, H. A.; Packer, M. S.; Badran, A. H.; Bryson, D. I.; Liu, D. R. Programmable Base Editing of A$\cdot$T to G$\cdot$C in Genomic DNA without DNA Cleavage. *Nature* 2017, 551 (7681), 464-471.

(39) Hochrein, L. M.; Li, H.; Pierce, N. A. High-Performance Allosteric Conditional Guide RNAs for Mammalian Cell-Selective Regulation of CRISPR/Cas. *ACS Synth. Biol.* 2021, 10 (5), 964-971.

(40) Zadeh, J. N.; Steenberg, C. D.; Bois, J. S.; Wolfe, B. R.; Pierce, M. B.; Khan, A. R.; Dirks, R. M.; Pierce, N. A. NUPACK: Analysis and Design of Nucleic Acid Systems. *J. Comput. Chem.* 2011, 32 (1), 170-173.

(41) Wolfe, B. R.; Porubsky, N. J.; Zadeh, J. N.; Dirks, R. M.; Pierce, N. A. Constrained Multistate Sequence Design for Nucleic Acid Reaction Pathway Engineering. *J. Am. Chem. Soc.* 2017, 139 (8), 3134-3144.

(42) Wang, D.; Zhang, C.; Wang, B.; Li, B.; Wang, Q.; Liu, D.; Wang, H.; Zhou, Y.; Shi, L.; Lan, F.; Wang, Y. Optimized CRISPR Guide RNA Design for Two High-Fidelity Cas9 Variants by Deep Learning. *Nat Commun* 2019, 10 (1), 4284.

(43) Misteli, T.; Spector, D. L. Applications of the Green Fluorescent Protein in Cell Biology and Biotechnology. *Nat Biotech* 1997, 15 (10), 961-964.

(44) Tsien, R. Y. The Green Fluorescent Protein. *Annu Rev Biochem* 1998, 67 (1), 509-544.

(45) Zimmer, M. Green Fluorescent Protein (GFP): Applications, Structure, and Related Photophysical Behavior. *Chem Rev* 2002, 102 (3), 759-782.

(46) Gao, Z.; Herrera-Carrillo, E.; Berkhout, B. Delineation of the Exact Transcription Termination Signal for Type 3 Polymerase III. *Mol. Ther. Nucleic Acids* 2018, 10, 36-44.

(47) Kieft, J. S.; Rabe, J. L.; Chapman, E. G. New Hypotheses Derived from the Structure of a Flaviviral Xrn1-Resistant RNA: Conservation, Folding, and Host Adaptation. *RNA Biol* 2015, 12 (11), 1169-1177.

(48) Chavez, A.; Scheiman, J.; Vora, S.; Pruitt, B. W.; Tuttle, M.; Iyer, E. P. R.; Lin, S.; Kiani, S.; Guzman, C. D.; Wiegand, D. J.; Ter-Ovanesyan, D.; Braff, J. L.; Davidsohn, N.; Housden, B. E.; Perrimon, N.; Weiss, R.; Aach, J.; Collins, J. J.; Church, G. M. Highly Efficient Cas9-Mediated Transcriptional Programming. *Nat. Methods* 2015, 12 (4), 326-328.

(49) Mali, P.; Aach, J.; Stranges, P. B.; Esvelt, K. M.; Moosburner, M.; Kosuri, S.; Yang, L.; Church, G. M. CAS9 Transcriptional Activators for Target Specificity Screening and Paired Nickases for Cooperative Genome Engineering. *Nat. Biotechnol.* 2013, 31, 833-838.

(50) Nissim, L.; Perli, S. D.; Fridkin, A.; Perez-Pinera, P.; Lu, T. K. Multiplexed and Programmable Regulation of Gene Networks with an Integrated RNA and CRISPR/Cas Toolkit in Human Cells. *Mol. Cell* 2014, 54 (4), 698-710.

(51) Shagin, D. A.; Barsova, E. V.; Yanushevich, Y. G.; Fradkov, A. F.; Lukyanov, K. A.; Labas, Y. A.; Semenova, T. N.; Ugalde, J. A.; Meyers, A.; Nunez, J. M.; Widder, E. A.; Lukyanov, S. A.; Matz, M. V. GFP-like Proteins as Ubiquitous Metazoan Superfamily: Evolution of Functional Features and Structural Complexity. *Mol. Biol. Evol.* 2004, 21 (5), 841-850.

(52) Nissim, L.; Perli, S. D.; Fridkin, A.; Perez-Pinera, P.; Lu, T. K. Multiplexed and Programmable Regulation of Gene Networks with an Integrated RNA and CRISPR/Cas Toolkit in Human Cells. *Mol Cell* 2019, 54 (4), 698-710.

(53) Zadeh, J. N.; Wolfe, B. R.; Pierce, N. A. Nucleic Acid Sequence Design via Efficient Ensemble Defect Optimization. *J. Comput. Chem.* 2011, 32, 439-452.

(54) Wolfe, B. R.; Pierce, N. A. Sequence Design for a Test Tube of Interacting Nucleic Acid Strands. *ACS Synth. Biol.* 2015, 4 (10), 1086-1100.

What is claimed is:

1. An allosteric conditional guide RNA (cgRNA) comprising a 5' fragment (cg5) and a 3' fragment (cg3), cg5 comprising a target-binding region and a trigger-binding region, and cg3 comprising a cognate RNA trigger:
   a. wherein the trigger-binding region is non-overlapping with the target-binding region and is not configured to bind either the target-binding region or 5' of the target-binding region;
   b. wherein cg5 and cg3 are inactive when not bound to each other; and
   c. wherein upon hybridization of cg3 to cg5 to form a cg5:cg3 complex comprising a terminator duplex, the cgRNA is activated, mediating the function of a Cas protein effector on a target gene that binds the target-binding region, wherein:
   fragment cg5 comprises a trigger-binding region comprising a 5' portion of a stem of the terminator duplex; and
   fragment cg3 comprises a 3' portion of the stem of the terminator duplex, such that hybridization of cg5 to cg3 forms the terminator duplex, activating the cgRNA.

2. The allosteric cgRNA of claim 1 wherein the fragment cg5 further comprises a Cas handle wherein the target-binding region is 5' of the Cas handle and the trigger-binding region is 3' of the Cas handle.

* * * * *

SEQUENCE LISTING

<160> NUMBER OF SEQ ID NOS: 108

<210> SEQ ID NO 1
<211> LENGTH: 129
<212> TYPE: DNA
<213> ORGANISM: Artificial Sequence
<220> FEATURE:
<223> OTHER INFORMATION: cgRNA A

```
<400> SEQUENCE: 1
aactttcagt ttagcggtct gttttagagc tagaaatagc aagttaaaat aaggctagtc    60
cgatcaaacg ggtaaacaaa caggataatt aaggaggcag tacccgggca ccgagtcggt   120
gcttttttt                                                          129

<210> SEQ ID NO 2
<211> LENGTH: 129
<212> TYPE: DNA
<213> ORGANISM: Artificial Sequence
<220> FEATURE:
<223> OTHER INFORMATION: cgRNA B

<400> SEQUENCE: 2
aactttcagt ttagcggtct gttttagagc tagaaatagc aagttaaaat aaggctagtc    60
cgtatcatgg ggttgtgtgt tgttgtaagt gtgtgtgtgt tgccccggca ccgagtcggt   120
gcttttttt                                                          129

<210> SEQ ID NO 3
<211> LENGTH: 129
<212> TYPE: DNA
<213> ORGANISM: Artificial Sequence
<220> FEATURE:
<223> OTHER INFORMATION: cgRNA C

<400> SEQUENCE: 3
aactttcagt ttagcggtct gttttagagc tagaaatagc aagttaaaat aaggctagtc    60
cgaatatagg ggaagagaaa gaagaagaga agagaaagat gtccccggca ccgagtcggt   120
gcttttttt                                                          129

<210> SEQ ID NO 4
<211> LENGTH: 40
<212> TYPE: DNA
<213> ORGANISM: Artificial Sequence
<220> FEATURE:
<223> OTHER INFORMATION: Trigger XA

<400> SEQUENCE: 4
tactgcctcc ttaattatcc tgtttgttta cccgtttgat                          40

<210> SEQ ID NO 5
<211> LENGTH: 40
<212> TYPE: DNA
<213> ORGANISM: Artificial Sequence
<220> FEATURE:
<223> OTHER INFORMATION: Trigger XB

<400> SEQUENCE: 5
caacacacac acacttacaa caacacacaa ccccatgata                          40

<210> SEQ ID NO 6
<211> LENGTH: 40
<212> TYPE: DNA
<213> ORGANISM: Artificial Sequence
<220> FEATURE:
<223> OTHER INFORMATION: Trigger XC

<400> SEQUENCE: 6
acatctttct cttctcttct tctttctctt cccctatatt                          40

<210> SEQ ID NO 7
<211> LENGTH: 165
```

```
<212> TYPE: DNA
<213> ORGANISM: Artificial Sequence
<220> FEATURE:
<223> OTHER INFORMATION: cgRNA A

<400> SEQUENCE: 7
catctaattc aacaagaatt gttttagagc tacaccttac gccggttcaa ttccaagtcc    60
cttccagtag caagttaaaa taaggctagt ccgttatcaa cttaacaccc tttacaaacc   120
ttcctcttcc tttaccctaa gtggcaccga gtcggtgctt ttttt                   165

<210> SEQ ID NO 8
<211> LENGTH: 165
<212> TYPE: DNA
<213> ORGANISM: Artificial Sequence
<220> FEATURE:
<223> OTHER INFORMATION: cgRNA B

<400> SEQUENCE: 8
catctaattc aacaagaatt gttttagagc tagtaatcga atcatagtaa atttcccatc    60
gtcataatag caagttaaaa taaggctagt ccgttatcaa cttcatacgg gtctgaagta   120
gttcattctt atacagtcaa gtggcaccga gtcggtgctt ttttt                   165

<210> SEQ ID NO 9
<211> LENGTH: 165
<212> TYPE: DNA
<213> ORGANISM: Artificial Sequence
<220> FEATURE:
<223> OTHER INFORMATION: cgRNA C

<400> SEQUENCE: 9
catctaattc aacaagaatt gttttagagc tagtcgttac cttatcaata tcaacctccg    60
catacactag caagttaaaa taaggctagt ccgttatcaa cttgcacata ggacccaaca   120
tgccaacaga gaagagttaa gtggcaccga gtcggtgctt ttttt                   165

<210> SEQ ID NO 10
<211> LENGTH: 70
<212> TYPE: DNA
<213> ORGANISM: Artificial Sequence
<220> FEATURE:
<223> OTHER INFORMATION: Trigger XA

<400> SEQUENCE: 10
agggtaaagg aagaggaagg tttgtaaagg gtgttctgga agggacttgg aattgaaccg    60
gcgtaaggtg                                                          70

<210> SEQ ID NO 11
<211> LENGTH: 70
<212> TYPE: DNA
<213> ORGANISM: Artificial Sequence
<220> FEATURE:
<223> OTHER INFORMATION: Trigger XB

<400> SEQUENCE: 11
gactgtataa gaatgaacta cttcagaccc gtatgttatg acgatgggaa atttactatg    60
attcgattac                                                          70

<210> SEQ ID NO 12
<211> LENGTH: 70
<212> TYPE: DNA
<213> ORGANISM: Artificial Sequence
<220> FEATURE:
```

<223> OTHER INFORMATION: Trigger XC

<400> SEQUENCE: 12
aactcttctc tgttggcatg ttgggtccta tgtgcgtgta tgcggaggtt gatattgata     60
aggtaacgac     70

<210> SEQ ID NO 13
<211> LENGTH: 129
<212> TYPE: DNA
<213> ORGANISM: Artificial Sequence
<220> FEATURE:
<223> OTHER INFORMATION: cgRNA Q

<400> SEQUENCE: 13
gagtcgcgtg tagcgaagca gttttagagc tagaaatagc aagttaaaat aaggctagtc     60
cgatctttgc gcgttagttt cgttcgtatt tctgtcatgt ttgcgcggca ccgagtcggt    120
gcttttttt    129

<210> SEQ ID NO 14
<211> LENGTH: 129
<212> TYPE: DNA
<213> ORGANISM: Artificial Sequence
<220> FEATURE:
<223> OTHER INFORMATION: cgRNA R

<400> SEQUENCE: 14
gagtcgcgtg tagcgaagca gttttagagc tagaaatagc aagttaaaat aaggctagtc     60
cgtatcgccg ggttcaagca gatgtggcat ttcagtgtag ttcccgggca ccgagtcggt    120
gcttttttt    129

<210> SEQ ID NO 15
<211> LENGTH: 129
<212> TYPE: DNA
<213> ORGANISM: Artificial Sequence
<220> FEATURE:
<223> OTHER INFORMATION: cgRNA S

<400> SEQUENCE: 15
gagtcgcgtg tagcgaagca gttttagagc tagaaatagc aagttaaaat aaggctagtc     60
cgtccattcg ggtttactat tacaatctta cgtgttctca ttcccgggca ccgagtcggt    120
gcttttttt    129

<210> SEQ ID NO 16
<211> LENGTH: 129
<212> TYPE: DNA
<213> ORGANISM: Artificial Sequence
<220> FEATURE:
<223> OTHER INFORMATION: cgRNA T

<400> SEQUENCE: 16
gagtcgcgtg tagcgaagca gttttagagc tagaaatagc aagttaaaat aaggctagtc     60
cggataaagg gaaagatgaa gtgatgtgaa gatagagttg gatcccggca ccgagtcggt    120
gcttttttt    129

<210> SEQ ID NO 17
<211> LENGTH: 117
<212> TYPE: DNA
<213> ORGANISM: Artificial Sequence
<220> FEATURE:
<223> OTHER INFORMATION: Trigger XQ

<400> SEQUENCE: 17
agtcaggcca cttgtgccac ggtttgagca aaccgtgctg cctgtagctc cgccaataat    60
gggaggcgta aacatgacag aaatacgaac gaaactaacg cgcaaagatc ttttttt      117

<210> SEQ ID NO 18
<211> LENGTH: 117
<212> TYPE: DNA
<213> ORGANISM: Artificial Sequence
<220> FEATURE:
<223> OTHER INFORMATION: Trigger XR

<400> SEQUENCE: 18
agtcaggcca cttgtgccac ggtttgagca aaccgtgctg cctgtagctc cgccaataat    60
gggaggcgta actacactga aatgccacat ctgcttgaac ccggcgatac ttttttt      117

<210> SEQ ID NO 19
<211> LENGTH: 117
<212> TYPE: DNA
<213> ORGANISM: Artificial Sequence
<220> FEATURE:
<223> OTHER INFORMATION: Trigger XS

<400> SEQUENCE: 19
agtcaggcca cttgtgccac ggtttgagca aaccgtgctg cctgtagctc cgccaataat    60
gggaggcgta atgagaacac gtaagattgt aatagtaaac ccgaatggac ttttttt      117

<210> SEQ ID NO 20
<211> LENGTH: 117
<212> TYPE: DNA
<213> ORGANISM: Artificial Sequence
<220> FEATURE:
<223> OTHER INFORMATION: Trigger XT

<400> SEQUENCE: 20
agtcaggcca cttgtgccac ggtttgagca aaccgtgctg cctgtagctc cgccaataat    60
gggaggcgtt ccaactctat cttcacatca cttcatcttt ccctttatcc ttttttt      117

<210> SEQ ID NO 21
<211> LENGTH: 117
<212> TYPE: DNA
<213> ORGANISM: Artificial Sequence
<220> FEATURE:
<223> OTHER INFORMATION: Trigger XQ - 40 nt

<400> SEQUENCE: 21
agtcaggcca cttgtgccac ggtttgagca aaccgtgctg cctgtagctc cgccaataat    60
gggaggcgta aacatgacag aaatacgaac gaaactaacg cgcaaagatc ttttttt      117

<210> SEQ ID NO 22
<211> LENGTH: 127
<212> TYPE: DNA
<213> ORGANISM: Artificial Sequence
<220> FEATURE:
<223> OTHER INFORMATION: 50 nt Trigger - Center

<400> SEQUENCE: 22
agtcaggcca cttgtgccac ggtttgagca aaccgtgctg cctgtagctc cgccaataat    60
gggaggcgtg ccgaaaacat gacagaaata cgaacgaaac taacgcgcaa agattccagc   120
ttttttt                                                             127

<210> SEQ ID NO 23
<211> LENGTH: 127
<212> TYPE: DNA
<213> ORGANISM: Artificial Sequence
<220> FEATURE:
<223> OTHER INFORMATION: 50 nt Trigger - 40 nt XQ at 3'

<400> SEQUENCE: 23
agtcaggcca cttgtgccac ggtttgagca aaccgtgctg cctgtagctc cgccaataat      60
gggaggcgtg ccgatccaga aacatgacag aaatacgaac gaaactaacg cgcaaagatc     120
ttttttt                                                                127

<210> SEQ ID NO 24
<211> LENGTH: 127
<212> TYPE: DNA
<213> ORGANISM: Artificial Sequence
<220> FEATURE:
<223> OTHER INFORMATION: 50 nt Trigger - 40 nt XQ at 5'

<400> SEQUENCE: 24
agtcaggcca cttgtgccac ggtttgagca aaccgtgctg cctgtagctc cgccaataat      60
gggaggcgta aacatgacag aaatacgaac gaaactaacg cgcaaagatg ccgatccagc     120
ttttttt                                                                127

<210> SEQ ID NO 25
<211> LENGTH: 147
<212> TYPE: DNA
<213> ORGANISM: Artificial Sequence
<220> FEATURE:
<223> OTHER INFORMATION: 70 nt Trigger - Center

<400> SEQUENCE: 25
agtcaggcca cttgtgccac ggtttgagca aaccgtgctg cctgtagctc cgccaataat      60
gggaggcgtg ccgagccgag ccgaaaacat gacagaaata cgaacgaaac taacgcgcaa     120
agatgccgag ccgatccagc ttttttt                                          147

<210> SEQ ID NO 26
<211> LENGTH: 147
<212> TYPE: DNA
<213> ORGANISM: Artificial Sequence
<220> FEATURE:
<223> OTHER INFORMATION: 70 nt Trigger - 40 nt XQ at 3'

<400> SEQUENCE: 26
agtcaggcca cttgtgccac ggtttgagca aaccgtgctg cctgtagctc cgccaataat      60
gggaggcgtg ccgatccagg ccgatccagg ccgatccaga aacatgacag aaatacgaac     120
gaaactaacg cgcaaagatc ttttttt                                          147

<210> SEQ ID NO 27
<211> LENGTH: 147
<212> TYPE: DNA
<213> ORGANISM: Artificial Sequence
<220> FEATURE:
<223> OTHER INFORMATION: 70 nt Trigger - 40 nt XQ at 5'

<400> SEQUENCE: 27
agtcaggcca cttgtgccac ggtttgagca aaccgtgctg cctgtagctc cgccaataat      60
gggaggcgta aacatgacag aaatacgaac gaaactaacg cgcaaagatg ccgatccagg     120
ccgatccagg ccgatccagc ttttttt                                          147

```
<210> SEQ ID NO 28
<211> LENGTH: 177
<212> TYPE: DNA
<213> ORGANISM: Artificial Sequence
<220> FEATURE:
<223> OTHER INFORMATION: 100 nt Trigger - Center

<400> SEQUENCE: 28
agtcaggcca cttgtgccac ggtttgagca aaccgtgctg cctgtagctc cgccaataat    60
gggaggcgtg ccgatccagg ccgatccagg ccgatccaga acatgacag aaatacgaac    120 gaaactaacg cgcaaagatg ccgatccagg ccgatccagg ccgatccagc ttttttt      177

<210> SEQ ID NO 29
<211> LENGTH: 177
<212> TYPE: DNA
<213> ORGANISM: Artificial Sequence
<220> FEATURE:
<223> OTHER INFORMATION: 100 nt Trigger - 40 nt XQ at 3'

<400> SEQUENCE: 29
agtcaggcca cttgtgccac ggtttgagca aaccgtgctg cctgtagctc cgccaataat    60
gggaggcgtg ccgatccagg ccgatccagg ccgatccagg ccgatccagg ccgatccagg   120
ccgatccaga acatgacag aaatacgaac gaaactaacg cgcaaagatc ttttttt       177

<210> SEQ ID NO 30
<211> LENGTH: 177
<212> TYPE: DNA
<213> ORGANISM: Artificial Sequence
<220> FEATURE:
<223> OTHER INFORMATION: 100 nt Trigger - 40 nt XQ at 5'

<400> SEQUENCE: 30
agtcaggcca cttgtgccac ggtttgagca aaccgtgctg cctgtagctc cgccaataat    60
gggaggcgta aacatgacag aaatacgaac gaaactaacg cgcaaagatg ccgatccagg   120
ccgatccagg ccgatccagg ccgatccagg ccgatccagg ccgatccagc ttttttt      177

<210> SEQ ID NO 31
<211> LENGTH: 227
<212> TYPE: DNA
<213> ORGANISM: Artificial Sequence
<220> FEATURE:
<223> OTHER INFORMATION: 150 nt Trigger - Center

<400> SEQUENCE: 31
agtcaggcca cttgtgccac ggtttgagca aaccgtgctg cctgtagctc cgccaataat    60
gggaggcgtg ccgatccagg ccgatccagg ccgagccgat ccaggccgat ccaggccgat   120
ccagaaacat gacagaaata cgaacgaaac taacgcgcaa agatgccgat ccaggccgat   180
ccaggccgag ccgatccagg ccgatccagg ccgatccagc ttttttt                 227

<210> SEQ ID NO 32
<211> LENGTH: 227
<212> TYPE: DNA
<213> ORGANISM: Artificial Sequence
<220> FEATURE:
<223> OTHER INFORMATION: 150 nt Trigger - 40 nt XQ at 3'

<400> SEQUENCE: 32
agtcaggcca cttgtgccac ggtttgagca aaccgtgctg cctgtagctc cgccaataat    60
```

```
gggaggcgtg ccgatccagg ccgatccagg ccgatccagg ccgatccagg ccgatccagg    120
ccgatccagg ccgatccagg ccgatccagg ccgatccagg ccgatccagg ccgatccaga    180
aacatgacag aaatacgaac gaaactaacg cgcaaagatc ttttttt                  227
```

<210> SEQ ID NO 33
<211> LENGTH: 227
<212> TYPE: DNA
<213> ORGANISM: Artificial Sequence
<220> FEATURE:
<223> OTHER INFORMATION: 150 nt Trigger - 40 nt XQ at 5'

<400> SEQUENCE: 33

```
agtcaggcca cttgtgccac ggttttgagca aaccgtgctg cctgtagctc cgccaataat    60
gggaggcgta aacatgacag aaatacgaac gaaactaacg cgcaaagatg ccgatccagg    120
ccgatccagg ccgatccagg ccgatccagg ccgatccagg ccgatccagg ccgatccagg    180
ccgatccagg ccgatccagg ccgatccagg ccgatccagc ttttttt                  227
```

<210> SEQ ID NO 34
<211> LENGTH: 90
<212> TYPE: DNA
<213> ORGANISM: Artificial Sequence
<220> FEATURE:
<223> OTHER INFORMATION: cgRNA M

<400> SEQUENCE: 34

```
gagtcgcgtg tagcgaagca gtttaagagc tatgctggaa acagcatagc aagtttaaat    60
aaggctagtc cgttatcagc accttttttt                                     90
```

<210> SEQ ID NO 35
<211> LENGTH: 90
<212> TYPE: DNA
<213> ORGANISM: Artificial Sequence
<220> FEATURE:
<223> OTHER INFORMATION: cgRNA N

<400> SEQUENCE: 35

```
gagtcgcgtg tagcgaagca gtttaagagc tatgctggaa acagcatagc aagtttaaat    60
aaggctagtc cgttatcagg ccctttttt                                      90
```

<210> SEQ ID NO 36
<211> LENGTH: 90
<212> TYPE: DNA
<213> ORGANISM: Artificial Sequence
<220> FEATURE:
<223> OTHER INFORMATION: cgRNA O

<400> SEQUENCE: 36

```
gagtcgcgtg tagcgaagca gtttaagagc tatgctggaa acagcatagc aagtttaaat    60
aaggctagtc cgttatcacc cacttttttt                                     90
```

<210> SEQ ID NO 37
<211> LENGTH: 27
<212> TYPE: DNA
<213> ORGANISM: Artificial Sequence
<220> FEATURE:
<223> OTHER INFORMATION: Trigger XM

<400> SEQUENCE: 37

```
gtgcggcacc gagtcggtgc ttttttt                                        27
```

```
<210> SEQ ID NO 38
<211> LENGTH: 27
<212> TYPE: DNA
<213> ORGANISM: Artificial Sequence
<220> FEATURE:
<223> OTHER INFORMATION: Trigger XN

<400> SEQUENCE: 38
ggccggcacc gagtcggtgc tttttt                                          27

<210> SEQ ID NO 39
<211> LENGTH: 27
<212> TYPE: DNA
<213> ORGANISM: Artificial Sequence
<220> FEATURE:
<223> OTHER INFORMATION: Trigger XO

<400> SEQUENCE: 39
tgggggcacc gagtcggtgc tttttt                                          27

<210> SEQ ID NO 40
<211> LENGTH: 96
<212> TYPE: DNA
<213> ORGANISM: Artificial Sequence
<220> FEATURE:
<223> OTHER INFORMATION: cgRNA M

<400> SEQUENCE: 40
gagtcgcgtg tagcgaagca gtttaagagc tatgctggaa acagcatagc aagtttaaat    60
aaggctagtc cgttatcagc acatcccact tttttt                              96

<210> SEQ ID NO 41
<211> LENGTH: 96
<212> TYPE: DNA
<213> ORGANISM: Artificial Sequence
<220> FEATURE:
<223> OTHER INFORMATION: cgRNA N

<400> SEQUENCE: 41
gagtcgcgtg tagcgaagca gtttaagagc tatgctggaa acagcatagc aagtttaaat    60
aaggctagtc cgttatcagg ccaggttcct tttttt                              96

<210> SEQ ID NO 42
<211> LENGTH: 96
<212> TYPE: DNA
<213> ORGANISM: Artificial Sequence
<220> FEATURE:
<223> OTHER INFORMATION: cgRNA O

<400> SEQUENCE: 42
gagtcgcgtg tagcgaagca gtttaagagc tatgctggaa acagcatagc aagtttaaat    60
aaggctagtc cgttatcacc cagaacacct tttttt                              96

<210> SEQ ID NO 43
<211> LENGTH: 102
<212> TYPE: DNA
<213> ORGANISM: Artificial Sequence
<220> FEATURE:
<223> OTHER INFORMATION: Trigger XM

<400> SEQUENCE: 43
agtcaggcca cttgtgccac ggtttgagca aaccgtgctg cctgtagctc cgccaataat    60
gggaggcgtt gggatgtgcg gcaccgagtc ggtgcttttt tt                       102
```

<210> SEQ ID NO 44
<211> LENGTH: 102
<212> TYPE: DNA
<213> ORGANISM: Artificial Sequence
<220> FEATURE:
<223> OTHER INFORMATION: Trigger XN

<400> SEQUENCE: 44
agtcaggcca cttgtgccac ggtttgagca aaccgtgctg cctgtagctc cgccaataat    60
gggaggcgtg aacctggccg gcaccgagtc ggtgcttttt tt                      102

<210> SEQ ID NO 45
<211> LENGTH: 102
<212> TYPE: DNA
<213> ORGANISM: Artificial Sequence
<220> FEATURE:
<223> OTHER INFORMATION: Trigger XO

<400> SEQUENCE: 45
agtcaggcca cttgtgccac ggtttgagca aaccgtgctg cctgtagctc cgccaataat    60
gggaggcgtg tgttctgggg gcaccgagtc ggtgcttttt tt                      102

<210> SEQ ID NO 46
<211> LENGTH: 96
<212> TYPE: DNA
<213> ORGANISM: Artificial Sequence
<220> FEATURE:
<223> OTHER INFORMATION: cgRNA M

<400> SEQUENCE: 46
gagtcgcgtg tagcgaagca gtttaagagc tatgctggaa acagcatagc aagtttaaat    60
aaggctagtc cgttatcagc acatcccact tttttt                             96

<210> SEQ ID NO 47
<211> LENGTH: 96
<212> TYPE: DNA
<213> ORGANISM: Artificial Sequence
<220> FEATURE:
<223> OTHER INFORMATION: cgRNA N

<400> SEQUENCE: 47
gagtcgcgtg tagcgaagca gtttaagagc tatgctggaa acagcatagc aagtttaaat    60
aaggctagtc cgttatcagg ccaggttcct tttttt                             96

<210> SEQ ID NO 48
<211> LENGTH: 96
<212> TYPE: DNA
<213> ORGANISM: Artificial Sequence
<220> FEATURE:
<223> OTHER INFORMATION: cgRNA O

<400> SEQUENCE: 48
gagtcgcgtg tagcgaagca gtttaagagc tatgctggaa acagcatagc aagtttaaat    60
aaggctagtc cgttatcacc cagaacacct tttttt                             96

<210> SEQ ID NO 49
<211> LENGTH: 102
<212> TYPE: DNA
<213> ORGANISM: Artificial Sequence
<220> FEATURE:
<223> OTHER INFORMATION: Trigger XM

<400> SEQUENCE: 49
agtcaggcca cttgtgccac ggtttgagca aaccgtgctg cctgtagctc cgccaataat       60
gggaggcgtt gggatgtgcg gcaccgagtc ggtgcttttt tt                          102

<210> SEQ ID NO 50
<211> LENGTH: 102
<212> TYPE: DNA
<213> ORGANISM: Artificial Sequence
<220> FEATURE:
<223> OTHER INFORMATION: Trigger XN

<400> SEQUENCE: 50
agtcaggcca cttgtgccac ggtttgagca aaccgtgctg cctgtagctc cgccaataat       60
gggaggcgtg aacctggccg gcaccgagtc ggtgcttttt tt                          102

<210> SEQ ID NO 51
<211> LENGTH: 102
<212> TYPE: DNA
<213> ORGANISM: Artificial Sequence
<220> FEATURE:
<223> OTHER INFORMATION: Trigger XO

<400> SEQUENCE: 51
agtcaggcca cttgtgccac ggtttgagca aaccgtgctg cctgtagctc cgccaataat       60
gggaggcgtg tgttctgggg gcaccgagtc ggtgcttttt tt                          102

<210> SEQ ID NO 52
<211> LENGTH: 94
<212> TYPE: DNA
<213> ORGANISM: Artificial Sequence
<220> FEATURE:
<223> OTHER INFORMATION: cgRNA M

<400> SEQUENCE: 52
gagtcgcgtg tagcgaagca gtttaagagc tatgctggaa acagcatagc aagtttaaat       60
aaggctagtc cgttatcagc acatcccttt tttt                                   94

<210> SEQ ID NO 53
<211> LENGTH: 94
<212> TYPE: DNA
<213> ORGANISM: Artificial Sequence
<220> FEATURE:
<223> OTHER INFORMATION: cgRNA N

<400> SEQUENCE: 53
gagtcgcgtg tagcgaagca gtttaagagc tatgctggaa acagcatagc aagtttaaat       60
aaggctagtc cgttatcagg ccaggtcttt tttt                                   94

<210> SEQ ID NO 54
<211> LENGTH: 94
<212> TYPE: DNA
<213> ORGANISM: Artificial Sequence
<220> FEATURE:
<223> OTHER INFORMATION: cgRNA O

<400> SEQUENCE: 54
gagtcgcgtg tagcgaagca gtttaagagc tatgctggaa acagcatagc aagtttaaat       60
aaggctagtc cgttatcacc cagaaccttt tttt                                   94

<210> SEQ ID NO 55
<211> LENGTH: 100
<212> TYPE: DNA

<213> ORGANISM: Artificial Sequence
<220> FEATURE:
<223> OTHER INFORMATION: Trigger XM

<400> SEQUENCE: 55

```
agtcaggcca cttgtgccac ggtttgagca aaccgtgctg cctgtagctc cgccaataat      60
gggaggcgtg gatgtgcggc accgagtcgg tgcttttttt                          100
```

<210> SEQ ID NO 56
<211> LENGTH: 100
<212> TYPE: DNA
<213> ORGANISM: Artificial Sequence
<220> FEATURE:
<223> OTHER INFORMATION: Trigger XN

<400> SEQUENCE: 56

```
agtcaggcca cttgtgccac ggtttgagca aaccgtgctg cctgtagctc cgccaataat      60
gggaggcgta cctggccggc accgagtcgg tgcttttttt                          100
```

<210> SEQ ID NO 57
<211> LENGTH: 100
<212> TYPE: DNA
<213> ORGANISM: Artificial Sequence
<220> FEATURE:
<223> OTHER INFORMATION: Trigger XO

<400> SEQUENCE: 57

```
agtcaggcca cttgtgccac ggtttgagca aaccgtgctg cctgtagctc cgccaataat      60
gggaggcgtg ttctgggggc accgagtcgg tgcttttttt                          100
```

<210> SEQ ID NO 58
<211> LENGTH: 92
<212> TYPE: DNA
<213> ORGANISM: Artificial Sequence
<220> FEATURE:
<223> OTHER INFORMATION: cgRNA M

<400> SEQUENCE: 58

```
gagtcgcgtg tagcgaagca gtttaagagc tatgctggaa acagcatagc aagtttaaat      60
aaggctagtc cgttatcagc acatcttttt tt                                   92
```

<210> SEQ ID NO 59
<211> LENGTH: 92
<212> TYPE: DNA
<213> ORGANISM: Artificial Sequence
<220> FEATURE:
<223> OTHER INFORMATION: cgRNA N

<400> SEQUENCE: 59

```
gagtcgcgtg tagcgaagca gtttaagagc tatgctggaa acagcatagc aagtttaaat      60
aaggctagtc cgttatcagg ccagcttttt tt                                   92
```

<210> SEQ ID NO 60
<211> LENGTH: 92
<212> TYPE: DNA
<213> ORGANISM: Artificial Sequence
<220> FEATURE:
<223> OTHER INFORMATION: cgRNA O

<400> SEQUENCE: 60

```
gagtcgcgtg tagcgaagca gtttaagagc tatgctggaa acagcatagc aagtttaaat      60
aaggctagtc cgttatcacc cagacttttt tt                                   92
```

<210> SEQ ID NO 61
<211> LENGTH: 98
<212> TYPE: DNA
<213> ORGANISM: Artificial Sequence
<220> FEATURE:
<223> OTHER INFORMATION: Trigger XM

<400> SEQUENCE: 61
agtcaggcca cttgtgccac ggtttgagca aaccgtgctg cctgtagctc cgccaataat    60
gggaggcgta tgtgcggcac cgagtcggtg cttttttt                           98

<210> SEQ ID NO 62
<211> LENGTH: 98
<212> TYPE: DNA
<213> ORGANISM: Artificial Sequence
<220> FEATURE:
<223> OTHER INFORMATION: Trigger XN

<400> SEQUENCE: 62
agtcaggcca cttgtgccac ggtttgagca aaccgtgctg cctgtagctc cgccaataat    60
gggaggcgtc tggccggcac cgagtcggtg cttttttt                           98

<210> SEQ ID NO 63
<211> LENGTH: 98
<212> TYPE: DNA
<213> ORGANISM: Artificial Sequence
<220> FEATURE:
<223> OTHER INFORMATION: Trigger XO

<400> SEQUENCE: 63
agtcaggcca cttgtgccac ggtttgagca aaccgtgctg cctgtagctc cgccaataat    60
gggaggcgtt ctgggggcac cgagtcggtg cttttttt                           98

<210> SEQ ID NO 64
<211> LENGTH: 125
<212> TYPE: DNA
<213> ORGANISM: Artificial Sequence
<220> FEATURE:
<223> OTHER INFORMATION: cgRNA 40

<400> SEQUENCE: 64
agtcgcgtgt agcgaagcag tttaagagct atgctggaaa cagcatagca agtttaaata    60
aggctagtcc gttatcacat atcccatcca cctccacctc cacctccaca ttcccacctt   120
ttttt                                                              125

<210> SEQ ID NO 65
<211> LENGTH: 115
<212> TYPE: DNA
<213> ORGANISM: Artificial Sequence
<220> FEATURE:
<223> OTHER INFORMATION: cgRNA 30

<400> SEQUENCE: 65
agtcgcgtgt agcgaagcag tttaagagct atgctggaaa cagcatagca agtttaaata    60
aggctagtcc gttatcacat atcccatcca cctccacctc cacctccctt ttttt        115

<210> SEQ ID NO 66
<211> LENGTH: 105
<212> TYPE: DNA
<213> ORGANISM: Artificial Sequence
<220> FEATURE:

<223> OTHER INFORMATION: cgRNA 20

<400> SEQUENCE: 66
agtcgcgtgt agcgaagcag tttaagagct atgctggaaa cagcatagca agtttaaata    60
aggctagtcc gttatcacat atcccatcca cctccacctt ttttt    105

<210> SEQ ID NO 67
<211> LENGTH: 95
<212> TYPE: DNA
<213> ORGANISM: Artificial Sequence
<220> FEATURE:
<223> OTHER INFORMATION: cgRNA 10

<400> SEQUENCE: 67
agtcgcgtgt agcgaagcag tttaagagct atgctggaaa cagcatagca agtttaaata    60
aggctagtcc gttatcacat atcccatctt ttttt    95

<210> SEQ ID NO 68
<211> LENGTH: 132
<212> TYPE: DNA
<213> ORGANISM: Artificial Sequence
<220> FEATURE:
<223> OTHER INFORMATION: Trigger X40

<400> SEQUENCE: 68
agtcaggcca cttgtgccac ggtttgagca aaccgtgctg cctgtagctc cgccaataat    60
gggaggcgtg tgggaatgtg gaggtggagg tggaggtgga tgggatatgg gcaccgagtc    120
ggtgcttttt tt    132

<210> SEQ ID NO 69
<211> LENGTH: 122
<212> TYPE: DNA
<213> ORGANISM: Artificial Sequence
<220> FEATURE:
<223> OTHER INFORMATION: Trigger X30

<400> SEQUENCE: 69
agtcaggcca cttgtgccac ggtttgagca aaccgtgctg cctgtagctc cgccaataat    60
gggaggcgtg gaggtggagg tggaggtgga tgggatatgg gcaccgagtc ggtgcttttt    120
tt    122

<210> SEQ ID NO 70
<211> LENGTH: 113
<212> TYPE: DNA
<213> ORGANISM: Artificial Sequence
<220> FEATURE:
<223> OTHER INFORMATION: Trigger X20

<400> SEQUENCE: 70
agtcaggcca cttgtgccac ggtttgagca aaccgtgctg cctgtagctc cgccaataat    60
gggaggcgtg tggaggtgga tgggatatgg gcaccgagtc ggtgcttttt ttt    113

<210> SEQ ID NO 71
<211> LENGTH: 102
<212> TYPE: DNA
<213> ORGANISM: Artificial Sequence
<220> FEATURE:
<223> OTHER INFORMATION: Trigger X10

<400> SEQUENCE: 71
agtcaggcca cttgtgccac ggtttgagca aaccgtgctg cctgtagctc cgccaataat    60

```
gggaggcgta tgggatatgg gcaccgagtc ggtgcttttt tt                  102

<210> SEQ ID NO 72
<211> LENGTH: 103
<212> TYPE: DNA
<213> ORGANISM: Artificial Sequence
<220> FEATURE:
<223> OTHER INFORMATION: Standard gRNA

<400> SEQUENCE: 72
gagtcgcgtg tagcgaagca gttttagagc tagaaatagc aagttaaaat aaggctagtc   60
cgttatcaac ttgaaaaagt ggcaccgagt cggtgctttt ttt                   103

<210> SEQ ID NO 73
<211> LENGTH: 83
<212> TYPE: DNA
<213> ORGANISM: Artificial Sequence
<220> FEATURE:
<223> OTHER INFORMATION: No-target gRNA

<400> SEQUENCE: 73
gttttagagc tagaaatagc aagttaaaat aaggctagtc cgttatcaac ttgaaaaagt   60
ggcaccgagt cggtgctttt ttt                                          83

<210> SEQ ID NO 74
<211> LENGTH: 95
<212> TYPE: DNA
<213> ORGANISM: Artificial Sequence
<220> FEATURE:
<223> OTHER INFORMATION: 8 nt deletion

<400> SEQUENCE: 74
gagtcgcgtg tagcgaagca gttttagagc tagaaatagc aagttaaaat aaggctagtc   60
cgttatcaac ttgaaaaagt ggcaccgctt ttttt                             95

<210> SEQ ID NO 75
<211> LENGTH: 80
<212> TYPE: DNA
<213> ORGANISM: Artificial Sequence
<220> FEATURE:
<223> OTHER INFORMATION: 23 nt deletion

<400> SEQUENCE: 75
gagtcgcgtg tagcgaagca gttttagagc tagaaatagc aagttaaaat aaggctagtc   60
cgttatcaac ttcttttttt                                              80

<210> SEQ ID NO 76
<211> LENGTH: 71
<212> TYPE: DNA
<213> ORGANISM: Artificial Sequence
<220> FEATURE:
<223> OTHER INFORMATION: 32 nt deletion

<400> SEQUENCE: 76
gagtcgcgtg tagcgaagca gttttagagc tagaaatagc aagttaaaat aaggctagtc   60 cgtcttttttt t                                                      71

<210> SEQ ID NO 77
<211> LENGTH: 58
<212> TYPE: DNA
<213> ORGANISM: Artificial Sequence
<220> FEATURE:
```

<223> OTHER INFORMATION: 45 nt deletion

<400> SEQUENCE: 77
gagtcgcgtg tagcgaagca gttttagagc tagaaatagc aagttaaaat cttttttt    58

<210> SEQ ID NO 78
<211> LENGTH: 129
<212> TYPE: DNA
<213> ORGANISM: Artificial Sequence
<220> FEATURE:
<223> OTHER INFORMATION: cgRNA A

<400> SEQUENCE: 78
aactttcagt ttagcggtct gttttagagc tagaaatagc aagttaaaat aaggctagtc    60
cgatcaaacg ggtaaacaaa caggataatt aaggaggcag tacccgggca ccgagtcggt   120
gcttttttt                                                          129

<210> SEQ ID NO 79
<211> LENGTH: 129
<212> TYPE: DNA
<213> ORGANISM: Artificial Sequence
<220> FEATURE:
<223> OTHER INFORMATION: cgRNA E

<400> SEQUENCE: 79
aactttcagt ttagcggtct gttttagagc tagaaatagc aagttaaaat aaggctagtc    60
cgacacaagg ggaaattaac aacacaacac acacaacaca ggccccggca ccgagtcggt   120
gcttttttt                                                          129

<210> SEQ ID NO 80
<211> LENGTH: 1849
<212> TYPE: DNA
<213> ORGANISM: Artificial Sequence
<220> FEATURE:
<223> OTHER INFORMATION: Trigger XA

<400> SEQUENCE: 80
tggctaaaga aagaggagaa aaggtttatg gtagcaggtc atgcctctgg cagccccgca    60
ttcgggaccg cctctcattc gaattgcgaa catgaagaga tccacctcgc cggctcgatc   120
cagccgcatg gcgcgcttct ggtcgtcagc gaacatgatc atcgcgtcat ccaggccagc   180
gccaacgccg cggaatttct gaatctcgga agcgtactcg gcgttccgct cgccgagatc   240
gacggcgatc tgttgatcaa gatcctgccg catctcgatc ccaccgccga aggcatgccg   300
gtcgcggtgc gctgccggat cggcaatccc tctacggagt actgcggtct gatgcatcgg   360
cctccggaag gcgggctgat catcgaactc gaacgtgccg gcccgtcgat cgatctgtca   420
ggcacgctgg cgccggcgct ggagcggatc cgcacggcgg ttcactgcg cgcgctgtgc   480 gatgacaccg tgctgctgtt tcagcagtgc accggctacg accgggtgat ggtgtatcgt   540
ttcgatgagc aaggccacgg cctggtattc tccgagtgcc atgtgcctgg gctcgaatcc   600
tatttcggca accgctatcc gtcgtcgact gtcccgcaga tggcgcggca gctgtacgtg   660
cggcagcgcg tccgcgtgct ggtcgacgtc acctatcagc cggtgccgct ggagccgcgg   720
ctgtcgccgc tgaccgggcg cgatctcgac atgtcgggct gcttcctgcg ctcgatgtcg   780
ccgtgccatc tgcagttcct gaaggacatg gcgtgcgcg ccaccctggc ggtgtcgctg   840
gtggtcggcg gcaagctgtg gggcctggtt gtctgtcacc attatctgcc gcgcttcatc   900
cgtttcgagc tgcgggcgat ctgcaaacgg ctcgccgaaa ggatcgcgac gcggatcacc   960

```
gcgcttgaga gcgaattcgg tggtggtggt tctggtggtg gtggttctat gagtgtcaac    1020
ttagcttccc agttgcggga agggacgaaa aaatcccact ccatggcgga gaacgtcggc    1080
tttgtcaaat gcttcctcaa gggcgttgtc gagaaaaatt cctaccgtaa gctggttggc    1140
aatctctact ttgtctacag tgccatgaaa gaggaaatgg caaaatttaa ggaccatccc    1200
atcctcagcc acatttactt ccccgaactc aaccgcaaac aaagcctaga gcaagacctg    1260
caattctatt acggctccaa ctggcggcaa gaagtgaaaa tttctgccgc tggccaagcc    1320
tatgtggacc gagtccggca agtggccgct acggcccctg aattgttggt ggcccattcc    1380
tacacccgtt acctggggga tctttccggc ggtcaaattc tcaagaaaat tgcccaaaat    1440
gccatgaatc tccacgatgg tggcacagct ttctatgaat ttgccgacat tgatgacgaa    1500
aaggctttta aaaatacccta ccgtcaagct atgaatgatc tgcccattga ccaagccacc    1560
gccgaacgga ttgtggatga agccaatgac gcctttgcca tgaacatgaa aatgttcaac    1620
gaacttgaag caacctgat caaggcgatc ggcattatgg tgttcaacag cctcacccgt    1680
cgccgcagtc aaggcagcac cgaagttggc ctcgccacct ccgaaggcta gtaaacgtcg    1740
actctcgagt gagattgttg acggtaccgt attttttactg cctccttaat tatcctgttt    1800
gtttacccgt ttgatcgcaa aaaccccgc ttcggcgggg tttttttcgc                1849
```

<210> SEQ ID NO 81
<211> LENGTH: 1849
<212> TYPE: DNA
<213> ORGANISM: Artificial Sequence
<220> FEATURE:
<223> OTHER INFORMATION: Trigger XE

<400> SEQUENCE: 81

```
tggctaaaga aagaggagaa aaggtttatg gtagcaggtc atgcctctgg cagccccgca      60
ttcgggaccg cctctcattc gaattgcgaa catgaagaga tccacctcgc cggctcgatc     120
cagccgcatg gcgcgcttct ggtcgtcagc gaacatgatc atcgcgtcat ccaggccagc     180
gccaacgccg cggaatttct gaatctcgga agcgtactcg gcgttccgct cgccgagatc     240
gacggcgatc tgttgatcaa gatcctgccg catctcgatc ccaccgccga aggcatgccg     300
gtcgcggtgc gctgccggat cggcaatccc tctacggagt actgcggtct gatgcatcgg     360
cctccggaag gcgggctgat catcgaactc gaacgtgccg gcccgtcgat cgatctgtca     420
ggcacgctgg cgccggcgct ggagcggatc cgcacggcgg gttcactgcg cgcgctgtgc     480
gatgacaccg tgctgctgtt tcagcagtgc accggctacg accgggtgat ggtgtatcgt     540
ttcgatgagc aaggccacgg cctggtattc tccgagtgcc atgtgcctgg gctcgaatcc     600
tatttcggca accgctatcc gtcgtcgact gtcccgcaga tggcgcggca gctgtacgtg     660
cggcagcgcg tccgcgtgct ggtcgacgtc acctatcagc cggtgccgct ggagccgcgg     720
ctgtcgccgc tgaccgggcg cgatctcgac atgtcgggct gcttcctgcg ctcgatgtcg     780
ccgtgccatc tgcagttcct gaaggacatg ggcgtgcgcg ccaccctggc ggtgtcgctg     840
gtggtcggcg gcaagctgtg gggcctggtt gtctgtcacc attatctgcc gcgcttcatc     900
cgtttcgagc tgcgggcgat ctgcaaacgg ctcgccgaaa ggatcgcgac gcggatcacc     960
gcgcttgaga gcgaattcgg tggtggtggt tctggtggtg gtggttctat gagtgtcaac    1020
ttagcttccc agttgcggga agggacgaaa aaatcccact ccatggcgga gaacgtcggc    1080
tttgtcaaat gcttcctcaa gggcgttgtc gagaaaaatt cctaccgtaa gctggttggc    1140
```

```
aatctctact ttgtctacag tgccatggaa gaggaaatgg caaaatttaa ggaccatccc    1200
atcctcagcc acatttactt ccccgaactc aaccgcaaac aaagcctaga gcaagacctg    1260
caattctatt acggctccaa ctggcggcaa gaagtgaaaa tttctgccgc tggccaagcc    1320
tatgtggacc gagtccggca gtggccgct acggccctg aattgttggt ggcccattcc      1380
tacacccgtt acctggggga tctttccggc ggtcaaattc tcaagaaaat tgcccaaaat    1440
gccatgaatc tccacgatgg tggcacagct ttctatgaat ttgccgacat tgatgacgaa    1500
aaggctttta aaataccta ccgtcaagct atgaatgatc tgcccattga ccaagccacc     1560
gccgaacgga ttgtggatga agccaatgac gcctttgcca tgaacatgaa aatgttcaac    1620
gaacttgaag gcaacctgat caaggcgatc ggcattatgg tgttcaacag cctcacccgt    1680
cgccgcagtc aaggcagcac cgaagttggc ctcgccacct ccgaaggcta gtaaacgtcg    1740
actctcgagt gagattgttg acggtaccgt attttcctgt gttgtgtgtg ttgtgttgtt    1800
aatttcccct tgtgtcgcaa aaaccccgc ttcggcgggg ttttttcgc                 1849
```

<210> SEQ ID NO 82
<211> LENGTH: 129
<212> TYPE: DNA
<213> ORGANISM: Artificial Sequence
<220> FEATURE:
<223> OTHER INFORMATION: cgRNA

<400> SEQUENCE: 82

```
gagtcgcgtg tagcgaagca gttttagagc tagaaatagc aagttaaaat aaggctagtc    60
cgtccattcg ggtttactat tacaatctta cgtgttctca ttcccgggca ccgagtcggt    120
gcttttttt                                                            129
```

<210> SEQ ID NO 83
<211> LENGTH: 117
<212> TYPE: DNA
<213> ORGANISM: Artificial Sequence
<220> FEATURE:
<223> OTHER INFORMATION: Non-cognate trigger (X')

<400> SEQUENCE: 83

```
agtcaggcca cttgtgccac ggtttgagca aaccgtgctg cctgtagctc cgccaataat    60
gggaggcgta acatgacag aaatacgaac gaaactaacg cgcaaagatc ttttttt        117
```

<210> SEQ ID NO 84
<211> LENGTH: 117
<212> TYPE: DNA
<213> ORGANISM: Artificial Sequence
<220> FEATURE:
<223> OTHER INFORMATION: Cognate-trigger (X)

<400> SEQUENCE: 84

```
agtcaggcca cttgtgccac ggtttgagca aaccgtgctg cctgtagctc cgccaataat    60
gggaggcgta atgagaacac gtaagattgt aatagtaaac ccgaatggac ttttttt       117
```

<210> SEQ ID NO 85
<211> LENGTH: 96
<212> TYPE: DNA
<213> ORGANISM: Artificial Sequence
<220> FEATURE:
<223> OTHER INFORMATION: cgRNA

<400> SEQUENCE: 85

```
gagtcgcgtg tagcgaagca gtttaagagc tatgctggaa acagcatagc aagtttaaat    60
```

```
aaggctagtc cgttatcagg ccaggttcct tttttt                               96

<210> SEQ ID NO 86
<211> LENGTH: 102
<212> TYPE: DNA
<213> ORGANISM: Artificial Sequence
<220> FEATURE:
<223> OTHER INFORMATION: Non-cognate trigger (X')

<400> SEQUENCE: 86
agtcaggcca cttgtgccac ggtttgagca aaccgtgctg cctgtagctc cgccaataat    60
gggaggcgtt gggatgtgcg gcaccgagtc ggtgcttttt tt                       102

<210> SEQ ID NO 87
<211> LENGTH: 102
<212> TYPE: DNA
<213> ORGANISM: Artificial Sequence
<220> FEATURE:
<223> OTHER INFORMATION: Cognate trigger (X)

<400> SEQUENCE: 87
agtcaggcca cttgtgccac ggtttgagca aaccgtgctg cctgtagctc cgccaataat    60
gggaggcgtg aacctggccg gcaccgagtc ggtgcttttt tt                       102

<210> SEQ ID NO 88
<211> LENGTH: 72
<212> TYPE: DNA
<213> ORGANISM: Artificial Sequence
<220> FEATURE:
<223> OTHER INFORMATION: cgRNA M

<400> SEQUENCE: 88
catctaattc aacaagaatt gttttagagc tagaaatagc aagttaaaat aaggctagtc    60
cgttatcagc ac                                                        72

<210> SEQ ID NO 89
<211> LENGTH: 72
<212> TYPE: DNA
<213> ORGANISM: Artificial Sequence
<220> FEATURE:
<223> OTHER INFORMATION: cgRNA N

<400> SEQUENCE: 89
catctaattc aacaagaatt gttttagagc tagaaatagc aagttaaaat aaggctagtc    60
cgttatcagg cc                                                        72

<210> SEQ ID NO 90
<211> LENGTH: 72
<212> TYPE: DNA
<213> ORGANISM: Artificial Sequence
<220> FEATURE:
<223> OTHER INFORMATION: cgRNA O

<400> SEQUENCE: 90
catctaattc aacaagaatt gttttagagc tagaaatagc aagttaaaat aaggctagtc    60
cgttatcacc ca                                                        72

<210> SEQ ID NO 91
<211> LENGTH: 19
<212> TYPE: DNA
<213> ORGANISM: Artificial Sequence
<220> FEATURE:
```

<223> OTHER INFORMATION: Trigger XM

<400> SEQUENCE: 91
gtgcggcacc gagtcggtg                                                19

<210> SEQ ID NO 92
<211> LENGTH: 19
<212> TYPE: DNA
<213> ORGANISM: Artificial Sequence
<220> FEATURE:
<223> OTHER INFORMATION: Trigger XN

<400> SEQUENCE: 92
ggccggcacc gagtcggtg                                                19

<210> SEQ ID NO 93
<211> LENGTH: 19
<212> TYPE: DNA
<213> ORGANISM: Artificial Sequence
<220> FEATURE:
<223> OTHER INFORMATION: Trigger XO

<400> SEQUENCE: 93
tgggggcacc gagtcggtg                                                19

<210> SEQ ID NO 94
<211> LENGTH: 96
<212> TYPE: DNA
<213> ORGANISM: Artificial Sequence
<220> FEATURE:
<223> OTHER INFORMATION: cg5

<400> SEQUENCE: 94
gagtcgcgtg tagcgaagca gttttagagc tagaaatagc aagttaaaat aaggctagtc    60
cgtcccatcg tccgtcccat caatttccct tttttt                              96

<210> SEQ ID NO 95
<211> LENGTH: 43
<212> TYPE: DNA
<213> ORGANISM: Artificial Sequence
<220> FEATURE:
<223> OTHER INFORMATION: cg3

<400> SEQUENCE: 95
aatataatac gggacggacg ggcaccgagt cggtgctttt ttt                      43

<210> SEQ ID NO 96
<211> LENGTH: 97
<212> TYPE: DNA
<213> ORGANISM: Artificial Sequence
<220> FEATURE:
<223> OTHER INFORMATION: Trigger

<400> SEQUENCE: 96
agtcaggcca cttgtgccac ggtttgagca aaccgtgctg cctgtagctc cgccaataat    60
gggaggcgtc gtccgtcccg tattatattc ttttttt                             97

<210> SEQ ID NO 97
<211> LENGTH: 106
<212> TYPE: DNA
<213> ORGANISM: Artificial Sequence
<220> FEATURE:
<223> OTHER INFORMATION: cg5

<400> SEQUENCE: 97

```
gagtcgcgtg tagcgaagca gttttagagc tagaaatagc aagttaaaat aaggctagtc    60
cgatatatac aaacacaaca cacacacaac aacaaacact tttttt                  106

<210> SEQ ID NO 98
<211> LENGTH: 132
<212> TYPE: DNA
<213> ORGANISM: Artificial Sequence
<220> FEATURE:
<223> OTHER INFORMATION: cg3

<400> SEQUENCE: 98
agtcaggcca cttgtgccac ggtttgagca aaccgtgctg cctgtagctc cgccaataat    60
gggaggcgtt gtctagaatt gtttgttgtt gtgtgtgtgt tgtgtttgtg gcaccgagtc   120
ggtgcttttt tt                                                      132

<210> SEQ ID NO 99
<211> LENGTH: 117
<212> TYPE: DNA
<213> ORGANISM: Artificial Sequence
<220> FEATURE:
<223> OTHER INFORMATION: Trigger

<400> SEQUENCE: 99
agtcaggcca cttgtgccac ggtttgagca aaccgtgctg cctgtagctc cgccaataat    60
gggaggcgta caaacacaac acacacacaa caacaaacaa ttctagacac tttttttt    117

<210> SEQ ID NO 100
<211> LENGTH: 146
<212> TYPE: DNA
<213> ORGANISM: Artificial Sequence
<220> FEATURE:
<223> OTHER INFORMATION: cg5

<400> SEQUENCE: 100
aactttcagt ttagcggtct gttttagagc tagaaatagc aagttaaaat aaggctagtc    60
cgatatatac aaacacaaca cacacacaac aacaaacaca acccaaccag agcgcaaaaa   120
accccgcttc ggcggggttt tttcgc                                       146

<210> SEQ ID NO 101
<211> LENGTH: 67
<212> TYPE: DNA
<213> ORGANISM: Artificial Sequence
<220> FEATURE:
<223> OTHER INFORMATION: cg3

<400> SEQUENCE: 101
tgtctagaat tgtttgttgt tgtgtgtgtg ttgtgtttgt ggcaccgagt cggtgctttt    60
tttcgcc                                                            67

<210> SEQ ID NO 102
<211> LENGTH: 34
<212> TYPE: DNA
<213> ORGANISM: Artificial Sequence
<220> FEATURE:
<223> OTHER INFORMATION: No-trigger control

<400> SEQUENCE: 102
cgcaaaaaac cccgcttcgg cggggttttt tcgc                               34

<210> SEQ ID NO 103
```

```
<211> LENGTH: 74
<212> TYPE: DNA
<213> ORGANISM: Artificial Sequence
<220> FEATURE:
<223> OTHER INFORMATION: Trigger X (Mechanism 4B)

<400> SEQUENCE: 103
ggttgggttg tgtttgttgt tgtgtgtgtg ttgtgtttgt cgcaaaaaac cccgcttcgg      60
cggggttttt tcgc                                                        74

<210> SEQ ID NO 104
<211> LENGTH: 74
<212> TYPE: DNA
<213> ORGANISM: Artificial Sequence
<220> FEATURE:
<223> OTHER INFORMATION: Trigger X (Mechanism 4C)

<400> SEQUENCE: 104
acaaacacaa cacacacaca acaacaaaca attctagaca cgcaaaaaac cccgcttcgg      60
cggggttttt tcgc                                                        74

<210> SEQ ID NO 105
<211> LENGTH: 146
<212> TYPE: DNA
<213> ORGANISM: Artificial Sequence
<220> FEATURE:
<223> OTHER INFORMATION: cg5

<400> SEQUENCE: 105
ttgtttaagg ctatggtgag aactttcagt ttagcggtct gttttagagc tagaaatagc      60
aagttaaaat aaggctagtc cgtaaataaa agcccaccct caccatagag agcgcaaaaa     120
accccgcttc ggcggggttt tttcgc                                          146

<210> SEQ ID NO 106
<211> LENGTH: 95
<212> TYPE: DNA
<213> ORGANISM: Artificial Sequence
<220> FEATURE:
<223> OTHER INFORMATION: cg3

<400> SEQUENCE: 106
ccaccctcac cataggtgct atggtgaggg tgggctttgg caccgagtcg gtgcttttt       60 tcgcaaaaaa ccccgcttcg gcggggtttt ttcgc                                 95

<210> SEQ ID NO 107
<211> LENGTH: 34
<212> TYPE: DNA
<213> ORGANISM: Artificial Sequence
<220> FEATURE:
<223> OTHER INFORMATION: No-trigger control

<400> SEQUENCE: 107
cgcaaaaaac cccgcttcgg cggggttttt tcgc                                  34
```

```
<210> SEQ ID NO 108
<211> LENGTH: 54
<212> TYPE: DNA
<213> ORGANISM: Artificial Sequence
<220> FEATURE:
<223> OTHER INFORMATION: Trigger X

<400> SEQUENCE: 108
ctcaccatag ccttgaacaa cgcaaaaaac cccgcttcgg cggggttttt tcgc          54
```